US011441153B2

(12) United States Patent
Dietrich et al.

(10) Patent No.: US 11,441,153 B2
(45) Date of Patent: Sep. 13, 2022

(54) COMPOSITIONS AND METHODS FOR IMPROVING CROP YIELDS THROUGH TRAIT STACKING

(71) Applicant: Monsanto Technology LLC, St. Louis, MO (US)

(72) Inventors: Charles R. Dietrich, Chesterfield, MO (US); Natalia Ivleva, Webster Groves, MO (US); Thomas L. Slewinski, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 260 days.

(21) Appl. No.: 16/276,620

(22) Filed: Feb. 15, 2019

(65) Prior Publication Data

US 2019/0249185 A1 Aug. 15, 2019

Related U.S. Application Data

(60) Provisional application No. 62/631,221, filed on Feb. 15, 2018.

(51) Int. Cl.
*C12N 15/82* (2006.01)

(52) U.S. Cl.
CPC ..... *C12N 15/8261* (2013.01); *C12N 15/8218* (2013.01); *C12N 15/8297* (2013.01)

(58) Field of Classification Search
None
See application file for complete search history.

(56) References Cited

U.S. PATENT DOCUMENTS

| | | |
|---|---|---|
| 5,159,135 A | 10/1992 | Umbeck et al. |
| 5,188,958 A | 2/1993 | Moloney |
| 5,322,938 A | 6/1994 | McPherson et al. |
| 5,352,605 A | 10/1994 | Fraley et al. |
| 5,463,174 A | 10/1995 | Moloney et al. |
| 5,510,474 A | 4/1996 | Quail et al. |
| 5,538,880 A | 7/1996 | Lundquist et al. |
| 5,550,318 A | 8/1996 | Adams et al. |
| 5,591,616 A | 1/1997 | Hiei et al. |
| 5,641,876 A | 6/1997 | Elroy et al. |
| 5,750,871 A | 5/1998 | Moloney et al. |
| 5,824,877 A | 10/1998 | Hinchee et al. |
| 5,850,019 A | 12/1998 | Maiti et al. |
| 6,153,812 A | 11/2000 | Fry et al. |
| 6,160,208 A | 12/2000 | Lundquist et al. |
| 6,194,636 B1 | 2/2001 | McElroy |
| 6,225,529 B1 | 5/2001 | Lappegard |
| 6,232,526 B1 | 5/2001 | McElroy et al. |
| 6,372,211 B1 | 4/2002 | Isaac et al. |
| 6,376,750 B1 | 4/2002 | Yu et al. |
| 6,384,301 B1 | 5/2002 | Martinell et al. |
| 6,399,861 B1 | 6/2002 | Anderson et al. |
| 6,420,547 B1 | 7/2002 | Maiti et al. |
| 6,429,357 B1 | 8/2002 | McElroy et al. |
| 6,723,897 B2 | 4/2004 | Brown et al. |
| 7,049,490 B2 | 5/2006 | Tanaka et al. |
| 7,057,088 B2 | 6/2006 | Tanaka et al. |
| 7,154,028 B2 | 12/2006 | Tanaka et al. |
| 7,491,813 B2 | 2/2009 | Wu et al. |
| 7,518,035 B2 | 4/2009 | Cheikh et al. |
| 7,547,774 B2 | 6/2009 | Flasinski et al. |
| 8,835,353 B2 | 9/2014 | Fugiel et al. |
| 9,309,512 B2 | 4/2016 | Allen et al. |
| 2002/0053095 A1 | 5/2002 | Brown et al. |
| 2003/0233679 A1 | 12/2003 | Brown et al. |
| 2004/0053411 A1 | 3/2004 | Cullen et al. |
| 2004/0121321 A1 | 6/2004 | Brown et al. |
| 2004/0216189 A1 | 10/2004 | Houmard et al. |
| 2004/0268441 A1 | 12/2004 | Vance et al. |
| 2005/0037988 A1 | 2/2005 | Zamore et al. |
| 2005/0064474 A1 | 3/2005 | Umov et al. |
| 2005/0144669 A1 | 6/2005 | Reinhart et al. |
| 2005/0197253 A1 | 9/2005 | Stoller et al. |
| 2005/0251883 A1 | 11/2005 | Amasino et al. |
| 2006/0200878 A1 | 9/2006 | Lutfiyya et al. |
| 2006/0253933 A1 | 11/2006 | Brown et al. |
| 2007/0174931 A1 | 7/2007 | Brown et al. |
| 2007/0174938 A1 | 7/2007 | Vanderkimpen et al. |

(Continued)

FOREIGN PATENT DOCUMENTS

| | | |
|---|---|---|
| CN | 102174519 A | 9/2011 |
| CN | 103451200 A | 12/2013 |

(Continued)

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
Doerks et al., (TIG, 14:248-250, 1998).*

(Continued)

*Primary Examiner* — Vinod Kumar

(74) *Attorney, Agent, or Firm* — Morrison & Foerster LLP

(57) ABSTRACT

The present disclosure provides modified, transgenic, or genome edited/mutated corn plants that are semi-dwarf and have one or more improved ear traits relative to a control plant, such as increase in ear diameter, single kernel weight, ear fresh weight, ear area, ear volume, ear length, number of kernels per ear, and yield. The modified, transgenic, or genome edited/mutated corn plants comprise a transgene encoding one or more MADS-box polypeptides and have a reduced expression of one or more GA20 or GA3 oxidase genes. Also provided are methods for producing the modified, transgenic, or genome edited/mutated corn plants.

39 Claims, 14 Drawing Sheets

Specification includes a Sequence Listing.

(56) References Cited

U.S. PATENT DOCUMENTS

| | | |
|---|---|---|
| 2007/0294789 A1 | 12/2007 | Ghiglione et al. |
| 2008/0034453 A1 | 2/2008 | Cheikh et al. |
| 2008/0131581 A1 | 6/2008 | Schneeberger et al. |
| 2009/0031441 A1 | 1/2009 | Matsuoka et al. |
| 2009/0070898 A1 | 3/2009 | Allen et al. |
| 2009/0117617 A1 | 5/2009 | Holmes et al. |
| 2009/0313725 A1 | 12/2009 | Yu et al. |
| 2010/0095406 A1 | 4/2010 | Yu et al. |
| 2011/0004958 A1 | 1/2011 | Aloni et al. |
| 2011/0035839 A1 | 2/2011 | Lutfiyya et al. |
| 2011/0145940 A1 | 6/2011 | Voytas et al. |
| 2011/0167517 A1 | 7/2011 | Danilevskaya et al. |
| 2011/0185456 A1 | 7/2011 | Cheikh et al. |
| 2011/0296555 A1 | 12/2011 | Ivashuta et al. |
| 2011/0301073 A1 | 12/2011 | Gregory et al. |
| 2012/0142062 A1 | 6/2012 | Doyon et al. |
| 2012/0216318 A1 | 8/2012 | La Rosa et al. |
| 2013/0117869 A1 | 5/2013 | Duchateau et al. |
| 2013/0283461 A1 | 10/2013 | Abad et al. |
| 2014/0165228 A1 | 6/2014 | Danilevskaya et al. |
| 2014/0344996 A1 | 11/2014 | Inze et al. |
| 2015/0052634 A1 | 2/2015 | Park et al. |
| 2015/0247154 A1 | 9/2015 | Ivashuta et al. |
| 2015/0307889 A1 | 10/2015 | Petolino et al. |
| 2015/0376641 A1 | 12/2015 | Etzioni et al. |
| 2016/0010109 A1 | 1/2016 | Albertsen et al. |
| 2016/0017349 A1 | 1/2016 | Ayele et al. |
| 2016/0046956 A1 | 2/2016 | Yu et al. |
| 2016/0050920 A1 | 2/2016 | Ott et al. |
| 2016/0076046 A1 | 3/2016 | Alexandrov et al. |
| 2017/0114356 A1 | 4/2017 | Li et al. |

FOREIGN PATENT DOCUMENTS

| | | |
|---|---|---|
| EP | 1398382 B1 | 11/2005 |
| KR | 20150045611 A | 4/2015 |
| WO | WO 1994/28141 A1 | 12/1994 |
| WO | WO 1995/015389 | 6/1995 |
| WO | WO 1995/023230 | 8/1995 |
| WO | WO 1999/09174 A1 | 2/1999 |
| WO | WO 1999/016890 | 4/1999 |
| WO | WO 1999/66029 A2 | 12/1999 |
| WO | WO 2000/009722 A2 | 2/2000 |
| WO | WO 2000/012733 | 3/2000 |
| WO | WO 2002/055725 A2 | 7/2002 |
| WO | WO 2003/008540 A2 | 1/2003 |
| WO | WO 2004/070039 | 8/2004 |
| WO | WO 2006/032916 A2 | 3/2006 |
| WO | WO 2009/126470 | 10/2009 |
| WO | WO 2010/002984 A1 | 1/2010 |
| WO | WO 2013/037959 A1 | 3/2013 |
| WO | WO 2013/086499 A2 | 6/2013 |
| WO | WO 2014/055477 A2 | 4/2014 |
| WO | WO 2015/168124 A1 | 11/2015 |
| WO | PCT/US2017/047405 | 8/2017 |

OTHER PUBLICATIONS

Smith et al. (Nature Biotechnology, 15:1222-1223, 1997).*
Bork et al. (TIG, 12:425-427, 1996).*
Heuer et al. (Plant physiology, 127:33-45; 2001).*
Rounsley et al. (Plant Cell, 7:1259-1269, 1995).*
Alvarez-Buylla et al. (PNAS., 97:5328-5333, Published May 2000).*
Yang et al. (Molecular Genetics and Genomics; 289:873-883; 2014).*
Kaufmann et al. (Gene, 347:183-198, 2005).*
Petti et al. (Plant Physiol., 169:705-716; Sep. 2015).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Nunes et al. (Planta 224:125-132; 2006).*
Arziman et al. (Nucleic Acids Research, 33:582-588, 2005).*
Bonawitz et al., (Annu. Rev. Genet. 44: 337-363, 2010).*
Paul et al., Plant Cell Reports; 35:1417-1427; 2016.*
Nishimura et al. (Plant Cell Physiol., 41(5):583-590, 2000).*
Yang et al. (PNAS, 98:11438-11443, 2001).*
McConnell et al. (Nature, 411:709-713, 2001).*
Qiao et al. (Plant Mol Biol Reporter, 29:952-960, 2011).*
Wills et al. (Journal of Heredity, 109(3): pp. 333-338; published Sep. 5, 2017).*
Yang et al. (GenBank Sequence Accession No. EU179378.1; pp. 1-2, Published 2009).*
Wingen et al. (NCBI, GenBank Sequence Accession No. AJ850299.1; pp. 1-2, Published May 10, 2012).*
Albani et al, The Plant Cell 9:171-184 (1997).
Allen et al., "Evolution of microRNA genes by inverted duplication of target gene sequences in *Arabidopsis thaliana*," *Nat. Genet.*, 36:1282-1290 (2004).
Allen et al., "microRNA-directed phasing during trans-acting siRNA biogenesis in plants," *Cell*, 121(2):207-221 (2005).
Altschul et al., "Basic local alignment search tool," *J. Mol. Biol.*, 215(3):403-410 (1990).
Altschul et al., "Gapped BLAST and PSI-BLAST: a new generation of protein database search programs," *Nucleic Acids Res.*, 25(17):3389-3402 (1997).
Ashikari et al., "Loss-of-function of a Rice Gibberellin Biosynthetic Gene, GA20 oxidase (GA20ox-2), Led to the Rice 'Green Revolution'," *Breeding Science*, 52:143-150 (2002).
Axtell et al., "A two-hit trigger for siRNA biogenesis in plants," *Cell*, 127:565-577 (2006).
Beurdeley et al., "Compact designer TALENs for efficient genome engineering," *Nature Communications*, 4:1762 (2013).
Carrera et al., "Changes in GA 20-oxidase gene expression strongly affect stem length, tuber induction and tuber yield of potato plants," *Plant J.*, 22:247-256 (2000).
Cermak et al., "Efficient design and assembly of custom TALEN and other TAL effector-based constructs for DNA targeting," *Nucleic Acids Research*, 39(12):e82 (2011).
Chen et al., "Identification and Functional Analysis of Flowering Related microRNAs in Common Wild Rice (*Oryza rufipogon* Griff.)," *PLoS ONE*, 8:e82844 (2013).
Chen et al., "The Maize DWARF1 Encodes a Gibberellin 3-Oxidase and is Dual Localized to the Nucleus and Cytosol," *Plant Physiology*, 166:2028-2039 (2014).
Chenna et al., "Multiple sequence alignment with the Clustal series of programs," *Nucleic Acids Research*, 31:3497-3500 (2003).
Cho et al., Theor Appl Gen 98:1253-62 (1999).
Colbert et al., *Plant Physiol* 126:480-484 (2001).
Coles et al., "Modification of gibberellin production and plant development in *Arabidopsis* by sense and antisense expression of gibberellin 20-oxidase genes," *Plant J.*, 17:547-556 (1999).
Colot et al., Mol Gen Genet 216:81-90 (1989).
Doyle et al., "Nucleic Acids TAL Effector-Nucleotide Targeter (TALE-NT) 2.0: tools for TAL effector design and target prediction," *Research*, 40:W117-122 (2012).
Du et al., "Cloning and characterization of an up-regulated GA 20-oxidase gene in hyblid maize," *Natural Science*, 19:161-166 (2009).
Fagoaga et al., "Engineering of gibberellin levels in citrus by sense and antisense overexpression of a GA 20-oxidase gene modifies plant architecture," *Journal of Experimental Botany*, 58(6):1407-1420 (2007).
Franco-Zorrilla et al., "Target mimicry provides a new mechanism for regulation of microRNA activity," *Nature Genetics*, 39:1033-1037 (2007).
Gabsalilow et al., "Site- and strand-specific nicking of DNA by fusion proteins derived from MutH and I-SceI or TALE repeats," *Nucleic Acids Research*, 41(7):e83:1-11 (2013).
Gaj et al., "ZFN, TALEN and CRISPR/Cas-based methods for genome engineering," *Trends Biotechnol.*, 31(7):397-405 (2013).
Griffiths-Jones et al., "Rfam: an RNA family database," *Nucleic Acids Res.*, 31:439-441 (2003).

(56) References Cited

OTHER PUBLICATIONS

Jones-Rhoades et al., "Computational Identification of Plant MicroRNAs and Their Targets, Including a Stress-Induced miRNA," *Mol. Cell*, 14:787-799 (2004).
Katoh et al., "Specific residues at every third position of siRNA shape its efficient RNAi activity," *Nucleic Acids Res.*, 35(4):e27:1-14 (2007).
Khvorova et al., "Functional siRNAs and miRNAs Exhibit Strand Bias," *Cell*, 115(2):209-216 (2003).
Kim, "MicroRNA biogenesis: coordinated cropping and dicing," Nature *Rev. Mol. Cell. Biol.*, 6:376-385 (2005).
Larkin et al., "Clustal W and Clustal X version 2.0," *Bioinformatics*, 23(21):2947-48 (2007).
Last et al., *Theor. Appl. Genet.*, 81:581 (1991).
Mena et al, The Plant Journal, 116(1): 53-62 (1998).
Muller et al., The Plant Journal 4(2):343-355 (1993).
Nakase et al. Plant Mol. Biol. 33(3):513-S22 (1997).
Opsahl-Ferstad et al., Plant J. 12(1): 235-46 (1997).
Parizotto et al., "In vivo investigation of the transcription, processing, endonucleolytic activity, and functional relevance of the spatialdistiibution of a plant miRNA," *Genes Dev.*, 18:2237-2242 (2004).
Postma-Haarsma et al, Plant Mol. Biol. 39(2): 257-71 (1999).
Qiao et al., "Modification of plant height via RNAi suppression of OsGA20oxZ gene in rice," *Euphytica*, 158-35-45 (2007).
Rafalski et al., EMBO J 3(6):1409-15 (1984).
Reynolds et al., "Rational siRNA design for RNA interference," *Nature Biotechnol.*, 22(3):326-330 (2004).
Aryan et al., Mol and Gen Genet 225(1):65-71 (1991).
Atanassova et al., Plant Mol Biol, 37: 275-285 (1998).
Cai et al., "Molecular Cloning, Characterization, and Expression Analysis of Genes Encoding Gibberellin 20-Oxidase in Dasypymm villosum Dwarf Mutant," *Plant Mol Biol Rep*, 30:1110-1116 (2012).
Cejudo et al., Plant Mol Biol 20(5): 849-856 (1992.
Chen et al., "New insight in the Gibberellin biosynthesis and signal transduction," *Plant Signaling & Behavior*, 10(5):e1000140-1-e1000140-3:(2015).
Ciampitti et al., "A comprehensive study of plant density consequences on nitrogen uptake dynamics of maize plants from vegetative to reproductive stages," *Field Crops Research*, 121:2-18 (2011).
Conkling et al., "Isolation of Transcriptionally Regulated Root-Specific Genes from Tobacco," *Plant Physiol.*, 93:1203-1211 (1990).
Davis et al., "Gibberellin Biosynthesis in Maize. Metabolic Studies with $GA_{15}$, $GA_{24}$, $GA_{25}$, $GA_7$, and 2,3-Dehydro-$GA_9^1$," *Plant Physiology*, 121:1037-1045 (1999).
Derose et al., Plant Mol Biol 32(6):1029-35 (1997).
Diaz et al., Mol Gen Genet 248(5): 592-8 (1995).
Eriksson et al., "$GA_4$ is the Active Gibberellin in the Regulation of LEAFY Transcription and *Arabidopsis* Floral Initiation," *The Plant Cell*, 18:2172-2181 (2006).
Fambrini et al., "The extreme dwarf phenotype of the GA-sensitive mutant of sunflower, dwarf2, is generated by a deletion in the ent-kaurenoic acid oxidase 1 (HaKAO1) gene sequence," *Plant Mol Biol*, 75:431-450 (2011).
Furtado et al., Plant Biotechnol J 6(7):679-93 (2008).
Furtado et al., Plant Biotechnol J 7(3):240-53 (2009).
GenBank Accession No. AY105651.1 *Zea mays* PCO130567 mRNA sequence (2002).
Gramzow and Theissen, *Genome Biol.*, 11: 214 (2010).
Gupta et al., "Gibberellic acid in plant Still a mystery unresolved," *Plant Signaling & Behavior*, 8(9):e25504-1-e25504-5 (2013).
Hedden, "Gibberellin Biosynthesis: Enzymes, Genes and Their Regulation," *Annu. Rev. Plant Physiol. Plant Mol. Biol.*, 48:431-60 (1997).
Hedden, "The genes of the Green Revolution," *TRENDS in Genetics*, 19(1):5-9 (2003).
Horvath et al., PNAS 97(4): 1914-19 (2000).
Huang et al., "A Gibberellin-Mediated DELLA-NAC Signaling Cascade Regulates Cellulose Synthesis in Rice," *The Plant Cell*, 27:1681-1696 (2015).

International Search Report and Written Opinion dated Dec. 28, 2017, in International Application No. PCT/US2017/047405.
International Search Report and Written Opinion dated Jul. 9, 2019, in International Application No. PCT/US2019/018136.
Jia et al., "GA-20 oxidase as a candidate for the semidwarf gene sdw 1/denso in barley," *Funct Integr Genomics*, 9:255-262 (2009).
Jia et al., "Molecular characterization and functional analysis of barley semi-dwarf mutant Riso No. 9265," *BMC Genomics*, 16(927)1-11 (2015).
Joshi et al., Physiol Mol Biol Plants, 21(1): 35-42 (2015).
Kalla et al., The Plant J. 6(6): 849-60 (1994).
King et al., "Selective Deactivation of Gibberellins below the Shoot Apex is Critical to Flowering but Not to Stem Elongation of *Lolium*," *Molecular Plant*, 1(2):295-307 (2008).
Kobayashi et al., "Gibberellin Metabolism in Maize," *Plant Physiol.*, 110:413-418 (1996).
Kosugi et al., Nucl. Acids Res. 19: 1571-1576 (1991).
Kusaba et al., "Isolation and expression analysis of gibberellin 20-oxidase homologous gene in apple," *Journal of Experimental Botany*, 52(335):375-376 (2001).
Lagrimini, L.M. (editor), Maize: Methods and Protocols (Humana Press), Chapter 4: A Brief History of Promoter Development for Use in Transgenic Maize Applications, vol. 1676, pp. 61-93 (2017).
Lam et al., PNAS USA, 86:7890-7894 (1989).
Lamacchia et al., J Exp Bot 52(355):243-50 (2001).
Lanahan et al, The Plant Cell 4: 203-211 (1992).
Leah et al., Plant J. 6(4): 579-89, 1994).
Matzke et al., Plant Mol Biol, 14(3): 323-32 (1990).
McCallum et al., *Nat. Biotechnol.*, 18:455-457 (2000).
McCormick et al., *Plant Cell Reports* 5:81-84 (1986).
McElroy et al., "Construction of expression vectors based on the rice actin 1 (Act1) 5' region for use in monocot transformation," *Mol. Gen. Genet.*, 231:150-160 (1991).
Merida et al., Plant Physiol. 120(2):401-410 (1999).
Mitchum et al., "Distinct and overlapping roles of two gibberellin 3-oxidases in *Arabidopsis* development," *The Plant Journal*, 45:804-818 (2006).
Molina et al., "Transformation of a Dwarf *Arabidopsis* Mutant Illustrates Gibberellin Hormone Physiology and the Function of a Green Revolution Gene," *Biochemistry and Molecular Biology Education*, 37(3):170-177 (2009).
Mutasa-G ttgens et al., "Gibberellin as a factor in floral regulatory networks," *Journal of Experimental Botany*, 60(7):1979-1989 (2009).
Ohtsubo et al., Pant Mol Biol 23(3):553-565 (1993).
Oikawa et al., "A role of OsGA20ox1, encoding an isoform of gibberellin 20-oxidase, for regulation of plant stature in rice," *Plant Molecular Biology*, 55:687-700 (2004).
Onate et al., J Biol Chem 274(14): 9175-82 (1999).
Osvald et al., In Vitro Cellular & Dev Biol. Plant 44(1): 1-7 (2008).
Pater et al., "The promoter of the rice gene GOS2 is active in various different monocot tissues and binds rice nuclear factor ASF-1," *The Plant Journal*, 2(6):837-844 (1992).
Peiffer et al., "The Genetic Architecture of Maize Height," *Genetics*, 196:1337-1356 (2014).
Peng et al., "'Green revolution' genes encode mutant gibberellin response modulators," *Nature*, 400:256-261 (1999).
Petti et al., "Mapping of a Cellulose-Deficient Mutant Named dwarf1-1 in Sorghum bicolor to the Green Revolution Gene gibberellin20-oxidase Reveals a Positive Regulatory Association between Gibberellin and Cellulose Biosynthesis," *Plant Physiology*, 169:705-716 (2015).
Piston et al., Mol Breed 23(4):655-667 (2009).
Plackett et al., "Analysis of the Developmental Roles of the *Arabidopsis*Gibberellin 20-Oxidases Demonstrates That GA20ox1, -2 and -3 are the Dominant Paralogs," *The Plant Cell*, 24:941-960 (2012).
Qiao et al., "The Influence of RNAi Targeting of OsGA200x2 Gene on Plant Height in Rice," *Plant Molecular Biology Reporter*, 29(4):952-960 (2011).
Qiao et al., "Alteration of rice growth and development via anti-sense expression of OsGA20ox2 gene," *African Journal of Biotechnology*, 12(5):3898-3904 (2013).

(56) References Cited

OTHER PUBLICATIONS

Qin et al., "Gibberellin 20-Oxidase Gene OsGA20ox3 Regulates Plant Stature and Disease Development in Rice," *MPMI*, 26(2):227-239 (2013).
Qu et al., J Exp Bot 59(9):2417-2424 (2008).
Qu et al., Plant Biotechnol. J. 2: 113-125 (2004).
Rhoades et al., "Prediction of Plant MicroRNA Targets," *Cell*, 110(4):513-520 (2002).
Rieu et al., "The gibberellin biosynthetic genes AtGA20ox1 and AtGA20ox2 act, partially redundantly, to promote growth and development throughout the *Arabidopsis* life cycle," *The Plant Journal*, 53:488-504 (2008).
Ross et al., "Gibberellin mutants," *Physiologia Plantarum*, 100:550-560 (1997).
Sarkar et al., "Relationship between gibberellins, height, and stress tolerance in barely (*Hordeum vulgare* L.) seedlings," *Plant Growth Regulation*, 42:125-135 (2004).
Sasaki et al., "A mutant gibberellin-synthesis gene in rice," *Nature*, 416:701-702 (2002).
Sato et al., PNAS USA 93(15): 8117-8122 (1996).
Selinger et al., Genetics 149(2); 1125-38 (1998).
Singh, "The green revolution and the evolution of agricultural education and research in India," *Genome*, 42:557-561 (1999).
Skriver et al., PNAS USA 88(16): 7266-7270 (1991).
Song et al., "Flowering time regulation: photoperiod- and temperature-sensing in leaves," *Trends in Plant Science*, 18(10):575-583 (2013).
Sorensen et al., Mol and Gen Genet 250(6):750-60 (1996).
Sun, "Gibberellin Metabolism, Perception and Signaling Pathways in *Arabidopsis*," *The Arabidopsis Book*, pp. 1-28 (2008).
Sunkar et al., "Novel and Stress-Regulated MicroRNAs and Other Small RNAs from *Arabidopsis*," *Plant Cell*, 16:2001-2019 (2004).
Thilmony et al., GM Crops Food, 5(1): 36-43 (2014).
Thompson et al., "CLUSTAL W: Improving the sensitivity of progressive multiple sequence alignment through sequence weighting, position-specific gap penalties and weight matrix choice," *Nucleic Acids Research*, 22:4673-4680 (1994).
Tollenaar et al., "Effect of Defoliation on Kernel Development in Maize," *Can. J. Plant Sci.*, 58:207-212 (1978).
Tong et al., "REPLY: Brassinosteroid Promotes Cells Elongation by Regulating Both Synthesis and Signaling of Gibberellin: Critical Comments on Ross and Quittenden's Letter," *Plant Cell Advance Publication*, pp. 1-7 (2016).
Traore et al., "Corn: BT and Non-Bt Maize Growth and Development as Affected by Temperature and Drought Stress," *Agron. J.*, 92:1027-1035 (2000).
UniProtKB Accession No. Q84V78_MAIZE, Putative MADS-domain transcription factor (2003).
Unterholzner et al., "REPLY: Interaction Between Brassinosteroids and Gibberellins: Synthesis or Signaling? In *Arabidopsis* Both!," *Plant Cell Advance Publication*, pp. 1-8 (2016).

Urakami et al., "Immunomodulation of gibberellin biosynthesis using an anti-precursor gibberellin antibody confers gibberellin-deficient phenotypes," *Planta*, 228:863-873 (2008).
VanHerpen et al., AnnBot 102(3) 331-342 (2008).
Vaucheret, *Science STKE*, 2005:pe43 (2005).
Wagner et al., The Plant Cell 13(2): 303-318 (2001).
Wang et al., "Gibberellin Biosynthetic Deficiency is Responsible for Maize Dominant Dwarf11 (D11) Mutant Phenotype: Physiological and Transcriptomic Evidence," *PLoS One*, 8(6):e66466:1-8 (2013).
Weng et al., "Genome-Wide Association Study Identifies Candidate Genes That Affect Plant Height in Chinese Elite Maize (*Zea mays* L.) Inbred Lines," *PLoS One*, 6(12):e29229:1-8 (2011).
Wills et al., "Defining the Role of the MADS-Box Gene, *Zea Agamous-like1*, a Target of Selection During Maize Domestication," *Journal of Heredity*, 109(3):333-338 (2017).
Woo, et al., "Genomics Analysis of Genes Expressed in Maize endosperm Identifies Novel Seed Proteins and Clarifies Patterns of Zein Gene Expression," *The Plant Cell*, 13(10): 2297-2318 (2001).
Wu et al. Int. J. Dev. Biol. 57: 535-543 (2013).
Wu et al, J. Biochem 123: 386-391 (1998).
Wu et al., "Target specificity of the CRISPR-Cas9 system," *Quant Biol.*, 2(2):59-70 (2014).
Wu et al., Plant Cell Physiology 39(8) 885-889 (1998).
Xu et al., "Charactertization of a rice gene family encoding root-specific proteins," *Plant Mol Biol.* 27(2): 237-48 (1995).
Yamaguchi et al., "Gibberellin Acts Positively Then Negatively to Control Onset of Flower Formation in *Arabidopsis*," *Science*, 344:638-641 (2014).
Yamaguchi, "Gibberellin Metabolism and its Regulation," *Annu. Rev. Plant Biol.*, 59:225-251 (2008).
Yanik et al., "TALE-PvuII Fusion Proteins—Novel Tools for Gene Targeting," *PLoS One*, 8(12):e82539:1-13 (2013).
Yin et al., "In-Season Prediction of Corn Yield Using Plant Height under Major Production Systems," *Agronomy Journal*, 103(3):923-929 (2011).
Yoshikawa et al., "A pathway for the biogenesis of trans-acting siRNAs in *Arabidopsis*," *Genes Dev.*, 19:2164-2175 (2005).
Yu et al., Gene 122(2): 247-253 (1992).
Zeng et al., "Both Natural and Designed Micro RNAs Can Inhibit the Expression of Cognate mRNAs When Expressed in Human Cells," *Mol. Cell*, 9(6):1327-1333 (2002).
J. Craig Venter Institute, Maize Cell Genomics Database, http://maize.jcvi.org/cellgenomics/index.php, accessed Jan. 3, 2020.
Xiao et al., "Dissection of GA 20-oxidase members affecting tomato morphology by RNAi-mediated silencing," *Plant Growth Regulation*, 50:179-189 (2006).
Anonymous. (Jan. 1, 1998). "Dwarf Corn Earns Tall Praise," Retrieved from the Internet:URL:https ://www.farmprogress.com/dwarf-corn-earns-tall-prai se[retrieved on Sep. 21, 2021].
European Extended Search Report, dated Oct. 5, 2021 for European Patent Application No. 19753661.8, 9 pages.
Hedden, P. et al. (2012). "Gibberellin biosynthesis and its regulation," Biochem. J. 444:11-25.

* cited by examiner

COMPOSITIONS AND METHODS FOR IMPROVING CROP YIELDS THROUGH TRAIT STACKING

CROSS-REFERENCE TO RELATED APPLICATION

This application claims benefit under 35 U.S.C. § 119(e) of U.S. Provisional Appln. No. 62/631,221, filed Feb. 15, 2018, herein incorporated by reference in its entirety.

INCORPORATION OF SEQUENCE LISTING

A sequence listing contained in the file named "GA20Ox_ZMM19_Sequence Listing_P34601US01.txt" which is 387,608 bytes (measured in MS-Windows®) and was created on Feb. 13, 2019, is filed electronically herewith and incorporated by reference in its entirety.

FIELD

The present disclosure relates to modified, transgenic, and/or genome edited or mutated corn plants that are semi-dwarf and have one or more improved ear traits relative to a control plant, as well as methods for producing transgenic and/or genome edited or mutated corn plants through stacking.

BACKGROUND

Cereal crop yields have been steadily increasing over the past decades due to improved agronomic practices and traits. However, there continues to be a need in the art for improved corn yield through intrinsic yield gains and/or reduced yield losses from improved lodging resistance, stress tolerances and other traits.

SUMMARY

Figure 1:
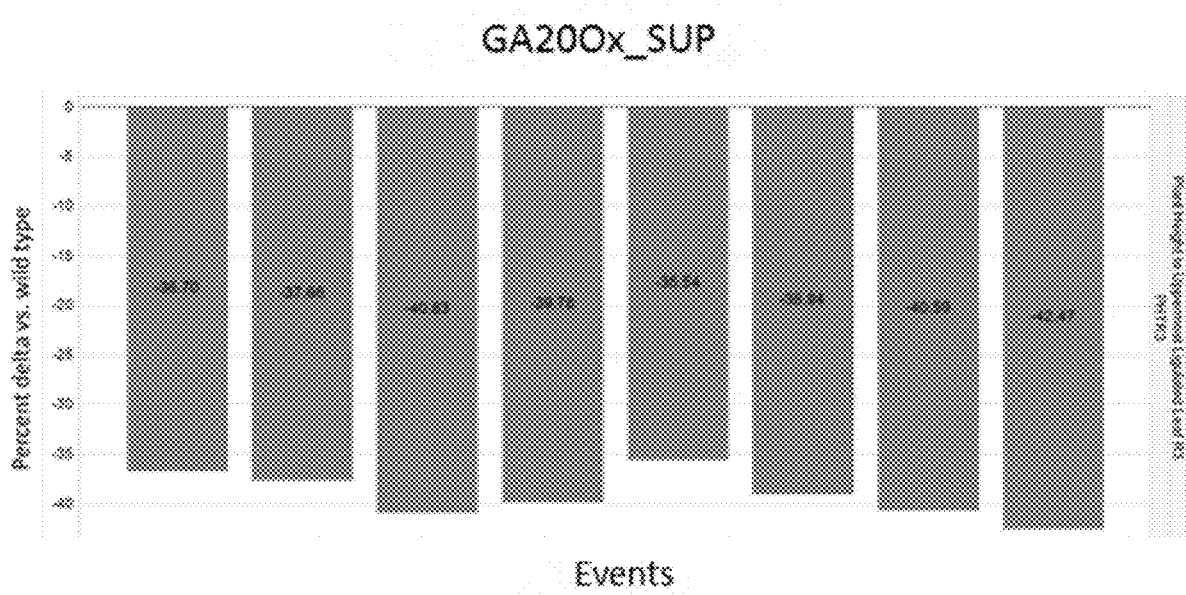
FIG. 1 shows plant heights of corn plants comprising a DNA sequence encoding an miRNA for the suppression of GA20 oxidase ("GA20Ox_SUP single") across eight transformation events, relative to control corn plants.

The present specification provides a modified corn plant or a plant part thereof comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a MADS-box polypeptide.

The present specification also provides a plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a MADS-box polypeptide.

Also provided by the present specification is a method for producing a modified corn plant, the method comprising: a) introducing into a corn cell a first recombinant expression cassette comprising a DNA sequence encoding a MADS-box polypeptide, wherein the corn cell comprises a second recombinant expression cassette comprising a transcribable DNA sequence encoding a non-coding RNA for suppression of one or more GA3 oxidase genes and/or one or more GA20 oxidase genes; and b) regenerating or developing a modified corn plant from the corn cell, wherein the modified corn plant comprises the first and second recombinant expression cassettes.

Further provided by the present specification is a method for producing a modified corn plant, the method comprising a) introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a MADS-box polypeptide; and b) regenerating or developing a modified corn plant from the corn cell, wherein the modified corn plant comprises the first and second recombinant expression cassettes.

In an aspect, the present specification provides a method for producing a modified corn plant, the method comprising a) introducing into a corn cell a first recombinant expression cassette comprising a transcribable DNA sequence encoding a non-coding RNA for suppression of one or more GA3 oxidase genes and/or GA20 oxidase genes; b) introducing into the corn cell of step (a) a second recombinant expression cassette comprising a DNA sequence encoding a MADS-box polypeptide to create a modified corn cell; and c) regenerating or developing a modified corn plant from the modified corn cell of step (b), wherein the modified corn plant comprises the first and second recombinant expression cassettes In another aspect, the present specification provides a method for producing a modified corn plant, the method comprising a) introducing into a corn cell a first recombinant expression cassette comprising a DNA sequence encoding a MADS-box polypeptide; b) introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and c) regenerating or developing a modified corn plant from the modified corn cell of step (b), wherein the modified corn plant comprises the first and second recombinant expression cassettes.

In yet another aspect, the present specification provides a method for producing a modified corn plant, the method comprising: a) crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a MADS-box polypeptide; and b) producing a progeny corn plant comprising the recombinant expression cassette and has the reduced expression of the one or more endogenous GA3 oxidase genes and/or GA20 oxidase genes.

The present specification provides a method for producing a modified corn plant, the method comprising: a) introducing into a corn cell a recombinant expression cassette comprising a DNA sequence encoding a MADS-box polypeptide, wherein the DNA sequence is operably linked to a plant-expressible promoter, and wherein the corn cell comprises one or more mutations and/or edits in one or more endogenous GA3 oxidase and/or GA20 oxidase genes; and b) regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

The present specification also provides a method for producing a modified corn plant, the method comprising: a) mutating or editing one or more endogenous GA3 oxidase genes and/or one or more GA20 oxidase genes in a corn cell, wherein the corn cell comprises a recombinant expression cassette encoding a MADS-box polypeptide, wherein the DNA sequence is operably linked to a plant-expressible promoter; and b) regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

Also provided by the present specification is a modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a MADS-box polypeptide, wherein the DNA sequence is operably linked to a plant-expressible promoter.

Further provided by the present specification is a plurality of modified corn plants in a field, each modified corn plant comprising 1) one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and 2) a recombinant expression cassette comprising a DNA sequence encoding a MADS-box polypeptide, wherein the DNA sequence is operably linked to a plant-expressible promoter.

In an aspect, the present specification provides a recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a MADS-box polypeptide, wherein the DNA sequence is operably linked to a plant-expressible promoter.

In an aspect, the present specification provides a recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a MADS-box polypeptide, wherein the DNA sequence is operably linked to a plant-expressible promoter.

DESCRIPTION

Definitions

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007.

Any references cited herein, including, e.g., all patents, published patent applications, and non-patent publications, are incorporated by reference in their entirety. To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, a "plant" includes an explant, plant part, seedling, plantlet or whole plant at any stage of regeneration or development. The term "cereal plant" as used herein refers a monocotyledonous (monocot) crop plant that is in the Poaceae or Gramineae family of grasses and is typically harvested for its seed, including, for example, wheat, corn, rice, millet, barley, sorghum, oat and rye. As commonly understood, a "corn plant" or "maize plant" refers to any plant of species Zea mays and includes all plant varieties that can be bred with corn, including wild maize species.

As used herein, a "plant part" can refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure can be viable, nonviable, regenerable, and/or non-regenerable. A "propagule" can include any plant part that can grow into an entire plant.

As used herein, a "transgenic plant" refers to a plant whose genome has been altered by the integration or insertion of a recombinant DNA molecule, construct, cassette or sequence for expression of a non-coding RNA molecule, mRNA and/or protein in the plant. A transgenic plant includes an $R_0$ plant developed or regenerated from an originally transformed plant cell(s) as well as progeny transgenic plants in later generations or crosses from the $R_0$ transgenic plant that comprise the recombinant DNA molecule, construct, cassette or sequence. A plant having an integrated or inserted recombinant DNA molecule, construct, cassette or sequence is considered a transgenic plant even if the plant also has other mutation(s) or edit(s) that would not themselves be considered transgenic.

A plant cell is a biological cell of a plant, taken from a plant or derived through culture from a cell taken from a plant. As used herein, a "transgenic plant cell" refers to any plant cell that is transformed with a stably-integrated recombinant DNA molecule, construct, cassette, or sequence. A transgenic plant cell can include an originally-transformed plant cell, a transgenic plant cell of a regenerated or developed $R_0$ plant, a transgenic plant cell cultured from another transgenic plant cell, or a transgenic plant cell from any progeny plant or offspring of the transformed $R_0$ plant, including cell(s) of a plant seed or embryo, or a cultured plant cell, callus cell, etc.

As used herein, the term "transcribable DNA sequence" refers to a DNA sequence that can be transcribed into an RNA molecule. The RNA molecule can be coding or non-coding and may or may not be operably linked to a promoter and/or other regulatory sequences.

For purposes of the present disclosure, a "non-coding RNA molecule" is a RNA molecule that does not encode a protein. Non-limiting examples of a non-coding RNA molecule include a microRNA (miRNA), a miRNA precursor, a small interfering RNA (siRNA), a siRNA precursor, a small RNA (18-26 nt in length) and precursors encoding the same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA).

The terms "suppressing"/"suppression" or "reduced"/"reduction" when used in reference to a gene(s), refers to a lowering, reduction, or elimination of the expression level of a mRNA and/or protein encoded by the gene(s), and/or a lowering, reduction, or elimination of the activity of a protein encoded by the gene(s) in a plant, plant cell or plant tissue at one or more stage(s) of plant development, as compared to the expression level of such target mRNA and/or protein, and/or the activity of such encoded protein in a wild-type or control plant, cell or tissue at the same stage(s) of plant development.

As used herein, the term "consecutive" in reference to a polynucleotide or protein sequence means without deletions or gaps in the sequence.

As commonly understood in the art, a "mutation" refers to any alteration of the nucleotide sequence of the genome, extrachromosomal DNA, or other genetic element of an organism (e.g., a gene or regulatory element operably linked to a gene in a plant), such as a nucleotide insertion, deletion, inversion, substitution, duplication, etc.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" can also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

It is recognized that residue positions of proteins that are not identical often differ by conservative amino acid substitutions, where amino acid residues are substituted for other amino acid residues with similar size and chemical properties (e.g., charge, hydrophobicity, polarity, etc.), and therefore may not change the functional properties of the molecule. When sequences differ in conservative substitutions, the percent sequence similarity can be adjusted upwards to correct for the conservative nature of the non-identical substitution(s). Sequences that differ by such conservative substitutions are said to have "sequence similarity" or "similarity." Thus, "percent similarity" or "percent similar" as used herein in reference to two or more protein sequences is calculated by (i) comparing two optimally aligned protein sequences over a window of comparison, (ii) determining the number of positions at which the same or similar amino acid residue occurs in both sequences to yield the number of matched positions, (iii) dividing the number of matched positions by the total number of positions in the window of comparison (or the total length of the reference or query protein if a window of comparison is not specified), and then (iv) multiplying this quotient by 100% to yield the percent similarity. Conservative amino acid substitutions for proteins are known in the art.

For optimal alignment of sequences to calculate their percent identity or similarity, various pair-wise or multiple sequence alignment algorithms and programs are known in the art, such as ClustalW, or Basic Local Alignment Search Tool® (BLAST®), etc., that can be used to compare the sequence identity or similarity between two or more nucleotide or protein sequences. Although other alignment and comparison methods are known in the art, the alignment between two sequences (including the percent identity ranges described above) can be as determined by the ClustalW or BLAST® algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s).

As commonly understood in the art, the term "promoter" can generally refer to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present disclosure can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or most tissues of the plant are referred to as "constitutive" promoters. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. An "inducible" promoter is a promoter that initiates transcription in response to an environmental stimulus such as cold, drought or light, or other stimuli, such as wounding or chemical application. A promoter can also be classified in terms of its origin, such as being heterologous, homologous, chimeric, synthetic, etc.

As used herein, a "plant-expressible promoter" or a "heterologous plant-expressible promoter" refers to a promoter that can initiate, assist, affect, cause, and/or promote the transcription and expression of its associated transcribable DNA sequence, coding sequence or gene in a corn plant cell or tissue.

As used herein, a "heterologous plant-expressible promoter" refers to a plant-expressible promoter which does not naturally occur adjacent to or associated with the referenced gene or nucleic acid sequence in its natural environment, but which is positioned by laboratory manipulation.

As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue(s) can comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters.

As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature—e.g., the promoter or regulatory sequence has a different origin relative to the associated polynucleotide sequence and/or the promoter or regulatory sequence is not naturally occurring in a plant species to be transformed with the promoter or regulatory sequence.

As used herein, a "functional portion" of a promoter sequence refers to a part of the promoter sequence that provides essentially the same or similar expression pattern of an operably linked coding sequence or gene as the full promoter sequence. For this definition, "essentially the same or similar" means that the pattern and level of expression of a coding sequence operably linked to the functional portion of the promoter sequence closely resembles the pattern and level of expression of the same coding sequence operably linked to the full promoter sequence.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, the term "isolated" refers to at least partially separating a molecule from other molecules typically associated with it in its natural state. In an aspect, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

As used herein, an "encoding region" or "coding region" refers to a portion of a polynucleotide that encodes a functional unit or molecule (e.g., without being limiting, a mRNA, protein, or non-coding RNA sequence or molecule).

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more gene(s) relative to a wild-type or control plant, plant seed, plant part, plant cell, and/or plant genome, such as via a transgenic event or a genome editing event or mutation affecting the expression level or activity of one or more genes. Modified plants, plant parts, seeds, etc., can be subjected to or created by mutagenesis, genome editing or site-directed integration (e.g., without being limiting, via methods using site-specific nucleases), genetic transformation (e.g., without being limiting, via methods of *Agrobacterium* transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more genes. A modified seed provided herein can give rise to a modified plant provided herein. A modified plant, plant seed, plant part, plant cell, or plant genome provided herein can comprise a recombinant DNA construct or vector or genome edit as provided herein. A "modified plant product" can be any product made from a modified plant, plant part, plant cell, or plant chromosome provided herein, or any portion or component thereof.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a transgene, expression cassette, mutation, and/or genome edit affecting one or more genes. For purposes of comparison to a modified plant, plant seed, plant part, plant cell and/or plant genome, a "wild-type plant" (or likewise a "wild-type" plant seed, plant part, plant cell and/or plant genome) refers to a non-transgenic, non-mutated, and non-genome edited control plant, plant seed, plant part, plant cell and/or plant genome. Alternatively as can be specified herein, such a "control plant" (or likewise a "control" plant seed, plant part, plant cell and/or plant genome) can refer to a plant (or plant seed, plant part, plant cell and/or plant genome) that (i) is used for comparison to a modified plant (or modified plant seed, plant part, plant cell and/or plant genome) having a stack of two or more transgene(s), expression cassette(s), mutation(s) and/or genome edit(s), (ii) has the same or similar genetic background (e.g., same parental lines, hybrid cross, inbred line, testers, etc.) as the modified plant (or plant seed, plant part, plant cell and/or plant genome), but (iii) lacks at least one of the two or more transgene(s), expression cassette(s), mutation(s) and/or genome edit(s) of the modified plant (e.g., a stack in comparison to a single of one of the members of the stack). As used herein, such a "control" plant, plant seed, plant part, plant cell and/or plant genome can also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, "crossed" or "cross" means to produce progeny via fertilization (e.g., cells, seeds or plants) and includes crosses between plants (sexual) and self-fertilization (selfing).

As used herein, "ear trait" of a corn plant refers to a characteristic of an ear of a corn plant. In an aspect, an ear trait can include, but is not limited to, ear diameter, single kernel weight, ear fresh weight, ear area, ear volume, ear length, number of kernels per ear, and/or yield. In another aspect, an ear trait can include, but is not limited to, ear tip void, ear void, kernel number, kernel number per row, kernels per field area, kernel rank, kernel row number, kernel weight, number of florets, and/or grain yield estimate. In yet another aspect, an ear trait can include, but is not limited to, ear attitude, ear cob color, ear cob diameter, ear cob strength, ear dry husk color, ear fresh husk color, ear husk bract, ear husk cover, ear husk opening, ear number per stalk, ear shank length, ear shelling percent, ear silk color, ear taper, ear weight, ear rot rating, kernel aleurone color, kernel cap color, kernel endosperm color, kernel endosperm type, kernel grade, kernel length, kernel pericarp color, kernel row direction, kernel side color, kernel thickness, kernel type, kernel width, cob weight, and/or prolificacy. A modified or genome edited/mutated corn plant of the present disclosure exhibits one or more improved ear trait compared to a control corn plant. In an aspect, a modified or genome edited/mutated corn plant exhibits an increased ear diameter relative to a control corn plant. In an aspect, a modified or genome edited/mutated corn plant exhibits increased single kernel weight relative to a control corn plant. In an aspect, a modified or genome edited/mutated corn plant exhibits an increased ear fresh weight relative to a control corn plant. In an aspect, a modified or genome edited/mutated corn plant exhibits an increased ear area relative to a control corn plant. In an aspect, a modified or genome edited/mutated corn plant exhibits an increased ear volume relative to a control corn plant. In an aspect, a modified or genome edited/mutated corn plant exhibits an increased ear length relative to a control corn plant. In an aspect, a modified or genome edited/mutated corn plant exhibits an increased number of kernels per ear relative to a control corn plant. In an aspect, a modified or genome edited/mutated corn plant exhibits an increased yield relative to a control corn plant.

As used herein, "yield" refers to the total amount of an agricultural product (e.g., seeds, fruit, etc.) produced or harvested from a plurality of crop plants per unit area of land cultivation (e.g., a field of crop plants) as understood in the art. Yield can be measured or estimated in a greenhouse, in a field, or under specific environment, treatment and/or stress conditions. For example, as known and understood in the art, yield can be measured in units of kilograms per hectare, bushels per acre, or the like. Indeed, yield can be measured in terms of "broad acreage yield" or "BAY" as known and understood in the art.

As used herein, "root trait" of a corn plant refers to characteristics of the root of a corn plant, including, but is not limited to, root growth rate, root length, root thickness, root branching, root anchorage, crown root lateral root density rating, and/or root dry weight. A transgenic or genome edited/mutated corn plant of the present disclosure exhibits one or more improved root traits compared to a control corn plant.

As used herein, "comparable conditions" for plants refers to the same or similar environmental conditions and agronomic practices for growing and making meaningful comparisons between two or more plant genotypes so that neither environmental conditions nor agronomic practices would significantly contribute to, or explain, any differences observed between the two or more plant genotypes. Environmental conditions include, for example, light, temperature, water, humidity, soil, and nutrition (e.g., nitrogen and phosphorus).

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase.

As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence using a targeted genome editing technique. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant using a targeted genome editing technique.

As used herein, a "target site" for genome editing refers to the location of a polynucleotide sequence within a plant genome that is targeted and cleaved by a site-specific nuclease introducing a double stranded break (or single-stranded nick) into the nucleic acid backbone of the polynucleotide sequence and/or its complementary DNA strand. A site-specific nuclease can bind to a target site, such as via a non-coding guide RNA (e.g., without being limiting, a CRISPR RNA (crRNA) or a single-guide RNA (sgRNA) as described further below). A non-coding guide RNA provided herein can be complementary to a target site (e.g., complementary to either strand of a double-stranded nucleic acid molecule or chromosome at the target site). A "target site" also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some aspects a target region can be subjected to a mutation, deletion, insertion or inversion. As used herein, "flanked" when used to describe a target region of a polynucleotide sequence or molecule, refers to two or more target sites of the polynucleotide sequence or molecule surrounding the target region, with one target site on each side of the target region.

Apart from genome editing, the term "target site" can also be used in the context of gene suppression to refer to a portion of a mRNA molecule (e.g., a "recognition site") that is complementary to at least a portion of a non-coding RNA molecule (e.g., a miRNA, siRNA, etc.) encoded by a suppression construct. As used herein, a "target site" for a RNA-guided nuclease can comprise the sequence of either complementary strand of a double-stranded nucleic acid (DNA) molecule or chromosome at the target site. It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA can be tolerated.

As used herein, a "donor molecule", "donor template", or "donor template molecule" (collectively a "donor template"), which can be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" can be used for site-directed integration of a transgene or suppression construct, or as a template to introduce a mutation, such as an insertion, deletion, etc., into a target site within the genome of a plant. A targeted genome editing technique provided herein can comprise the use of one or more, two or more, three or more, four or more, or five or more donor molecules or templates. A donor template can be a single-stranded or double-stranded DNA or RNA molecule or plasmid. A donor template can also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template. Further, the donor template can be linear or circular, and can be single-stranded or double-stranded. A donor template can be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively.

An insertion sequence of a donor template can comprise one or more genes or sequences that each encode a transcribed non-coding RNA or mRNA sequence and/or a translated protein sequence. A transcribed sequence or gene of a donor template can encode a protein or a non-coding RNA molecule. An insertion sequence of a donor template can comprise a polynucleotide sequence that does not comprise a functional gene or an entire gene sequence (e.g., the donor template can simply comprise regulatory sequences, such as a promoter sequence, or only a portion of a gene or coding sequence), or may not contain any identifiable gene expression elements or any actively transcribed gene sequence. An insertion sequence of a donor template provided herein can comprise a transcribable DNA sequence that can be transcribed into an RNA molecule, which can be non-coding and may or may not be operably linked to a promoter and/or other regulatory sequence.

As used herein, the term "guide RNA" or "gRNA" is a short RNA sequence comprising (1) a structural or scaffold RNA sequence necessary for binding or interacting with an RNA-guided nuclease and/or with other RNA molecules (e.g., tracrRNA), and (2) an RNA sequence (referred to herein as a "guide sequence") that is identical or complementary to a target sequence or a target site. A "single-chain guide RNA" (or "sgRNA") is a RNA molecule comprising a crRNA covalently linked a tracrRNA by a linker sequence, which can be expressed as a single RNA transcript or molecule. The guide RNA comprises a guide or targeting sequence (a "guide sequence") that is identical or complementary to a target site within the plant genome, such as at or near a GA oxidase gene. A protospacer-adjacent motif (PAM) can be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. The genomic PAM sequence on the sense (+) strand adjacent to the target site (relative to the targeting sequence of the guide RNA) can comprise 5'-NGG-3'. However, the corresponding sequence of the guide RNA (i.e., immediately downstream (3') to the targeting sequence of the guide RNA) can generally not be complementary to the genomic PAM sequence. The guide RNA can typically be a non-coding RNA molecule that does not encode a protein.

As used herein, an "RNA-guided nuclease" refers to an RNA-guided DNA endonuclease associated with the CRISPR system. Non-limiting examples of RNA-guided nucleases include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In an aspect, the RNA-guided nuclease is Cas9. In an aspect, the RNA-guided nuclease comprises the N and C terminal nuclear localization sequences (NLS).

DESCRIPTION

The present disclosure provides certain stacked combinations of transgenes and/or mutations or edits in corn plants, plant parts, etc., comprising a transgene that encodes one or more MADS-box polypeptides, such as maize ZMM19, in addition to a reduction in the expression level of one or more GA20 and/or GA3 oxidase genes through suppression, mutation and/or editing of the GA oxidase genes, wherein the corn plants have a semi-dwarf phenotype and one or more improved traits related to yield, lodging resistance, and/or stress tolerance. As described in co-pending PCT Application No. PCT/US2017/047405, the entire contents and disclosure of which are incorporated herein by reference, reducing the level of active GAs in corn or other cereal plants, such as through suppression, mutation or editing of one or more GA20 and/or GA3 oxidase genes, can result in a semi-dwarf phenotype with improved agronomic traits, such as lodging resistance and/or increased yield. However, it is proposed herein that lower active GA levels can be combined with an expression cassette or transgene encoding a MADS-box protein, such as ZMM19, to produce a semi-dwarf corn plant having positive ear traits leading to further increased yield, thus providing greater agronomic benefits than either MADS-box gene expression or lower active GA levels alone.

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20$^{th}$ century, which was largely responsible for the Green Revolution. However, successful yield gains in other cereal crops, such as corn, have not been realized through manipulation of the GA pathway. Corn or maize is unique among the grain-producing grasses in that it forms separate male (tassel) and female (ear) inflorescences, and mutations in the GA pathway in corn have been shown to negatively impact reproductive development. Indeed, some mutations in the GA pathway genes in corn have been associated with various off-types that are incompatible with yield, which has led researchers away from finding semi-dwarf, high-yielding corn varieties via manipulation of the GA pathway.

Despite these prior difficulties in achieving higher grain yields in corn through manipulation of the GA pathway, co-pending PCT Application No. PCT/US2017/047405 describes a way to manipulate active GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants with reduced GA levels can also have one or more additional yield and/or stress tolerance traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Active or bioactive gibberellic acids (i.e., "active gibberellins" or "active GAs") are known in the art for a given plant species, as distinguished from inactive GAs. For example, active GAs in corn and higher plants include the following: GA1, GA3, GA4, and GA7. Thus, an "active GA-producing tissue" is a plant tissue that produces one or more active GAs.

Certain biosynthetic enzymes (e.g., GA20 oxidase and GA3 oxidase) and catabolic enzymes (e.g., GA2 oxidase) in the GA pathway participate in GA synthesis and degradation, respectively, to affect active GA levels in plant tissues. Thus, in addition to suppression of certain GA20 oxidase genes, it is further proposed that suppression of a GA3 oxidase gene in a constitutive or tissue-specific or tissue-preferred manner can also produce corn plants having a short stature phenotype and increased lodging resistance, with possible increased yield, but without off-types in the ear.

Without being bound by theory, it is proposed that incomplete suppression of GA20 or GA3 oxidase gene(s) and/or targeting of a subset of one or more GA oxidase gene(s) can be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, can be sufficient to produce a short-stature plant with increased lodging resistance, but without significant off-types in reproductive tissues. Expression of a GA20 or GA3 oxidase suppression element in a tissue-specific or tissue-preferred manner can be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) can be targeted for suppression using a vascular promoter, such as a rice tungro bacilliform virus (RTBV) promoter, that drives expression in vascular tissues of plants. The expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn plant that produce active GAs can reduce plant height and increase lodging resistance, and off-types can be avoided in those plants if active GA levels are not also significantly impacted or lowered in reproductive tissues, such as the developing female organ or ear of the plant. If active GA levels could be reduced in the stalk, stem, or internode(s) of corn or cereal plants without significantly affecting GA levels in reproductive tissues (e.g., the female or male reproductive organs or inflorescences), then corn or cereal plants having reduced plant height and increased lodging resistance could be created without off-types in the reproductive tissues of the plant.

Without being limited by theory, it is further proposed that short stature, semi-dwarf phenotypes in corn plants can result from a sufficient level of expression of a suppression construct targeting certain GA oxidase gene(s) in active GA-producing tissue(s) of the plant. For targeted suppression of certain GA20 oxidase genes in corn, restricting the pattern of expression to avoid reproductive ear tissues may not be necessary to avoid reproductive off-types in the developing ear. However, expression of a GA20 oxidase suppression construct at low levels, and/or in a limited number of plant tissues, can be insufficient to cause a significant short stature, semi-dwarf phenotype. Given that the observed semi-dwarf phenotype with targeted GA20 oxidase suppression is the result of shortening the stem internodes of the plant, it was surprisingly found that suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), can be sufficient to produce semi-dwarf plants, even though the short stature trait is due to shortening of the stem internodes. Given that GAs can migrate through the vasculature of the plant, manipulating GA oxidase genes in plant tissue(s) where active GAs are produced can result in a short stature, semi-dwarf plant, even though this can be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues causes a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. A semi-dwarf phenotype was also observed with expression of the same GA20 oxidase suppression construct using other vascular promoters and with various constitutive promoters without any observable off-types.

By targeting a subset of one or more endogenous GA3 or GA20 oxidase genes for suppression within a plant, a more pervasive pattern of expression (e.g., with a constitutive promoter) can be used to produce semi-dwarf plants without significant reproductive off-types and/or other undesirable traits in the plant, even with expression of the suppression construct in reproductive tissue(s). Indeed, suppression elements and constructs are provided herein that selectively target the GA20 oxidase_3 and/or GA20 oxidase_5 genes for suppression, which can be operably linked to a vascular, leaf and/or constitutive promoter.

Thus, recombinant DNA constructs and modified corn plants are provided herein comprising a GA20 or GA3 oxidase suppression element or sequence operably linked to a plant expressible promoter, which can be a constitutive or tissue-specific or tissue-preferred promoter. Such a tissue-specific or tissue-preferred promoter can drive expression of its associated GA oxidase suppression element or sequence in one or more active GA-producing tissue(s) of the plant to suppress or reduce the level of active GAs produced in those tissue(s). Such a tissue-specific or tissue-preferred promoter can drive expression of its associated GA oxidase suppression construct or transgene during one or more vegetative stage(s) of development. Such a tissue-specific or tissue-preferred promoter can also have little or no expression in one or more cell(s) or tissue(s) of the developing female organ or ear of the plant to avoid the possibility of off-types in those reproductive tissues. According to an aspect, the tissue-specific or tissue-preferred promoter is a vascular promoter, such as the RTBV promoter. The sequence of the RTBV promoter is provided herein as SEQ ID NO: 65, and a truncated version of the RTBV promoter is further provided herein as SEQ ID NO: 66. However, other types of tissue-specific or tissue preferred promoters can potentially be used for GA3 oxidase suppression in active GA-producing tissues of a corn or cereal plant to produce a semi-dwarf phenotype without significant off-types. As introduced above, instead of suppressing one or more GA oxidase gene(s), active GA levels can also be reduced in a corn plant by mutation or editing of one or more GA20 and/or GA3 oxidase gene(s).

Corn has a family of at least nine GA20 oxidase genes that includes GA20 oxidase 1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1, and the DNA and protein sequences by SEQ ID NOs for each of these GA3 oxidase genes are provided in Table 2.

TABLE 1

DNA and protein sequences by sequence identifier for GA20 oxidase genes in corn.

| GA20 oxidase Gene | cDNA | Coding Sequence (CDS) | Protein |
| --- | --- | --- | --- |
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
|---|---|---|---|
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |

In addition to lowering active GA levels in corn plants through suppression, mutation or editing of GA oxidase gene(s), such corn plants as provided herein may further comprise an ectopically expressed transgene expressing one or more MADS-box polypeptides.

MADS-box polypeptides typically have transcription factor activity and are involved in controlling all major aspects of the life of land plants. The MADS-box polypeptides, encoded by the MADS box gene, are characterized by the highly conserved DNA-binding MADS domain (about 58 amino acids), and is named after MCM1, AGAMOUS, DEFICIENS and SRF (serum response factor) proteins.

Without being bound by any theory, MADS-box polypeptides can be classified into type I and type II subfamilies. Type I polypeptides do not have distinct conserved domains other than the SRF-like MADS domain. Type II polypeptides are commonly referred to as MIKC-type polypeptides after their domain structure: MADS domain, intervening (I) domain, keratin-like (K) domain, and carboxyl-terminal (C) domains. Type I polypeptides do not have K domain. See Gramzow and Theissen, *Genome Biol.*, 11: 214 (2010), the content and disclosure of which are incorporated by reference.

Without being bound by any theory, MADS-box polypeptides can bind to DNA as dimers and/or multimeric complexes and can thus regulate target gene by direct transcriptional activation or repression. Dimers of MADS-box polypeptides can bind to CArG-boxes, i.e., stretches of DNA with a consensus sequence of 5'-CC[A/T]$_6$GG-3', or very similar sequences thereof. The number of CArG-boxes in genomes is enormous, and different MADS-box polypeptides can recognize different sets of target genes, and thus play a universal role in plant development and/or growth.

Without being bound by any theory, in plants, type II MADS-box polypeptides are suggested to be able to 1) control various aspects of sporophyte development, 2) determine flowering time, 3) specify floral meristem identify, floral organ identity, fruit formation, and seed pigmentation, and/or 4) play generally critical roles in gametophyte development.

As used herein, a MADS-box polynucleotide refers to a polynucleotide, gene or coding sequence encoding a polypeptide containing at least one SRF-TF MADS-box Pfam domain and a K-box Pfam domain, and encompasses any variants (e.g., polymorphisms), isoforms, homologs, orthologs, and/or paralogs thereof. On the sequence level, the SRF-TF MADS-box domain is located on the N-terminal side of the K-box domain, or stated differently, the K-box domain is located on the C-terminal side of the SRF-TF MADS-box domain.

In an aspect, a MADS-box polypeptide of the present disclosure is a maize ZMM19 polypeptide or homologs, orthologs, and/or paralogs thereof. In an aspect, a MADS-box polypeptide of the present disclosure comprises an amino acid sequence comprising SEQ ID NO: 168, or a functional fragment thereof. In another aspect, a MADS-box polynucleotide provided herein comprises an amino acid sequence selected from the group consisting of SEQ ID NOs: 175-199, and any homologs, orthologs, and paralogs thereof.

According to another aspect, a modified corn plant or a plant part thereof is provided comprising 1) a first recombinant expression cassette (or a construct) comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette (or a construct) comprising a DNA sequence encoding an MADS-box polypeptide.

According to another aspect, a plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding an MADS-box polypeptide. In an aspect, the modified corn plants have increased yield relative to control corn plants. In another aspect, the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

Such modified corn plants can have semi-dwarf plant height in addition to one or more improved yield-related traits as described further herein, relative to control corn plant(s) that do not have the first and second expression cassettes or the combination of MADS-box transgene and edited/mutated GA oxidase gene(s). Modified corn plants comprising a combination of the first and second expression cassettes, or a combination of an expression cassette comprising a MADS-box transgene and one or more mutated or edited GA oxidase genes, can each be referred to as a "stack" or "stacked" combination. Such stacked combinations for the reduction of active GA levels and expression of a MADS-box transgene can be brought together in the same corn plant, or population of corn plants, by (1) crossing a first plant comprising a GA oxidase suppression element(s), edit(s) and/or mutation(s) to a second plant comprising a MADS-box transgene, (2) co-transformation of a plant or plant part with a GA oxidase suppression element(s) and a MADS-box transgene, (3) transformation of a plant or plant part already having a GA oxidase suppression element(s), edit(s) and/or mutation(s) with a MADS-box transgene, (4) transformation of a plant or plant part already having a MADS-box transgene with a GA oxidase suppression element(s), or (5) editing or mutating a GA oxidase gene(s) in a plant or plant part already having a MADS-box transgene, each of which can be followed by further crosses to obtain a desired genotype, plant parts can be regenerated, grown or developed into plants, and plant parts can be taken from any of the foregoing plants.

As provided above, a corn plant or plant part can comprise a first expression cassette comprising a first sequence encoding a non-coding RNA molecule that targets one or more GA20 or GA3 oxidase gene(s) for suppression. In an aspect, the non-coding RNA molecule can target one or more GA20 oxidase gene(s) for suppression, such as a GA20 oxidase_3 gene, a GA20 oxidase_4 gene, a GA20 oxidase_5 gene, or any combination thereof. According to an aspect, the first expression cassette comprises a first transcribable DNA sequence encoding a non-coding RNA targeting a GA20 oxidase_3 gene for suppression. According to another aspect, the first expression cassette comprises a first transcribable DNA sequence encoding a non-coding RNA targeting a GA20 oxidase_5 gene for suppression. According to another aspect, the first expression cassette comprises a first transcribable DNA sequence encoding a non-coding RNA that targets both the GA20 oxidase_3 gene and the GA20 oxidase_5 gene for suppression. In addition to targeting a mature mRNA sequence (including either or both of the untranslated or exonic sequences), a non-coding RNA molecule can also target the intronic sequences of a GA20 oxidase gene or transcript.

A genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

A genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

For suppression of a GA20 oxidase_3 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 7 and 8.

For suppression of a GA20 oxidase_4 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 10 and 11.

For suppression of a GA20 oxidase_5 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 13 and 14.

For suppression of a GA20 oxidase_3 gene and a GA20 oxidase_5 gene, a transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 7 and 8; and the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 13 and 14.

In an aspect, a non-coding RNA molecule encoded by a transcribable DNA sequence comprises (i) a sequence that is at least 95%, at least 96%, at least 97%, at least 98%, at least 99%, at least 99.5%, or 100% complementary to SEQ ID NO: 39, 41, 43 or 45, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 40, 42, 44 or 46. According to an aspect, the non-coding RNA molecule encoded by a transcribable DNA sequence can comprise a sequence with one or more mismatches, such as 1, 2, 3, 4, 5 or more complementary mismatches, relative to the sequence of a target or recognition site of a targeted GA20 oxidase gene mRNA, such as a sequence that is nearly complementary to SEQ ID NO: 40 but with one or more complementary mismatches relative to SEQ ID NO: 40. According to a particular aspect, the non-coding RNA molecule encoded by the transcribable DNA sequence comprises a sequence that is 100% identical to SEQ ID NO: 40, which is 100% complementary to a target sequence within the cDNA and coding sequences of the GA20 oxidase_3 (i.e., SEQ ID NOs: 7 and 8, respectively), and/or to a corresponding sequence of a mRNA encoded by an endogenous GA20 oxidase_3 gene. However, the sequence of a non-coding RNA molecule encoded by a transcribable DNA sequence that is 100% identical to SEQ ID NO: 40, 42, 44 or 46 may not be perfectly complementary to a target sequence within the cDNA and coding sequences of the GA20 oxidase_5 gene (i.e., SEQ ID NOs: 13 and 14, respectively), and/or to a corresponding sequence of a mRNA encoded by an endogenous GA20 oxidase_5 gene. For example, the closest complementary match between the non-coding RNA molecule or miRNA sequence in SEQ ID NO: 40 and the cDNA and coding sequences of the GA20 oxidase_5 gene can include one mismatch at the first position of SEQ ID NO: 39 (i.e., the "C" at the first position of SEQ ID NO: 39 is replaced with a "G"; i.e., GTCCATCATGCGGTGCAACTA). However, the non-coding RNA molecule or miRNA sequence in SEQ ID NO: 40 can still bind and hybridize to the mRNA encoded by the endogenous GA20 oxidase_5 gene despite this slight mismatch.

For suppression of a GA20 oxidase_1 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 1 and 2.

For suppression of a GA20 oxidase_2 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 4 and 5.

For suppression of a GA2 oxidase_6, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 16 and 17.

For suppression of a GA20 oxidase_7 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 19 and 20.

For suppression of a GA20 oxidase_8 gene, a first transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 22 and 23.

For suppression of a GA20 oxidase_9 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 25 and 26.

A non-coding RNA can target an intron sequence of a GA20 oxidase gene instead of, or in addition to, an exonic, 5' UTR or 3' UTR of the GA20 oxidase gene. Thus, a non-coding RNA targeting the GA20 oxidase_3 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 34, and/or of nucleotides 3666-3775 or 4098-5314 of SEQ ID NO: 34.

In another aspect, a non-coding RNA molecule targeting the GA20 oxidase_5 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 35, and/or of nucleotides 3792-3906 or 4476-5197 of SEQ ID NO: 35.

In another aspect, a non-coding RNA molecule targeting the GA20 oxidase_4 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 38, and/or of nucleotides 1996-2083 or 2412-2516 of SEQ ID NO: 38.

In another aspect, a first expression cassette comprises a first transcribable DNA sequence encoding a non-coding RNA targeting a GA3 oxidase gene(s) for suppression in corn, such as a GA3 oxidase_1 gene or a GA3 oxidase_2 gene. In another aspect, a first transcribable DNA sequence encoding a non-coding RNA targets both the GA3 oxidase_1 gene and the GA3 oxidase_2 gene for suppression. In addition to targeting a mature mRNA sequence (including either or both of the untranslated or exonic sequences), a non-coding RNA molecule can also target the intronic sequences of a GA3 oxidase gene or transcript.

The genomic DNA sequence of GA3 oxidase_1 is provided in SEQ ID NO: 36, and the genomic DNA sequence of GA3 oxidase_2 is provided in SEQ ID NO: 37. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon; nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. For the GA3 oxidase_2 gene, nucleotides 1-38 of SEQ ID NO: 37 correspond to the 5-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR.

For suppression of a GA3 oxidase_1 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 28 and 29.

As mentioned above, a non-coding RNA molecule can target an intron sequence of a GA3 oxidase gene instead of, or in addition to, an exonic, 5' UTR or 3' UTR of the GA oxidase gene. Thus, a non-coding RNA molecule targeting the GA3 oxidase_1 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 36, and/or of nucleotides 515-879 or 1039-1158 of SEQ ID NO: 36.

For suppression of a GA3 oxidase_2 gene, a first transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 31 and 32.

As mentioned above, a non-coding RNA molecule can target an intron sequence of a GA3 oxidase gene instead of, or in addition to, an exonic, 5' UTR or 3' UTR of the GA3 oxidase gene. Thus, a non-coding RNA molecule targeting the GA3 oxidase_2 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 37, and/or of nucleotides 533-692 or 852-982 of SEQ ID NO: 37.

For suppression of a GA3 oxidase_1 gene and a GA3 oxidase_2 gene, a transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 28 and 29; and the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 31 and 32.

In an aspect, a transcribable DNA sequence for the suppression of a GA20 oxidase gene and/or a GA3 oxidase comprises a sequence selected from the group consisting of SEQ ID NOs: 47, 49, 51, 53, 55, 57, 59, 61, and 63. In another aspect, a transcribable DNA sequence for the suppression of a GA20 oxidase gene and/or a GA3 oxidase encodes a non-coding RNA sequence, wherein the non-coding RNA sequence comprises a sequence selected from the group consisting of SEQ ID NOs: 48, 50, 52, 54, 56, 58, 60, 62, and 64.

In an aspect, an expression cassette is provided comprising a second DNA sequence encoding a MADS-box polypeptide. In an aspect, an expression cassette is provided comprising a second DNA sequence encoding ZMM19. In another aspect, the second DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NO: 169. In another aspect, the second DNA sequence comprises a sequence encoding a polypeptide that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof. The second DNA sequence encoding a MADS-box polypeptide is operatively linked to a plant-expressible promoter. In an aspect, such a plant-expressible promoter operably linked to a DNA sequence encoding a MADS-box polypeptide is a root promoter, such as a root-specific or root-preferred promoter. In another aspect, such a plant-expressible promoter operably linked to a DNA sequence encoding a MADS-box polypeptide is a meristem promoter, such as a meristem-specific promoter or a meristem-preferred promoter. In an aspect, such a plant-expressible promoter operably linked to a DNA sequence encoding a MADS-box polypeptide is a seed or kernel promoter, such as a seed-preferred promoter, a seed-specific promoter, or a seed-germinating promoter.

In an aspect, such a root promoter is an *Oryza sativa* Rcc3 gene promoter. In an aspect, such a root promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 170, or a functional portion thereof. In an aspect, such a seed or kernel promoter is from a maize putative embryo-specific (Esp) gene promoter. In an aspect, such a seed or kernel promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 174, or a functional portion thereof.

In an aspect, an expression cassette is provided comprising a second DNA sequence encoding a MADS-box polypeptide. In another aspect, the second DNA sequence encodes a protein that comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to an amino acid sequence selected from the group consisting of SEQ ID NOs: 175-199, or a functional fragment thereof. The second DNA sequence encoding a MADS-box polypeptide is operatively linked to a plant-expressible promoter. In an aspect, such a plant-expressible promoter operably linked to a DNA sequence encoding a MADS-box polypeptide is a root promoter, such as a root-specific or root-preferred promoter. In another aspect, such a plant-expressible promoter operably linked to a DNA sequence encoding a MADS-box polypeptide is a meristem promoter, such as a meristem-specific promoter or a meristem-preferred promoter. In another aspect, such a plant-expressible promoter operably linked to a DNA sequence encoding a MADS-box polypeptide is a kernel or seed promoter, such as a seed-preferred or seed-specific promoter. Examples of a root promoter, a meristem promoter, and a seed or kernel promoter are provided herein.

In addition to targeting a mature mRNA sequence, a non-coding RNA molecule can instead target an intronic sequence of a GA oxidase gene or mRNA transcript, or a GA oxidase mRNA sequence overlapping coding and non-coding sequences. According to other aspects, a recombinant DNA molecule, vector or construct is provided comprising a transcribable DNA sequence encoding a non-coding RNA (precursor) molecule that is cleaved or processed into a mature non-coding RNA molecule that binds or hybridizes to a target mRNA in a plant cell, wherein the target mRNA molecule encodes a GA20 or GA3 oxidase protein, and wherein the transcribable DNA sequence is operably linked to a constitutive or tissue-specific or tissue-preferred promoter.

Any method known in the art for suppression of a target gene can be used to suppress GA oxidase gene(s) according to aspects of the present disclosure including expression of antisense RNAs, double stranded RNAs (dsRNAs) or inverted repeat RNA sequences, or via co-suppression or RNA intereference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules can be used that target the non-coding genomic sequences or regions within or near a gene to cause silencing of the gene. Accordingly, any of these methods can be used for the targeted suppression of an endogenous GA oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

In an aspect, an expression level(s) of one or more endogenous GA20 oxidase and/or GA3 oxidase gene(s) is/are reduced or eliminated in the modified corn plant, thereby suppressing the endogenous GA20 oxidase and/or GA3 oxidase gene(s).

According to an aspect, a modified or transgenic plant is provided having the expression level(s) of one or more GA20 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant.

According to an aspect, a modified or transgenic plant is provided having the expression level(s) of one or more GA3 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant.

According to an aspect, a modified or transgenic plant is provided having the expression level(s) of one or more GA20 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

According to an aspect, a modified or transgenic plant is provided having the expression level(s) of one or more GA3 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-'75%, 30%-80%, or 10%-75%, as compared to a control plant.

According to an aspect, the at least one tissue of a modified or transgenic plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In an aspect, the non-coding RNA is a precursor miRNA or siRNA capable of being processed or cleaved to form a mature miRNA or siRNA.

In an aspect, suppression of an endogenous GA20 oxidase gene or a GA3 oxidase gene is tissue-specific (e.g., only in leaf and/or vascular tissue). Suppression of a GA20 oxidase gene can be constitutive and/or vascular or leaf tissue specific or preferred. In other aspects, suppression of a GA20 oxidase gene or a GA3 oxidase gene is constitutive and not tissue-specific. According to an aspect, expression of an endogenous GA20 oxidase gene and/or a GA3 oxidase gene is reduced in one or more tissue types (e.g., in leaf and/or vascular tissue(s)) of a modified or transgenic plant as compared to the same tissue(s) of a control plant.

Engineered miRNAs can be useful for targeted gene suppression with increased specificity. See, e.g., Parizotto et al., *Genes Dev.* 18:2237-2242 (2004), and U.S. Patent Application Publication Nos. 2004/0053411, 2004/0268441, 2005/0144669, and 2005/0037988, the contents and disclosures of which are incorporated herein by reference. miRNAs are non-protein coding RNAs. When a miRNA precursor molecule is cleaved, a mature miRNA is formed that is typically from about 19 to about 25 nucleotides in length (commonly from about 20 to about 24 nucleotides in length in plants), such as 19, 20, 21, 22, 23, 24, or 25 nucleotides in length, and has a sequence corresponding to the gene targeted for suppression and/or its complement. Mature miRNA hybridizes to target mRNA transcripts and guides the binding of a complex of proteins to the target transcripts, which can function to inhibit translation and/or result in degradation of the transcript, thus negatively regulating or suppressing expression of the targeted gene. miRNA precursors are also useful in plants for directing in-phase production of siRNAs, trans-acting siRNAs (ta-siRNAs), in a process that requires a RNA-dependent RNA polymerase to cause suppression of a target gene. See, e.g., Allen et al., *Cell*, 121:207-221 (2005), Vaucheret, *Science STKE,* 2005: pe43 (2005), and Yoshikawa et al. *Genes Dev.,* 19:2164-2175 (2005), the contents and disclosures of which are incorporated herein by reference.

Without being limited by any scientific theory, plant miRNAs regulate their target genes by recognizing and binding to a complementary or near-perfectly complementary sequence (miRNA recognition site) in the target mRNA transcript, followed by cleavage of the transcript by RNase III enzymes, such as ARGONAUTE1. In plants, certain mismatches between a given miRNA recognition site and the corresponding mature miRNA are typically not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) *Nature Genetics,* 39:1033-1037; and Axtell et al. (2006) *Cell,* 127:565-577.

Many microRNA genes (MIR genes) have been identified and made publicly available in a database ("miRBase", available on line at microrna.sanger.ac.uk/sequences; also see Griffiths-Jones et al. (2003) *Nucleic Acids Res.,* 31:439-441). MIR genes have been reported to occur in intergenic regions, both isolated and in clusters in the genome, but can also be located entirely or partially within introns of other genes (both protein-coding and non-protein-coding). For a review of miRNA biogenesis, see Kim (2005) *Nature Rev. Mol. Cell. Biol.,* 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (foldback structures containing a stem-loop arrangement that is processed to the mature miRNA) as well as the usual 5'

"cap" and polyadenylated tail of an mRNA. See, for example, FIG. 1 in Kim (2005) *Nature Rev. Mol. Cell. Biol.,* 6:376-385.

Transgenic expression of miRNAs (whether a naturally occurring sequence or an artificial sequence) can be employed to regulate expression of the miRNA's target gene or genes. Recognition sites of miRNAs have been validated in all regions of a mRNA, including the 5' untranslated region, coding region, intron region, and 3' untranslated region, indicating that the position of the miRNA target or recognition site relative to the coding sequence may not necessarily affect suppression (see, e.g., Jones-Rhoades and Bartel (2004). *Mol. Cell,* 14:787-799, Rhoades et al. (2002) *Cell,* 110:513-520, Allen et al. (2004) *Nat. Genet.,* 36:1282-1290, Sunkar and Zhu (2004) Plant Cell, 16:2001-2019). miRNAs are important regulatory elements in eukaryotes, and transgenic suppression with miRNAs is a useful tool for manipulating biological pathways and responses. A description of native miRNAs, their precursors, recognition sites, and promoters is provided in U.S. Patent Application Publication No. 2006/0200878, the contents and disclosures of which are incorporated herein by reference.

Designing an artificial miRNA sequence can be achieved by substituting nucleotides in the stem region of a miRNA precursor with a sequence that is complementary to the intended target, as demonstrated, for example, by Zeng et al. (2002) *Mol. Cell,* 9:1327-1333. According to many aspects, the target can be a sequence of a GA20 oxidase gene or a GA3 oxidase gene. One non-limiting example of a general method for determining nucleotide changes in a native miRNA sequence to produce an engineered miRNA precursor for a target of interest includes the following steps: (a) selecting a unique target sequence of at least 18 nucleotides specific to the target gene, e.g., by using sequence alignment tools such as BLAST (see, for example, Altschul et al. (1990) *J. Mol. Biol.,* 215:403-410; Altschul et al. (1997) *Nucleic Acids Res.,* 25:3389-3402); cDNA and/or genomic DNA sequences can be used to identify target transcript orthologues and any potential matches to unrelated genes, thereby avoiding unintentional silencing or suppression of non-target sequences; (b) analyzing the target gene for undesirable sequences (e.g., matches to sequences from non-target species), and score each potential target sequence for GC content, Reynolds score (see Reynolds et al. (2004) *Nature Biotechnol.,* 22:326-330), and functional asymmetry characterized by a negative difference in free energy ("ΔΔG") (see Khvorova et al. (2003) *Cell,* 115:209-216). Preferably, target sequences (e.g., 19-mers) can be selected that have all or most of the following characteristics: (1) a Reynolds score >4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. In an aspect, a non-coding RNA molecule used here to suppress a target gene (e.g., a GA20 or GA3 oxidase gene) is designed to have a target sequence exhibiting one or more, two or more, three or more, four or more, or five or more of the foregoing characteristics. Positions at every third nucleotide of a suppression element can be important in influencing RNAi efficacy; for example, an algorithm, "siExplorer" is publicly available at rna.chem.t.u-tokyo.acjp/siexplorer.htm (see Katoh and Suzuki (2007) *Nucleic Acids Res.,* 10.1093/nar/gkl1120); (c) determining a reverse complement of the selected target sequence (e.g., 19-mer) to use in making a modified mature miRNA. Relative to a 19-mer sequence, an additional nucleotide at position 20 can be matched to the selected target or recognition sequence, and the nucleotide at position 21 can be chosen to either be unpaired to prevent spreading of silencing on the target transcript or paired to the target sequence to promote spreading of silencing on the target transcript; and (d) transforming the artificial miRNA into a plant.

Multiple sense and/or anti-sense suppression elements for more than one GA oxidase target can be arranged serially in tandem or arranged in tandem segments or repeats, such as tandem inverted repeats, which can also be interrupted by one or more spacer sequence(s), and the sequence of each suppression element can target one or more GA oxidase gene(s). Furthermore, a sense or anti-sense sequence of the suppression element may not be perfectly matched or complementary to the targeted GA oxidase gene sequence, depending on the sequence and length of the suppression element. Even shorter RNAi suppression elements from about 19 nucleotides to about 27 nucleotides in length can have one or more mismatches or non-complementary bases, yet still be effective at suppressing the target GA oxidase gene. Accordingly, a sense or anti-sense suppression element sequence can be at least 80%, at least 85%, at least 90%, at least 95%, at least 96%, at least 97%, at least 98%, at least 99%, at least 99.5% or 100% identical to a corresponding sequence of at least a segment or portion of the targeted GA oxidase gene, or its complementary sequence, respectively.

For suppression of GA oxidase gene(s) using an inverted repeat or a transcribed dsRNA, a transcribable DNA sequence or suppression element can comprise a sense sequence that comprises a segment or portion of a targeted GA oxidase gene and an anti-sense sequence that is complementary to a segment or portion of the targeted GA oxidase gene, where the sense and anti-sense DNA sequences are arranged in tandem. The sense and/or anti-sense sequences, respectively, can each be less than 100% identical or complementary to a segment or portion of the targeted GA oxidase gene as described above. A sense and anti-sense sequences can be separated by a spacer sequence, such that the RNA molecule transcribed from the suppression element forms a stem, loop or stem-loop structure between the sense and anti-sense sequences. A suppression element can instead comprise multiple sense and anti-sense sequences that are arranged in tandem, which can also be separated by one or more spacer sequences. Suppression elements comprising multiple sense and anti-sense sequences can be arranged as a series of sense sequences followed by a series of anti-sense sequences, or as a series of tandemly arranged sense and anti-sense sequences. Alternatively, one or more sense DNA sequences can be expressed separately from the one or more anti-sense sequences (i.e., one or more sense DNA sequences can be expressed from a first transcribable DNA sequence, and one or more anti-sense DNA sequences can be expressed from a second transcribable DNA sequence, wherein the first and second transcribable DNA sequences are expressed as separate transcripts).

For suppression of GA oxidase gene(s) using a microRNA (miRNA), the transcribable DNA sequence or suppression element can comprise a DNA sequence derived from a miRNA sequence native to a virus or eukaryote, such as an animal or plant, or modified or derived from such a native miRNA sequence. Such native or native-derived miRNA sequences can form a fold back structure and serve as a scaffold for the precursor miRNA (pre-miRNA), and can correspond to the stem region of a native miRNA precursor sequence, such as from a native (or native-derived) primary-miRNA (pri-miRNA) or pre-miRNA sequence. However, in addition to these native or native-derived miRNA scaffold or preprocessed sequences, engineered or synthetic miRNAs of the present aspects further comprise a sequence corresponding to a segment or portion of the targeted GA oxidase gene(s). Thus, in addition to the pre-processed or scaffold miRNA sequences, the suppression element can further comprise a sense and/or anti-sense sequence that corresponds to a segment or portion of a targeted GA oxidase gene, and/or a sequence that is complementary thereto, although one or more sequence mismatches can be tolerated.

GA oxidase gene(s) can also be suppressed using one or more small interfering RNAs (siRNAs). The siRNA pathway involves the non-phased cleavage of a longer double-stranded RNA intermediate ("RNA duplex") into small interfering RNAs (siRNAs). The size or length of siRNAs ranges from about 19 to about 25 nucleotides or base pairs, but common classes of siRNAs include those containing 21 or 24 base pairs. Thus, a transcribable DNA sequence or suppression element can encode a RNA molecule that is at least about 19 to about 25 nucleotides (or more) in length, such as at least 19, 20, 21, 22, 23, 24, or 25 nucleotides in length. For siRNA suppression, a recombinant DNA molecule, construct or vector can be provided comprising a transcribable DNA sequence and suppression element encoding a siRNA molecule for targeted suppression of a GA oxidase gene(s). A transcribable DNA sequence and suppression element can be at least 19 nucleotides in length and have a sequence corresponding to one or more GA oxidase gene(s), and/or a sequence complementary to one or more GA oxidase gene(s).

GA oxidase gene(s) can also be suppressed using one or more trans-acting small interfering RNAs (ta-siRNAs). In the ta-siRNA pathway, miRNAs serve to guide in-phase processing of siRNA primary transcripts in a process that requires an RNA-dependent RNA polymerase for production of a double-stranded RNA precursor. ta-siRNAs are defined by lack of secondary structure, a miRNA target site that initiates production of double-stranded RNA, requirements of DCL4 and an RNA-dependent RNA polymerase (RDR6), and production of multiple perfectly phased ~21-nt small RNAs with perfectly matched duplexes with 2-nucleotide 3' overhangs (see Allen et al. (2005) Cell, 121:207-221). The size or length of ta-siRNAs ranges from about 20 to about 22 nucleotides or base pairs, but are mostly commonly 21 base pairs. A transcribable DNA sequence or suppression element of the present invention can encode a RNA molecule that is at least about 20 to about 22 nucleotides in length, such as 20, 21, or 22 nucleotides in length. For ta-siRNA suppression, a recombinant DNA molecule, construct or vector is thus provided comprising a transcribable DNA sequence or suppression element encoding a ta-siRNA molecule for targeted suppression of a GA oxidase gene(s). Such a transcribable DNA sequence and suppression element can be at least 20 nucleotides in length and have a sequence corresponding to one or more GA oxidase gene(s) and/or a sequence complementary to one or more GA oxidase gene(s). For methods of constructing suitable ta-siRNA scaffolds, see, e.g., U.S. Pat. No. 9,309,512, which is incorporated herein by reference in its entirety.

According to an aspect of the present disclosure, a seed of the modified corn plant is produced, in which the seed comprises a first expression cassette and DNA sequence encoding a non-coding RNA for suppression of one more GA20 oxidase genes and/or one or more GA3 oxidase genes, or one or more mutated or edited GA20 and/or GA3 oxidase genes, and a second expression cassette and DNA sequence encoding one or more MADS-box polypeptides. In an aspect, a progeny plant grown from the seed is semi-dwarf and has one or more improved ear traits, relative to a control corn plant that does not have the suppression element, mutation or edit and the MADS-box transgene. In another aspect, a commodity or commodity product is produced from the seed of the modified corn plant comprising the first transcribable DNA sequence encoding a non-coding RNA for suppression of one more GA20 oxidase genes and/or one or more GA3 oxidase genes, or one or more mutated or edited GA20 and/or GA3 oxidase genes, and the second DNA sequence encoding one or more MADS-box polypeptides.

A transgenic plant can be produced by any suitable transformation method as provided herein to produce a transgenic $R_0$ plant, which can then be selfed or crossed to other plants to generate $R_1$ seed and subsequent progeny generations and seed through additional crosses, etc. Aspects of the present disclosure further include a plant cell, tissue, explant, plant part, etc., comprising one or more transgenic cells having a transformation event or genomic insertion of a recombinant DNA or polynucleotide sequence comprising a transcribable DNA sequence encoding a non-coding RNA molecule that targets an endogenous GA3 or GA20 oxidase gene for suppression and a transgene encoding a MADS-box polypeptide Transgenic plants, plant cells, seeds, and plant parts of the present disclosure can be homozygous or hemizygous for a transgenic event or insertion in at least one plant cell thereof, or a targeted genome editing event or mutation, and plants, plant cells, seeds, and plant parts of the present disclosure can contain any number of copies of such transgenic event(s), insertion(s) mutation(s), and/or edit(s). The dosage or amount of expression of a transgene or transcribable DNA sequence can be altered by its zygosity and/or number of copies, which can affect the degree or extent of phenotypic changes in the transgenic plant, etc.

Transgenic plants provided herein can include a variety of monocot cereal plants, including crop plants, such as corn, wheat, rice and sorghum. Indeed, recombinant DNA molecules or constructs of the present disclosure can be used to create beneficial traits in cereal plants such as corn without off-types using only a single copy of the transgenic event, insertion or construct.

Aspects of the present disclosure further include methods for making or producing transgenic plants, such as by transformation, crossing, etc., wherein the method comprises introducing a recombinant DNA molecule, construct or sequence into a plant cell, and then regenerating or developing the transgenic plant from the transformed or edited plant cell, which can be performed under selection pressure favoring a transgenic event.

Provided in the present disclosure is a method for producing a modified corn plant, the method comprising: introducing into a corn cell a first recombinant expression cassette comprising a DNA sequence encoding a MADS-box polypeptide, wherein the corn cell comprises a second recombinant expression cassette comprising a transcribable DNA sequence encoding a non-coding RNA for suppression of one or more GA3 oxidase genes and/or one or more GA20 oxidase genes; and regenerating or developing a modified corn plant from the corn cell, wherein the modified corn plant comprises the first and second recombinant expression cassettes.

Also provided in the present disclosure is a method for producing a transgenic corn plant, the method comprising: (a) introducing into a first corn cell a transgene that encodes one or more MADS-box polypeptides to create a transgenic corn cell, wherein the first corn cell comprises a transcribable DNA sequence encoding a non-coding RNA for suppression of one or more GA3 oxidase genes or GA20 oxidase genes; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising: introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a MADS-box polypeptide; and regenerating or developing a modified corn plant from the corn cell, wherein the modified corn plant comprises the first and second recombinant expression cassettes.

Also provided in the present disclosure is a method for producing a transgenic corn plant, the method comprising: (a) introducing into a first corn cell a transcribable DNA sequence encoding a non-coding RNA for suppression of one or more GA3 oxidase genes or GA20 oxidase genes to create a transgenic corn cell, wherein the first corn cell comprises a transgene that encodes one or more MADS-box polypeptides; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a MADS-box polypeptide; and regenerating or developing a modified corn plant from the corn cell, wherein the modified corn plant comprises the first and second recombinant expression cassettes.

Also provided in the present disclosure is a method for producing a transgenic corn plant, the method comprising (a) introducing into a first corn cell 1) a transcribable DNA sequence encoding a non-coding RNA for suppression of one or more GA3 oxidase genes or GA20 oxidase genes and 2) a transgene that encodes one or more MADS-box polypeptides, to create a transgenic corn cell; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising introducing into a corn cell a first recombinant expression cassette comprising a transcribable DNA sequence encoding a non-coding RNA for suppression of one or more GA3 oxidase genes and/or GA20 oxidase genes; introducing into the corn cell of step (a) a second recombinant expression cassette comprising a DNA sequence encoding a MADS-box polypeptide to create a modified corn cell; and regenerating or developing a modified corn plant from the modified corn cell of step (b), wherein the modified corn plant comprises the first and second recombinant expression cassettes.

Also provided in the present disclosure is a method for producing a modified corn plant, the method comprising introducing into a corn cell a first recombinant expression cassette comprising a DNA sequence encoding a MADS-box polypeptide; introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and regenerating or developing a modified corn plant from the modified corn cell of step (b), wherein the modified corn plant comprises the first and second recombinant expression cassettes.

Also provided in the present disclosure is a method for producing a transgenic corn plant, the method comprising (a) introducing into a first corn cell a transcribable DNA sequence encoding a non-coding RNA for suppression of one or more GA3 oxidase genes and/or one or more GA20 oxidase genes to create a transgenic corn cell, wherein the first corn cell is genome edited or mutated and comprises a transgene that encodes one or more MADS-box polypeptides; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the DNA sequence and the transgene.

Also provided in the present disclosure is a method for producing a transgenic corn plant, the method comprising (a) introducing into a first corn cell a DNA sequence that encodes one or more MADS-box polypeptides to create a transgenic corn cell, wherein the first corn cell is genome edited or mutated and has a reduced expression of one or more endogenous GA3 oxidase genes and/or one or more GA20 oxidase genes; and (b) generating a transgenic corn plant from the transgenic corn cell. In an aspect, the first corn cell comprises one or more mutation(s) or edit(s) at or near one or more endogenous GA20 oxidase and/or GA3 oxidase gene(s) (e.g., a mutation or edit in two or more endogenous GA20 oxidase and/or GA3 oxidase gene(s), wherein the expression of the endogenous GA20 oxidase and/or GA3 oxidase gene(s) is reduced relative to a wildtype control. In an aspect, the method further comprises identifying a transgenic corn plant with a desired trait. In another aspect, the identified transgenic corn plant is semi-dwarf and has one or more improved ear traits, relative to a control corn plant not having both the DNA sequence and the reduced expression of the one or more endogenous GA3 oxidase and/or GA20 oxidase genes.

Also provided in the present disclosure is a method for producing a modified corn plant, the method comprising: crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a MADS-box polypeptide; and producing a progeny corn plant comprising the recombinant expression cassette and has the reduced expression of the one or more endogenous GA3 oxidase genes and/or GA20 oxidase genes.

Also provided in the present disclosure is a method for producing a transgenic corn plant, the method comprising (a) crossing a first corn plant with a second corn plant to create a modified corn plant, wherein the expression of one or more endogenous GA3 oxidase gene(s) and/or one or more GA20 oxidase gene(s) is reduced in the first corn plant relative to a wildtype control, and wherein the second corn plant comprises a transgene encoding one or more MADS-box polypeptides; and (b) producing an offspring of the transgenic corn plant of step (a). In an aspect, the method further comprises identifying a modified corn plant with a desired trait. In another aspect, the identified modified corn plant is semi-dwarf and has one or more improved ear traits, relative to a control corn plant not having both the transgene and a reduced expression of the one or more endogenous GA3 oxidase and/or GA20 oxidase gene(s).

According to an aspect of the present disclosure, methods are provided for transforming a cell, tissue or explant with a recombinant DNA molecule or construct comprising DNA sequences or transgenes operably linked to one or more promoters to produce a transgenic or genome edited cell. According to other aspects of the present disclosure, methods are provided for transforming a plant cell, tissue or explant with a recombinant DNA molecule or construct comprising transcribable DNA sequences or transgenes operably linked to one or more plant-expressible promoters to produce a transgenic or genome edited plant or plant cell.

Numerous methods for transforming chromosomes or plastids in a plant cell with a recombinant DNA molecule or construct are known in the art, which can be used according to methods of the present disclosure to produce a transgenic plant cell and plant. Any suitable method or technique for transformation of a plant cell known in the art can be used according to present methods.

Effective methods for transformation of plants include bacterially mediated transformation, such as *Agrobacterium*-mediated or *Rhizobium*-mediated transformation and microprojectile particle bombardment-mediated transformation. A variety of methods are known in the art for transforming explants with a transformation vector via bacterially mediated transformation or microprojectile particle bombardment and then subsequently culturing, etc., those explants to regenerate or develop transgenic plants.

In an aspect, the methods for producing a transgenic or modified corn plant disclosed in the present disclosure comprise obtaining the first corn cell and the transgenic corn cell via *Agrobacterium*-mediated transformation.

In another aspect, the methods for producing a transgenic or modified corn plant disclosed in the present disclosure comprise obtaining the first corn cell and the transgenic corn cell via microprojectile particle bombardment-mediated transformation.

In yet another aspect, the methods for producing a transgenic corn plant disclosed in the present disclosure comprises (1) introducing into a first corn cell a transgene via site-directed integration to create a modified or mutated corn cell, wherein the transgene encodes one or more MADS-box polypeptides, and (2) introducing into the modified or mutated corn cell a transcribable DNA sequence via transformation to create a transgenic corn cell, wherein the transcribable DNA sequence encodes a non-coding RNA for suppression of one or more GA3 oxidase genes and/or one or more GA20 oxidase genes. In an aspect, the transformation can be *Agrobacterium*-mediated transformation or microprojectile particle bombardment-mediated transformation.

In still another aspect, the methods for producing a transgenic corn plant disclosed in the present disclosure comprise (1) obtaining a modified corn cell via genome editing, wherein the modified corn cell has a reduced expression of one or more GA3 oxidase genes and/or one or more GA20 oxidase genes; and (2) introducing into the modified corn cell a transgene via transformation to create a transgenic corn cell, wherein the transgene encodes one or more MADS-box polypeptides. In an aspect, the transformation can be *Agrobacterium*-mediated transformation or microprojectile particle bombardment-mediated transformation.

Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile particle bombardment with particles coated with recombinant DNA are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

In an aspect, described herein are methods of integrating an insertion sequence encoding one or more MADS-box polypeptides into the genome of a plant cell via site-directed integration. Such methods comprise creating a double-stranded break (DSB) in the genome of the plant cell such that the insertion sequence is integrated at the site of the DSB. In an aspect, the insertion/donor sequence encoding one or more MADS-box polypeptides can be integrated in a targeted manner into the genome of a cell at the location of a DSB. DSBs can be created by any mechanism, including but are not limited to, zinc finger nucleases (ZFN), transcription activator-like effector nuclease (TALEN), meganucleases, recombinases, transposases, and RNA-guided nucleases (e.g., Cas9 and Cpf1) in a CRISPR based genome editing system.

When Cas9 cleaves targeted DNA, endogenous double stranded break (DSB) repair mechanisms are activated. DSBs can be repaired via non-homologous end joining (NHEJ), which can incorporate insertions or deletions (indels) into the targeted locus. If two DSBs flanking one target region are created, the breaks can be repaired by reversing the orientation of the targeted DNA. Alternatively, if an insertion sequence of a donor template with homology to the target DNA sequence is provided, the DSB can be repaired via homology-directed repair or homologous recombination (HR). This repair mechanism allows for the precise integration of an insertion sequence into the targeted DNA sequence.

As used herein, an "insertion sequence" of a donor template is a sequence designed for targeted insertion into the genome of a plant cell, which can be of any suitable length. For example, an insertion sequence can be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length.

According to some aspects, a donor template may not comprise a sequence for insertion into a genome, and instead comprise one or more homology sequences that include(s) one or more mutations, such as an insertion, deletion, substitution, etc., relative to the genomic sequence at a target site within the genome of a plant. Alternatively, a donor template can comprise a sequence that does not comprise a coding or transcribable DNA sequence, wherein the insertion sequence is used to introduce one or more mutations into a target site within the genome of a plant.

A donor template provided herein can comprise at least one, at least two, at least three, at least four, at least five, at least six, at least seven, at least eight, at least nine, or at least ten genes or transcribable DNA sequences. Alternatively, a donor template can comprise no genes. Without being limiting, a gene or transcribable DNA sequence of a donor template can include, for example, an insecticidal resistance gene, an herbicide tolerance gene, a nitrogen use efficiency gene, a water use efficiency gene, a nutritional quality gene, a DNA binding gene, a selectable marker gene, an RNAi or suppression construct, a site-specific genome modification enzyme gene, a single guide RNA of a CRISPR/Cas9 system, a geminivirus-based expression cassette, or a plant viral expression vector system. A donor template can comprise a promoter, such as a tissue-specific or tissue-preferred promoter, a constitutive promoter, or an inducible promoter. A donor template can comprise a leader, enhancer, promoter, transcriptional start site, 5'-UTR, one or more exon(s), one or more intron(s), transcriptional termination site, region or sequence, 3'-UTR, and/or polyadenylation signal. The leader, enhancer, and/or promoter can be operably linked to a gene or transcribable DNA sequence encoding a non-coding RNA, a guide RNA, an mRNA and/or protein.

In an aspect, an insertion sequence of a donor template of the present disclosure comprises a DNA sequence encoding a MADS-box polypeptide, wherein the MADS-box polypeptide is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 175-199.

In an aspect, an insertion sequence of a donor template of the present disclosure comprises a DNA sequence encoding a maize ZMM19 polypeptide, wherein the DNA sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

In an aspect, a "modified plant(s)," "modified corn plant(s)," "transgenic plant(s)," or "transgenic corn plant(s)" produced according to a method disclosed in the present disclosure comprises (1) a first transcribable DNA sequence encoding a non-coding RNA for suppression of one or more GA20 oxidase genes and/or one or more GA3 oxidase genes, and (2) a second DNA sequence encoding one or more MADS-box polypeptides.

In another aspect, a "modified plant(s)," "modified corn plant(s)," "transgenic plant(s)," or "transgenic corn plant(s)" produced according to a method disclosed in the present disclosure comprises (1) a DNA sequence encoding one or more MADS-box polypeptides, and (2) a reduced expression of one or more endogenous GA3 oxidase genes or GA20 oxidase genes relative to a wildtype control. In an aspect, the reduced expression of the one or more endogenous GA20 oxidase genes or GA3 oxidase genes is caused by a mutation or edit at or near the one or more endogenous GA20 oxidase genes or GA3 oxidase genes.

Transgenic or modified plants produced by transformation methods can be chimeric or non-chimeric for the transformation event depending on the methods and explants used. Methods are further provided for expressing a non-coding RNA molecule that targets an endogenous GA oxidase gene for suppression in one or more plant cells or tissues under the control of a plant-expressible promoter, such as a constitutive, tissue-specific, tissue-preferred, vascular and/or leaf promoter as provided herein. Such methods can be used to create transgenic cereal or corn plants having a shorter, semi-dwarf stature, reduced internode length, increased stalk/stem diameter, and/or improved lodging resistance. Such transgenic cereal or corn plants can further have other traits that can be beneficial for yield, such as reduced green snap, deeper roots, increased leaf area, earlier canopy closure, improved drought tolerance, increased nitrogen use efficiency, increased water use efficiency, higher stomatal conductance, lower ear height, increased foliar water content, reduced anthocyanin content and/or area in leaves under normal or nitrogen or water limiting stress conditions, increased ear weight, increased seed or kernel number, increased seed or kernel weight, increased yield, and/or increased harvest index, relative to a wild type or control plant. As used herein, "harvest index" refers to the mass of the harvested grain divided by the total mass of the above-ground biomass of the plant over a harvested area.

Alternatively, nucleotide sequences of the disclosure can be introduced into an organism and allowed to undergo recombination with homologous regions of the organism's genome. Such homologous recombination approaches are well known to those of ordinary skill in the art and can be used to stably incorporate sequences of the disclosure into an organism. In an aspect, nucleotide sequences of the disclosure can be used to introduce "knockout mutations" into a specific gene of an organism that shares substantial homology to the sequences of the disclosure. A knockout mutation is any mutation in the sequence of a gene that eliminates or substantially reduces the function or the level of the product encoded by the gene. Methods involving transformation of an organism followed by homologous recombination to stably integrate the sequences of the disclosure into the genome organism are encompassed by the disclosure. The disclosure is particularly directed to methods where sequences of the disclosure are utilized to alter the growth of an organism. Such methods encompass use of the sequences of the disclosure to interfere with the function of one or more GA20 oxidase genes or GA3 oxidase genes. In an aspect, a knockout mutation of one or more GA20 oxidase or GA3 oxidase genes can be introduced into a corn cell via recombination to reduce the expression of the one or more of GA20 oxidase or GA3 oxidase genes in the corn cell.

Cells that have been transformed can be grown into plants in accordance with conventional ways. See, for example, McCormick et al. (1986) *Plant Cell Reports* 5:81-84. These plants can then be grown, and either pollinated with the same transformed strain or different strains, and the resulting hybrid having constitutive expression of the desired phenotypic characteristic identified. Two or more generations can be grown to ensure that constitutive expression of the desired phenotypic characteristic is stably maintained and inherited and then seeds harvested to ensure constitutive expression of the desired phenotypic characteristic has been achieved.

In an aspect, the methods for producing a transgenic or modified corn plant further comprises culturing the transgenic corn plant of step (b) or a plant part thereof in the presence of a selection agent. In another aspect, the selection agent is kanamycin.

Recipient cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell.

Transformation of a target plant material or explant can be practiced in tissue culture on nutrient media, for example a mixture of nutrients that allow cells to grow in vitro or cell culture. Transformed explants, cells or tissues can be subjected to additional culturing steps, such as callus induction, selection, regeneration, etc., as known in the art. Transformation can also be carried out without creation or use of a callus tissue. Transformed cells, tissues or explants containing a recombinant DNA sequence insertion or event can be grown, developed or regenerated into transgenic plants in culture, plugs, or soil according to methods known in the art. Transgenic plants can be further crossed to themselves or other plants to produce transgenic seeds and progeny. A transgenic plant can also be prepared by crossing a first plant comprising the recombinant DNA sequence or transformation event with a second plant lacking the insertion. For example, a recombinant DNA construct or sequence can be introduced into a first plant line that is amenable to transformation, which can then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line, but for the introduction of the recombinant DNA construct or sequence.

Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference.

Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In an aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction.

Transgenic plants can be further crossed to themselves or other plants to produce transgenic seeds and progeny. A transgenic plant can also be prepared by crossing a first plant comprising the recombinant DNA sequence or transformation event with a second plant lacking the insertion. For example, a recombinant DNA construct or sequence can be introduced into a first plant line that is amenable to transformation, which can then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line but for the introduction of the recombinant DNA construct or sequence.

A plant, cell, or explant provided herein can be of an elite variety or an elite line. An elite variety or an elite line refers to any variety that has resulted from breeding and selection for superior agronomic performance. A plant, cell, or explant provided herein can be a hybrid plant, cell, or explant. As used herein, a "hybrid" is created by crossing two plants from different varieties, lines, or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

For *Agrobacterium*-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. In other words, the transgene, a transcribable DNA sequence, transgene or expression cassette encoding the site-specific nuclease(s), and/or sgRNA(s) or crRNA(s) would be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant.

A plant selectable marker transgene in a transformation vector or construct of the present disclosure can be used to assist in the selection of transformed cells or tissue due to the presence of a selection agent, such as an antibiotic or herbicide, wherein the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_0$ plant.

A plant selectable marker transgene in a transformation vector or construct of the present disclosure can be used to assist in the selection of transformed cells or tissue due to the presence of a selection agent, such as an antibiotic or herbicide, wherein the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes can also be used, which provide an ability to visually screen for transformants, such as luciferase or green fluorescent protein (GFP), or a gene expressing a beta glucuronidase or uidA gene (GUS) for which various chromogenic substrates are known. In some aspects, a vector or polynucleotide provided herein comprises at least one selectable marker gene selected from the group consisting of nptII, aph IV, aadA, aac3, aacC4, bar, pat, DMO, EPSPS, aroA, GFP, and GUS. Plant transformation can also be carried out in the absence of selection during one or more steps or stages of culturing, developing or regenerating transformed explants, tissues, plants and/or plant parts.

An aspect of the present disclosure relate to screening cells, tissues or plants for mutations, targeted edits or transgenes and selecting cells or plants comprising targeted edits or transgenes. Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In an aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified or transgenic plants or plant cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, marker genotyping, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

Modified corn plants of the present disclosure having a reduced plant height and improved ear traits relative to a wild-type or control plant can comprise a mutation (e.g., an insertion, deletion, substitution, etc.) introduced through other plant mutagenesis technique or genome editing, wherein expression of one or more GA20 or GA3 oxidase gene is reduced or eliminated in one or more tissues of the modified plant. Modified corn plants of the present disclosure having a reduced plant height and improved ear traits relative to a wild-type or control plant can comprise a transgene encoding one or more MADS-box polypeptides. The transgene can be introduced through other plant mutagenesis technique or genome editing.

Plant mutagenesis techniques (excluding genome editing) can include chemical mutagenesis (i.e., treatment with a chemical mutagen, such as an azide, hydroxylamine, nitrous acid, acridine, nucleotide base analog, or alkylating agent— e.g., EMS (ethylmethane sulfonate), MNU (N-methyl-N-nitrosourea), etc.), physical mutagenesis (e.g., gamma rays, X-rays, UV, ion beam, other forms of radiation, etc.), and insertional mutagenesis (e.g., transposon or T-DNA insertion). Plants or various plant parts, plant tissues or plant cells can be subjected to mutagenesis. Treated plants can be reproduced to collect seeds or produce a progeny plant, and treated plant parts, plant tissues or plant cells can be developed or regenerated into plants or other plant tissues. Mutations generated with chemical or physical mutagenesis techniques can include a frameshift, missense or nonsense mutation leading to loss of function or expression of a targeted gene, such as a GA3 or GA20 oxidase gene.

One method for mutagenesis of a gene is called "TILLING" (for targeting induced local lesions in genomes), in which mutations are created in a plant cell or tissue, preferably in the seed, reproductive tissue or germline of a plant, for example, using a mutagen, such as an EMS treatment. The resulting plants are grown and self-fertilized, and the progeny are used to prepare DNA samples. PCR amplification and sequencing of a nucleic acid sequence of a GA20 or GA3 oxidase gene can be used to identify whether a mutated plant has a mutation in the GA oxidase gene. Plants having mutations in the GA20 or GA3 oxidase gene can then be tested for an altered trait, such as reduced plant height. Alternatively, mutagenized plants can be tested for an altered trait, such as reduced plant height, and then PCR amplification and sequencing of a nucleic acid sequence of a GA20 or GA3 oxidase gene can be used to determine whether a plant having the altered trait also has a mutation in the GA oxidase gene. See, e.g., Colbert et al., 2001, *Plant Physiol* 126:480-484; and McCallum et al., 2000, *Nat. Biotechnol.*, 18:455-457. TILLING can be used to identify mutations that alter the expression a gene or the activity of proteins encoded by a gene, which can be used to introduce and select for a targeted mutation in a GA20 or GA3 oxidase gene of a corn or cereal plant.

Provided in the present disclosure is a recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a MADS-box polypeptide, wherein the DNA sequence is operably linked to a plant-expressible promoter. In an aspect, the first and second expression cassettes are in a single T-DNA segment of a transformation vector. In another aspect, the first and second expression cassettes are in two different T-DNA segments of a transformation vector.

In an aspect, the transcribable DNA sequence encodes a non-coding RNA for suppression of a GA3 oxidase_1 gene, a GA3 oxidase_2 gene, or both. In another aspect, the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37. In another aspect, the transcribable DNA sequence encodes a non-coding RNA comprising a sequence that is 80% complementary to at least 15 consecutive nucleotides of one or more of SEQ ID NOs: 28, 29, 31, 32, 36, and 37.

In another aspect, the transcribable DNA sequence encodes a non-coding RNA for suppression of a GA20 oxidase_3 gene, a GA20 oxidase_4 gene, a GA20 oxidase_5 gene, or a combination thereof. In another aspect, the transcribable DNA sequence comprises a sequence that is at least 80% complementary to at least 15 consecutive nucleotides of SEQ ID NO: 39, 53, or 55. In another aspect, the transcribable DNA sequence encodes a sequence that is at least 80% complementary to at least 15 consecutive nucleotides of SEQ ID NO: 40, 54, or 56.

In an aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9, 12, 15, 30, or 33.

In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

In an aspect, the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199, or a functional fragment thereof.

In an aspect, the DNA sequence comprised in the second expression cassette encodes a maize ZMM19 polypeptide. In another aspect, the MADS-box polypeptide comprises an amino acid sequence that is at least 60% identical to SEQ ID NO: 168, or a functional fragment thereof. In another aspect, the DNA sequence comprises a sequence that is at least 60% identical to SEQ ID NO: 169.

Also provided herein is a recombinant DNA construct comprising 1) a first transcribable DNA sequence encoding a non-coding RNA for suppression of one or more GA20 oxidase or one or more GA3 oxidase genes, and 2) a second DNA sequence encoding one or more MADS-box polypeptides.

In an aspect, a recombinant DNA construct of the present disclosure comprises a transcribable DNA sequence encoding a non-coding RNA for suppression of one or more GA20 oxidase or one or more GA3 oxidase genes, wherein the DNA sequence is operably linked to a plant-expressible promoter. Such a recombinant DNA construct can be used to transform a corn plant cell expressing a transgene encoding one or more MADS-box polypeptides to create a transgenic corn plant with desired traits. In another aspect, desired traits comprise semi-dwarf and improved ear traits as compared to a control corn plant not having the transgene and the DNA sequence.

In an aspect, a recombinant DNA construct of the present disclosure comprises a DNA sequence encoding one or more MADS-box polypeptides, wherein the DNA sequence is operably linked to a plant-expressible promoter. Such a recombinant DNA construct can be used to transform a corn plant cell having a reduced expression of one or more GA20 oxidase genes and/or one or more GA3 oxidase genes to create a transgenic corn plant with desired traits. In another aspect, desired traits comprise semi-dwarf and improved ear traits as compared to a control corn plant not having the DNA sequence and the reduced expression of the one or more GA20 oxidase genes and/or GA3 oxidase genes.

Also provided in the present disclosure is a transgenic corn plants comprising the recombinant DNA construct. In an aspect, the first and second DNA sequences are in a single T-DNA molecule. In another aspect, the first and second DNA sequences are in two different T-DNA molecules. In an aspect, the first transcribable DNA sequence is operably linked to a plant-expressible promoter.

In an aspect, a recombinant DNA construct of the present disclosure comprises a transcribable DNA sequence encoding a non-coding RNA molecule, wherein the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9, 12, 15, 30 or 33, and wherein the transcribable DNA sequence is operably linked to a plant-expressible promoter. In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31 or 32.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 15. In yet another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or SEQ ID NO: 14.

In another aspect, the non-coding RNA molecule comprises a sequence that is (i) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9; and/or (ii) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 15.

In another aspect, the non-coding RNA molecule comprises a sequence that is (i) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 or 8; and/or (ii) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or 14.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 12.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 10 or 11.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein, the endogenous GA3 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 30 or 33.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 28, 29, 31 or 32.

In an aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 3, 6, 9, 12, 15, 18, 21, 24, 27, 30 and 33.

In another aspect, the non-coding RNA molecule comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 1, 2, 4, 5, 7, 8, 10, 11, 13, 14, 16, 17, 19, 20, 22, 23, 25, 26, 28, 29, 31, and 32.

In an aspect, a recombinant DNA molecule, vector or construct is provided for suppression of an endogenous GA oxidase (or GA oxidase-like) gene in a corn or cereal plant, the recombinant DNA molecule, vector or construct comprising a transcribable DNA sequence encoding a non-coding RNA molecule, wherein the non-coding RNA molecule comprises a sequence that is (i) at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of any one or more of SEQ ID NO: 84, 85, 87, 88, 89, 91, 92, 93, 95, 96, 98, 99, 100, 102, 103, 105, 106, 107, 109, 110, 111, 113, 114, 115, 117, 119, 120, 122, 123, 124, 126, 127, 128, 130, 131, 132, 134, 135, and/or 137, and/or (ii) at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding a protein in the cereal plant that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to any one or more of SEQ ID NO: 86, 90, 94, 97, 101, 104, 108, 112, 116, 118, 121, 125, 129, 133, and/or 136. Likewise, a non-coding RNA molecule can target an endogenous GA oxidase (or GA oxidase-like) gene in a cereal plant having a percent identity to the GA oxidase gene(s) shown to affect plant height in corn. Thus, a non-coding RNA molecule is further provided comprising a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous protein in a cereal plant that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to any one or more of SEQ ID NO: 9, 12, 15, 30, and/or 33. As mentioned above, the non-coding RNA molecule can target an exon, intron and/or UTR sequence of a GA oxidase (or GA oxidase-like) gene.

A recombinant DNA construct of the present disclosure can comprise or be included within a DNA transformation vector for use in transformation of a target plant cell, tissue or explant. Such a transformation vector of the present disclosure can generally comprise sequences or elements necessary or beneficial for effective transformation in addition to at least one selectable marker gene, at least one expression cassette and/or transcribable DNA sequence encoding one or more site-specific nucleases, and, optionally, one or more sgRNAs or crRNAs.

According to an aspect of the present disclosure, suitable tissue-specific or tissue preferred promoters can include those promoters that drive or cause expression of its associated suppression element or sequence at least in the vascular and/or leaf tissue(s) of a corn or cereal plant, or possibly other tissues.

Expression of the GA oxidase suppression element or construct with a tissue-specific or tissue-preferred promoter can also occur in other tissues of the cereal or corn plant outside of the vascular and leaf tissues, but active GA levels in the developing reproductive tissues of the plant (particularly in the female reproductive organ or ear) are preferably not significantly reduced or impacted (relative to wild type or control plants), such that development of the female organ or ear can proceed normally in the transgenic plant without off-types in the ear and a loss in yield potential.

According to some aspects, constructs and transgenes are provided comprising the first transcribable DNA sequence and the second DNA sequence that are operably linked to a constitutive or tissue-specific or tissue-preferred promoter, such as a vascular or leaf promoter.

In an aspect, the plant-expressible promoter is a vascular promoter. Any vascular promoters known in the art can potentially be used as the tissue-specific or tissue-preferred promoter. Examples of vascular promoters include the RTBV promoter, a known sucrose synthase gene promoter, such as a corn sucrose synthase-1 (Sus1 or Sh1) promoter, a corn Sh1 gene paralog promoter, a barley sucrose synthase promoter (Ss1) promoter, a rice sucrose synthase-1 (RSs1) promoter, or a rice sucrose synthase-2 (RSs2) promoter, a known sucrose transporter gene promoter, such as a rice sucrose transporter promoter (SUT1), or various known viral promoters, such as a *Commelina* yellow mottle virus (CoYMV) promoter, a wheat dwarf geminivirus (WDV) large intergenic region (LIR) promoter, a maize streak geminivirus (MSV) coat protein (CP) promoter, or a rice yellow stripe 1 (YS1)-like or OsYSL2 promoter, and any functional sequence portion or truncation of any of the foregoing promoters with a similar pattern of expression, such as a truncated RTBV promoter.

In another aspect, the vascular promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 67, SEQ ID NO: 68, SEQ ID NO: 69, SEQ ID NO: 70, SEQ ID NO: 71, or a functional portion thereof.

In another aspect, the plant-expressible promoter is a rice tungro bacilliform virus (RTBV) promoter. In an aspect, the RTBV promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 65 or SEQ ID NO: 66, or a functional portion thereof.

In another aspect, the plant-expressible promoter is a leaf promoter. Any leaf promoters known in the art can potentially be used as the tissue-specific or tissue-preferred promoter. Examples of leaf promoters include a corn pyruvate phosphate dikinase or PPDK promoter, a corn fructose 1,6 bisphosphate aldolase or FDA promoter, and a rice Nadh-Gogat promoter, and any functional sequence portion or truncation of any of the foregoing promoters with a similar pattern of expression. Other examples of leaf promoters from monocot plant genes include a ribulose biphosphate carboxylase (RuBisCO) or RuBisCO small subunit (RBCS) promoter, a chlorophyll a/b binding protein gene promoter, a phosphoenolpyruvate carboxylase (PEPC) promoter, and a Myb gene promoter, and any functional sequence portion or truncation of any of these promoters with a similar pattern of expression.

In another aspect, the leaf promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 72, SEQ ID NO: 73 or SEQ ID NO: 74, or a functional portion thereof.

In another aspect, the plant-expressible promoter is a constitutive promoter. Examples of constitutive promoters that can be used in monocot plants, such as cereal or corn plants, include, for example, various actin gene promoters, such as a rice Actin 1 promoter (see, e.g., U.S. Pat. No. 5,641,876) and a rice Actin 2 promoter (see, e.g., U.S. Pat. No. 6,429,357), a CaMV 35S or 19S promoter (see, e.g., U.S. Pat. No. 5,352,605), a maize ubiquitin promoter (see, e.g., U.S. Pat. No. 5,510,474), a Coix lacryma-jobi polyubiquitin promoter, a rice or maize Gos2 promoter (see, e.g., Pater et al., Plant J., 2(6): 837-44 1992), a FMV 35S promoter (see, e.g., U.S. Pat. No. 6,372,211), a dual enhanced CMV promoter (see, e.g., U.S. Pat. No. 5,322,938), a MMV promoter (see, e.g., U.S. Pat. No. 6,420,547), a PCLSV promoter (see, e.g., U.S. Pat. No. 5,850,019), an Emu promoter (see, e.g., Last et al., Theor. Appl. Genet., 81:581 (1991); and Mcelroy et al., Mol. Gen. Genet., 231: 150 (1991)), a tubulin promoter from maize, rice or other species, a nopaline synthase (nos) promoter, an octopine synthase (ocs) promoter, a mannopine synthase (mas) promoter, or a plant alcohol dehydrogenase (e.g., maize Adh1) promoter, any other promoters including viral promoters known or later-identified in the art to provide constitutive expression in a cereal or corn plant, any other constitutive promoters known in the art that can be used in monocot or cereal plants, and any functional sequence portion or truncation of any of the foregoing promoters.

In another aspect, the constitutive promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

Tissue-specific and tissue-preferred promoters that drive, etc., a moderate or strong level of expression of their associated transcribable DNA sequence in active GA-producing tissue(s) of a plant can be preferred. Furthermore, such tissue-specific and tissue-preferred should drive, etc., expression of their associated transcribable DNA sequence during one or more vegetative stage(s) of plant development when the plant is growing and/or elongating including one or more of the following vegetative stage(s): $V_E$, V1, V2, V3, V4, V5, V6, V7, V8, V9, V10, V11, V12, V13, V14, Vn, $V_T$, such as expression at least during V3-V12, V4-V12, V5-V12, V6-V12, V7-V12, V8-V12, V3-V14, V5-V14, V6-V14, V7-V14, V8-V14, V9-V14, V10-V14, etc., or during any other range of vegetative stages when growth and/or elongation of the plant is occurring.

According to an aspect, the plant-expressible promoter can preferably drive expression constitutively or in at least a portion of the vascular and/or leaf tissues of the plant. Different promoters driving expression of a suppression element targeting the endogenous GA20 oxidase_3 and/or GA20 oxidase_5 gene(s), the GA20 oxidase_4 gene, the GA3 oxidase_1 and/or GA3 oxidase_2 gene(s) in corn, or similar genes and homologs in other cereal plants, can be effective at reducing plant height and increasing lodging resistance to varying degrees depending on their particular pattern and strength of expression in the plant. However, some tissue-specific and tissue-preferred promoters driving expression of a GA20 or GA3 oxidase suppression element in a plant may not produce a short stature or anti-lodging phenotypes due to the spatial-temporal pattern of expression of the promoter during plant development, and/or the amount or strength of expression of the promoter being too low or weak. Furthermore, some suppression constructs can only reduce and not eliminate expression of the targeted GA20 or GA3 oxidase gene(s) when expressed in a plant, and thus depending on the pattern and strength of expression with a given promoter, the pattern and level of expression of the GA20 or GA3 oxidase suppression construct with such a promoter may not be sufficient to produce an observable plant height and lodging resistance phenotype in plants.

Any other vascular and/or leaf promoters known in the art can also be used, including promoter sequences from related genes (e.g., sucrose synthase, sucrose transporter, and viral gene promoter sequences) from the same or different plant species or virus that have a similar pattern of expression. Further provided are promoter sequences with a high degree of homology to any of the foregoing. Examples of vascular and/or leaf promoters can further include other known, engineered and/or later-identified promoter sequences shown to have a pattern of expression in vascular and/or leaf tissue(s) of a cereal or corn plant. Furthermore, any known or later-identified constitutive promoter can also be used for expression of a GA20 oxidase or GA3 oxidase suppression element.

According to some aspects, recombinant expression cassettes, constructs, transgenes, and recombinant DNA donor template molecules are provided comprising a DNA sequence encoding a MADS-box polypeptide operably linked to a meristem promoter, a root promoter, or a seed or kernel promoter. For a review or resource of some promoter types and examples available in the art, see, e.g., Lagrimini, L. M. (editor), Maize: Methods and Protocols (Humana Press), Chapter 4: A Brief History of Promoter Development for Use in Transgenic Maize Applications, Vol. 1676, pp. 61-93 (2017); and the Maize Cell Genomics Database, the entire contents and disclosures of which are incorporated herein by reference.

In an aspect, a DNA sequence encoding a MADS-box polypeptide is operably linked to a meristem promoter, such as a meristem-specific promoter or a meristem-preferred promoter. A meristem-preferred promoter refers to a promoter that preferentially or predominantly causes or drives expression of a gene (or transgene) operably linked to the promoter in one or more meristem tissues of a corn or maize plant although the meristem-preferred promoter may also cause or drive expression of the gene (or transgene) operably linked to the promoter in other tissues. A meristem-specific promoter refers to a promoter that causes or drives expression of a gene (or transgene) operably linked to the promoter specifically in one or more meristem tissues of a corn plant. As used herein, a "meristem promoter" refers to any meristem-preferred promoter or meristem-specific promoter. A meristem promoter includes any promoter which causes or drives, or can cause or drive, meristem-specific or meristem-preferred expression of a gene or transgene operably linked to the promoter in a corn or maize seed, including any such promoter from a monocot or Poaceae plant, such as maize, barley, wheat, oat, millet, sorghum, rice, etc.

According to present embodiments, a meristem promoter can include any meristem promoter known in the art to cause or drive expression of a gene (or transgene) in one or more meristem tissues of a corn or maize plant, such as for example, a promoter from a WAK1 or WAK2 gene (see, e.g., Wagner et al., The Plant Cell 13(2): 303-318 (2001)), a metallothionein gene, a rice OSH1 gene (see, e.g., Sato et al, PNAS USA 93(15): 8117-8122 (1996)), a PCNA gene (see, e.g., Kosugi et al., Nucl. Acids Res. 19: 1571-1576 (1991)), a histone gene, such as a maize histone H3C4 gene (see, e.g., Ohtsubo et al., Pant Mol Biol 23(3):553-565 (1993); and Atanassova et al., Plant Mol Biol, 37: 275-285 (1998)), a maize WUSCHEL gene or a maize RAMOSA3 gene (see, e.g., Wu et al Int. J. Dev. Biol. 57: 535-543 (2013)), or a functional portion of any of the foregoing known meristem promoters, or a promoter sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to any of the foregoing known seed promoters, or any functional portion thereof. All of the above-cited references are incorporated herein by reference in their entirety. In another aspect, a meristem promoter comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 200-205, or a functional portion thereof.

In an aspect, a DNA sequence encoding a MADS-box polypeptide is operably linked to a root promoter, such as a root-specific promoter or a root-preferred promoter. Such a root promoter can confer transcription in root tissue, e.g., root endodermis, root epidermis, and/or root vascular tissues. A root-preferred promoter refers to a promoter that preferentially or predominantly causes or drives expression of a gene (or transgene) operably linked to the promoter in one or more root tissues of a corn or maize plant, such as the root endodermis, root epidermis, root vascular tissue, etc., although the root-preferred promoter may also cause or drive expression of the gene (or transgene) operably linked to the promoter in other tissues. A root-specific promoter refers to a promoter that causes or drives expression of a gene (or transgene) operably linked to the promoter specifically in one or more root tissues of a corn plant, such as the root endodermis, root epidermis, root vascular tissue, etc. As used herein, a "root promoter" refers to any root-preferred promoter or root-specific promoter. A root promoter includes any promoter which causes or drives, or can cause or drive, root-specific or root-preferred expression of a gene or transgene operably linked to the promoter in a corn or maize seed, including any such promoter from a monocot or Poaceae plant, such as maize, barley, wheat, oat, millet, sorghum, rice, etc.

According to present embodiments, a root promoter can include any root promoter known in the art to cause or drive expression of a gene (or transgene) in one or more root tissues of a corn or maize plant, such as for example, a root-specific subdomain of the CaMV 35S promoter (see, e.g., Lam et al., PNAS USA, 86:7890-7894 (1989)) or other root cell specific promoters (see, e.g., *Plant Physiol.*, 93:1203-1211 (1990)), one of the YP0128, YP0275, PT0625, PT0660, PT0683, PT0758, PT0613, PT0672, PT0678, PT0688, and PT0837 promoters (see, e.g., US Patent Pub. No. 2008/0131581), a GL5 promoter (see, e.g., US Patent Pub. No. 2007/174938), or a promoter from an acid chitanase gene, a RCc2 or RCc3 gene (see, e.g., U.S. Pat. No. 7,547,774 (rice); PCT Pub. No. WO 2009/126470 (millet); and Plant Mol Biol. 27(2): 237-48 (1995)), or a Zm.PIIG gene (see, e.g., U.S. Pat. No. 7,491,813), or a functional portion of any of the foregoing known root promoters, or a promoter sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to any of the foregoing known root promoters, or any functional portion thereof. In another aspect, a root promoter comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 206-209, or a functional portion thereof.

In an aspect, a DNA sequence encoding a MADS-box polypeptide is operably linked to a seed or kernel promoter, such as a seed- or kernel-specific promoter or a seed- or kernel-preferred promoter. A seed-preferred or kernel-preferred promoter refers to a promoter that preferentially or predominantly causes or drives expression of a gene (or transgene) operably linked to the promoter in one or more tissues of a seed or kernel of a corn or maize plant, such as in one or more of a seed endosperm, embryo, scutellum, etc., although the seed-preferred or kernel-preferred promoter may also cause or drive expression of the gene (or transgene) operably linked to the promoter in other tissues. A seed-specific or kernel-specific promoter refers to a promoter that causes or drives expression of a gene (or transgene) operably linked to the promoter specifically in one or more tissues of a seed or kernel of a corn or maize plant, such as in one or more of a seed endosperm, embryo, scutellum, etc. As used herein, a "seed promoter" or a "kernel promoter" refers to any seed-preferred (or kernel-preferred) promoter or any seed-specific (or kernel-specific) promoter. A seed or kernel promoter includes any promoter which causes or drives, or can cause or drive, seed-specific or seed-preferred expression of a gene or transgene operably linked to the promoter in a corn or maize seed, including any such promoter from a monocot or Poaceae plant, such as maize, barley, wheat, oat, millet, sorghum, rice, etc.

According to present embodiments, a seed or kernel promoter can include any seed or kernel promoter known in the art to cause or drive expression of a gene (or transgene) in one or more tissues of a corn or maize seed, such as for example, a promoter from a zein gene (see, e.g., Matzke et al., Plant Mol Biol, 14(3): 323-32 (1990); The Plant Cell, 13(10): 2297-2318 (2001); and Joshi et al., Physiol Mol Biol Plants, 21(1): 35-42 (2015)), such as alpha-zeins, gamma-zeins, and delta-zeins, including maize 15 kDa zein, 19 kDa zein, 22 kDa zein, or 27 kDa zein, or other prolamin gene, such as a B1-, C- or D-hordein gene, an alpha-, beta- or gamma-gliadin gene, a secalin gene, a kafirin gene, an avenin gene, etc. (see, e.g., Horvath et al., PNAS 97(4): 1914-19 (2000); Cho et al., Theor Appl Gen 98:1253-62 (1999); Muller et al., The Plant Journal 4(2):343-355 (1993); Sorensen et al., Mol and Gen Genet 250(6):750-60 (1996); Van Herpen et al., Ann Bot 102(3) 331-342 (2008); Aryan et al., Mol and Gen Genet 225(1):65-71 (1991); Rafalski et al., EMBO J 3(6):1409-15 (1984); Piston et al., Mol Breed 23(4):655-667 (2009); Derose et al., Plant Mol Biol 32(6): 1029-35 (1997); and PCT Application Pub. No. WO 1999/016890); a granule bound starch synthase (waxy) gene (see, e.g., Merida et al., Plant Physiol. 120(2):401-410 (1999)), a LMW or HMW glutenin or glutelin gene (see, e.g., Thilmony et al., GM Crops Food, 5(1): 36-43 (2014); Furtado et al., Plant Biotechnol J 7(3):240-53 (2009); Furtado et al., Plant Biotechnol J 6(7):679-93 (2008); Lamacchia et al., J Exp Bot 52(355):243-50 (2001); Osvald et al., In Vitro Cellular & Dev Biol. Plant 44(1): 1-7 (2008); Qu et al., J Exp Bot 59(9):2417-2424 (2008); and Colot et al., Mol Gen Genet 216:81-90 (1989)), a Cim1 (cytokinin-induced message) gene, a seed-preferred ADP-glucose pyrophosphorylase gene, such as a maize shrunken gene, a globulin-1 (Glb-1) or alpha-globulin gene (see, e.g., Wu et al., Plant Cell Physiology 39(8) 885-889 (1998); and Nakase et al. Plant Mol. Biol. 33(3):513-522 (1997)), a REB1/OHP-1 gene, a DOF gene (see, e.g., Mena et al, The Plant Journal, 116(1): 53-62 (1998), a lipid transfer protein (ltp) gene, such as a Ltp1 or Ltp2 gene (see, e.g., PCT Application Pub Nos. WO 1995/15389 and WO 1995/23230; and Kalla et al., The Plant J. 6(6): 849-60 (1994)), a SPA gene (see, e.g., Albani et al, The Plant Cell 9:171-184 (1997), a rice OSH1 gene (see, e.g., Sato et al, PNAS USA 93(15): 8117-8122 (1996)), an oleosin gene (see, e.g., Wu et al, J. Biochem 123: 386-391 (1998)), an ESR gene (see, e.g., Opsahl-Ferstad et al., Plant J. 12(1): 235-46 (1997), a KNOX gene (see, e.g., Postma-Haarsma et al, Plant Mol. Biol. 39(2): 257-71 (1999)), an amylase gene (see, e.g., Lanahan et al, The Plant Cell 4: 203-211 (1992); Yu et al., Gene 122(2): 247-253 (1992); and Skriver et al, PNAS USA 88(16): 7266-7270 (1991)), cathepsin Beta-like gene (see, e.g., Cejudo et al., Plant Mol Biol 20(5): 849-856 (1992)), chitinase or Chi26 gene (see, e.g., Leah et al., Plant J. 6(4): 579-89, 1994), B-Peru gene allele (see, e.g., Selinger et al., Genetics 149(2); 1125-38 (1998)), blz2 gene (see, e.g., Onate et al., J Biol Chem 274(14): 9175-82 (1999)), a trypsin inhibitor gene, such as Itr1 (see, e.g., Diaz et al., Mol Gen Genet 248(5): 592-8 (1995)), an end1 or end2 gene (see, e.g., PCT Application Pub No. WO 2000/12733), an alanine aminotransferase gene (see, e.g., Qu et al., Plant Biotechnol. J. 2: 113-125 (2004)), a glycine rich RNA binding (GRP) protein (see, e.g., U.S. Pat. No. 6,376,750), a ZM.39486 gene (see, e.g., U.S. Pat. No. 7,518,035), or a milps (myo-inositol-1-phosphate synthase) gene (see, e.g., U.S. Pat. No. 6,225,529), or a PRO0005, PRO0058, PRO0095, PRO0117, PRO0151, PRO0173, or PRO0175 promoter (see, e.g., WO 2004/070039), or a functional portion of any of the foregoing known seed promoters, or a promoter sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to any of the foregoing known seed promoters, or any functional portion thereof. All of the above-cited references are incorporated herein by reference in their entirety. In another aspect, a seed or kernel promoter comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 210-217, or a functional portion thereof. In another aspect, a seed or kernel promoter is from a maize putative embryo-specific (Esp) gene promoter and/or comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 174, or a functional portion thereof.

The following are exemplary promoters of the present specification.

TABLE 3

Exemplary promoters

| SEQ ID NO. | Expression Pattern | Sequence Name | Source organism |
|---|---|---|---|
| 200 | Meristem Preferred | P-Zm.H2a-1-1:1:1 | Zea mays |
| 201 | Meristem Preferred | P-At.Erl1:3 | Arabidopsis thaliana |
| 202 | Meristem Preferred | P-Zm.Wus1 | Zea mays |

TABLE 3-continued

Exemplary promoters

| SEQ ID NO. | Expression Pattern | Sequence Name | Source organism |
|---|---|---|---|
| 203 | Meristem Preferred | P-Zm.RAMOSA3 | Zea mays |
| 204 | Meristem Preferred | P-Zm.PCNA2 | Zea mays |
| 205 | Meristem Preferred | P-Zm.WAK | Zea mays |
| 206 | Root Preferred | P-Os.Rcc3-1:1:24 | Oryza sativa |
| 207 | Root Preferred | P-SETit.Ifr-1:1:2 | Setaria italica |
| 208 | Root Preferred | P-At.Mt-1a-1:1:1 | Arabidopsis thaliana |
| 209 | Root Preferred | P-Zm.RCC3 | Zea mays |
| 210 | Seed Preferred | P-At.rd29b-1:1:8 | Arabidopsis thaliana |
| 211 | Seed Preferred | P-Zm.Nac-1:1:2 | Zea mays |
| 212 | Seed Preferred | P-Zm.Esp-1:1:1 | Zea mays |
| 213 | Seed Preferred | P-At.Cab1-1:1:1 | Arabidopsis thaliana |
| 214 | Seed Preferred | P-Zm.Bt1-1:1:1 | Zea mays |
| 215 | Seed Preferred | P-Zm.Zein | Zea mays |
| 216 | Seed endosperm Preferred | P-Zm.39486-1:1:1 | Zea mays |
| 217 | Seed endosperm Preferred | P-Zm.miR167g-1:1:8 | Zea mays |

In addition to its associated promoter, a transcribable DNA sequence or a transgene can also be operatively linked to one or more additional regulatory element(s), such as an enhancer(s), leader, transcription start site (TSS), linker, 5' and 3' untranslated region(s) (UTRs), intron(s), polyadenylation signal, termination region or sequence, etc., that are suitable, necessary or preferred for strengthening, regulating or allowing expression of the transcribable DNA sequence in a plant cell. Such additional regulatory element(s) can be optional and/or used to enhance or optimize expression of the transgene or transcribable DNA sequence. As provided herein, an "enhancer" can be distinguished from a "promoter" in that an enhancer typically lacks a transcription start site, TATA box, or equivalent sequence and is thus insufficient alone to drive transcription. As used herein, a "leader" can be defined generally as the DNA sequence of the 5'-UTR of a gene (or transgene) between the transcription start site (TSS) and 5' end of the transcribable DNA sequence or protein coding sequence start site of the transgene.

In an aspect, the second DNA sequence encoding one or more MADS-box polypeptides comprised in a recombinant DNA construct of the present application is operably linked to a plant-expressible promoter, such as a constitutive or tissue-specific promoter. According to an aspect, the plant-expressible promoter is a medium or high-constitutive promoter with a high-constitutive promoter having a relatively more robust or strong constitutive expression. In an aspect, the plant-expressible promoter is a constitutive promoter, which can be selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

In an aspect, a transformation vector comprising the recombinant DNA construct is produced. In another aspect, a transgenic corn plant or a plant part thereof comprising the recombinant DNA construct is produced. In still another aspect, the transgenic corn plant is semi-dwarf and has one or more improved ear traits, relative to a control corn plant not having both the first transcribable DNA sequence and the second DNA sequence.

A recombinant DNA molecule or construct of the present disclosure can comprise or be included within a DNA transformation vector for use in transformation of a target plant cell, tissue or explant. Such a transformation vector can generally comprise sequences or elements necessary or beneficial for effective transformation in addition to at least one transgene, expression cassette and/or transcribable DNA sequence.

For Agrobacterium-mediated, Rhizobia-mediated or other bacteria-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. Thus, a transcribable DNA sequence, transgene or expression cassette can be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant. According to alternative aspects, the transcribable DNA sequence, transgene or expression cassette encoding a non-coding RNA molecule targeting an endogenous GA oxidase gene for suppression and the plant selectable marker transgene (or other gene of agronomic interest) can be present in separate T-DNA segments on the same or different recombinant DNA molecule(s), such as for co-transformation. A transformation vector or construct can further comprise prokaryotic maintenance elements, which can be located in the vector outside of the T-DNA region(s).

The present disclosure provides a modified corn plant with a semi-dwarf phenotype and one or more improved ear traits relative to a control plant. The modified corn plant has its expression of one or more GA20 oxidase genes and/or one or more GA3 oxidase genes reduced and comprises a transgene expressing one or more MADS-box polypeptides. In an aspect, the reduced expression of the one or more GA20 oxidase genes and/or one or more GA3 oxidase genes is caused by a mutation or edit at or near the one or more GA20 oxidase genes and/or GA3 oxidase genes introduced via genome editing. In another aspect, the reduced expression of one or more GA20 oxidase genes and/or one or more GA3 oxidase genes is caused by a site-directed integration of a transcribable DNA sequence encoding a non-coding RNA for suppression of the one or more GA20 oxidase genes and/or one or more GA3 oxidase genes. In an aspect, the site-directed integration is mediated by genome editing. In an aspect, the introduction of the transgene expressing one or more MADS-box polypeptides is caused by a site-directed integration of a sequence comprising the transgene. In another aspect, the site-directed integration is mediated by genome editing.

In an aspect, a genome editing system provided herein comprises a CRISPR system. The CRISPR systems are based on RNA-guided engineered nucleases that use complementary base pairing to recognize DNA sequences at target sites. In an aspect, a vector provided herein can comprise any combination of a nucleic acid sequence encoding a RNA-guided nuclease.

In an aspect, a method and/or composition provided herein comprises one or more, two or more, three or more, four or more, or five or more Cas9 nucleases. In an aspect, a method and/or composition provided herein comprises one or more polynucleotides encoding one or more, two or more, three or more, four or more, or five or more Cas9 nucleases. In another aspect, a Cas9 nuclease provided herein is capable of generating a targeted DSB. In an aspect, a method and/or composition provided herein comprises one or more, two or more, three or more, four or more, or five or more Cpf1 nucleases. In an aspect, a method and/or composition provided herein comprises one or more polynucleotides encoding one or more, two or more, three or more, four or more, or five or more Cpf1 nucleases. In another aspect, a Cpf1 nuclease provided herein is capable of generating a targeted DSB.

In an aspect, a vector or construct provided herein comprises polynucleotides encoding at least 1, at least 2, at least 3, at least 4, at least 5, at least 6, at least 7, at least 8, at least 9, or at least 10 site-specific nuclease. In another aspect, a cell provided herein already comprises a site-specific nuclease. In an aspect, a polynucleotide encoding a site-specific nuclease provided herein is stably transformed into a cell. In another aspect, a polynucleotide encoding a site-specific nuclease provided herein is transiently transformed into a cell. In another aspect, a polynucleotide encoding a site-specific nuclease is under the control of a regulatable promoter, a constitutive promoter, a tissue specific promoter, or any promoter useful for expression of the site-specific nuclease.

In an aspect, vectors comprising polynucleotides encoding a site-specific nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

In an aspect, a vector comprises in cis a cassette encoding a site-specific nuclease and an insertion sequence such that when contacted with the genome of a cell, the site-specific nuclease enables site-specific integration of the insertion sequence. In an aspect, a first vector comprises a cassette encoding a site-specific nuclease and a second vector comprises an insertion sequence such that when contacted with the genome of a cell, the site-specific nuclease provided in trans enables site-specific integration of the insertion sequence.

Site-specific nucleases provided herein can be used as part of a targeted editing technique. Non-limiting examples of site-specific nucleases used in methods and/or compositions provided herein include meganucleases, zinc finger nucleases (ZFNs), transcription activator-like effector nucleases (TALENs), RNA-guided nucleases (e.g., Cas9 and Cpf1), a recombinase (without being limiting, for example, a serine recombinase attached to a DNA recognition motif, a tyrosine recombinase attached to a DNA recognition motif), a transposase (without being limiting, for example, a DNA transposase attached to a DNA binding domain), or any combination thereof. In an aspect, a method provided herein comprises the use of one or more, two or more, three or more, four or more, or five or more site-specific nucleases to induce one, two, three, four, five, or more than five DSBs at one, two, three, four, five, or more than five target sites.

In an aspect, a genome editing system provided herein (e.g., a meganuclease, a ZFN, a TALEN, a CRISPR/Cas9 system, a CRISPR/Cpf1 system, a recombinase, a transposase), or a combination of genome editing systems provided herein, is used in a method to introduce one or more insertions, deletions, substitutions, or inversions to a locus in a cell to introduce a mutation, or generate a dominant negative allele or a dominant positive allele.

Site-specific nucleases, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), Cas9 nucleases (non-limiting examples of RNA-guided nucleases include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof), induce a double-strand DNA break at the target site of a genomic sequence that is then repaired by the natural processes of HR or NHEJ. Sequence modifications then occur at the cleaved sites, which can include inversions, deletions, or insertions that result in gene disruption in the case of NHEJ, or integration of nucleic acid sequences by HR.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1.

In another aspect a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof. In another aspect, an RNA-guided nuclease provided herein is selected from the group consisting of a Cas9 or a Cpf1.

In another aspect an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof.

In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, C5m5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof, an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, modified versions thereof), a DNA guide for an Argonaute protein, and any combination thereof. In another aspect, an RNA-guided nuclease provided herein is selected from the group consisting of Cas9 and Cpf1.

In another aspect, an RNA-guided nuclease provided herein comprises Cas9. In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In an aspect a site-specific nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo. In another aspect, an RNA-guided nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can also be positioned upstream or downstream of a sequence encoding a leader, an enhancer, a transcriptional start site, a promoter, a 5'-UTR, an exon, an intron, a 3'-UTR, a polyadenylation site, or a termination sequence. In an aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

In an aspect, a target site bound by an RNA-guided nuclease is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In an aspect, a targeted genome editing technique described herein can comprise the use of a recombinase. In an aspect, a tyrosine recombinase attached to a DNA recognition motif is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA binding domain. The Flp-FRT site-directed recombination system comes from the 2µ plasmid from the baker's yeast *Saccharomyces cerevisiae*. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif.

ZFNs are synthetic proteins consisting of an engineered zinc finger DNA-binding domain fused to the cleavage domain of the FokI restriction nuclease. ZFNs can be designed to cleave almost any long stretch of double-stranded DNA for modification by the zinc finger DNA-binding domain. ZFNs form dimers from monomers composed of a non-specific DNA cleavage domain of FokI nuclease fused to a zinc finger array engineered to bind a target DNA sequence.

DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

FokI nuclease domain requires dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs can be introduced as ZFN proteins, as polynucleotides encoding ZFN proteins, and/or as combinations of proteins and protein-encoding polynucleotides.

In an aspect, a method and/or composition provided herein comprises one or more, two or more, three or more, four or more, or five or more ZFNs. In another aspect, a ZFN provided herein is capable of generating a targeted DSB. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or *Agrobacterium*-mediated transformation).

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some aspects, a meganuclease can comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease can be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI and FokI, AlwI, MlyI, SbfI, SdaI, StsI, CleDORF, Clo051, Pept071. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation).

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase.

Provided in the present disclosure is a modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a MADS-box polypeptide, wherein the DNA sequence is operably linked to a plant-expressible promoter. In an aspect, the modified corn plant is semi-dwarf and has one or more improved ear traits, relative to a control corn plant that does not comprise both the one or more mutations or edits and the recombinant expression cassette. In another aspect, the one or more mutations or edits are selected from the group consisting of an insertion, a substitution, an inversion, a deletion, a duplication, and a combination thereof. In yet another aspect, the one or more mutations or edits are introduced using a meganuclease, a zinc-finger nuclease (ZFN), a RNA-guided endonuclease, a TALE-endonuclease (TALEN), a recombinase, or a transposase.

Also provided is a plurality of modified corn plants in a field, each modified corn plant comprising one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and a recombinant expression cassette comprising a DNA sequence encoding a MADS-box polypeptide, wherein the DNA sequence is operably linked to a plant-expressible promoter. In an aspect, the modified corn plants have increased yield relative to control corn plants. In another aspect, the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants. In an aspect, such a plant-expressible promoter is a root promoter, such as a root-specific or root-preferred promoter. In another aspect, such a plant-expressible promoter is a meristem promoter, such as a meristem-specific promoter or a meristem-preferred promoter. In another aspect, such a plant-expressible promoter is a kernel or seed promoter, such as a seed-preferred or seed-specific promoter. In an aspect, a root promoter is an *Oryza sativa* Rcc3 gene promoter. In an aspect, a plant-expressible or root promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 170, or a functional portion thereof. In an aspect, a seed or kernel promoter is a maize putative embryo-specific (Esp) gene promoter. In an aspect, a plant-expressible or seed or kernel promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 174, or a functional portion thereof.

Also provided is a genome edited or mutated corn plant comprising (1) a mutation or edit at or near an endogenous GA20 oxidase or GA3 oxidase gene, wherein the expression of the endogenous GA20 oxidase or GA3 oxidase gene is reduced relative to a wildtype control, and (2) a heterologous DNA sequence encoding a MADS-box polypeptide. In an aspect, the genome edited or mutated corn plant is semi-dwarf and has one or more improved ear traits, relative to a control corn plant that does not comprise both the mutation and the heterologous DNA sequence. In an aspect, a genome edited or mutated corn cell is obtained via a CRISPR based genome editing system.

Aspects of the present disclosure further include methods for making or producing modified plants, such as by genome editing, crossing, etc., wherein the method comprises editing the genomic locus of an endogenous GA3 or GA20 oxidase gene and introducing a transgene encoding one or more MADS-box polypeptide, and then regenerating or developing the modified plant from the edited plant cell.

In an aspect, a method comprises introducing a mutation or edit via CRISPR based genome editing at or near one or more endogenous GA3 or GA20 oxidase genes to reduce the expression of the one or more endogenous GA3 or GA20 oxidase genes. The method comprises creating a double-stranded break (DSB) in the genome of the plant cell, wherein a mutation or edit is introduced therein, thereby reducing the expression of the one or more endogenous GA3 or GA20 oxidase genes. In an aspect, the mutation or edit can be created (or integrated with a donor template) in a targeted manner into the genome of a cell at the location of a DSB via RNA-guided nucleases (e.g., Cas9 and Cpf1). In another aspect, a guide RNA recognizes a target site and acts in association with an RNA-guided nuclease that creates a DSB at the target site, wherein a mutation or edit is created (or integrated with a donor template) into the target site. In another aspect, the target site is near or at one or more endogenous GA3 or GA20 oxidase genes.

In an aspect, a method comprises introducing an insertion sequence encoding one or more MADS-box polypeptides into the genome of a plant cell via site-directed integration. Such a method comprises creating a DSB in the genome of the plant cell such that the insertion sequence is integrated at the site of the DSB. In an aspect, the insertion sequence encoding one or more MADS-box polypeptides can be inserted or integrated in a targeted manner into the genome of a cell at the location of a DSB via RNA-guided nucleases (e.g., Cas9 and Cpf1) in a CRISPR based genome editing system. In another aspect, a guide RNA recognizes a target site and acts in association with an RNA-guided nuclease that creates a double-stranded break at the target site, wherein the insertion sequence encoding one or more MADS-box polypeptides inserts or integrates into the target site.

In an aspect, an insertion sequence of a donor template of the present disclosure comprises a DNA sequence encoding a MADS-box polypeptide, wherein the MADS-box polypeptide sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 175-199 and a functional fragment thereof.

In an aspect, an insertion sequence of a donor template of the present disclosure comprises a DNA sequence encoding a ZMM19 polypeptide, wherein the DNA sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169. In another aspect, an insertion sequence of the present disclosure comprises a DNA sequence encoding a polypeptide comprising an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof.

Provided in the present disclosure is a method for producing a modified corn plant, the method comprising: introducing into a corn cell a recombinant expression cassette comprising a DNA sequence encoding a MADS-box polypeptide, wherein the DNA sequence is operably linked to a plant-expressible promoter, and wherein the corn cell comprises one or more mutations and/or edits in one or more endogenous GA3 oxidase and/or GA20 oxidase genes; and regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits. In an aspect, the method further comprises introducing a recombinant DNA construct encoding a guide RNA that targets the one or more endogenous GA3 oxidase and/or GA20 oxidase genes. In an aspect, such a plant-expressible promoter is a root promoter, such as a root-specific or root-preferred promoter. In another aspect, such a plant-expressible promoter is a meristem promoter, such as a meristem-specific promoter or a meristem-preferred promoter. In another aspect, such a plant-expressible promoter is a kernel or seed promoter, such as a seed-preferred or seed-specific promoter. In an aspect, a root promoter is an *Oryza sativa* Rcc3 gene promoter. In an aspect, a plant-expressible or root promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 170, or a functional portion thereof. In an aspect, a seed or kernel promoter is from a maize putative embryo-specific (Esp) gene promoter. In an aspect, a plant-expressible or seed or kernel promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 174, or a functional portion thereof.

In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes. In another aspect, In yet another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto. In an aspect, the guide RNA is a CRISPR RNA (crRNA) or a single-chain guide RNA (sgRNA), or the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

Also provided is a method for producing a genome edited or mutated corn plant, the method comprising: (a) introducing into a first corn cell a transgene that encodes one or more MADS-box polypeptides to create a genome edited or mutated corn cell, wherein the first corn cell has its expression of one or more endogenous GA3 oxidase genes or GA20 oxidase genes reduced relative to a wildtype control; and (b) generating a genome edited or mutated corn plant from the genome edited or mutated corn cell. In an aspect, the method further comprises identifying a genome edited or mutated corn plant with a desired trait. In another aspect, the identified genome edited or mutated corn plant is semi-dwarf and has one or more improved ear traits, relative to a control corn plant not having both the transgene and a reduced expression of one or more endogenous GA3 oxidase genes or GA20 oxidase genes.

In another aspect, the first corn cell of step (a) is obtained by being provided with a first guide RNA and a first RNA-guided nuclease, and wherein the genome edited or mutated corn cell of step (b) is obtained by being provided with a second guide RNA, an insertion sequence, and a second RNA-guided nuclease.

In another aspect, the first guide RNA recognizes a target site in a GA20 oxidase, wherein the first guide RNA acts in association with the first RNA-guided nuclease that creates a double-stranded break at the target site, and whereby the expression of the endogenous GA20 oxidase is reduced.

In another aspect, the method further comprises integrating into the double-stranded break at least one insertion, at least one substitution, at least one inversion, at least one deletion, at least one duplication, or a combination thereof.

In yet another aspect, the second guide RNA recognizes a target site and acts in association with the second RNA-guided nuclease that creates a double-stranded break at the target site, wherein the insertion sequence integrates into the target site, and wherein the donor/insertion sequence encodes a MADS-box polypeptide, such as ZMM19 polypeptide.

Provided in the present disclosure is A method for producing a modified corn plant, the method comprising: mutating or editing one or more endogenous GA3 oxidase genes and/or one or more GA20 oxidase genes in a corn cell, wherein the corn cell comprises a recombinant expression cassette encoding a MADS-box polypeptide, wherein the DNA sequence is operably linked to a plant-expressible promoter; and regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

In an aspect, the mutating or editing is obtained by using a site-specific nuclease selected from the group consisting of a RNA-guided endonuclease, a meganuclease, a zinc-finger nuclease (ZFN), a TALE-endonuclease (TALEN), a recombinase, and a transposase. In another aspect, a method further comprises introducing a recombinant DNA construct encoding a guide RNA that targets the one or more endogenous GA3 oxidase and/or GA20 oxidase genes. In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto. In another aspect, the guide RNA is a CRISPR RNA (crRNA) or a single-chain guide RNA (sgRNA). In yet another aspect, the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

Also provided is a method for producing a genome edited or mutated corn plant, the method comprising: (a) reducing the expression of one or more endogenous GA3 oxidase genes or GA20 oxidase genes in a first corn cell to create a genome edited or mutated corn cell, wherein the first corn cell comprises a transgene that encodes one or more MADS-box polypeptides; and (b) generating a genome edited or mutated corn plant from the genome edited or mutated corn cell. In an aspect, the method further comprises identifying a genome edited or mutated corn plant with a desired trait. In another aspect, the identified genome edited or mutated corn plant is semi-dwarf and has one or more improved ear traits, relative to a control corn plant not having both the transgene and a reduced expression of one or more endogenous GA3 oxidase genes or GA20 oxidase genes.

In an aspect, the first corn cell of step (a) is obtained by being provided with a first guide RNA, an insertion sequence, and a first RNA-guided nuclease, and wherein the genome edited or mutated corn cell of step (b) is obtained by being provided with a second guide RNA and a second RNA-guided nuclease.

In another aspect, the first guide RNA recognizes a target site and acts in association with the first RNA-guided nuclease that creates a double-stranded break at the target site, wherein the insertion sequence integrates into the target site, and wherein the insertion sequence encodes a ZMM19 polypeptide.

In another aspect, the second guide RNA recognizes a target site in a GA20 oxidase, wherein the second guide RNA acts in association with the second RNA-guided nuclease that creates a double-stranded break at the target site, and whereby the expression level of the endogenous GA20 oxidase is reduced.

The gRNA can be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. The guide sequence of the guide RNA can be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence can be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

For genome editing at or near the GA20 oxidase_3 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 34 or a sequence complementary thereto (e.g., 12, 13, 14, 15, 16, 17, 18, 19, 20, 21, 22, 23, 24, 25 or more consecutive nucleotides of SEQ ID NO: 34 or a sequence complementary thereto).

For genome editing at or near the GA20 oxidase_4 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 38 or a sequence complementary thereto (e.g., 12, 13, 14, 15, 16, 17, 18, 19, 20, 21, 22, 23, 24, 25 or more consecutive nucleotides of SEQ ID NO: 38 or a sequence complementary thereto).

For genome editing at or near the GA20 oxidase_5 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 35 or a sequence complementary thereto (e.g., 10, 11, 12, 13, 14, 15, 16, 17, 18, 19, 20, 21, 22, 23, 24, 25 or more consecutive nucleotides of SEQ ID NO: 35 or a sequence complementary thereto).

In an aspect, a guide RNA for targeting an endogenous GA20 oxidase_3 and/or GA20 oxidase_5 gene is provided comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 138-167.

For genome editing at or near the GA3 oxidase_1 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 36 or a sequence complementary thereto (e.g., 10, 11, 12, 13, 14, 15, 16, 17, 18, 19, 20, 21, 22, 23, 24, 25 or more consecutive nucleotides of SEQ ID NO: 36 or a sequence complementary thereto).

For genome editing at or near the GA3 oxidase_2 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 37 or a sequence complementary thereto (e.g., 10, 11, 12, 13, 14, 15, 16, 17, 18, 19, 20, 21, 22, 23, 24, 25 or more consecutive nucleotides of SEQ ID NO: 37 or a sequence complementary thereto).

In an aspect, a guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 87, 91, 95, 98, 105, 109, 113, 117, 122, 126, 130 or 137, or a sequence complementary thereto.

In an aspect, a guide RNA comprises a sequence complementary to a protospacer adjacent motif (PAM) sequence present in the genome of a corn plant immediately adjacent to a target DNA sequence at or near the genomic locus of one or more endogenous GA20 or GA3 oxidase gene.

In addition to the guide sequence, a guide RNA can further comprise one or more other structural or scaffold sequence(s), which can bind or interact with an RNA-guided endonuclease. Such scaffold or structural sequences can further interact with other RNA molecules (e.g., tracrRNA). Methods and techniques for designing targeting constructs and guide RNAs for genome editing and site-directed integration at a target site within the genome of a plant using an RNA-guided endonuclease are known in the art.

Mutations such as deletions, insertions, inversions and/or substitutions can be introduced at a target site via imperfect repair of the DSB or nick to produce a knock-out or knock-down of a GA oxidase gene. Such mutations can be generated by imperfect repair of the targeted locus even without the use of a donor template molecule. A "knock-out" of a GA oxidase gene can be achieved by inducing a DSB or nick at or near the endogenous locus of the GA oxidase gene that results in non-expression of the GA oxidase protein or expression of a non-functional protein, whereas a "knock-down" of a GA oxidase gene can be achieved in a similar manner by inducing a DSB or nick at or near the endogenous locus of the GA oxidase gene that is repaired imperfectly at a site that does not affect the coding sequence of the GA oxidase gene in a manner that would eliminate the function of the encoded GA oxidase protein.

For example, the site of the DSB or nick within the endogenous locus can be in the upstream or 5' region of the GA oxidase gene (e.g., a promoter and/or enhancer sequence) to affect or reduce its level of expression. Similarly, such targeted knock-out or knock-down mutations of a GA oxidase gene can be generated with a donor template molecule to direct a particular or desired mutation at or near the target site via repair of the DSB or nick.

The donor template molecule can comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a GA oxidase gene can be achieved by deleting or inverting at least a portion of the gene or by introducing a frame shift or premature stop codon into the coding sequence of the gene. A deletion of a portion of a GA oxidase gene can also be introduced by generating DSBs or nicks at two target sites and causing a deletion of the intervening target region flanked by the target sites.

Provided herein is a recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a MADS-box polypeptide, wherein the DNA sequence is operably linked to a plant-expressible promoter.

In an aspect, the DNA donor template molecule comprises two of the homology sequences, wherein the two homology sequences flank the insertion sequence. In another aspect, the insertion sequence comprises a recombinant DNA construct or expression cassette comprising a DNA sequence encoding a MADS-box polypeptide, wherein the MADS-box polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199, or a functional fragment thereof.

In another aspect, the MADS-box polypeptide comprises a maize ZMM19 polypeptide. In another aspect, the DNA sequence comprised in the expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169. In another aspect, the MADS-box polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof. In another aspect, a recombinant DNA construct or expression cassette comprising a DNA sequence encoding a MADS-box polypeptide operably linked to a plant-expressible promoter. The plant-expressible promoter can comprise a DNA sequence that is at least 80%, at least 85%, at least 90%, at least 95%, at least 96%, at least 97%, at least 98%, at least 99%, at least 99.5% or 100% identical to SEQ ID NO: 170, 174, or a functional portion thereof. In another aspect, the plant-expressible promoter is selected from the group consisting of a meristem promoter, a root promoter, a seed or kernel promoter, and a combination thereof.

In another aspect, a DNA donor template molecule further comprises a transcribable DNA sequence encoding a non-coding RNA for suppression of one or more GA20 oxidase genes and/or one or more GA3 oxidase genes, wherein the transcribable DNA sequence is operably linked to a promoter.

In an aspect, a donor template comprising at least one homology sequence or homology arm, wherein the at least one homology sequence or homology arm is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of an endogenous GA oxidase gene of a corn or cereal plant.

In another aspect, the at least one homology sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In an aspect, a donor template comprising two homology arms including a first homology arm and a second homology arm, wherein the first homology arm comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a first flanking DNA sequence, wherein the second homology arm comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a second flanking DNA sequence, and wherein the first flanking DNA sequence and the second flanking DNA sequence are genomic sequences at or near the genomic locus of an endogenous GA oxidase gene of a corn or cereal plant.

In another aspect, each of the two homology arms is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In another aspect, the method further comprises integrating into the double-stranded break at least one insertion, at least one substitution, at least one inversion, at least one deletion, at least one duplication, or a combination thereof.

In yet another aspect, an insertion sequence of a donor template comprises a sequence encoding a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NOs: 168, or a functional fragment thereof. In still another aspect, an insertion sequence of a donor template comprises a sequence encoding a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 175-199 and a functional fragment thereof.

Further provided is a method for producing a modified corn plant, the method comprising: (a) crossing a first corn plant with a second corn plant to create a modified corn plant, wherein the expression of one or more endogenous GA3 oxidase genes or GA20 oxidase genes is reduced in the first corn plant relative to a wildtype control, and wherein the second corn plant comprising a transgene encoding one or more MADS-box polypeptides; and (b) producing an offspring of the modified corn plant of step (a). In an aspect, the method further comprises identifying a modified corn plant with a desired trait. In another aspect, the identified modified corn plant is semi-dwarf and has one or more improved ear traits, relative to a control corn plant not having both the transgene and a reduced expression of one or more endogenous GA3 oxidase genes or GA20 oxidase genes.

In an aspect, a target site can comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides.

In an aspect, the target site is a GA3 oxidase_1 gene. In another aspect, the target site is a GA3 oxidase_2 gene. In yet another aspect, the target site is a combination of the GA3 oxidase_1 and GA3 oxidase_2 genes. In still another aspect, the target site is within the open reading frame of the GA3 oxidase_1 or GA3 oxidase_2 gene. In still another aspect, the target site is within the promoter/enhancer of the GA3 oxidase_1 or GA3 oxidase_2 gene. In still another aspect, the target site is within the intron of the GA3 oxidase_1 or GA3 oxidase_2 gene. In still another aspect, the target site is within the 5'UTR of the GA3 oxidase_1 or GA3 oxidase_2 gene. In still another aspect, the target site is within the 3'UTR of the GA3 oxidase_1 or GA3 oxidase_2 gene.

In an aspect, the target site is a GA20 oxidase_3 gene. In another aspect, the target site is a GA20 oxidase_4 gene. In another aspect, the target site is a GA20 oxidase_5 gene. In yet another aspect, the target site is a combination of the GA20 oxidase_3 gene, GA20 oxidase_4 gene, and GA20 oxidase_5 gene. In still another aspect, the target site is within the open reading frame of the GA20 oxidase_3, GA20 oxidase_4, or GA20 oxidase_5 gene. In still another aspect, the target site is within the promoter/enhancer of the GA20 oxidase_3, GA20 oxidase_4, or GA20 oxidase_5 gene. In still another aspect, the target site is within the intron of the GA20 oxidase_3, GA20 oxidase_4, or GA20 oxidase_5 gene. In still another aspect, the target site is within the 5'UTR of the GA20 oxidase_3, GA20 oxidase_4, or GA20 oxidase_5 gene. In still another aspect, the target site is within the 3'UTR of the GA20 oxidase_3, GA20 oxidase_4, or GA20 oxidase_5 gene.

In an aspect, the target site comprises a nucleotide sequence selected from the group consisting of SEQ ID NOs: 34, 35, and 38.

A targeted genome editing technique provided herein can comprise the use of one or more, two or more, three or more, four or more, or five or more donor molecules or templates. A "donor template" can be a single-stranded or double-stranded DNA or RNA molecule or plasmid.

According to other aspects, an insertion sequence of a donor template can comprise a transcribable DNA sequence that encodes a non-coding RNA molecule, which targets one or more GA oxidase gene(s), such as a GA3 oxidase or GA20 oxidase gene(s), for suppression. In an aspect, the transcribable DNA sequence that encodes a non-coding RNA for the suppression of the GA3 oxidase and/or GA20 oxidase gene(s) is selected from the group consisting of SEQ ID NOs: 35-38. In another aspect, an insertion sequence of a donor template can comprise a DNA sequence encoding one or more MADS-box polypeptides, wherein the DNA sequence encodes protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and 175-199. In yet another aspect, an insertion sequence of a donor template can comprise a first transcribable DNA sequence encoding a non-coding RNA molecule for the suppression of the one or more GA3 oxidase or GA20 oxidase gene(s), wherein the first transcribable DNA sequence is selected from the group consisting of SEQ ID NOs: 35-38; and an insertion sequence of a donor template can comprise a second DNA sequence encoding one or more MADS-box polypeptides, wherein the second DNA sequence encodes a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and 175-199, or a functional fragment thereof.

An insertion sequence provided herein can be of any length. For example, a donor or insertion sequence provided herein is between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000 or between 20 and 10,000 nucleotides in length.

In an aspect, a sequence can be inserted into a double-stranded break created by a CRISPR based genome editing system without the presence of a donor template. In an aspect, at least one insertion, at least one substitution, at least one deletion, at least one duplication, and/or at least one inversion can be inserted/introduced into a double-stranded break created by a CRISPR based genome editing system via non-homologous end joining (NHEJ) without a donor template. In an aspect, at least one insertion, at least one substitution, at least one deletion, at least one duplication, and/or at least one inversion can be inserted/introduced into a double-stranded break created by a CRISPR based genome editing system via homologous recombination (HR) with a donor template.

According to other aspects, at least one insertion is integrated into the double-stranded break at the GA3 oxidase or GA20 oxidase locus and introduces a premature stop codon therein which leads to truncation of the GA3 oxidase or GA20 oxidase proteins and subsequent suppression of the GA3 oxidase or GA20 oxidase genes. In an aspect, the at least one insertion is a single nucleobase insertion. In another aspect, the single nucleobase insertion is selected from the group consisting of guanine, cytosine, adenine, thymine, and uracil. In an aspect, the at least one insertion is inserted within the open reading frame of the GA3 oxidase or GA20 oxidase gene. In another aspect, the at least one insertion is inserted within the promoter/enhancer, intron, 5'UTR, 3'UTR, or a combination thereof.

In another aspect, the at least one insertion at the GA3 oxidase or GA20 oxidase locus comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

According to an aspect, at least one substitution is integrated into the double-stranded break at the GA3 oxidase or GA20 oxidase locus that leads to the suppression of the GA3 oxidase or GA20 oxidase gene. In an aspect, the at least one substitution is integrated within the open reading frame of the GA3 oxidase or GA20 oxidase gene. In another aspect, the at least one substitution is integrated within the promoter/enhancer, intron, 5'UTR, 3'UTR, or a combination thereof.

According to an aspect, at least one deletion is introduced into the double-stranded break at the GA3 oxidase or GA20 oxidase locus that leads to the suppression of the GA3 oxidase or GA20 oxidase gene. In an aspect, the at least one deletion is introduced within the open reading frame of the GA3 oxidase or GA20 oxidase gene. In another aspect, the at least one deletion is introduced within the promoter/enhancer, intron, 5'UTR, 3'UTR, or a combination thereof.

According to an aspect, at least one duplication is introduced into the double-stranded break at the GA3 oxidase or GA20 oxidase locus that leads to the suppression of the GA3 oxidase or GA20 oxidase gene. In an aspect, the at least one duplication is introduced within the open reading frame of the GA3 oxidase or GA20 oxidase gene. In another aspect, the at least one duplication is introduced within the promoter/enhancer, intron, 5'UTR, 3'UTR, or a combination thereof.

According to an aspect, at least one inversion is integrated into the double-stranded break at the GA3 oxidase or GA20 oxidase locus that leads to the suppression of the GA3 oxidase or GA20 oxidase gene. In an aspect, the at least one inversion is integrated within the open reading frame of the GA3 oxidase or GA20 oxidase gene. In another aspect, the at least one inversion is integrated within the promoter/enhancer, intron, 5'UTR, 3'UTR, or a combination thereof.

According to an aspect, a recombinant DNA construct or vector can comprise a first polynucleotide sequence encoding a site-specific nuclease and a second polynucleotide sequence encoding a guide RNA that can be introduced into a plant cell together via plant transformation techniques. Alternatively, two recombinant DNA constructs or vectors can be provided including a first recombinant DNA construct or vector and a second DNA construct or vector that can be introduced into a plant cell together or sequentially via plant transformation techniques, where the first recombinant DNA construct or vector comprises a polynucleotide sequence encoding a site-specific nuclease and the second recombinant DNA construct or vector comprises a polynucleotide sequence encoding a guide RNA.

According to an aspect, a recombinant DNA construct or vector comprising a polynucleotide sequence encoding a site-specific nuclease can be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA can be introduced via plant transformation techniques into a plant cell that already comprises (or is transformed with) a recombinant DNA construct or vector comprising a polynucleotide sequence encoding a site-specific nuclease. According to yet further aspects, a first plant comprising (or transformed with) a recombinant DNA construct or vector comprising a polynucleotide sequence encoding a site-specific nuclease can be crossed with a second plant comprising (or transformed with) a recombinant DNA construct or vector comprising a polynucleotide sequence encoding a guide RNA. Such recombinant DNA constructs or vectors can be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Dwarf or semi-dwarf corn disclosed herein can have characteristics that make it suitable for grain and forage production, especially, production in short-season environments. In particular, limited heat units in short-season environments reduce grain yield and lessen the probability of the crop reaching physiological maturity in a given year. The disclosed dwarf or semi-dwarf corn plants require fewer heat units (e.g., required 10%) than conventional hybrids to reach anthesis and generally reach physiological maturity earlier than conventional cultivars. Semi-dwarf corn plants disclosed herein are less prone to stalk and root lodging due to the shorter stalks and lower ear placement. Corn plants disclosed herein also have the potential to produce high-quality forage due to its high ear-to-stover ratio.

Short stature or semi-dwarf corn plants can also have one or more additional traits, including, but not limited to, increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, increased seed number, increased seed weight, and increased prolificacy, and/or increased harvest index.

According to aspects of the present disclosure, modified, transgenic, or genome edited/mutated cereal or corn plants are provided that have at least one beneficial agronomic trait and at least one female reproductive organ or ear that is substantially or completely free of off-types. The beneficial agronomic trait can include, but is not limited to, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. As used herein, "harvest index" refers to the mass of the harvested grain divided by the total mass of the above-ground biomass of the plant over a harvested area.

In an aspect, a modified, transgenic, or genome edited/mutated corn plant exhibits improved lodging resistance, reduced green snap, or both, relative to a control corn plant.

In an aspect, the height at maturity of a modified, transgenic, or genome edited/mutated corn plant exhibiting semi-dwarf phenotype is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, relative to a control corn plant grown under comparable conditions.

According to another aspect of the present disclosure, a modified, transgenic, or genome edited/mutated corn plant provided herein comprises a height that is between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 15%, between 1% and 10%, between 1% and 5%, or between 1% and 2%, of that of a control plant grown under comparable conditions.

According to another aspect of the present disclosure, a modified, transgenic, or genome edited/mutated corn plant provided herein comprises a height that is between 2% and 75%, between 5% and 75%, between 10% and 75%, between 15% and 75%, between 20% and 75%, between 25% and 75%, between 30% and 75%, between 35% and 75%, between 40% and 75%, between 45% and 75%, between 50% and 75%, between 55% and 75%, between 60% and 75%, between 65% and 75%, or between 70% and 75%, of that of a control plant grown under comparable conditions.

According to another aspect of the present disclosure, a modified, transgenic, or genome edited/mutated corn plant provided herein comprises a height that is between 2% and 70%, between 5% and 65%, between 10% and 60%, between 15% and 55%, between 20% and 50%, between 25% and 45%, or between 30% and 40%, of that of a control plant grown under comparable conditions.

According to another aspect of the present disclosure, a modified, transgenic, or genome edited/mutated corn plant provided herein comprises a height that is between 1% and 10%, between 10% and 20%, between 20% and 30%, between 30% and 40%, between 40% and 50%, between 50% and 60%, between 60% and 70%, or between 70% and 80%, of that of a control plant grown under comparable conditions.

In an aspect, the stalk or stem diameter of a transgenic corn plant or genome edited/mutated corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plan grown under comparable conditions.

According to another aspect of the present disclosure, a modified, transgenic, or genome edited/mutated corn plant provided herein comprises a stalk or stem diameter that is between 0.1% and 100%, between 0.2% and 100%, between 0.5% and 100%, between 1% and 100%, between 1.5% and 100%, between 2% and 100%, between 2.5% and 100%, between 3% and 100%, between 3.5% and 100%, between 4% and 100%, between 4.5% and 100%, between 5% and 100%, between 6% and 100%, between 7% and 100%, between 8% and 100%, between 9% and 100%, between 10% and 100%, between 15% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100%, greater than that of a control corn plan grown under comparable conditions.

According to another aspect of the present disclosure, a modified, transgenic, or genome edited/mutated corn plant provided herein comprises a stalk or stem diameter that is between 0.1% and 95%, between 0.1% and 90%, between 0.1% and 85%, between 0.1% and 80%, between 0.1% and 75%, between 0.1% and 70%, between 0.1% and 65%, between 0.1% and 60%, between 0.1% and 55%, between 0.1% and 50%, between 0.1% and 45%, between 0.1% and 40%, between 0.1% and 35%, between 0.1% and 30%, between 0.1% and 25%, between 0.1% and 20%, between 0.1% and 15%, between 0.1% and 10%, between 0.1% and 9%, between 0.1% and 8%, between 0.1% and 7%, between 0.1% and 6%, between 0.1% and 5%, between 0.1% and 4.5%, between 0.1% and 4%, between 0.1% and 3.5%, between 0.1% and 3%, between 0.1% and 2.5%, between 0.1% and 2%, between 0.1% and 1.5%, between 0.1% and 1%, between 0.1% and 0.5%, or between 0.1% and 0.2%, greater than that that of a control corn plan grown under comparable conditions.

According to another aspect of the present disclosure, a modified, transgenic, or genome edited/mutated corn plant provided herein comprises a stalk or stem diameter that is between 0.2% and 95%, between 0.5% and 90%, between 1% and 85%, between 1.5% and 80%, between 2% and 75%, between 2.5% and 70%, between 3% and 65%, between 3.5% and 60%, between 4% and 55%, between 4.5% and 50%, between 5% and 45%, between 6% and 40%, between 7% and 35%, between 8% and 30%, between 9% and 25%, or between 10% and 20%, greater than that of a control corn plan grown under comparable conditions.

According to another aspect of the present disclosure, a modified, transgenic, or genome edited/mutated corn plant provided herein comprises a stalk or stem diameter that is between 0.1% and 1%, between 1% and 5%, between 6% and 10%, between 20% and 30%, between 30% and 40%, between 40% and 50%, between 50% and 60%, between 60% and 70%, between 70% and 80%, between 80% and 90%, between 90% and 100%, greater than that that of a control corn plan grown under comparable conditions.

In another aspect, the yield of a modified, transgenic, or genome edited/mutated exhibiting semi-dwarf phenotype is equal to or more then the yield of a control plant grown under comparable conditions.

In another aspect, a modified, transgenic, or genome edited/mutated corn plant exhibiting semi-dwarf phenotype requires about 5%, 10%, 15%, 20%, or 25% fewer heat units than a control plant to reach anthesis.

In yet another aspect, a modified, transgenic, or genome edited/mutated corn plant exhibiting semi-dwarf phenotype has a relative maturity of about 10%, 15%, 20%, 25%, 30%, 35%, 40%, or 45% fewer days than the relative maturity of a control plant grown under comparable conditions.

According to an aspect of the present disclosure, a modified, transgenic, or genome edited/mutated corn plant provided herein comprises a height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm and an average stem diameter of at least 17.5 mm, at least 18 mm, at least 18.5 mm, at least 19 mm, at least 19.5 mm, at least 20 mm, at least 20.5 mm, at least 21 mm, at least 21.5 mm, or at least 22 mm. According to another aspect the modified corn plant further comprises at least one ear that is substantially free of mature male reproductive tissue.

According to aspects of the present disclosure, modified, transgenic, or genome edited/mutated corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant can be substantially free of off-types, such as male reproductive tissues or structures in one or more ears of the modified corn plant.

According to an aspect of the present disclosure a modified, transgenic, or genome edited/mutated corn plant provided herein comprises a height of between 1000 mm and 1600 mm, 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, or between 1000 mm and 1300 mm, and an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. According to another aspect the modified corn plant further comprises at least one ear that is substantially free of mature male reproductive tissue.

According to an aspect of the present disclosure, a modified, transgenic, or genome edited/mutated corn plant provided herein comprises a height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a control plant and a stalk or stem diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of a control plant.

According to an aspect of the present disclosure, a modified, transgenic, or genome edited/mutated corn plant provided herein comprises a fresh ear weight that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the fresh ear weight of a control plant.

According to an aspect of the present disclosure, a population of modified, transgenic, or genome edited/mutated corn plants provided herein comprises a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% lower as compared to a population of unmodified control plants. According to another aspect of the present disclosure, a population of modified corn plants provided herein comprises a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% lower as compared to a population of control plants.

According to an aspect of the present disclosure, modified, transgenic, or genome edited/mutated corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a control plant.

The "minus-2 internode" of a corn plant refers to the second internode below the ear of the plant, and the "minus-4 internode" of a corn plant refers to the fourth internode below the ear of the plant. According to many aspects, modified, transgenic, or genome edited/mutated corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a control plant.

A modified, transgenic, or genome edited/mutated corn plant can have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant can have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a control plant.

According to an aspect of the present disclosure, modified, transgenic, or genome edited/mutated corn plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant can have an increase in harvestable yield between 1 and 10, between 1 and 8, between 2 and 8, between 2 and 6, between 2 and 5, between 2.5 and 4.5, or between 3 and 4 bushels per acre. A modified corn plant can have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant can have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a control plant.

According to an aspect, the present disclosure provides a population of a modified, transgenic, or genome edited/mutated corn plants, where the population of a modified, transgenic, or genome edited/mutated corn plants shares ancestry with a single modified, transgenic, or genome edited/mutated corn plant, where the population of a modified, transgenic, or genome edited/mutated corn plants comprises an average height of 1500 mm or less, wherein the population of a modified, transgenic, or genome edited/mutated corn plants comprises an average stalk or stem diameter of 18 mm or more, wherein less than 5%, less than 10%, less than 15%, less than 20%, or less than 25% of the population of modified, transgenic, or genome edited/mutated corn plants comprises a height of greater than 1500 mm, and where less than 5%, less than 10%, less than 15%, less than 20%, or less than 25% of the population of a modified, transgenic, or genome edited/mutated corn plants comprises at least one ear comprising mature male reproductive tissue. In another aspect the population of a modified, transgenic, or genome edited/mutated corn plants comprises an average height of 1200 mm or less.

According to an aspect, the present disclosure provides a population of a modified, transgenic, or genome edited/mutated corn plants, where the population of a modified, transgenic, or genome edited/mutated corn plants share ancestry with a single modified corn plant, where the population of a modified, transgenic, or genome edited/mutated corn plants comprises an average height of 1500 mm or less, where less than 5%, less than 10%, less than 15%, less than 20%, or less than 25% of the population of modified corn plants comprises a height of greater than 1500 mm, and where the population of a modified, transgenic, or genome edited/mutated corn plants comprises a lodging frequency that is at least 5%, at least 10%, at least 20%, at least 30%, at least 40%, at least 50%, at least 60%, at least 70% at least 80%, at least 90%, or 100% lower as compared to a population of control corn plants.

According to an aspect, the present disclosure provides a modified, transgenic, or genome edited/mutated corn plant comprising a height of 1500 mm or less, where the a modified, transgenic, or genome edited/mutated corn plant further comprises a stalk or stem diameter of 18 mm or more, and where at least one ear of the a modified, transgenic, or genome edited/mutated corn plant is substantially free of mature male reproductive tissue.

According to an aspect, the present disclosure provides a modified, transgenic, or genome edited/mutated corn plant comprising a height of 1500 mm or less, wherein the a modified, transgenic, or genome edited/mutated corn plant further comprises a harvest index of at least 0.58, and where the a modified, transgenic, or genome edited/mutated corn plant further comprises at least one ear that is substantially free of mature male reproductive tissue.

According to an aspect of the present disclosure, modified, transgenic, or genome edited/mutated corn plants are provided having a significantly reduced or eliminated expression level of one or more GA3 oxidase and/or GA20 oxidase gene transcript(s) and/or protein(s) in one or more tissue(s), such as one or more stem, internode, leaf and/or vascular tissue(s), of the modified, transgenic, or genome edited/mutated plants, as compared to the same tissue(s) of wild-type or control plants. In an aspect, the level of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant can be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a control corn or cereal plant.

According to an aspect of the present disclosure, modified, transgenic, or genome edited/mutated cereal or corn plants are provided that have at least one beneficial agronomic trait and at least one female reproductive organ or ear that is substantially or completely free of off-types. The beneficial agronomic trait can include, for example, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. A modified, transgenic, or genome edited/mutated cereal or corn plant can have a female reproductive organ or ear that appears normal relative to a control or wild-type plant. Indeed, modified, transgenic, or genome edited/mutated cereal or corn plants are provided that comprise at least one reproductive organ or ear that does not have or exhibit, or is substantially or completely free of, off-types including male sterility, reduced kernel or seed number, and/or masculinized structure(s) in one or more female organs or ears.

A modified, transgenic, or genome edited/mutated cereal or corn plant is provided herein that lacks significant off-types in the reproductive tissues of the plant. Off-types can include male (tassel or anther) sterility, reduced kernel or seed number, and/or the presence of one or more masculinized or male (or male-like) reproductive structures in the female organ or ear (e.g., anther ear) of the plant.

As used herein, a female organ or ear of a plant, such as corn, is "substantially free" of male reproductive structures if male reproductive structures are absent or nearly absent in the female organ or ear of the plant based on visual inspection of the female organ or ear at later reproductive stages. A female organ or ear of a plant, such as corn, is "completely free" of mature male reproductive structures if male reproductive structures are absent or not observed or observable in the female organ or ear of the plant, such as a corn plant, by visual inspection of the female organ or ear at later reproductive stages.

In an aspect, a modified, transgenic, or genome edited/mutated corn plant exhibits increased ear area relative to a control corn plant.

According to an aspect of the present disclosure, a modified, transgenic, or genome edited/mutated corn plant exhibits an increase in ear area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear area that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear area that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear area that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear area that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased ear volume relative to a control corn plant grown under comparable conditions.

According to an aspect of the present disclosure, a modified, transgenic, or genome edited/mutated corn plant exhibits an increase in ear volume by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear volume that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear volume that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear volume that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear volume that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased ear diameter relative to a control corn plant grown under comparable conditions.

According to an aspect of the present disclosure, a modified, transgenic, or genome edited/mutated corn plant exhibits an ear diameter that is at least 0.2%, at least 0.4%, at least 0.6%, at least 0.8%, at least 1.0%, at least 1.2%, at least 1.4%, at least 1.6%, at least 1.8%, at least 2.0%, at least 2.2%, at least 2.4%, at least 2.6%, at least 2.8%, at least 3.0%, at least 3.2%, at least 3.4%, at least 3.6%, at least 3.8%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, at least 9.5%, at least 10.0%, relative to a control corn plant.

According to an aspect of the present disclosure, a modified, transgenic, or genome edited/mutated corn plant exhibits an ear diameter that is between 0.2% and 10.0%, between 0.4% and 10.0%, between 0.6% and 10.0%, between 0.8% and 10.0%, between 1.0% and 10.0%, between 1.2% and 10.0%, between 1.4% and 10.0%, between 1.6% and 10.0%, between 1.8% and 10.0%, between 2.0% and 10.0%, between 2.2% and 10.0%, between 2.4% and 10.0%, between 2.6% and 10.0%, between 2.8% and 10.0%, between 3.0% and 10.0%, between 3.2% and 10.0%, between 3.4% and 10.0%, between 3.6% and 10.0%, between 3.8% and 10.0%, between 4.0% and 10.0%, between 4.5% and 10.0%, between 5.0% and 10.0%, between 5.5% and 10.0%, between 6.0% and 10.0%, between 6.5% and 10.0%, between 7.0% and 10.0%, between 7.5% and 10.0%, between 8.0% and 10.0%, between 8.5% and 10.0%, between 9.0% and 10.0%, or between 9.5% and 10.0%, greater than that of a control corn plant grown under comparable conditions.

According to an aspect of the present disclosure, a modified, transgenic, or genome edited/mutated corn plant exhibits an ear diameter that is between 0.2% and 9.5%, between 0.2% and 9.0%, between 0.2% and 8.5%, between 0.2% and 8.0%, between 0.2% and 7.5%, between 0.2% and 7.0%, between 0.2% and 6.5%, between 0.2% and 6.0%, between 0.2% and 5.5%, between 0.2% and 5.0%, between 0.2% and 4.5%, between 0.2% and 4.0%, between 0.2% and 3.8%, between 0.2% and 3.6%, between 0.2% and 3.4%, between 0.2% and 3.2%, between 0.2% and 3.0%, between 0.2% and 2.8%, between 0.2% and 2.6%, between 0.2% and 2.4%, between 0.2% and 2.2%, between 0.2% and 2.0%, between 0.2% and 1.8%, between 0.2% and 1.6%, between 0.2% and 1.4%, between 0.2% and 1.2%, between 0.2% and 1.0%, between 0.2% and 0.8%, between 0.2% and 0.6%, or between 0.2% and 0.4%, greater than that of a control corn plant grown under comparable conditions.

According to an aspect of the present disclosure, a modified, transgenic, or genome edited/mutated corn plant exhibits an ear diameter that is between 0.4% and 9.5%, between 0.6% and 9.0%, between 0.8% and 8.5%, between 1.0% and 8.0%, between 1.2% and 7.5%, between 1.4% and 7.0%, between 1.6% and 6.5%, between 1.8% and 6.0%, between 2.0% and 5.5%, between 2.2% and 5.0%, between 2.4% and 4.5%, between 2.6% and 4.0%, between 2.8% and 3.8%, between 3.0% and 3.6%, or between 3.2% and 3.4%, greater than that of a control corn plant grown under comparable conditions.

According to an aspect of the present disclosure, a modified, transgenic, or genome edited/mutated corn plant exhibits an ear diameter that is between 0.2% and 0.6%, between 0.6% and 1.0%, between 1.0% and 1.4%, between 1.4% and 1.8%, between 1.8% and 2.2%, between 2.2% and 2.6%, between 2.6% and 3.0%, between 3.0% and 3.5%, between 3.5% and 4.0%, between 4.0% and 4.5%, between 4.5% and 5.0%, between 5.0% and 5.5%, between 5.5% and 6.0%, between 6.0% and 6.5%, between 6.5% and 7.0%, between 7.0% and 7.5%, between 7.5% and 8.0%, between 8.0% and 8.5%, between 8.5% and 9.0%, between 9.0% and 9.5%, or between 9.5% and 10.0%, greater than that of a control corn plant grown under comparable conditions.

In an aspect, a modified, transgenic, or genome edited/mutated corn plant exhibits increased ear length relative to a control corn plant grown under comparable conditions.

According to an aspect of the present disclosure, a modified, transgenic, or genome edited/mutated corn plant exhibits an increase in ear length by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear length that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a corn plant grown under comparable conditions.

According to an aspect of the present disclosure, a modified, transgenic, or genome edited/mutated corn plant exhibits an ear length that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear length that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear length that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits decreased ear tip void relative to a control corn plant grown under comparable conditions.

According to an aspect of the present disclosure, a modified, transgenic, or genome edited/mutated corn plant exhibits a decrease in ear tip void by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear tip void that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% less than that of a control corn plant grown under comparable conditions.

According to an aspect of the present disclosure, a modified, transgenic, or genome edited/mutated corn plant exhibits an ear tip void that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% less than that of a control corn plant grown under comparable conditions.

According to an aspect of the present disclosure, a modified, transgenic, or genome edited/mutated corn plant exhibits an ear tip void that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% less than that of a control corn plant grown under comparable conditions.

According to an aspect of the present disclosure, a modified, transgenic, or genome edited/mutated corn plant exhibits an ear tip void that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% less than that of a control corn plant grown under comparable conditions.

In an aspect, a modified, transgenic, or genome edited/mutated corn plant exhibits an increased number of kernels per ear relative to a control corn plant grown under comparable conditions.

According to an aspect of the present disclosure, a modified, transgenic, or genome edited/mutated corn plant exhibits an increase in number of kernels per ear by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits kernels per ear that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits kernels per ear that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits kernels per ear that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits kernels per ear that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased single kernel weight relative to a control corn plant grown under comparable conditions.

According to an aspect of the present disclosure, a modified, transgenic, or genome edited/mutated corn plant exhibits an increase in single kernel weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a single kernel weight that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a single kernel weight that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a single kernel weight that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a single kernel weight that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a single kernel weight that is between 1% and 2%, between 2% and 3%, between 3% and 4%, between 4% and 5%, between 5% and 6%, between 6% and 7%, between 7% and 8%, between 8% and 9%, or between 9% and 10% greater than that of a control corn plant grown under comparable conditions.

In an aspect, a modified, transgenic, or genome edited/mutated corn plant exhibits increased ear fresh weight relative to a control corn plant.

According to an aspect of the present disclosure, a modified, transgenic, or genome edited/mutated corn plant exhibits an increased ear fresh weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control corn plant grown under comparable conditions.

According to an aspect of the present disclosure, a modified, transgenic, or genome edited/mutated corn plant exhibits an ear fresh weight that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear fresh weight that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear fresh weight that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear fresh weight that is between 1% and 5%, between 5% and 10%, between 10% and 15%, between 15% and 20%, between 20% and 25%, between 25% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits an ear fresh weight that is between 1% and 2%, between 2% and 3%, between 3% and 4%, between 4% and 5%, between 5% and 6%, between 6% and 7%, between 7% and 8%, between 8% and 9%, between 9% and 10%, between 10% and 11%, between 11% and 12%, between 12% and 13%, between 13% and 14%, between 14% and 15%, between 15% and 16%, between 16% and 17%, between 17% and 18%, between 18% and 19%, between 19% and 20%, between 20% and 21%, between 21% and 22%, between 22% and 23%, between 23% and 24%, between 24% and 25%, between 25% and 26%, between 26% and 27%, between 27% and 28%, between 28% and 29%, between 29% and 30%, greater than that of a control corn plant grown under comparable conditions.

In an aspect, a modified, transgenic, or genome edited/mutated corn plant exhibits an increased yield relative to a control corn plant.

According to an aspect of the present disclosure, a modified, transgenic, or genome edited/mutated corn plant exhibits an increased yield by at least 1%, at least 3%, at least 5%, at least 7%, at least 9%, at least 11%, at least 13%, at least 15%, at least 17%, at least 19%, at least 21%, at least 23%, at least 25%, at least 27%, at least 29%, at least 31%, at least 33%, at least 35%, at least 37%, at least 39%, at least 41%, at least 43%, at least 45%, at least 47%, at least 49%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a yield that is between 1% and 100%, between 3% and 100%, between 5% and 100%, between 7% and 100%, between 9% and 100%, between 11% and 100%, between 13% and 100%, between 15% and 100%, between 17% and 100%, between 19% and 100%, between 21% and 100%, between 23% and 100%, between 25% and 100%, between 27% and 100%, between 29% and 100%, between 31% and 100%, between 33% and 100%, between 35% and 100%, between 37% and 100%, between 39% and 100%, between 41% and 100%, between 43% and 100%, between 45% and 100%, between 47% and 100%, between 49% and 100%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, greater than that of a control corn plant grown under comparable conditions.

According to an aspect of the present disclosure, a modified, transgenic, or genome edited/mutated corn plant exhibits a yield that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 49%, between 1% and 47%, between 1% and 45%, between 1% and 43%, between 1% and 41%, between 1% and 39%, between 1% and 37%, between 1% and 35%, between 1% and 33%, between 1% and 31%, between 1% and 29%, between 1% and 27%, between 1% and 25%, between 1% and 23%, between 1% and 21%, between 1% and 19%, between 1% and 17%, between 1% and 15%, between 1% and 13%, between 1% and 11%, between 1% and 9%, between 1% and 7%, between 1% and 5%, or between 1% and 3%, greater than that of a control corn plant grown under comparable conditions.

According to an aspect of the present disclosure, a modified, transgenic, or genome edited/mutated corn plant exhibits a yield that is between 3% and 95%, between 5% and 90%, between 7% and 85%, between 9% and 80%, between 11% and 75%, between 13% and 70%, between 15% and 65%, between 17% and 60%, between 19% and 55%, between 21% and 50%, between 23% and 49%, between 25% and 47%, between 27% and 45%, between 29% and 43%, between 31% and 41%, between 33% and 39%, or between 35% and 37%, greater than that of a control corn plant grown under comparable conditions.

According to an aspect of the present disclosure, a modified, transgenic, or genome edited/mutated corn plant exhibits a yield that is between 1% and 7%, between 7% and 13%, between 13% and 19%, between 19% and 25%, between 25% and 31%, between 31% and 37%, between 37% and 43%, between 43% and 49%, between 49% and 55%, between 55% and 60%, between 60% and 65%, between 65% and 70%, between 70% and 75%, between 75% and 80%, between 80% and 85%, between 85% and 90%, between 90% and 95%, or between 95% and 100%, greater than that of a control corn plant grown under comparable conditions.

In an aspect, modified, transgenic, or genome edited/mutated corn plants exhibit increased kernels per field area relative to control corn plants.

According to an aspect of the present disclosure, modified, transgenic, or genome edited/mutated corn plants exhibit increased kernels per field area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to control corn plants.

According to an aspect of the present disclosure, modified, transgenic, or genome edited/mutated corn plants exhibit kernels per field area that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of control corn plants grown under comparable conditions.

According to an aspect of the present disclosure, modified, transgenic, or genome edited/mutated corn plants exhibit kernels per field area that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of control corn plants grown under comparable conditions.

According to an aspect of the present disclosure, modified, transgenic, or genome edited/mutated corn plants exhibit kernels per field area that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of control corn plants grown under comparable conditions.

According to an aspect of the present disclosure, modified, transgenic, or genome edited/mutated corn plants exhibit kernels per field area that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of control corn plants grown under comparable conditions.

According to an aspect of the present disclosure, modified, transgenic, or genome edited/mutated corn plants exhibit kernels per field area that is between 1% and 3%, between 3% and 5%, between 5% and 7%, between 7% and 9%, between 9% and 11%, between 11% and 13%, between 13% and 15%, between 15% and 17%, between 17% and 19%, between 19% and 21%, between 21% and 23%, between 23% and 25%, between 25% and 27%, between 27% and 29%, or between 29% and 30% greater than that of control corn plants grown under comparable conditions.

In an aspect, a modified, transgenic, or genome edited/mutated corn plant disclosed in the present disclosure can exhibit one or more improved root traits relative to a control corn plant grown under comparable conditions.

In an aspect, a modified, transgenic, or genome edited/mutated corn plant exhibits increased crown root lateral root density rating at the V12 stage relative to a control corn plant grown under comparable conditions.

According to an aspect of the present disclosure, a modified, transgenic, or genome edited/mutated corn plant exhibits an increased crown root lateral root density rating at the V12 stage by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control corn plant grown under comparable conditions.

According to an aspect of the present disclosure, a modified, transgenic, or genome edited/mutated corn plant exhibits crown root lateral root density rating at the V12 stage that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits crown root lateral root density rating at the V12 stage that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits crown root lateral root density rating at the V12 stage that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits crown root lateral root density rating at the V12 stage that is between 1% and 5%, between 5% and 10%, between 10% and 15%, between 15% and 20%, between 20% and 25%, between 25% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits crown root lateral root density rating at the V12 stage that is between 1% and 2%, between 2% and 3%, between 3% and 4%, between 4% and 5%, between 5% and 6%, between 6% and 7%, between 7% and 8%, between 8% and 9%, between 9% and 10%, between 10% and 11%, between 11% and 12%, between 12% and 13%, between 13% and 14%, between 14% and 15%, between 15% and 16%, between 16% and 17%, between 17% and 18%, between 18% and 19%, between 19% and 20%, between 20% and 21%, between 21% and 22%, between 22% and 23%, between 23% and 24%, between 24% and 25%, between 25% and 26%, between 26% and 27%, between 27% and 28%, between 28% and 29%, between 29% and 30%, greater than that of a control corn plant grown under comparable conditions.

In an aspect, a modified, transgenic, or genome edited/mutated corn plant exhibits increased root dry weight at the V12 stage relative to a control corn plant grown under comparable conditions.

According to an aspect of the present disclosure, a modified, transgenic, or genome edited/mutated corn plant exhibits an increase in root dry weight at the V12 stage by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a root dry weight at the V12 stage that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a root dry weight at the V12 stage that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a root dry weight at the V12 stage that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a root dry weight at the V12 stage that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a root dry weight at the V12 stage that is between 1% and 2%, between 2% and 3%, between 3% and 4%, between 4% and 5%, between 5% and 6%, between 6% and 7%, between 7% and 8%, between 8% and 9%, or between 9% and 10% greater than that of a control corn plant grown under comparable conditions.

In an aspect, a modified, transgenic, or genome edited/mutated corn plant exhibits increased number of florets relative to a control corn plant.

According to an aspect of the present disclosure, a modified, transgenic, or genome edited/mutated corn plant exhibits increased number of florets by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant.

According to an aspect of the present disclosure, a modified, transgenic, or genome edited/mutated corn plant exhibits a number of florets that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a number of florets that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a number of florets that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a number of florets that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a number of florets that is between 1% and 3%, between 3% and 5%, between 5% and 7%, between 7% and 9%, between 9% and 11%, between 11% and 13%, between 13% and 15%, between 15% and 17%, between 17% and 19%, between 19% and 21%, between 21% and 23%, between 23% and 25%, between 25% and 27%, between 27% and 29%, or between 29% and 30% greater than that of a control corn plant grown under comparable conditions.

A modified, transgenic, or genome edited/mutated corn plant disclosed in the present disclosure can display a positive trait interaction in which a trait, such as a positive or negative trait, attributable to a transgene (or mutation or edit) can be enhanced, out-performed, neutralized, offset or mitigated due to the presence of a second transgene (or mutation or edit). Such a transgenic and/or genome edited/ mutated corn plant can exhibit improved ear traits as compared to a control corn plant comprising only one transgene (or mutation or edit). For example, GA20Ox_SUP/ZMM19 stack plants may have enhanced traits and/or positive trait interactions relative to ZMM19 single and/or GA20Ox_SUP single plants, in terms of increased ear diameter, single kernel weight, ear fresh weight, ear area, ear volume, ear length, kernels per ear, and/or yield.

In another aspect, a modified, transgenic, or genome edited/mutated corn plant of the present disclosure exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

In yet another aspect, a modified, transgenic, or genome edited/mutated corn plant of the present disclosure does not have any significant off-types in at least one female organ or ear.

According to an aspect of the present disclosure, a modified, transgenic, or genome edited/mutated corn plant has no or reduced adverse effect over a trait or phenotype selected from the group consisting of senescence, delayed flowering, fungal infection, and a combination thereof, relative to a control corn plant.

Short stature or semi-dwarf corn plants can also have one or more additional traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

According to an aspect of the present disclosure, a modified, transgenic, or genome edited/mutated corn plant provided herein comprises a harvest index of at least 0.57, at least 0.58, at least 0.59, at least 0.60, at least 0.61, at least 0.62, at least 0.63, at least 0.64, or at least 0.65. According to another aspect of the present disclosure a modified, transgenic, or genome edited/mutated corn plant provided herein comprises a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. According to yet another aspect of the present disclosure, a modified, transgenic, or genome edited/mutated corn plant provided herein comprises a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater as compared to an unmodified control plant. According to still another aspect of the present disclosure, a modified, transgenic, or genome edited/mutated corn plant provided herein comprises a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater as compared to a control plant.

According to another aspect of the present disclosure, methods are provided for planting a modified or transgenic plant(s) provided herein at a normal/standard or high density in field. According to some aspects, the yield of a crop plant per acre (or per land area) can be increased by planting a modified or transgenic plant(s) of the present disclosure at a higher density in the field. As described herein, modified or transgenic plants expressing a transcribable DNA sequence that encodes a non-coding RNA molecule targeting one or more endogenous GA20 and/or GA3 oxidase gene for suppression and a transgene encoding one or more MADS-box polypeptide, can have reduced plant height, shorter internode(s), increased stalk/stem diameter, and/or increased lodging resistance. Modified or transgenic plants described herein can tolerate high density planting conditions since an increase in stem diameter can resist lodging and the shorter plant height can allow for increased light penetrance to the lower leaves under high density planting conditions. Thus, modified or transgenic plants provided herein can be planted at a higher density to increase the yield per acre (or land area) in the field. For row crops, higher density can be achieved by planting a greater number of seeds/plants per row length and/or by decreasing the spacing between rows. In an aspect, the row spacing for high density planting of the modified, transgenic, or genome edited/mutated corn plants is less than or equal to 40 inches. In an aspect, the row spacing for high density planting of the modified, transgenic, or genome edited/mutated corn plants is less than or equal to 30 inches. In another aspect, the row spacing for high density planting of the modified, transgenic, or genome edited/mutated corn plants is less than or equal to 20 inches.

According to an aspect, seeds of a modified or transgenic crop plants can be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified or transgenic crop plant can be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre.

As an example, seeds of corn plants can be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

Exemplary Embodiments

1. A modified corn plant or a plant part thereof comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a MADS-box polypeptide.

2. The modified corn plant of embodiment 1, wherein the first and second recombinant expression cassettes are stably integrated into the genome of the corn plant or plant part thereof.

3. The modified corn plant or plant part thereof of embodiment 1, wherein the modified corn plant further exhibits one or more improved root traits, relative to a control corn plant that does not have the first or second recombinant expression cassette.

4. The modified corn plant or plant part thereof of embodiment 1, wherein the modified corn plant is semi-dwarf and has one or more improved ear traits, relative to a control corn plant that does not have the first or second recombinant expression cassette.

5. The modified corn plant or plant part thereof of embodiments 1 to 4, wherein the transcribable DNA sequence encodes a non-coding RNA for suppression of a GA3 oxidase gene.

6. The modified corn plant or plant part thereof of embodiment 5, wherein the transcribable DNA sequence encodes a non-coding RNA for suppression of a GA3 oxidase_1 gene, a GA3 oxidase_2 gene, or both.

7. The modified corn plant or plant part thereof of embodiment 6, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

8. The modified corn plant or plant part thereof of embodiment 6, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

9. The modified corn plant or plant part thereof of embodiments 1 to 4, wherein the transcribable DNA sequence encodes a non-coding RNA for suppression of a GA20 oxidase gene.

10. The modified corn plant or plant part thereof of embodiment 9, wherein the transcribable DNA sequence encodes a non-coding RNA for suppression of a GA20 oxidase_3 gene, a GA20 oxidase_4 gene, a GA20 oxidase_5 gene, or a combination thereof.

11. The modified corn plant or plant part thereof of embodiment 9, wherein the transcribable DNA sequence encodes a non-coding RNA for suppression of a GA20 oxidase_3 gene, a GA20 oxidase_5 gene, or both.

12. The modified corn plant or plant part thereof of embodiment 11, wherein the transcribable DNA sequence comprises a sequence that is at least 60% identical or complementary to at least 15 consecutive nucleotides of SEQ ID NO: 39, 53, or 55.

13. The modified corn plant or plant part thereof of embodiment 11, wherein the transcribable DNA sequence encodes a sequence that is at least 60% identical or complementary to at least 15 consecutive nucleotides of SEQ ID NO: 40, 54, or 56.

14. The modified corn plant or plant part thereof of any one of embodiments 5 to 11, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

15. The modified corn plant or plant part thereof of any one of embodiments 5 to 11, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

16. The modified corn plant or plant part thereof of embodiment 1, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 168.

17. The modified corn plant or plant part thereof of embodiment 1, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

18. The modified corn plant or plant part thereof of any one of embodiments 1 to 4, wherein the MADS-box polypeptide comprises a maize ZMM19 polypeptide.

19. The modified corn plant or plant part thereof of any one of embodiments 1 to 17, wherein the DNA sequence of the second recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

20. The modified corn plant or plant part thereof of embodiment 1 or 4, wherein the expression level of an endogenous GA20 oxidase or GA3 oxidase gene is reduced or eliminated in the modified corn plant or plant part thereof.

21. The modified corn plant or plant part thereof of embodiment 1 or 4, wherein the transcribable DNA sequence is operably linked to a heterologous plant-expressible promoter.

22. The modified corn plant or plant part thereof of embodiment 21, wherein the heterologous plant-expressible promoter is a vascular promoter.

23. The modified corn plant or plant part thereof of embodiment 22, wherein the vascular promoter is selected from the group consisting of a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, a rice yellow stripe 2 (OsYSL2) promoter, and a combination thereof.

24. The modified corn plant or plant part thereof of embodiment 23, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70 or SEQ ID NO: 71, or a functional portion thereof.

25. The modified corn plant or plant part thereof of embodiment 21, wherein the heterologous plant-expressible promoter is a rice tungro baciliform virus (RTBV) promoter.

26. The modified corn plant or plant part thereof of embodiment 25, wherein RTBV promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

27. The modified corn plant or plant part thereof of embodiment 21, wherein the heterologous plant-expressible promoter is a leaf promoter.

28. The modified corn plant or plant part thereof of embodiment 27, wherein the leaf promoter is selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, a Myb gene promoter, and a combination thereof.

29. The modified corn plant or plant part thereof of embodiment 28, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

30. The modified corn plant or plant part thereof of embodiment 21, wherein the heterologous plant-expressible promoter is a constitutive promoter.

31. The modified corn plant or plant part thereof of embodiment 30, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a *mirabilis* mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

32. The modified corn plant or plant part thereof of embodiment 31, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

33. The modified corn plant or plant part thereof of embodiment 1 or 4, wherein the non-coding RNA is a precursor miRNA or siRNA capable of being processed or cleaved to form a mature miRNA or siRNA.

34. The modified corn plant or plant part thereof of embodiment 1 or 4, wherein the DNA sequence comprised in the second recombinant expression cassette is operably linked to a heterologous plant-expressible promoter.

35. The modified corn plant or plant part thereof of embodiment 34, wherein the heterologous plant-expressible promoter is a constitutive promoter.

36. The modified corn plant or plant part thereof of embodiment 35, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a *mirabilis* mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

37. The modified corn plant or plant part thereof of embodiment 35, wherein the heterologous plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

38. The modified corn plant or plant part thereof of embodiment 35, wherein the heterologous plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 174 or a functional portion thereof.

39. The modified corn plant or plant part thereof of embodiment 35, wherein the heterologous plant-expressible promoter is selected from the group consisting of a meristem promoter, a root promoter, a seed or kernel promoter, and a combination thereof.

40. The modified corn plant or plant part thereof of any one of embodiments 1 to 36, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

41. The modified corn plant or plant part thereof of any one of embodiments 1 to 40, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

42. The modified corn plant or plant part thereof of any one of embodiments 1 to 41, wherein the modified corn plant exhibits improved lodging resistance, reduced green snap, or both, relative to a control corn plant.

43. The modified corn plant or plant part thereof of embodiments 1 to 42, wherein the modified corn plant exhibits increased ear diameter relative to the control corn plant.

44. The modified corn plant or plant part thereof of embodiment 43, wherein the modified corn plant exhibits an increase in ear diameter by at least 0.2%, at least 0.4%, at least 0.6%, at least 0.8%, at least 1.0%, at least 1.2%, at least 1.4%, at least 1.6%, at least 1.8%, at least 2.0%, at least 2.2%, at least 2.4%, at least 2.6%, at least 2.8%, at least 3.0%, at least 3.2%, at least 3.4%, at least 3.6%, at least 3.8%, or at least 4.0%, relative to the control corn plant.

45. The modified corn plant or plant part thereof of embodiments 1 to 44, wherein the modified corn plant exhibits increased single kernel weight relative to the control corn plant.

46. The modified corn plant or plant part thereof of embodiment 45, wherein the modified corn plant exhibits an increase in singe kernel weight by at least at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

47. The modified corn plant or plant part thereof of any one of embodiments 1 to 46, wherein the modified corn plant exhibits increased ear fresh weight relative to the control corn plant.

48. The modified corn plant or plant part thereof of embodiment 47, wherein the modified corn plant exhibits increased ear fresh weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, relative to the control corn plant.

49. The modified corn plant or plant part thereof of any one of embodiments 1 to 48, wherein the modified corn plant exhibits increased ear area relative to the control corn plant.

50. The modified corn plant or plant part thereof of embodiment 49, wherein the modified corn plant exhibits an increase in ear area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

51. The modified corn plant or plant part thereof of any one of embodiments 1 to 50, wherein the modified corn plant exhibits increased ear volume relative to the control corn plant.

52. The modified corn plant or plant part thereof of embodiment 51, wherein the modified corn plant exhibits an increase in ear volume by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

53. The modified corn plant or plant part thereof of any one of embodiments 1 to 52, wherein the modified corn plant exhibits increased ear length relative to the control corn plant.

54. The modified corn plant or plant part thereof of embodiment 53, wherein the modified corn plant exhibits an increase in ear length by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%, at least 16%, at least 17%, at least 18%, at least 19%, or at least 20%, relative to the control corn plant.

55. The modified corn plant or plant part thereof of any one of embodiments 1 to 54, wherein the modified corn plant exhibits increased number of kernels per ear relative to the control corn plant.

56. The modified corn plant or plant part thereof of embodiment 55, wherein the modified corn plant exhibits an increase in number of kernels per ear by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%, at least 16%, at least 17%, at least 18%, at least 19%, or at least 20%, relative to the control corn plant.

57. The modified corn plant or plant part thereof of any one of embodiments 1 to 56, wherein the modified corn plant exhibits increased yield relative to the control corn plant.

58. The modified corn plant or plant part thereof of embodiment 57, wherein the modified corn plant exhibits an increase in yield by at least 1%, at least 3%, at least 5%, at least 7%, at least 9%, at least 11%, at least 13%, at least 15%, at least 17%, at least 19%, at least 21%, at least 23%, at least 25%, at least 27%, at least 29%, at least 31%, at least 33%, at least 35%, at least 37%, at least 39%, at least 41%, at least 43%, or at least 45%, relative to the control corn plant.

59. The modified corn plant or plant part thereof of any one of embodiments 1 to 58, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to the control corn plant.

60. The modified corn plant or plant part thereof of any one of embodiments 1 to 59, wherein the modified corn plant exhibits increased crown root lateral root density rating at the V12 stage relative to the control corn plant.

61. The modified corn plant or plant part thereof of embodiment 60, wherein the modified corn plant exhibits an increase in crown root lateral root density rating at the V12 stage by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, relative to the control corn plant.

62. The modified corn plant or plant part thereof of any one of embodiments 1 to 61, wherein the modified corn plant exhibits increased root dry weight at the V12 stage relative to the control corn plant.

63. The modified corn plant or plant part thereof of embodiment 62, wherein the modified corn plant exhibits an increase in root dry weight at the V12 stage by at least at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

64. The modified corn plant or plant part thereof of any one of embodiments 1 to 59, wherein the modified corn plant does not have any significant off-types in at least one female organ or ear.

65. A seed of the modified corn plant of any one of embodiments 1 to 64, wherein the seed comprises the first and second recombinant expression cassettes.

66. The seed of embodiment 65, wherein a progeny plant grown from the seed is semi-dwarf and has one or more improved ear traits, relative to a control corn plant that does not comprise the first or second recombinant expression cassette.

67. The seed of embodiment 66, wherein a progeny plant grown from the seed has one or more improved root traits, relative to the control corn plant.

68. A commodity or commodity product produced from the seed of embodiment 65, comprising the first and second DNA sequence recombinant expression cassettes.

69. A method comprising planting the seed of embodiment 65 in a growth medium or soil.

70. The method of embodiment 69, further comprising planting a plurality of the seeds with a row spacing of less than or equal to 40 inches.

71. The method of embodiment 69, further comprising planting a plurality of the seeds with a row spacing of less than or equal to 30 inches.

72. The method of embodiment 71, wherein the row spacing is less than or equal to 20 inches.

73. The method of embodiment 69, further comprising growing a corn plant from the seed.

74. The method of embodiment 73, further comprising harvesting a seed from the corn plant.

75. The method of any one of embodiments 71 to 74, wherein the seed is planted at a density selected from the group consisting of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, and at least 56,000 plants per acre.

76. A plurality of modified corn plants in a field, each modified corn plant comprising
1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and
2) a second recombinant expression cassette comprising a DNA sequence encoding a MADS-box polypeptide.

77. The plurality of modified corn plants of embodiment 76, wherein the modified corn plants have increased yield relative to control corn plants.

78. The plurality of modified corn plants of embodiment 76 or 77, wherein the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

79. A method for producing a modified corn plant, the method comprising:
a. introducing into a corn cell a first recombinant expression cassette comprising a DNA sequence encoding a MADS-box polypeptide, wherein the corn cell comprises a second recombinant expression cassette comprising a transcribable DNA sequence encoding a non-coding RNA for suppression of one or more GA3 oxidase genes and/or one or more GA20 oxidase genes; and
b. regenerating or developing a modified corn plant from the corn cell, wherein the modified corn plant comprises the first and second recombinant expression cassettes.

80. The method of embodiment 79, wherein the introducing is via site-directed integration using a site-specific nuclease.

81. The method of embodiment 80, wherein the site-specific nuclease is selected from the group consisting of a RNA-guided endonuclease, a meganuclease, a zinc-finger nuclease (ZFN), a TALE-endonuclease (TALEN), a recombinase, and a transposase.

82. The method of embodiment 79, wherein the introducing is via *Agrobacterium*-mediated transformation.

83. The method of embodiment 79, wherein the introducing is via particle bombardment.

84. The method of any one of embodiments 79 to 83, wherein the transcribable DNA sequence encodes a non-coding RNA for suppression of a GA3 oxidase_1 gene, a GA3 oxidase_2 gene, or both.

85. The method of embodiment 84, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

86. The method of embodiment 84, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

87. The method of any one of embodiments 79 to 83, wherein the transcribable DNA sequence encodes a non-coding RNA for suppression of a GA20 oxidase gene.

88. The method of embodiment 87, wherein the transcribable DNA sequence encodes a non-coding RNA for suppression of a GA20 oxidase_3 gene, a GA20 oxidase_4 gene, a GA20 oxidase_5 gene, or a combination thereof.

89. The method of embodiment 88, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

90. The method of embodiment 88, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

91. The method of any one of embodiments 79 to 90, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

92. The method of any one of embodiments 79 to 90, wherein the MADS-box polypeptide comprises a maize ZMM19 polypeptide.

93. The method of any one of embodiments 79 to 90, wherein the DNA sequence comprised in the first recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

94. The method of any one of embodiments 79 to 90, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

95. The modified corn plant of embodiment 79, wherein the first and second recombinant expression cassettes are stably integrated into the genome of the corn cell.

96. The method of embodiment 79, further comprising selecting a modified corn plant having a desired trait.

97. The method of embodiment 96, wherein the selected modified corn plant is semi-dwarf and has one or more improved ear traits, relative to a control corn plant not having the first or the second recombinant expression cassettes.

98. The method of embodiment 97, wherein the selected modified corn plant has one or more improved root traits, relative to the control corn plant.

99. The method of embodiment 96 or 97, wherein the selecting a modified corn plant having a desired trait comprises the use of one or more molecular techniques.

100. The method of embodiment 99, wherein the one or more molecular techniques are selected from the group consisting of Southern analysis, polymerase chain reaction (PCR) amplification, Northern blots, RNase protection, primer extension, reverse transcription PCR (RT-PCR), Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

101. The method of any one of embodiments 79 to 100, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

102. The method of any one of embodiments 79 to 101, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

103. The method of any one of embodiments 79 to 101, wherein the modified corn plant exhibit an ear trait selected from the group consisting of increased ear diameter, increased single kernel weight, increased ear fresh weight, increased ear area, increased ear volume, increased ear length, increased number of kernels per ear, increased yield, and a combination thereof, relative to a control corn plant.

104. The method of any one of embodiments 79 to 101, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

105. A method for producing a modified corn plant, the method comprising:

106. introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a MADS-box polypeptide; and 107. regenerating or developing a modified corn plant from the corn cell, wherein the modified corn plant comprises the first and second recombinant expression cassettes.

108. The method of embodiment 105, wherein the introducing is via site-directed integration using a site-specific nuclease.

109. The method of embodiment 108, wherein the site-specific nuclease is selected from the group consisting of a RNA-guided endonuclease, a meganuclease, a zinc-finger nuclease (ZFN), a TALE-endonuclease (TALEN), a recombinase, and a transposase.

110. The method of embodiment 105, wherein the introducing is via *Agrobacterium*-mediated transformation.

111. The method of embodiment 105, wherein the introducing is via particle bombardment.

112. The method of any one of embodiments 105 to 111, wherein the transcribable DNA sequence encodes a non-coding RNA for suppression of a GA3 oxidase_1 gene, a GA3 oxidase_2 gene, or both.

113. The method of embodiment 112, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

114. The method of embodiment 112, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

115. The method of any one of embodiments 105 to 111, wherein the transcribable DNA sequence encodes a non-coding RNA for suppression of a GA20 oxidase gene.

116. The method of embodiment 115, wherein the transcribable DNA sequence encodes a non-coding RNA for suppression of a GA20 oxidase_3 gene, a GA20 oxidase_4 gene, a GA20 oxidase_5 gene, or a combination thereof.

117. The method of embodiment 116, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

118. The method of embodiment 116, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

119. The method of any one of embodiments 105 to 118, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

120. The method of any one of embodiments 105 to 118, wherein the MADS-box polypeptide comprises a maize ZMM19 polypeptide.

121. The method of any one of embodiments 105 to 118, wherein the DNA sequence comprised in the second recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

122. The method of any one of embodiments 105 to 118, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

123. The modified corn plant of embodiment 105, wherein the first and second recombinant expression cassettes are stably integrated into the genome of the corn cell.

124. The method of embodiment 105, further comprising selecting a modified corn plant having a desired trait.

125. The method of embodiment 124, wherein the selected modified corn plant is semi-dwarf and has one or more improved ear traits, relative to a control corn plant not having the first or the second recombinant expression cassette.

126. The method of embodiment 125, wherein the selected modified corn plant has one or more improved root traits, relative to the control corn plant.

127. The method of embodiment 124 or 125, wherein the selecting a modified corn plant having a desired trait comprises the use of one or more molecular techniques.

128. The method of embodiment 127, wherein the one or more molecular techniques are selected from the group consisting of Southern analysis, PCR amplification, Northern blots, RNase protection, primer extension, RT-PCR, Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

129. The method of any one of embodiments 105 to 128, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

130. The method of any one of embodiments 105 to 129, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

131. The method of any one of embodiments 105 to 130, wherein the modified corn plant exhibit an ear trait selected from the group consisting of increased ear diameter, increased single kernel weight, increased ear fresh weight, increased ear area, increased ear volume, increased ear length, increased number of kernels per ear, increased yield, and a combination thereof, relative to a control corn plant.

132. The method of any one of embodiments 105 to 131, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

133. A method for producing a modified corn plant, the method comprising
   a. introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a MADS-box polypeptide; and b. regenerating or developing a modified corn plant from the corn cell, wherein the modified corn plant comprises the first and second recombinant expression cassettes.

134. A method for producing a modified corn plant, the method comprising
   a. introducing into a corn cell a first recombinant expression cassette comprising a transcribable DNA sequence encoding a non-coding RNA for suppression of one or more GA3 oxidase genes and/or GA20 oxidase genes;
   b. introducing into the corn cell of step (a) a second recombinant expression cassette comprising a DNA sequence encoding a MADS-box polypeptide to create a modified corn cell; and
   c. regenerating or developing a modified corn plant from the modified corn cell of step (b), wherein the modified corn plant comprises the first and second recombinant expression cassettes.

135. A method for producing a modified corn plant, the method comprising
   a. introducing into a corn cell a first recombinant expression cassette comprising a DNA sequence encoding a MADS-box polypeptide;
   b. introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and
   c. regenerating or developing a modified corn plant from the modified corn cell of step (b), wherein the modified corn plant comprises the first and second recombinant expression cassettes.

136. A method for producing a modified corn plant, the method comprising:
   a. crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a MADS-box polypeptide; and
   b. producing a progeny corn plant comprising the recombinant expression cassette and has the reduced expression of the one or more endogenous GA3 oxidase genes and/or GA20 oxidase genes.

137. The method of embodiment 136, wherein the first and second modified corn plants are obtained via site-directed integration using a site-specific nuclease.

138. The method of embodiment 137, wherein the site-specific nuclease is selected from the group consisting of a RNA-guided endonuclease, a meganuclease, a zinc-finger nuclease (ZFN), a TALE-endonuclease (TALEN), a recombinase, and a transposase.

139. The method of embodiment 136, wherein the first and second modified corn plants are obtained via *Agrobacterium*-mediated transformation.

140. The method of embodiment 136, wherein the first and second modified corn plants are obtained via particle bombardment.

141. The method of embodiment 136 to 140, wherein the first modified corn plant and the progeny corn plant comprise a transcribable DNA sequence encoding a non-coding RNA for suppression of a GA3 oxidase_1 gene, a GA3 oxidase_2 gene, or both.

142. The method of embodiment 141, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

143. The method of embodiment 141, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

144. The method of any one of embodiments 136 to 140, wherein the transcribable DNA sequence encodes a non-coding RNA for suppression of a GA20 oxidase gene.

145. The method of embodiment 144, wherein the transcribable DNA sequence encodes a non-coding RNA for suppression of a GA20 oxidase_3 gene, a GA20 oxidase_4 gene, a GA20 oxidase_5 gene, or a combination thereof.

146. The method of embodiment 145, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

147. The method of embodiment 145, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

148. The method of any one of embodiments 136 to 147, wherein the second modified corn plant and the progeny corn plant comprise a recombinant expression cassette comprising a DNA sequence encoding a MADS-box polypeptide.

149. The method of embodiment 148, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

150. The method of any one of embodiments 136 to 147, wherein the MADS-box polypeptide comprises a maize ZMM19 polypeptide.

151. The method of any one of embodiments 136 to 147, wherein the DNA sequence comprised in the second modified corn plant comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

152. The method of any one of embodiments 136 to 147, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

153. The method of embodiment 136, further comprising selecting a progeny corn plant having a desired trait.

154. The method of embodiment 153, wherein the selected progeny corn plant is semi-dwarf and has one or more improved ear traits, relative to a control corn plant.

155. The method of embodiment 154, wherein the selected progeny corn plant has one or more improved root traits, relative to the control corn plant 156. The method of embodiment 153 or 154, wherein the selecting a progeny corn plant having a desired trait comprises the use of one or more molecular techniques.

157. The method of embodiment 156, wherein the one or more molecular techniques are selected from the group consisting of Southern analysis, PCR amplification, Northern blots, RNase protection, primer extension, RT-PCR, Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

158. The method of any one of embodiments 136 to 157, wherein the height at maturity of the progeny corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

159. The method of any one of embodiments 136 to 158, wherein the stalk or stem diameter of the progeny corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

160. The method of any one of embodiments 136 to 159, wherein the progeny corn plant exhibit an ear trait selected from the group consisting of increased ear diameter, increased single kernel weight, increased ear fresh weight, increased ear area, increased ear volume, increased ear length, increased number of kernels per ear, increased yield, and a combination thereof, relative to a control corn plant.

161. The method of any one of embodiments 136 to 160, wherein the progeny corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

162. A method for producing a modified corn plant, the method comprising:
  a. introducing into a corn cell a recombinant expression cassette comprising a DNA sequence encoding a MADS-box polypeptide, wherein the DNA sequence is operably linked to a plant-expressible promoter, and wherein the corn cell comprises one or more mutations and/or edits in one or more endogenous GA3 oxidase and/or GA20 oxidase genes; and
  b. regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

163. The method of embodiment 162, further comprising introducing a recombinant DNA construct encoding a guide RNA that targets the one or more endogenous GA3 oxidase and/or GA20 oxidase genes.

164. The method of embodiment 163, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

165. The method of embodiment 164, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto.

166. The method of any one of embodiments 163 to 165, wherein the guide RNA is a CRISPR RNA (crRNA) or a single-chain guide RNA (sgRNA).

167. The method of any one of embodiments 163 to 166, wherein the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

168. The method of any one of embodiments 163 to 167, wherein the one or more endogenous GA3 oxidase and/or GA20 oxidase genes encode a protein that is at least 80%, at least 85%, at least 90%, at least 95%, at least 96%, at least 97%, at least 98%, at least 99%, at least 99.5%, or 100% identical to SEQ ID NO: 9, 12, 15, 30, or 33.

169. The method of embodiment 162, wherein the introducing is via *Agrobacterium*-mediated transformation or particle bombardment.

170. The method of embodiment 169, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

171. The method of embodiment 169, wherein the MADS-box polypeptide comprises a maize ZMM19 polypeptide.

172. The method of any one of embodiments 162 to 171, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

173. The method of any one of embodiments 162 to 171, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

174. A method for producing a modified corn plant, the method comprising:
  a. mutating or editing one or more endogenous GA3 oxidase genes and/or one or more GA20 oxidase genes in a corn cell, wherein the corn cell comprises a recombinant expression cassette encoding a MADS-box polypeptide, wherein the DNA sequence is operably linked to a plant-expressible promoter; and
  b. regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

175. The method of embodiment 174, wherein the mutating or editing is obtained by using a site-specific nuclease selected from the group consisting of a RNA-guided endonuclease, a meganuclease, a zinc-finger nuclease (ZFN), a TALE-endonuclease (TALEN), a recombinase, and a transposase.

176. The method of embodiment 174 or 175, further comprising introducing a recombinant DNA construct encoding a guide RNA that targets the one or more endogenous GA3 oxidase and/or GA20 oxidase genes.

177. The method of embodiment 176, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

178. The method of embodiment 177, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto.

179. The method of any one of embodiments 176 to 178, wherein the guide RNA is a CRISPR RNA (crRNA) or a single-chain guide RNA (sgRNA).

180. The method of any one of embodiments 176 to 179, wherein the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

181. The method of any one of embodiments 176 to 180, wherein the one or more endogenous GA3 oxidase and/or GA20 oxidase genes encode a protein that is at least 80%, at least 85%, at least 90%, at least 95%, at least 96%, at least 97%, at least 98%, at least 99%, at least 99.5%, or 100% identical to SEQ ID NO: 9, 12, 15, 30, or 33.

182. The method of embodiment 174, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

183. The method of embodiment 174, wherein the recombinant expression cassette encodes a maize ZMM19 polypeptide.

184. The method of embodiment 174, wherein the recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

185. The method of embodiment 174, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

186. The method of any one of embodiments 174 to 185, further comprising selecting a modified corn plant having a desired trait.

187. The method of embodiment 186, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

188. The method of embodiment 187, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

189. The method of any one of embodiments 186 to 188, wherein the modified corn plant exhibit an ear trait selected from the group consisting of increased ear diameter, increased single kernel weight, increased ear fresh weight, increased ear area, increased ear volume, increased ear length, increased number of kernels per ear, increased yield, and a combination thereof, relative to a control corn plant.

190. The method of any one of embodiments 186 to 189, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

191. A modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a MADS-box polypeptide, wherein the DNA sequence is operably linked to a plant-expressible promoter.

192. The modified corn plant of embodiment 191, wherein the modified corn plant is semi-dwarf and has one or more improved ear traits, relative to a control corn plant that does not comprise both the one or more mutations or edits and the recombinant expression cassette.

193. The modified corn plant of embodiment 192, wherein the modified corn plant has one or more improved root traits, relative to the control corn plant 194. The modified corn plant of embodiment 191 or 192, wherein the one or more mutations or edits are selected from the group consisting of an insertion, a substitution, an inversion, a deletion, a duplication, and a combination thereof.

195. The modified corn plant of any one of embodiments 191 to 194, wherein the one or more mutations or edits are introduced using a meganuclease, a zinc-finger nuclease (ZFN), a RNA-guided endonuclease, a TALE-endonuclease (TALEN), a recombinase, or a transposase.

196. The modified corn plant of any one of embodiments 191 to 195, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

197. The modified corn plant of any one of embodiments 191 to 195, wherein MADS-box polypeptide comprises a maize ZMM19 polypeptide.

198. The modified corn plant of any one of embodiments 191 to 195, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

199. The modified corn plant of any one of embodiments 191 to 195, the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

200. The modified corn plant of any one of embodiments 191 to 199, wherein the recombinant expression cassette is stably integrated into the genome of the modified corn plant.

201. The modified corn plant of any one of embodiments 191 to 200, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

202. The modified corn plant of any one of embodiments 191 to 201, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

203. The modified corn plant of any one of embodiments 191 to 202, wherein the modified corn plant exhibits improved lodging resistance, reduced green snap, or both, relative to the control corn plant.

204. The modified corn plant of any one of embodiments 191 to 203, wherein the modified corn plant exhibits increased ear diameter relative to a control corn plant.

205. The modified corn plant of any one of embodiments 191 to 204, wherein the modified corn plant exhibits increased single kernel weight relative to a control corn plant.

206. The modified corn plant of any one of embodiments 191 to 205, wherein the modified corn plant exhibits increased ear fresh weight relative to a control corn plant.

207. The modified corn plant of any one of embodiments 191 to 206, wherein the modified corn plant exhibits increased ear area relative to a control corn plant.

208. The modified corn plant of any one of embodiments 191 to 207, wherein the modified corn plant exhibits increased ear volume relative to a control corn plant.

209. The modified corn plant of any one of embodiments 191 to 208, wherein the modified corn plant exhibits increased ear length relative to a control corn plant.

210. The modified corn plant of any one of embodiments 191 to 209, wherein the modified corn plant exhibits increased number of kernels per ear relative to a control corn plant.

211. The modified corn plant of any one of embodiments 191 to 210, wherein the modified corn plant exhibits increased yield relative to a control corn plant.

212. The modified corn plant of any one of embodiments 191 to 211, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

213. The modified corn plant of any one of embodiments 191 to 212, wherein the modified corn plant does not have any significant off-types in at least one female organ or ear.

214. A plurality of modified corn plants in a field, each modified corn plant comprising
1) one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and
2) a recombinant expression cassette comprising a DNA sequence encoding a MADS-box polypeptide, wherein the DNA sequence is operably linked to a plant-expressible promoter.

215. The plurality of modified corn plants of embodiment 214, wherein the modified corn plants have increased yield relative to control corn plants.

216. The plurality of modified corn plants of embodiment 214 or 215, wherein the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

217. A recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a MADS-box polypeptide, wherein the DNA sequence is operably linked to a plant-expressible promoter.

218. The recombinant DNA construct of embodiment 217, wherein the first and second expression cassettes are in a single T-DNA segment of a transformation vector.

219. The recombinant DNA construct of embodiment 217, wherein the first and second expression cassettes are in two different T-DNA segments of a transformation vector.

220. The recombinant DNA construct of any one of embodiments 217 to 219, wherein the transcribable DNA sequence encodes a non-coding RNA for suppression of a GA3 oxidase gene.

221. The recombinant DNA construct of embodiment 220, wherein the transcribable DNA sequence encodes a non-coding RNA for suppression of a GA3 oxidase_1 gene, a GA3 oxidase_2 gene, or both.

222. The recombinant DNA construct of embodiment 221, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

223. The recombinant DNA construct of embodiment 221, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

224. The recombinant DNA construct of embodiment 220, wherein the transcribable DNA sequence encodes a non-coding RNA for suppression of a GA20 oxidase gene.

225. The recombinant DNA construct of embodiment 224, wherein the transcribable DNA sequence encodes a non-coding RNA for suppression of a GA20 oxidase_3 gene, a GA20 oxidase_4 gene, a GA20 oxidase_5 gene, or a combination thereof.

226. The recombinant DNA construct of embodiment 224, wherein the transcribable DNA sequence encodes a non-coding RNA for suppression of a GA20 oxidase_3 gene, a GA20 oxidase_5 gene, or both.

227. The recombinant DNA construct of embodiment 226, wherein the transcribable DNA sequence comprises a sequence that is at least 80% identical or complementary to at least 15 consecutive nucleotides of SEQ ID NO: 39, 53, or 55.

228. The recombinant DNA construct of embodiment 227, wherein the transcribable DNA sequence encodes a sequence that is at least 80% complementary to at least 15 consecutive nucleotides of SEQ ID NO: 40, 54, or 56.

229. The recombinant DNA construct of any one of embodiments 217 to 228, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

230. The recombinant DNA construct of any one of embodiments to 217 to 229, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

231. The recombinant DNA construct of any one of embodiments 217 to 230, wherein the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

232. The recombinant DNA construct of any one of embodiments 217 to 230, wherein the DNA sequence comprised in the second expression cassette encodes a maize ZMM19 polypeptide.

233. The recombinant DNA construct of any one of embodiments 217 to 230, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

234. The recombinant DNA construct of any one of embodiments 217 to 230, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

235. The recombinant DNA construct of any one of embodiments 217 to 232, the plant-expressible promoter is a vascular promoter.

236. The recombinant DNA construct of embodiment 235, wherein the vascular promoter is selected from the group consisting of a sucrose synthase promoter, a sucrose transporter promoter, a Sh1 promoter, CoYMV promoter, a WDV large intergenic region (LIR) promoter, a MSV coat polypeptide (CP) promoter, a rice yellow stripe 1 (YS1)-like promoter, a rice yellow stripe 2 (OsYSL2) promoter, and a combination thereof.

237. The recombinant DNA construct of any one of embodiments 217 to 232, wherein the plant-expressible promoter is an RTBV promoter.

238. The recombinant DNA construct of any one of embodiments 217 to 232, wherein the plant-expressible promoter is a leaf promoter.

239. The recombinant DNA construct of embodiment 238, wherein the leaf promoter is selected from the group consisting of a RuBisCO promoter, a PPDK promoter, a FDA promoter, a Nadh-Gogat promoter, a chlorophyll a/b binding polypeptide gene promoter, a PEPC promoter, a Myb gene promoter, and a combination thereof.

240. The recombinant DNA construct of any one of embodiments 217 to 232, wherein the plant-expressible promoter is a constitutive promoter.

241. The recombinant DNA construct of embodiment 240, wherein the constitutive promoter is selected from the group consisting of an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

242. The recombinant DNA construct of any one of embodiments 217 to 232, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

243. The recombinant DNA construct of any one of embodiments 217 to 232, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 174 or a functional portion thereof.

244. The recombinant DNA construct of any one of embodiments 217 to 232, wherein the plant-expressible promoter is selected from the group consisting of a meristem promoter, a root promoter, a seed or kernel promoter, and a combination thereof.

245. The recombinant DNA construct of embodiment 217, wherein the non-coding RNA is a precursor miRNA or siRNA capable of being processed or cleaved to form a mature miRNA or siRNA.

246. A transformation vector comprising the recombinant DNA construct of any one of embodiments 217 to 245.

247. A modified corn plant or a plant part thereof comprising the recombinant DNA construct of embodiment 246.

248. The modified corn plant of embodiment 247, wherein the modified corn plant is semi-dwarf and has one or more improved ear traits, relative to a control corn plant not having both the first and second expression cassettes.

249. The modified corn plant of embodiment 248, wherein the modified corn plant has one or more improved root traits, relative to the control corn plant 250. The modified corn plant of embodiment 248, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to the control corn plant.

251. The modified corn plant of embodiment 248, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to the control corn plant.

252. The modified corn plant of embodiment 248, wherein the modified corn plant exhibits improved lodging resistance, reduced green snap, or both, relative to the control corn plant.

253. The modified corn plant of embodiment 248, wherein the modified corn plant exhibits increased ear diameter relative to the control corn plant.

254. The modified corn plant of embodiment 248, wherein the modified corn plant exhibits increased single kernel weight relative to the control corn plant.

255. The modified corn plant of embodiment 248, wherein the modified corn plant exhibits increased ear fresh weight relative to the control corn plant.

256. The modified corn plant of embodiment 248, wherein the modified corn plant exhibits increased ear area relative to the control corn plant.

257. The modified corn plant of embodiment 248, wherein the modified corn plant exhibits increased ear volume relative to the control corn plant.

258. The modified corn plant of embodiment 248, wherein the modified corn plant exhibits increased ear length relative to the control corn plant.

259. The modified corn plant of embodiment 248, wherein the modified corn plant exhibits increased number of kernels per ear relative to the control corn plant.

260. The modified corn plant of embodiment 248, wherein the modified corn plant exhibits increased yield relative to the control corn plant.

261. The modified corn plant of embodiment 248, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to the control corn plant.

262. The modified corn plant of embodiment 248, wherein the modified corn plant does not have any significant off-types in at least one female organ or ear.

263. A recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a MADS-box polypeptide, wherein the DNA sequence is operably linked to a plant-expressible promoter.

264. The recombinant DNA donor template molecule of embodiment 263, comprising two of the homology sequences, wherein the two homology sequences flank the insertion sequence.

265. The recombinant DNA donor template molecule of embodiment 263 or 264, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 175-199.

266. The recombinant DNA donor template molecule of embodiment 263 or 264, wherein the MADS-box polypeptide comprises a maize ZMM19 polypeptide.

267. The recombinant DNA donor template molecule of embodiment 263 or 264, wherein the DNA sequence comprised in the expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

268. The recombinant DNA donor template molecule of embodiment 263 or 264, wherein the MADS-box polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

269. The recombinant DNA donor template molecule of any one of embodiments 263 to 268, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

270. The recombinant DNA donor template molecule of any one of embodiments 263 to 268, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 174 or a functional portion thereof.

271. The recombinant DNA donor template molecule of any one of embodiments 263 to 268, wherein the plant-expressible promoter is selected from the group consisting of a meristem promoter, a root promoter, a seed or kernel promoter, and a combination thereof.

272. The recombinant DNA donor template molecule of any one of embodiments 263 to 269, further comprising a transcribable DNA sequence encoding a non-coding RNA for suppression of one or more GA20 oxidase genes and/or one or more GA3 oxidase genes, wherein the transcribable DNA sequence is operably linked to a promoter.

273. The recombinant DNA donor template molecule of embodiment 271, wherein the promoter is a vascular promoter.

274. The recombinant DNA donor template molecule of embodiment 272, wherein the vascular promoter is selected from the group consisting of a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, a rice yellow stripe 2 (OsYSL2) promoter, and a combination thereof.

275. The recombinant DNA donor template molecule of embodiment 273, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70, or SEQ ID NO: 71, or a functional portion thereof.

276. The recombinant DNA donor template molecule of any one of embodiments 263 to 268, wherein the promoter is a rice tungro bacilliform virus (RTBV) promoter.

277. The recombinant DNA donor template molecule of embodiment 275, wherein the RTBV promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

278. The recombinant DNA donor template molecule of any one of embodiments 263 to 268, wherein the promoter is a leaf promoter.

279. The recombinant DNA donor template molecule of embodiment 277, wherein the leaf promoter is selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, a Myb gene promoter, and a combination thereof.

280. The recombinant DNA donor template molecule of embodiment 278, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

281. The recombinant DNA donor template molecule of any one of embodiments 263 to 268, wherein the promoter is a constitutive promoter.

282. The recombinant DNA donor template molecule of embodiment 280, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a *mirabilis* mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

283. The recombinant DNA donor template molecule of embodiment 281, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO:

79, SEQ ID NO: 80, SEQ ID NO: 81, SEQ ID NO: 82 or SEQ ID NO: 83, or a functional portion thereof.

284. The modified corn plant of embodiment 1, wherein the first recombinant expression cassette comprises SEQ ID NO: 39, and the second recombinant expression cassette comprises SEQ ID NO: 169.

285. The modified corn plant of embodiment 284, wherein the modified corn plant is semi-dwarf and exhibits one or more improved ear traits, relative to a control plant that does not comprise the first or second recombinant expression cassette.

286. The modified corn plant of embodiment 285, wherein the one or more improved ear traits are selected from the group consisting of broad acreage yield, ear area, ear dry weight, ear tip void, single kernel weight, kernels per ear, ear fresh weight, and a combination thereof.

287. A modified corn plant or a plant part thereof comprising 1) a first transcribable DNA sequence comprising SEQ ID NO: 39, and 2) a second transcribable DNA sequence comprising SEQ ID NO: 169.

288. The modified corn plant of embodiment 287, wherein the modified corn plant is semi-dwarf and has one or more improved ear traits, relative to a control corn plant that does not have the first or second transcribable DNA sequence.

289. The modified corn plant of embodiment 288, wherein the one or more improved ear traits are selected from the group consisting of broad acreage yield, ear area, ear dry weight, ear tip void, single kernel weight, kernels per ear, ear fresh weight, and a combination thereof.

290. A method for producing a modified corn plant, the method comprising
  a. introducing into a corn cell a recombinant expression cassette comprising a first transcribable DNA sequence comprising SEQ ID NO: 39, and a second transcribable DNA sequence comprising SEQ ID NO: 169;
  b. regenerating or developing a modified corn plant from the corn cell, wherein the modified corn plant comprises the first and second transcribable DNA sequences.

291. The method of embodiment 290, wherein the modified corn plant is semi-dwarf and has one or more improved ear traits, relative to a control corn plant that does not have the first or second transcribable DNA sequence.

292. The method of embodiment 291, wherein the one or more improved ear traits are selected from the group consisting of broad acreage yield, ear area, ear dry weight, ear tip void, single kernel weight, kernels per ear, ear fresh weight, and a combination thereof.

293. A recombinant expression cassette comprising 1) a first transcribable DNA sequence comprising SEQ ID NO: 39, and 2) a second transcribable DNA sequence comprising SEQ ID NO: 169.

EXAMPLES

Example 1. Generation of the GA20Ox_SUP/ZMM19 Stack Plants

An inbred corn plant line was transformed via *Agrobacterium*-mediated transformation with a transformation vector having an expression construct comprising a miRNA-encoding DNA sequence (SEQ ID NO: 39) encoding a targeting sequence (SEQ ID NO: 40) under the control of a rice tungro bacilliform virus (RTBV) promoter (SEQ ID NO: 65) known to cause expression in vascular tissues of plants. The miRNA encoded by the construct comprises an RNA sequence that targets the GA20 oxidase_3 and GA20 oxidase_5 genes in corn plants. Several transformation events were generated therefrom. The resulting transformed/transgenic inbred line is herein referred to as GA20Ox_SUP or GA20Ox_SUP single.

Plant height was measured up to the uppermost ligulated leaf at the R3 stage. As shown in FIG. 1, statistically significant reductions in plant height between 35% and 45% are consistently observed in GA20Ox_SUP single plants relative to control plants (p-value≤0.2).

Similarly, an inbred corn plant line was transformed via *Agrobacterium*-mediated transformation with a transformation vector having an expression construct comprising an *Oryza sativa* Rcc3 gene promoter region (SEQ ID NO: 170), a leader sequence thereof (SEQ ID NO: 171), a *Zea mays* intron sequence (SEQ ID NO: 172), and an *Oryza sativa* UP2 terminator region (SEQ ID NO: 173), operably linked to a polynucleotide sequence (SEQ ID NO: 169) encoding maize ZMM19 polypeptide (SEQ ID NO: 168). Several transformation events were generated therefrom. The resulting transformed/transgenic inbred line is herein referred to as ZMM19, ZMM19 transgenic plant, or ZMM19 single.

Parental GA20Ox_SUP and ZMM19 singles were crossed to create a stacked transgenic progeny plant comprising both the ZMM19 transgene and the miRNA-encoding DNA sequence for the suppression of GA20 oxidase_3 and GA20 oxidase_5 genes. The stacked combination may be referred to as a breeding or crossing stack since the transgenes are brought together through crossing of two parental plants. The resulting stacked transgenic line is herein referred to as GA20Ox_SUP/ZMM19 stack. The GA20Ox_SUP/ZMM19 stack can be an inbred stack if the parental lines are of the same inbred line origin, or a hybrid when the parental lines are of different inbreds.

For each type of transgenic single and stack plants, the corresponding control plants were also produced for comparison having the same inbred line or same parental line combination, but without the transgenic GA20Ox_SUP and ZMM19 constructs.

Example 2. Reduced Height of the GA20Ox_SUP/ZMM19 Stack Plants

GA20Ox_SUP/ZMM19 stack plants were grown to maturity in a field under standard agronomic practice and their heights were measured. Plant height was measured as the plot average from the soil line to the base of highest collared leaf at the R3 stage. A sufficient number of plants were measured to meet statistical significance with p-value≤0.2. Control plants of the same parental inbred lines but without the GA20Ox_SUP and ZMM19 transgenic constructs were also grown under similar conditions.

Figure 2:
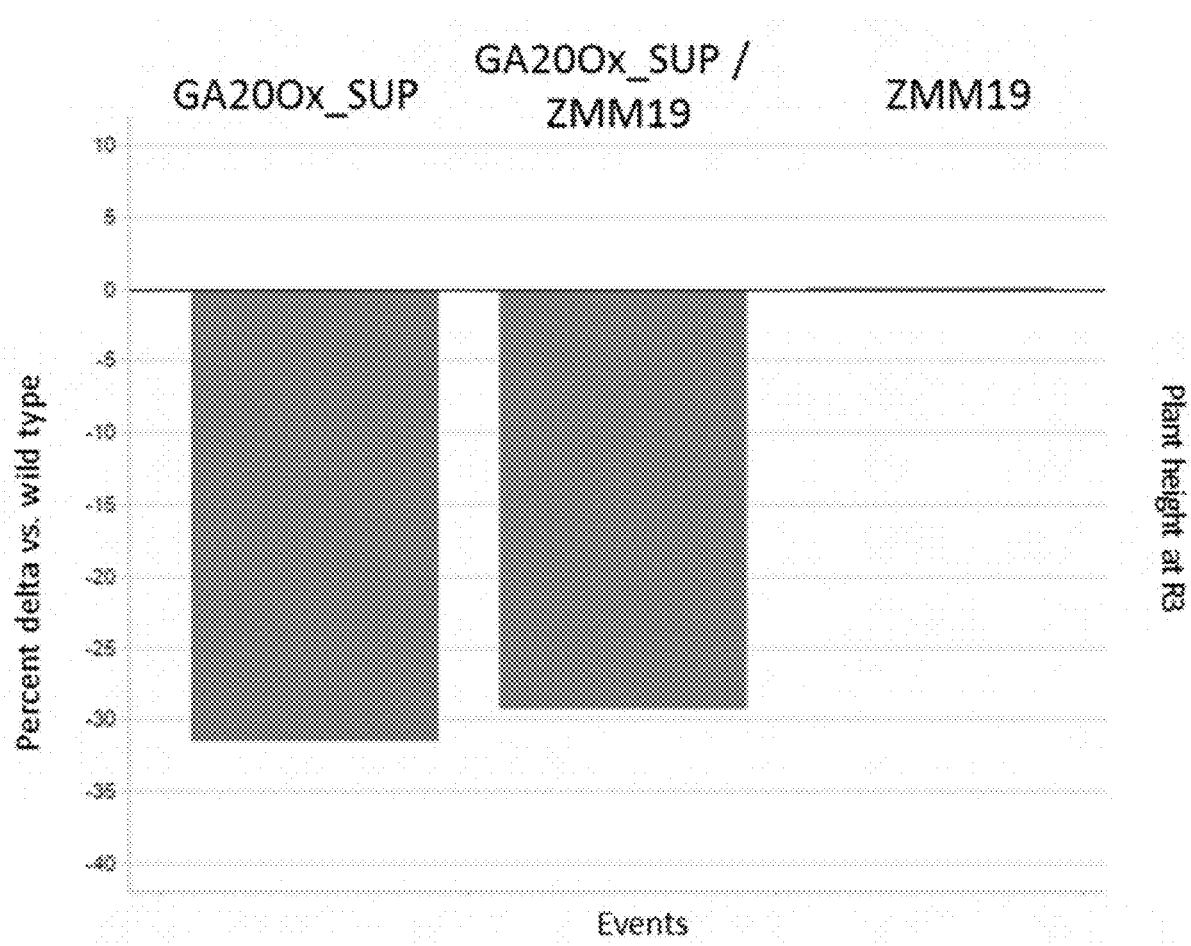
FIG. 2 shows plant heights of stacked transgenic corn plants comprising a DNA sequence encoding a miRNA for suppression of GA20 oxidase genes and a transgene encoding maize ZMM19 polypeptide ("GA20Ox_SUP/ZMM19 stack"), along with GA20Ox_SUP single corn plants, and ZMM19 single corn plants, each relative to control corn plants.

Average plant height reduction for the GA20Ox_SUP/ZMM19 stack, as well as the GA20Ox_SUP single and ZMM19 single, are shown in FIG. 2, each relative to control plants. As shown in FIG. 2, a statistically significant reduction in plant height averaging between 25 to 30% was consistently observed in GA20Ox_SUP/ZMM19 stack plants relative to control plants. In contrast, the plant height of ZMM19 single plants were relatively unchanged in comparison to control plants.

Example 3. Enhanced Root Traits and Ear Traits with Expression of the ZMM19 Gene The transgenic single and stack plants and control plants described in Example 1 were grown under standard agronomic practice. Several root traits were measured for the ZMM19 single plants. Crown lateral root density rating at the V12 stage (CLRV12) is measured as an average of two plants per plot, using a visual rating system score from 1-9, with 1 being the least complex looking root system and 9 being the most complex looking root system. Root dry weight at the V12 (RDWV12) stage is measured as the plot average (based on two plants) of root dry weight at the V12 stage.

Corn ear traits were measured for the ZMM19 single plants at the R6 stage. Ear area is measured as the plot average of the area of an ear from a two-dimensional view by imaging the ear and including kernels and tip void in the area measurement. Typically, 10 representative ears were measured per plot. Ear diameter is a measure of the plot average of the ear diameter measured as the maximal "wide" axis of an ear over its widest section. Ear length is a measure of the plot average of the length of an ear measured from the tip of the ear in a straight line to the base of the ear node. Ear volume is measured as the plot average of the volume of an ear calculated by measuring the diameter and estimating the resulting volume along the length of the ear (one row at a time), accounting for the shape/contour of the ear, but assuming that the ear is a perfect circle for each row.

Grain yield estimate is a conversion from the hand-harvested grain weight per area measurement, collected from a small section of a plot, to the equivalent number of bushels per acre, including adjustment to a standard moisture level. Number of kernels per ear is a measure of the plot average of the number of kernels divided by the number of ears.

Single kernel weight is measured as the plot average of weight per kernel, calculated as the sample kernel weight (adjusted to a standard moisture level)/sample kernel number. The sample kernel number can range from 350 to 850.

Figure 3A:
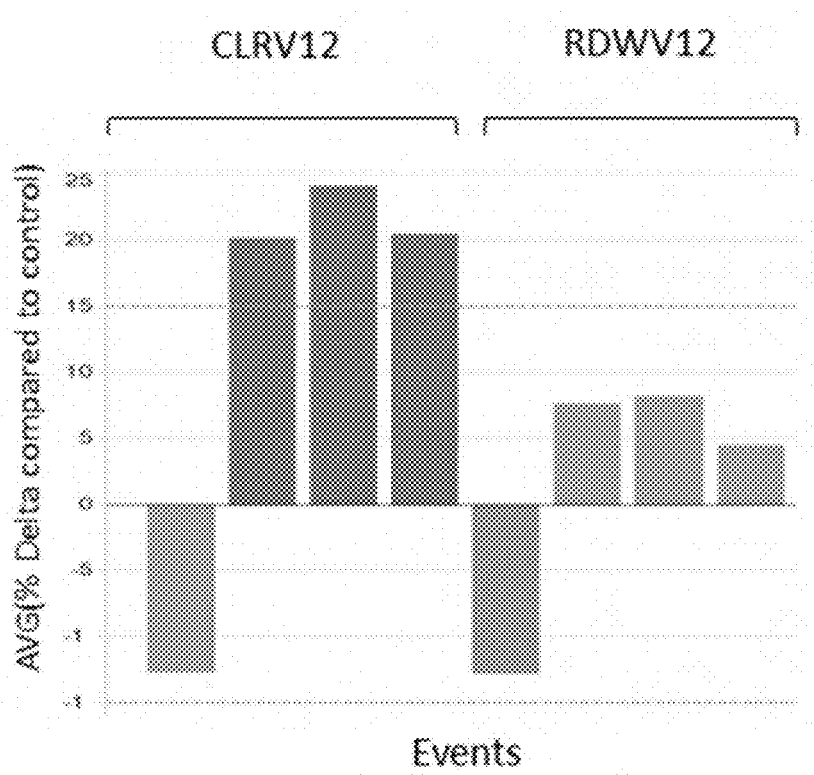
FIG. 3A shows root traits of transgenic corn plants comprising a transgene encoding maize ZMM19 polypeptide ("ZMM19 single") relative to control corn plants.

FIG. 3A shows root trait results for ZMM19 single plants. Results are shown as percent difference (delta) between ZMM19 single plants and control plants of the same inbred without the ZMM19 transgenic construct. Dark grey bars indicate statistically significant changes as compared to control plants (p-value≤0.2). As shown in FIG. 3A, in comparison to controls, ZMM19 single plants exhibited statistically significant increase in crown root lateral root density rating at the V12 stage (CLRV12) by about 20 to 25% across most events. ZMM19 single plants also exhibited numerical increase in root dry weight at the V12 stage (RDWV12) in comparison to controls.

Figure 3B:
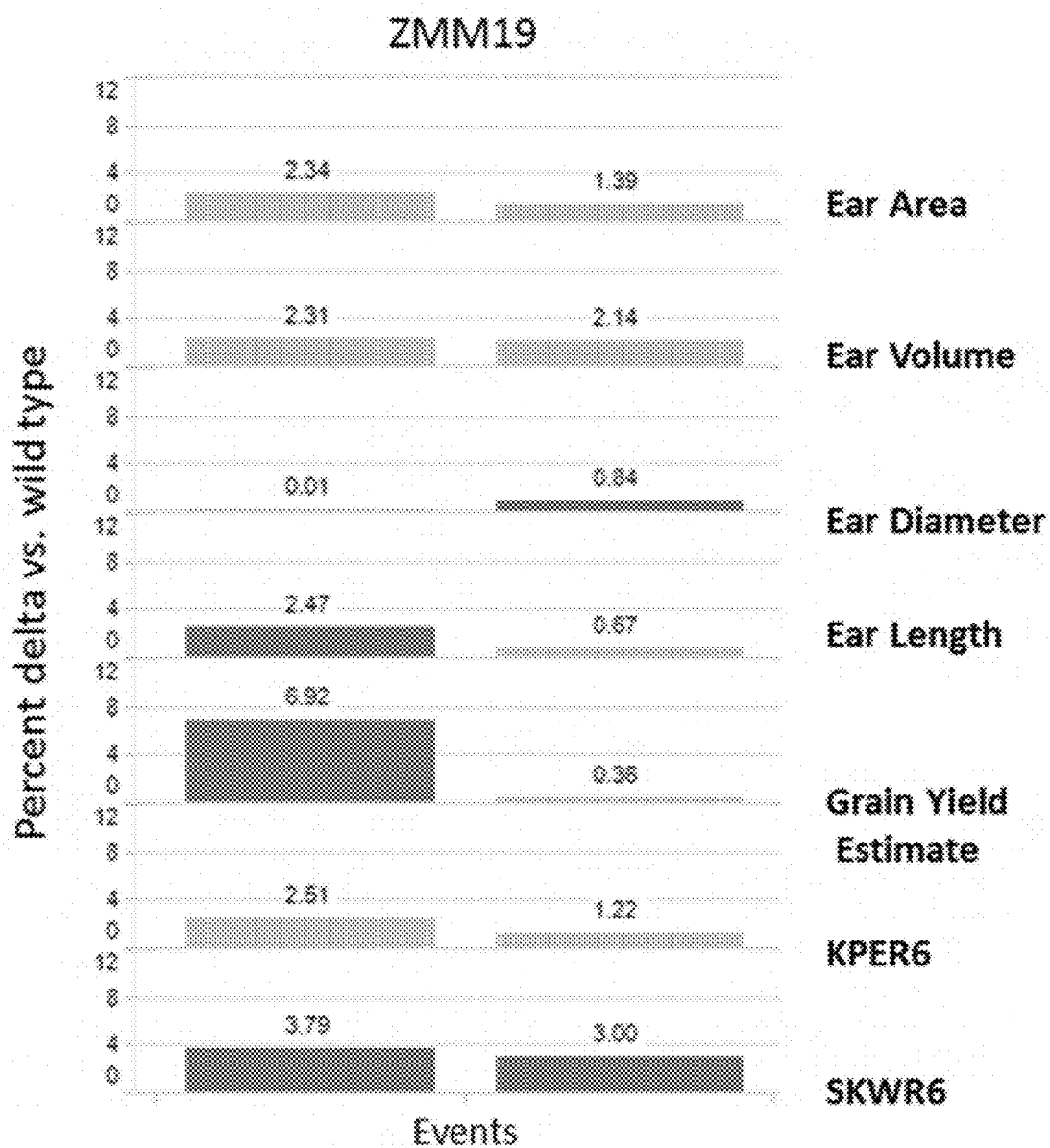
FIG. 3B shows ear traits of ZMM19 single plants relative to control corn plants.

FIG. 3B shows ear trait results for ZMM19 single plants. Results are shown as percent difference (delta) between ZMM19 single plants and control plants of the same inbred without the ZMM19 transgenic construct. Dark grey bars indicate statistically significant changes (positive or negative) as compared to control plants (p-value≤0.2). As shown in FIG. 3B, in comparison to controls, ZMM19 single plants exhibited statistically significant improvement in a number of ear traits, including increased ear diameter, increased ear length, increased grain yield estimate, and increased single kernel weight (SKWR6) depending on the transformation event. ZMM19 single plants also exhibited numerical increases in ear area, ear volume, and number of kernels per ear (KPER6) in comparison to control plants.

Figure 3C:
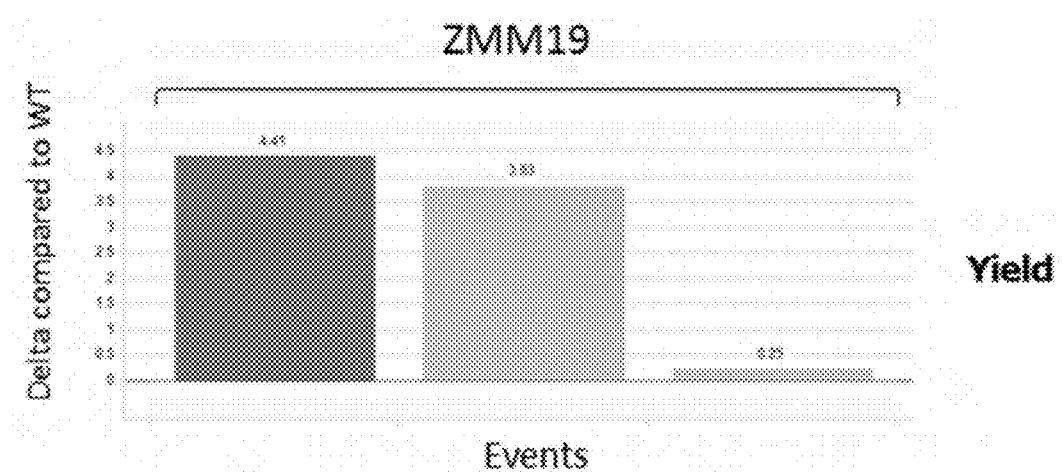
FIG. 3C shows yield of ZMM19 single plants relative to control corn plants.

As shown in FIG. 3C, ZMM19 single plants showed a slight to modest increase in yield (in bushels/acre) by as much as 4.5 bushels/acre in comparison to control plants. However, as shown below, GA20Ox_SUP/ZMM19 stack plants surprisingly exhibited statistically significant increase in yield of at least 8 bushels/acre in comparison to control plants depending on event and germplasm.

Example 4. Enhanced Ear Traits of the GA20Ox_SUP/ZMM19 Stack Plants

Figure 4A:
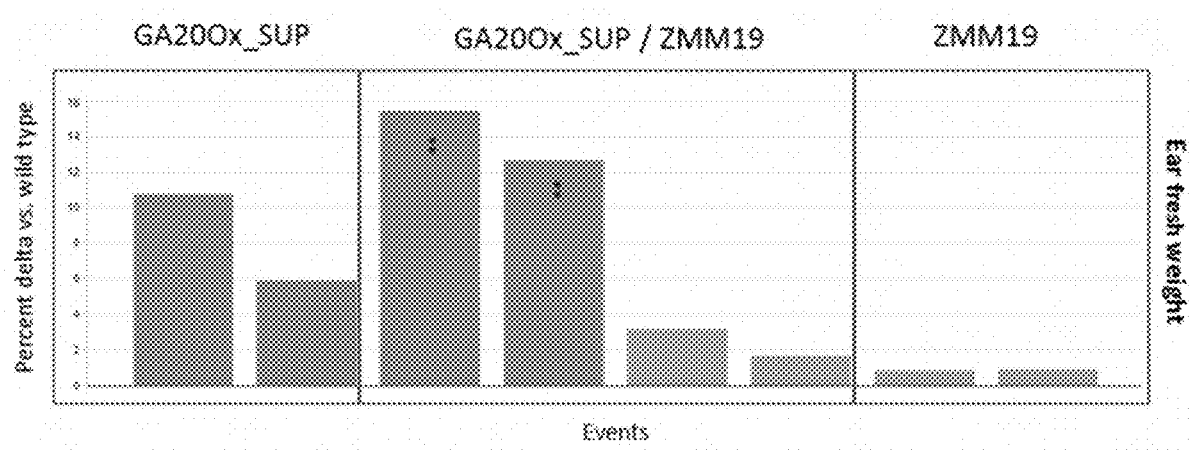
FIGS. 4A-4C show ear traits of GA20Ox_SUP/ZMM19 stack corn plants across four transformation events, GA20Ox_SUP single corn plants across two transformation events, and ZMM19 single corn plants across two transformation events, including ear fresh weight, ear area, ear volume, ear diameter, ear length, number of kernels per ear at the R6 stage, and single kernel weight at the R6 stage, under standard agronomic conditions in the field, relative to control corn plants.
Figure 4B:
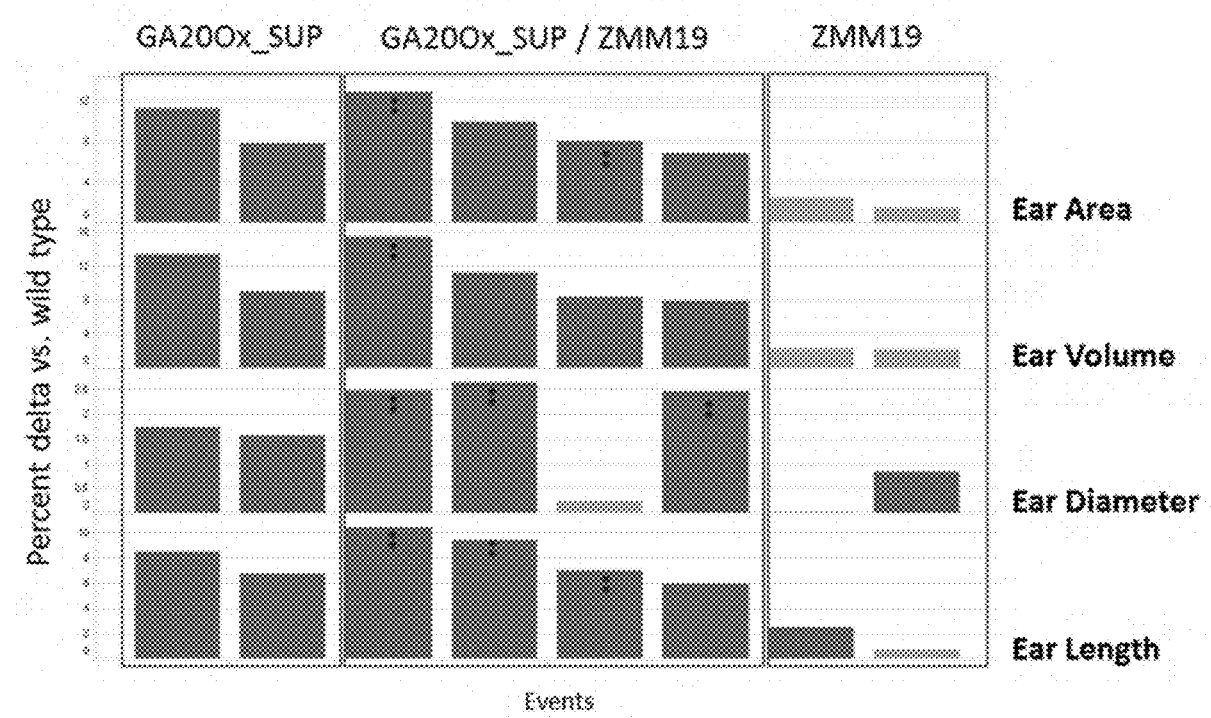
Figure 4C:
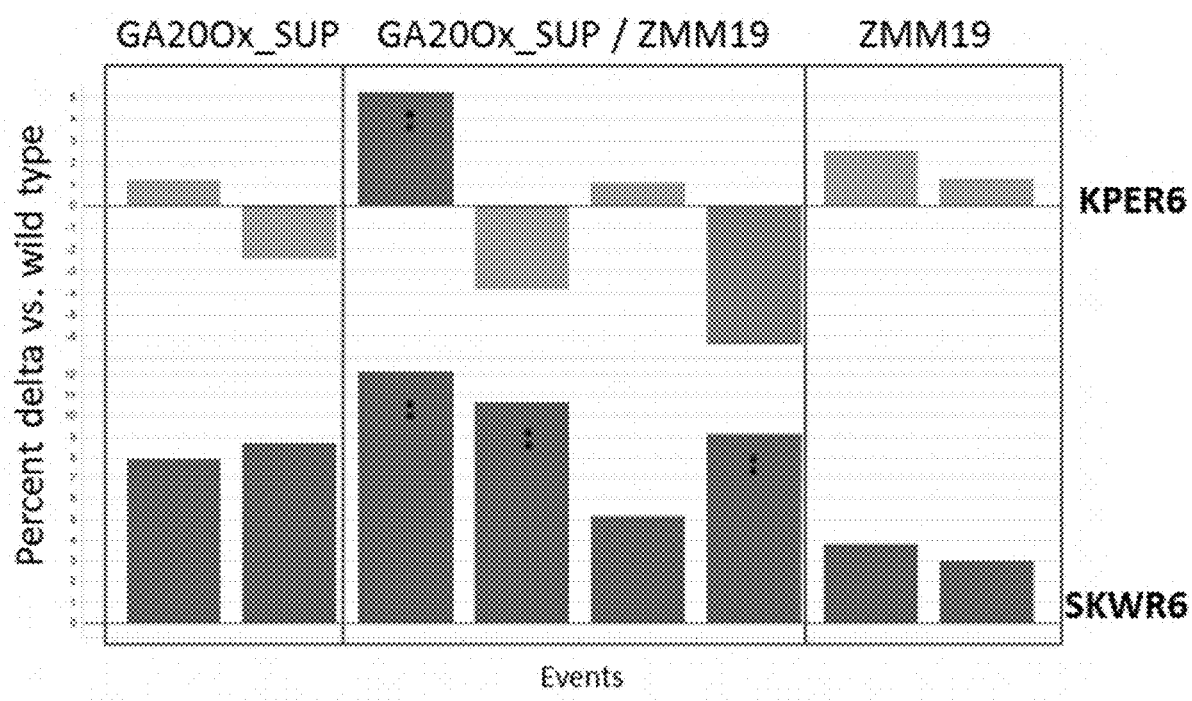

Positive trait interactions with regard to ear traits were observed when both the GA20Ox_SUP and ZMM19 constructs were present in the same plants. As shown in FIG. 4A-4C, ear traits such as ear fresh weight, ear area, ear volume, ear diameter, ear length, kernels per ear, and single kernel weight were measured in two events of GA20OX_SUP single, two events of ZMM19 single, and four event combinations of GA20Ox_SUP/ZMM19 stack plants grown in a single growing season. The definitions for ear area, ear volume, ear diameter, ear length, kernels per ear, and single kernel weight are provided above. Ear fresh weight is measured as the plot average of the weight of a fresh ear at the R6 stage. Each bar in FIG. 4A-4C indicates one transformation event (or stacked event combination). Bars with double asterisks (**) for stacked event combinations indicate a statistically significant change (increase) as compared to both GA20Ox_SUP and ZMM19 single plants.

Results in FIG. 4A-4C show that while GA20Ox_SUP and ZMM19 single events can have moderately improved ear fresh weight, ear area, ear volume, ear diameter, ear length, kernels per ear (KPER6), and/or single kernel weight (SKWR6) relative to control plants, GA20Ox_SUP/ZMM19 stack plants had a statistically significant increase in all seven ear traits relative to control plants. The average increase in all seven ear traits in GA20Ox_SUP/ZMM19 stack plants was numerically greater than that of the ZMM19 and GA20Ox_SUP single plants, with statistically significant increases in these ear traits over one or both of the ZMM19 and GA20Ox_SUP single plants with some events.

Figure 4D:
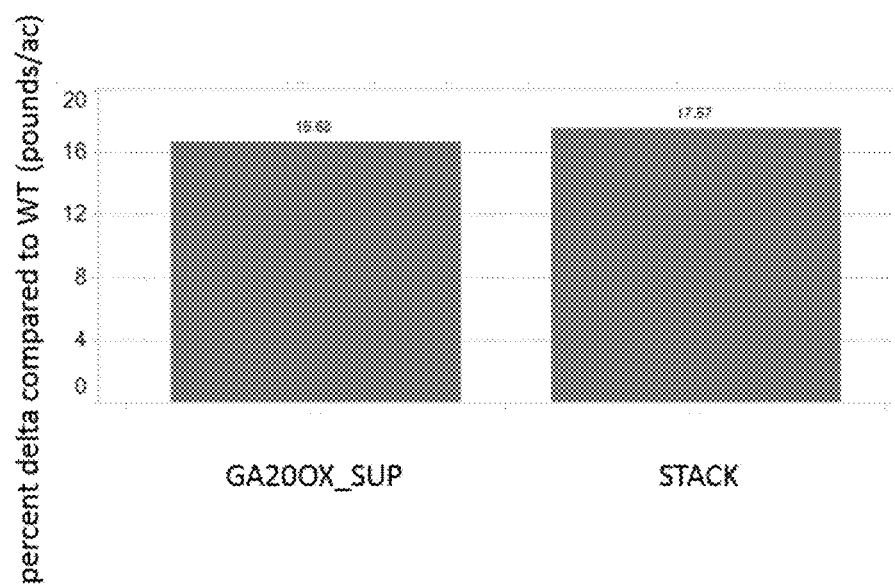
FIG. 4D shows grain yield estimate of GA20Ox_SUP single and GA20Ox_SUP/ZMM19 stack plants, relative to control corn plants.

FIG. 4D shows grain yield estimate as measured for plants grown in a single growing season having one event of the GA20Ox_SUP single, or one event combination for the GA20Ox_SUP/ZMM19 transgene stack, relative to control plants. The data in FIG. 4D is presented as the percentage difference between the grain yield estimate of GA20Ox_SUP single or GA20Ox_SUP/ZMM19 stack plants, relative to wildtype control plants. Dark gray bars indicate statistically significant positive changes (p-value≤0.2). As shown in FIG. 4D, GA20Ox_SUP/ ZMM19 stack plants showed a statistically significant increase in grain yield estimate relative to control plants, with an average increase greater than that of GA20Ox_SUP single plants.

Figure 4E:
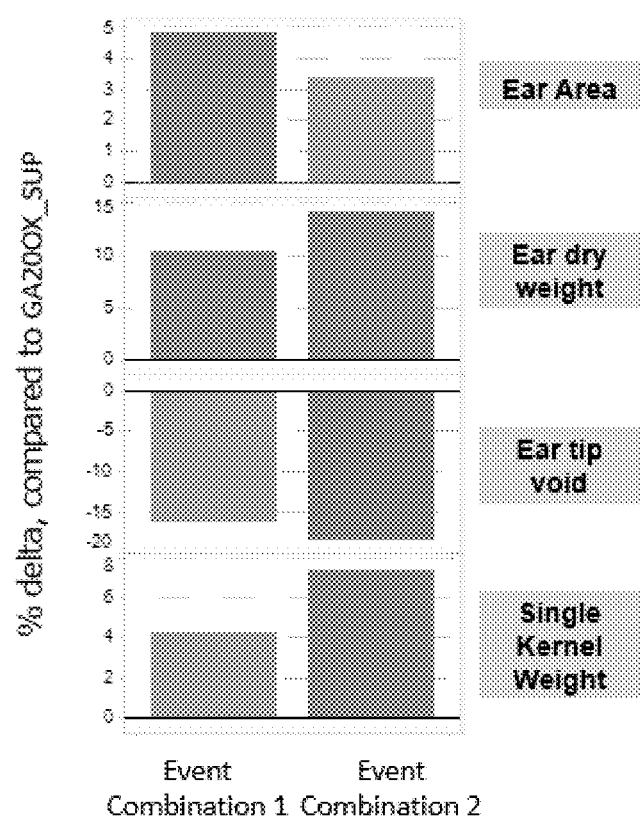
FIG. 4E shows ear area, ear dry weight, ear tip void, and single kernel weight of GA20Ox_SUP/ZMM19 stack plants in a drought reproductive assay, relative to GA20Ox_SUP single plants.

FIG. 4E shows ear area, ear dry weight, ear tip void, and single kernel weight with two event combinations of GA20Ox_SUP/ZMM19 stack plants in a drought reproductive assay in which drought stress was applied from the V8 to R1 developmental stages. The data in FIG. 4E is presented as the percentage difference between each of the above ear traits of GA20Ox_SUP/ZMM19 stack plants and that of GA20Ox_SUP single plants. Dark gray bars indicate statistically significant positive or negative changes (p-value≤0.1), and light gray bars indicate numerically positive or negative changes. As shown in FIG. 4E, GA20Ox_SUP/ZMM19 stack plants showed statistically significant increase in ear area, ear dry weight, and single kernel weight, relative to GA20Ox_SUP single plants. Further, GA20Ox_SUP/ZMM19 stack plants showed statistically significant decrease in ear tip void relative to GA20Ox_SUP single plants.

These results show that GA20Ox_SUP/ZMM19 stack plants have enhanced ear traits, such as ear fresh weight, ear area, ear dry weight, ear tip void, ear volume, ear diameter, ear length, kernels per ear, and single kernel weight, as compared to control plants and ZMM19 and/or GA20Ox_SUP single plants with statistically significant improvement in these traits in GA20Ox_SUP/ZMM19 stack plants depending on the particular event combinations.

Example 5. Increased Yield of GA20Ox_SUP/ZMM19 Stack Plants

Figure 5:
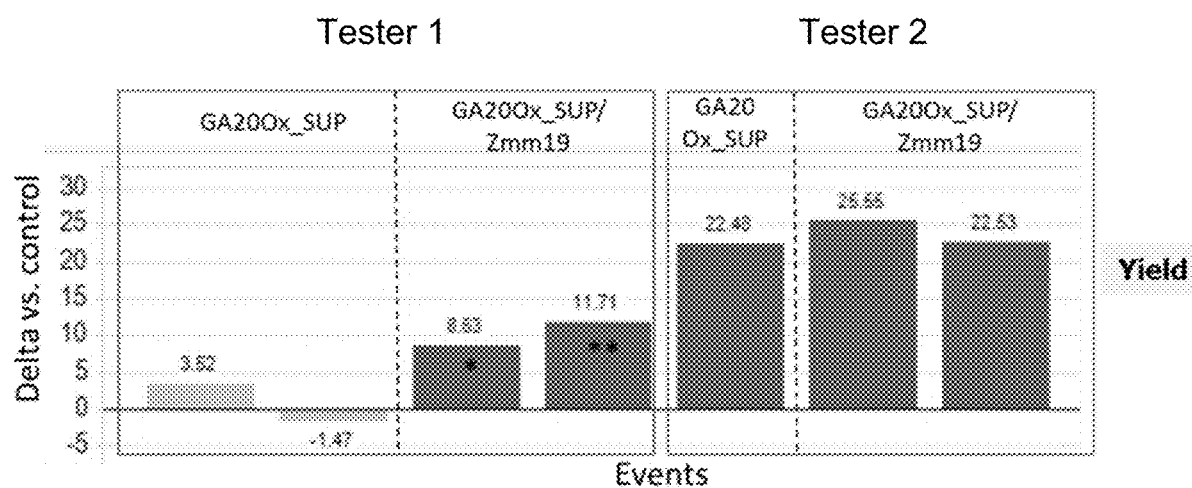
FIG. 5 shows yield of GA20Ox_SUP/ZMM19 stack corn plants and GA20Ox_SUP single corn plants under standard agronomic conditions in the field, relative to control corn plants.

FIG. 5 shows broad acre yield results in a field trial for GA20Ox_SUP single plants and GA20Ox_SUP/ZMM19 stack plants. Results are shown as the difference (delta) in yield (bushels/acre) as compared to control plants. Dark grey bars indicate values significantly different (increased) from control plants (p-value≤0.2). Bars with two asterisks (**) indicate values statistically different (increased) from GA20Ox_SUP single plants (p-value≤0.1), and bars with one asterisk (*) indicate values numerically different (increased) from GA20Ox_SUP single plants.

As shown in FIG. 5, statistically significant increases in yield for GA20Ox_SUP/ZMM19 stack plants were observed relative to control plants, and the average numerical increase was greater than that of GA20Ox_SUP single plants, although the amount of the increase was dependent on the particular corn hybrid germplasm (each box in FIG. 5 represents a different corn hybrid plant cross involving the same female parent but different male testers). Some of these yield results for GA20Ox_SUP/ZMM19 stack plants are surprising given the relatively modest increase in yield in ZMM19 single plants (shown in FIG. 3C above to be about 4.5 bushels per acre or less).

These results suggest that the positive ear traits described above in GA20Ox_SUP/ZMM19 stack plants may cause, or allow for, an increase in yield in GA20Ox_SUP/ZMM19 stack plants over control plants that can be greater than that of GA20Ox_SUP and/or ZMM19 singles.

Example 6. Identification of MADS-Box Gene Homologs

Twenty-five MADS-box homologs were identified from the following species: bread wheat, domesticated barley, Indian rice, Japanese rice, maize, perennial ryegrass, sorghum, and tall fescue. The Zea mays ZMM19 protein sequences were further searched in Genbank® to identify additional MADS-box homologs from various plant species using BlastP (e-value cutoff of 1e-10). Preliminary search results were then filtered to identify those having a full amino acid sequence with a starting methionine and SRF-TF and K-box Pfam domains having at least 70% sequence identity to Zea mays ZMM19 protein. Compiled results of these searches include proteins having amino acid sequences as set forth in SEQ ID NOs: 175-199.

Example 7. Generation of GA20Ox_SUP/ZMM19 Vector Stack Plants Using a Single Vector Constructs and vectors were created via molecular cloning each having an expression cassette comprising a DNA sequence encoding a miRNA that targets the GA20 oxidase_3 and GA20 oxidase_5 genes in corn plants and another expression cassette comprising a DNA sequence encoding a maize ZMM19 polypeptide. Two vectors (Vector 1 and Vector 2) were constructed comprising in order a miRNA-encoding DNA sequence (SEQ ID NO: 39) encoding a miRNA having a targeting sequence (SEQ ID NO: 40) for the GA20 oxidase_3 and GA20 oxidase_5 genes and a gene sequence encoding a maize ZMM19 polypeptide (SEQ ID NO: 169), wherein the two coding sequences are each operably linked to a promoter and a terminator sequence and are separated from each other by an intergenic sequence. A third vector (Vector 3) was constructed comprising in order a gene sequence encoding a maize ZMM19 polypeptide (SEQ ID NO: 169) and a miRNA-encoding DNA sequence (SEQ ID NO: 39) encoding a miRNA having a targeting sequence (SEQ ID NO: 40) for the GA20 oxidase_3 and GA20 oxidase_5 genes, wherein the two coding sequences are each operably linked to a promoter and a terminator sequence and are separated from each other by an intergenic sequence. The order of elements for each expression cassette is as provided above in Example 1.

Corn plants were transformed via Agrobacterium-mediated transformation with one of Vector 1, Vector 2, or Vector 3 to create transgenic corn plants. Transgenic corn plants transformed with Vector 1, Vector 2, or Vector 3 were then crossed as females to different male tester corn lines to create progeny plants comprising both the ZMM19 transgene and the miRNA-encoding DNA sequence for the suppression of the GA20 oxidase_3 and GA20 oxidase_5 genes. The resulting stacked transgenic progeny plants are herein referred to as GA20Ox_SUP/ZMM19 vector stack plants, as opposed to breeding or crossing stack plants where the transgenes are from different parents and are brought together in progeny plants by crossing the parents together.

Example 8. Increased Yield of GA20Ox_SUP/ZMM19 Vector Stack Plants Compared to Control Transgenic corn plants transformed with Vector 1 were crossed as females to two male tester corn lines ("Tester 1" or "Tester 2") to produce progeny GA20Ox_SUP/ZMM19 vector stack plants. Six transformation events were tested for broad acre yield (BAY) with two tester lines.

Figure 6:
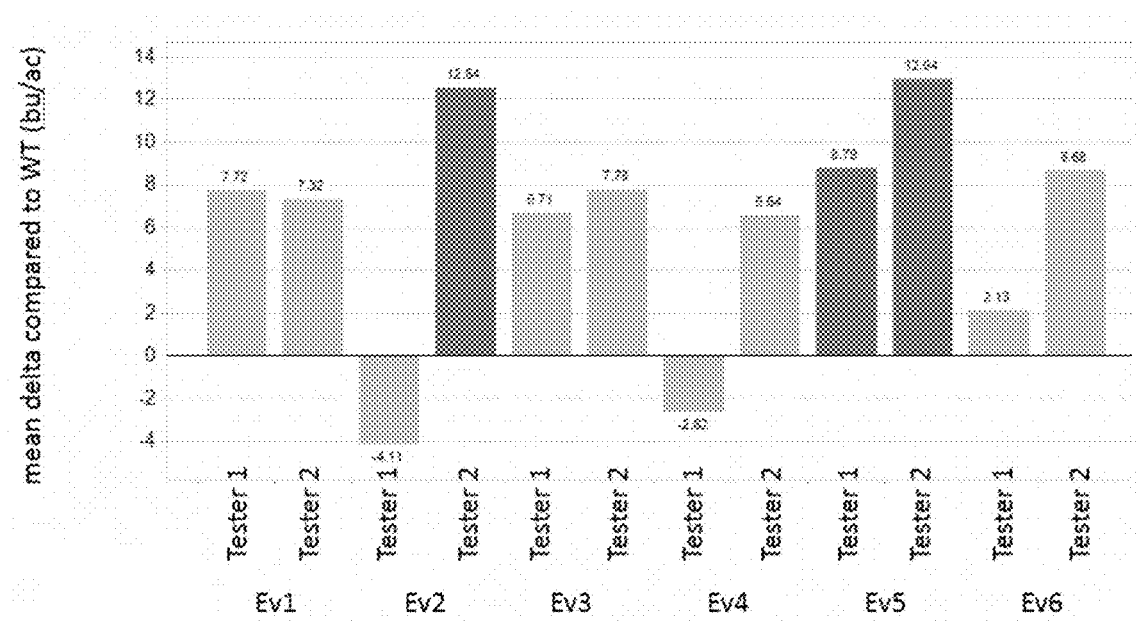
FIG. 6 shows broad acreage yield from six events of GA20Ox_SUP/ZMM19 vector stack plants, relative to control corn plants.

FIG. 6 shows BAY results in one growing season across 15 locations from six events of GA20Ox_SUP/ZMM19 vector stack plants containing a transformation event from Vector 1. BAY results are shown as the mean difference in bushels/acre between GA20Ox_SUP/ZMM19 vector stack plants and wildtype control plants. Each bar in FIG. 6 represents a transformation event. Dark gray bars in FIG. 6 are indicative of statistically significant positive changes (p-value≤0.1), and light gray bars are indicative of numerically positive or negative changes.

As shown in FIG. 6, two out of six events of GA20Ox_SUP/ZMM19 vector stack plants containing a transformation event from Vector 1 showed statistically significant increase in BAY relative to control plants (with at least one of the two testers), with an average increase of about 6 bushels/acre. The other four events of GA20Ox_SUP/ZMM19 vector stack plants containing a transformation event from Vector 1 showed a numerical increase in BAY relative to control plants, although two of these other four events showed a numerical decrease in BAY relative to control plants with one of the two male tester lines.

Figure 7:
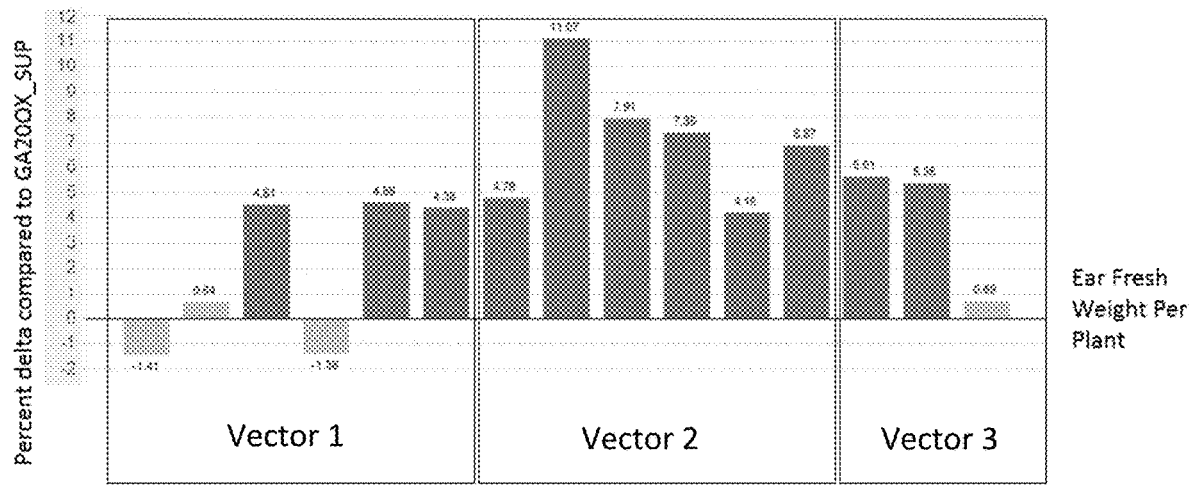
FIG. 7 shows ear fresh weight per plant of GA20Ox_SUP/ZMM19 vector stack plants, relative to GA20Ox_SUP single plants.

Example 9. Increased Ear Fresh Weight of the GA20Ox_SUP/ZMM19 Vector Stack Plants Compared to GA20Ox_SUP Single FIG. 7 shows ear fresh weight per plant for plants containing one of six events of the GA20Ox_SUP/ZMM19 vector stack made using Vector 1, one of six events of GA20Ox_SUP/ZMM19 vector stack made using Vector 2, or one of three events of GA20Ox_SUP/ZMM19 vector stack made using Vector 3. Results are shown as the percentage difference in ear fresh weight per plant between GA20Ox_SUP/ZMM19 vector stack plants and that of GA20Ox_SUP single plants. Each bar in FIG. 7 represents a single vector stack transformation event. Dark gray bars in FIG. 7 are indicative of statistically significant positive changes (p-value≤0.1), and light gray bars are indicative of numerically positive or negative changes.

As shown in the left panel of FIG. 7, plants containing one of three events of GA20Ox_SUP/ZMM19 vector stack made using Vector 1 showed a statistically significant increase in ear fresh weight per plant relative to GA20Ox_SUP single plants, and plants containing another event of GA20Ox_SUP/ZMM19 vector stack made from Vector 1 showed a numerical increase in ear fresh weight per plant relative to GA20Ox_SUP single plants, although plants containing one of two other events from Vector 1 showed a numerical (but not statistically significant) decrease in ear fresh weight per plant relative to GA20Ox_SUP single plants.

As shown in the middle panel of FIG. 7, plants containing any one of the six events of GA20Ox_SUP/ZMM19 vector stack from Vector 2 showed a statistically significant increase in ear fresh weight per plant relative to GA20Ox_SUP single plants.

As shown in the right panel of FIG. 7, plants containing one of two events of GA20Ox_SUP/ZMM19 vector stack plants made using Vector 3 showed a statistically significant increase in ear fresh weight per plant relative to GA20Ox_SUP single plants, and the other event of the GA20Ox_SUP/ZMM19 vector stack made from Vector 3 showed a numerical increase in ear fresh weight per plant relative to GA20Ox_SUP single plants.

Figure 8:
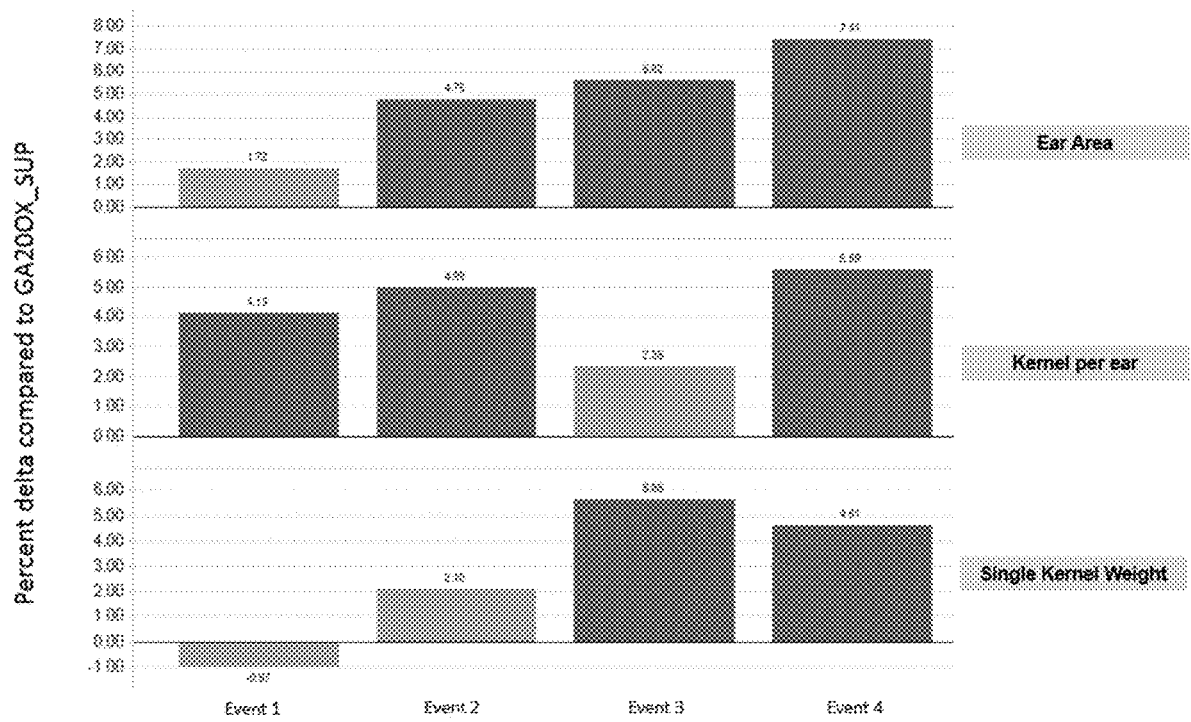
FIG. 8 shows ear area, kernels per ear, and single kernel weight of GA20Ox_SUP/ZMM19 vector stack plants, relative to GA20Ox_SUP single plants.

Example 10. Increased Ear Traits of the GA20Ox_SUP/ZMM19 Vector Stack Plants Compared to GA20Ox_SUP Single FIG. 8 shows ear area, kernels per ear, and single kernel weight traits, as measured with GA20Ox_SUP/ZMM19 vector stack plants containing one of four transformation events made using Vector 1 described above. Results are shown as the percentage difference between the ear area, kernels per ear, or single kernel weight of GA20Ox_SUP/ZMM19 vector stack plants and that of GA20Ox_SUP single plants. Each bar in FIG. 8 represents a single vector stack transformation event. Dark gray bars in FIG. 8 are indicative of statistically significant positive changes (p-value≤0.1), and light gray bars are indicative of numerically positive or negative changes.

As shown in the top panel of FIG. 8, plants containing one of three events of the GA20Ox_SUP/ZMM19 vector stack from Vector 1 showed a statistically significant increase in ear area relative to GA20Ox_SUP single plants, and plants containing the other event of the GA20Ox_SUP/ZMM19 vector stack from Vector 1 showed a numerical increase in ear area relative to GA20Ox_SUP single plants.

As shown in the middle panel of FIG. 8, plants containing one of three events of the GA20Ox_SUP/ZMM19 vector stack from Vector 1 showed a statistically significant increase in kernels per ear relative to GA20Ox_SUP single plants, and plants containing the other event of the GA20Ox_SUP/ZMM19 vector stack from Vector 1 showed a numerical increase in kernels per ear relative to GA20Ox_SUP single plants.

As shown in the bottom panel of FIG. 8, plants containing one of two (out of four) events of the GA20Ox_SUP/ZMM19 vector stack made from Vector 1 showed a statistically significant increase in single kernel weight relative to GA20Ox_SUP single plants, whereas one of the other events of the GA20Ox_SUP/ZMM19 vector stack made using Vector 1 showed a numerical increase in single kernel weight relative to GA20Ox_SUP single plants, and another event of the GA20Ox_SUP/ZMM19 vector stack made using Vector 1 showed a numerical decrease in single kernel weight relative to GA20Ox_SUP single plants.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples.

The invention claimed is:

1. A transgenic corn plant or a plant part thereof comprising (i) a first recombinant expression cassette comprising a first heterologous plant-expressible promoter operably linked to a transcribable DNA sequence encoding a non-coding RNA for suppression of one or more gibberellic acid 20 (GA20) oxidase genes, and ii) a second recombinant expression cassette comprising a DNA sequence encoding a MADS-box polypeptide having at least 95% amino acid sequence identity to the amino acid sequence as set forth in SEQ ID NO: 168; wherein the non-coding RNA comprises a targeting sequence that is (a) at least 95% complementary to at least 19 consecutive nucleotides of a first mRNA molecule encoding a first endogenous GA20 oxidase protein that has at least 95% amino acid sequence identity to the amino acid sequence as set forth in SEQ ID NO: 9, and (b) at least 95% complementary to at least 19 consecutive nucleotides of a second mRNA molecule encoding a second endogenous GA20 oxidase protein that has at least 95% amino acid sequence identity to the amino acid sequence as set forth in SEQ ID NO: 15; and wherein expression of said non-coding RNA and said MADS-box polypeptide in said transgenic corn plant results in a semi-dwarf phenotype, and an increase in one or more improved ear trait selected from the group consisting of ear diameter, single kernel weight, ear fresh weight, ear area, ear volume, ear length, kernels per ear, yield, grain yield estimate, broad acreage yield, ear dry weight, and ear tip void, as compared to a control wild-type corn plant grown under comparable conditions.

2. The transgenic corn plant or plant part thereof of claim 1, wherein the transcribable DNA sequence encoding said non-coding RNA comprises a nucleotide sequence that is 100% identical or complementary to at least 15 consecutive nucleotides of SEQ ID NO: 39.

3. The transgenic corn plant or plant part thereof of claim 1, wherein the MADS-box polypeptide comprises the amino acid sequence as set forth in SEQ ID NOs: 168.

4. The transgenic corn plant or plant part thereof of claim 1, wherein the DNA sequence encoding said MADS-box polypeptide comprises a nucleotide sequence that is at least 90% identical to the nucleotide sequence as set forth in SEQ ID NO: 169.

5. The transgenic corn plant or plant part thereof of claim 1, wherein the DNA sequence comprised in the second recombinant expression cassette is operably linked to a second heterologous plant-expressible promoter.

6. The transgenic corn plant or plant part thereof of claim 1, wherein the first heterologous plant-expressible promoter is selected from the group consisting of a vascular promoter a leaf promoter and a constitutive promoter.

7. The transgenic corn plant or plant part thereof of claim 6, wherein the first heterologous plant-expressible promoter is said vascular promoter selected from the group consisting of a sucrose synthase promoter, a sucrose transporter promoter, a sucrose synthase-1 (Sh 1) promoter, a *Commelina* yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, and a rice yellow stripe 2 (OsYSL2) promoter.

8. The transgenic corn plant or plant part thereof of claim 6, wherein the first heterologous plant-expressible promoter is said leaf promoter selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter and a Myb gene promoter.

9. The transgenic corn plant or plant part thereof of claim 6, wherein the first heterologous plant-expressible promoter is said constitutive promoter selected from the group consisting of an actin promoter, a Cauliflower mosaic virus (CaMV) 35S promoter, a CaMV 19S promoter, a plant ubiquitin promoter, a plant Gos2 promoter, a Figwort mosaic virus (FMV) promoter, a cytomegalovirus (CMV) promoter, a *mirabilis* mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, and a maize alcohol dehydrogenase.

10. The transgenic corn plant or plant part thereof of claim 1, wherein the first heterologous plant-expressible promoter is a rice tungro baciliform virus (RTBV) promoter.

11. The transgenic corn plant or plant part thereof of claim 10, wherein the RTBV promoter comprises a DNA sequence that is at least 95% identical to the nucleotide sequence as set forth in SEQ ID NO: 65 or SEQ ID NO: 66.

12. The transgenic corn plant or plant part thereof of claim 5, wherein the second heterologous plant-expressible promoter is selected from the group consisting of a root-specific promoter, a meristem promoter, a seed or kernel promoter, and a constitutive promoter.

13. The transgenic corn plant or plant part thereof of claim 12, wherein the second heterologous plant-expressible promoter is said root-specific promoter comprising a DNA sequence that is at least 95% identical to the nucleotide sequence as set forth in SEQ ID NO: 170.

14. The transgenic corn plant or plant part thereof of claim 5, wherein the second heterologous plant-expressible promoter comprises an Rcc3 gene promoter.

15. The transgenic corn plant or plant part thereof of claim 12, wherein the second heterologous plant-expressible promoter is said constitutive promoter selected from the group consisting of an actin promoter, a Cauliflower mosaic virus (CaMV) 35S promoter, a CaMV 19S promoter, a plant ubiquitin promoter, a plant Gos2 promoter, a Figwort mosaic virus (FMV) promoter, a cytomegalovirus (CMV) promoter, a *mirabilis* mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, and a maize alcohol dehydrogenase.

16. A transgenic corn seed or a part thereof of the transgenic corn plant of claim 1, wherein the transgenic corn seed comprises the first and second recombinant expression cassettes.

17. A commodity product produced from the transgenic corn plant or a part thereof of claim 1, wherein the commodity product comprises the first and second recombinant expression cassettes.

18. A recombinant DNA construct comprising (i) a first expression cassette comprising a first heterologous plant-expressible promoter operably linked to a transcribable DNA sequence encoding a non-coding RNA for suppression of one or more GA20 oxidase genes, and (ii) a second expression cassette comprising a second heterologous plant-expressible promoter operably to a DNA sequence encoding a MADS-box polypeptide having at least 95% amino acid sequence identity to the amino acid sequence as set forth in SEQ ID NO: 168; wherein the non-coding RNA comprises a targeting sequence that is (a) at least 95% complementary to at least 19 consecutive nucleotides of a first mRNA molecule encoding a first endogenous GA20 oxidase protein that has at least 95% amino acid sequence identity to the amino acid sequence as set forth in SEQ ID NO: 9, and (b) at least 95% complementary to at least 19 consecutive nucleotides of a second mRNA molecule encoding a second endogenous GA20 oxidase protein that has at least 95% amino acid sequence identity to the amino acid sequence as set forth in SEQ ID NO: 15; and wherein expression of said non-coding RNA and said MADS-box polypeptide in a corn plant results in a semi-dwarf phenotype, and an increase in one or more improved ear trait selected from the group consisting of ear diameter, single kernel weight, ear fresh weight, ear area, ear volume, ear length, kernels per ear, yield, grain yield estimate, broad acreage yield, ear dry weight, and ear tip void, as compared to a control wild-type corn plant grown under comparable conditions.

19. The recombinant DNA construct of claim 18, wherein the transcribable DNA sequence encoding said non-coding RNA comprises a nucleotide sequence that is 100% identical or complementary to at least 15 consecutive nucleotides of one or more of SEQ ID NO: 39.

20. The recombinant DNA construct of claim 18, wherein the MADS-box polypeptide comprises the amino acid sequence as set forth in SEQ ID NOs: 168.

21. The recombinant DNA construct of claim 18, wherein the DNA sequence encoding said MADS-box polypeptide comprises a nucleotide sequence that is at least 90% identical to the nucleotide sequence as set forth in SEQ ID NO: 169.

22. The recombinant DNA construct of claim 18, wherein the first heterologous plant-expressible promoter is selected from the group consisting of a vascular promoter, a leaf promoter, and a constitutive promoter.

23. The recombinant DNA construct of claim 22, wherein the first heterologous plant-expressible promoter is said vascular promoter selected from the group consisting of a sucrose synthase promoter, a sucrose transporter promoter, a sucrose synthase-1 (Sh 1) promoter, a *Commelina* yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, and a rice yellow stripe 2 (OsYSL2) promoter.

24. The recombinant DNA construct of claim 22, wherein the first heterologous plant-expressible promoter is said leaf promoter selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, and a Myb gene promoter.

25. The recombinant DNA construct of claim 22, wherein the first heterologous plant-expressible promoter is said constitutive promoter selected from the group consisting of an actin promoter, a Cauliflower mosaic virus (CaMV) 35S promoter, a CaMV 19S promoter, a plant ubiquitin promoter, a plant Gos2 promoter, a Figwort mosaic virus (FMV) promoter, a cytomegalovirus (CMV) promoter, a *mirabilis* mosaic virus (MMV) promoter, a peanut chlorotic streak caulimovirus (PCLSV) promoter, an Emu 9 promoter, a tubulin promoter, a nopaline synthase promoter, an octopine synthase promoter, a mannopine synthase promoter, and a maize alcohol dehydrogenase.

26. The recombinant DNA construct of claim 18, wherein the first heterologous plant-expressible promoter is a rice tungro bacilliform virus (RTBV) promoter.

27. The recombinant DNA construct of claim 18, wherein the RTBV promoter comprises a DNA sequence that is at least 95% identical to the nucleotide sequence as set forth in SEQ ID NO: 65 or SEQ ID NO: 66.

28. The recombinant DNA construct of claim 18, wherein the second heterologous plant-expressible promoter is selected from the group consisting of a root-specific promoter, a meristem promoter, a seed or kernel promoter, and a constitutive promoter.

29. The recombinant DNA construct of claim 28, wherein the second heterologous plant-expressible promoter is said root-specific promoter comprising a DNA sequence that is at least 95% identical to the nucleotide sequence as set forth in SEQ ID NO: 170.

30. The recombinant DNA construct of claim 18, wherein the second heterologous plant-expressible promoter comprises an Rcc3 gene promoter.

31. The recombinant DNA construct of claim 28, wherein the second heterologous plant-expressible promoter is said constitutive promoter selected from the group consisting of an actin promoter, a Cauliflower mosaic virus (CaMV) 35S promoter, a CaMV 19S promoter, a plant ubiquitin promoter, a plant Gos2 promoter, a Figwort mosaic virus (FMV) promoter, a cytomegalovirus (CMV) promoter, a *mirabilis* mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, and a maize alcohol dehydrogenase.

32. The transgenic corn plant or plant part thereof of claim 1, wherein the first heterologous plant-expressible promoter is a vascular promoter.

33. The transgenic corn plant or plant part thereof of claim 1, wherein the first heterologous plant-expressible promoter is a leaf promoter.

34. The transgenic corn plant or plant part thereof of claim 1, wherein the first heterologous plant-expressible promoter is a constitutive promoter.

35. The transgenic corn plant or plant part thereof of claim 5, wherein the second heterologous plant-expressible promoter is a root-specific promoter.

36. The transgenic corn plant or plant part thereof of claim 5, wherein the second heterologous plant-expressible promoter is a meristem promoter.

37. The transgenic corn plant or plant part thereof of claim 5, wherein the second heterologous plant-expressible promoter is a seed or kernel promoter.

38. The transgenic corn plant or plant part thereof of claim 5, wherein the second heterologous plant-expressible promoter is a constitutive promoter.

39. The transgenic corn plant or plant part thereof of claim 5, wherein the first heterologous plant-expressible promoter is a vascular promoter, and the second heterologous plant-expressible promoter is a root promoter.

* * * * *

SEQUENCE LISTING

```
<160> NUMBER OF SEQ ID NOS: 217

<210> SEQ ID NO 1
<211> LENGTH: 1741
<212> TYPE: DNA
<213> ORGANISM: Zea mays

<400> SEQUENCE: 1
gacggtagtt ttcatctaaa gtttattctt cgtcacatgg gatggccgtt tgcttgtttg      60
ttgcttccgg gaggcggtgg tgaattgaag cagatcgaca agcatggctg cccactggtc     120
```

-continued

```
tcgatcgatc ggcctgccat gccatgccat gccactagag tccgtcctga ctggccgccc      180
gttcccccgt ataaaaaggc aggcaggcag gcagagcggg gacgagcaag caagcagttg      240
cagttgcagc ggcctcctcc tctgcttcct ccctcctcct cctcaccatg gtgctggctg      300
cgcacgatcc ccctcccctt gtgttcgacg ctgcccgcct gagcggcctc tccgacatcc      360
cgcagcagtt catctggccg gcggacgaga gccccacccc ggactccgcc gaggagctgg      420
ccgtgccgct catcgacctc tccggggacg ccgccgaggt ggtccggcag gtccggcgcg      480
cctgcgacct gcacggcttc ttccaggtgg tgggcacgg catcgacgcg cgcgctgacgg      540
cggaggccca ccgctgcatg gacgccttct tcacgctgcc gctcccggac aagcagcgcg      600
cgcagcgccg ccaggggac agctgcggct acgccagcag cttcacgggc cggttcgcgt      660
ccaagctgcc ctggaaggag acgctgtcgt tccgctacac cgacgacgac gacggcgaca      720
agtccaagga cgtcgtggcg tcctacttcg tggacaagct gggcgagggg taccggcacc      780
acggggaggt gtacgggcgc tactgctctg agatgagccg tctgtcgctg agctcatgg      840
aggtgctagg cgagagcctg ggcgtgggcc ggcgccactt ccggcgcttc ttccagggga      900
acgactccat catgcgcctc aactactacc cgccgtgcca gcggccctac gacacgctgg      960
gcacggggcc gcattgcgac cccacgtcgc tcaccatcct gcaccaggac gacgtgggcg     1020
gactccaggt gttcgacgcc gccacgctcg cgtggcgctc catcaggccc cgcccgggcg     1080
ccttcgtcgt caacatcggc gacaccttca tggcgctctc caacgggcgc tacaggagct     1140
gcctccaccg cgccgtcgtc aacagccggg tggcacgccg ctcgctcgcc ttcttcctgt     1200
gccccggagat ggacaaggtg gtcaggccgc ccaaggagct ggtggacgac gccaacccga     1260
gggcgtaccc ggacttcacg tggaggacgc tgctggactt caccatgagg cactacaggt     1320
cggacatgag gacgctcgag gccttctcca actggctcag caccagtagc aatggcggac     1380
agcacctgct ggagaagaag taggcatgct atttgggtat ggaagatggt ggatgtaagc     1440
aaacaaagcc aaattaagca gagtaggtta attaaggttg gctgatgatc catttaggga     1500
aggagctgat ctccctgact ccctcctcca attttctcaa ccaaatttat atagtataat     1560
aataataata aaatagcaag taatagttgt atcgtattat tattaattaa tttattagct     1620
ggtaggcaag tagtattaaa taccatttgt agtacgatgg gcgtatttct attttggcgt     1680
tttgctctgt gttttttgac gttcctttg gatttggggg gacctcagat cagctcggcc     1740
t                                                                     1741
```

<210> SEQ ID NO 2
<211> LENGTH: 1116
<212> TYPE: DNA
<213> ORGANISM: Zea mays

<400> SEQUENCE: 2

```
atggtgctgg ctgcgcacga tccccctccc cttgtgttcg acgctgcccg cctgagcggc       60
ctctccgaca tcccgcagca gttcatctgg ccggcggacg agagccccac cccggactcc      120
gccgaggagc tggccgtgcc gctcatcgac ctctccgggg acgccgccga ggtggtccgg      180
caggtccggc gcgcctgcga cctgcacggc ttcttccagg tggtgggca ggcatcgac       240
gcggcgctga cggcggaggc ccaccgctgc atggacgcct tcttcacgct gccgctcccg      300
gacaagcagc gcgcgcagcg ccgccagggg gacagctgcg gctacgccag cagcttcacg      360
ggccggttcg cgtccaagct gccctggaag gagacgctgt cgttccgcta caccgacgac      420
gacgacggcg acaagtccaa ggacgtcgtg gcgtcctact tcgtggacaa gctgggcgag      480
```

-continued

```
gggtaccggc accacgggga ggtgtacggg cgctactgct ctgagatgag ccgtctgtcg    540
ctggagctca tggaggtgct aggcgagagc ctgggcgtgg gccggcgcca cttccggcgc    600
ttcttccagg ggaacgactc catcatgcgc ctcaactact acccgccgtg ccagcggccc    660
tacgacacgt gggcacgggc cgcattgc gaccccacgt cgctcaccat cctgcaccag     720
gacgacgtgg gcggactcca ggtgttcgac gccgccacgc tcgcgtggcg ctccatcagg    780
ccccgcccgg gcgccttcgt cgtcaacatc ggcgacacct tcatggcgct ctccaacggg    840
cgctacagga gctgcctcca ccgcgccgtc gtcaacagcc gggtggcacg ccgctcgctc    900
gccttcttcc tgtgcccgga gatggacaag gtggtcaggc cgcccaagga gctggtggac    960
gacgccaacc cgagggcgta cccggacttc acgtggagga cgctgctgga cttcaccatg   1020
aggcactaca ggtcggacat gaggacgctc gaggccttct ccaactggct cagcaccagt   1080
agcaatggcg gacagcacct gctggagaag aagtag                             1116
```

<210> SEQ ID NO 3
<211> LENGTH: 371
<212> TYPE: PRT
<213> ORGANISM: Zea mays

<400> SEQUENCE: 3

```
Met Val Leu Ala Ala His Asp Pro Pro Leu Val Phe Asp Ala Ala
1               5                  10                 15

Arg Leu Ser Gly Leu Ser Asp Ile Pro Gln Gln Phe Ile Trp Pro Ala
            20                  25                  30

Asp Glu Ser Pro Thr Pro Asp Ser Ala Glu Glu Leu Ala Val Pro Leu
        35                  40                  45

Ile Asp Leu Ser Gly Asp Ala Ala Glu Val Val Arg Gln Val Arg Arg
    50                  55                  60

Ala Cys Asp Leu His Gly Phe Phe Gln Val Val Gly His Gly Ile Asp
65                  70                  75                  80

Ala Ala Leu Thr Ala Glu Ala His Arg Cys Met Asp Ala Phe Phe Thr
                85                  90                  95

Leu Pro Leu Pro Asp Lys Gln Arg Ala Gln Arg Arg Gln Gly Asp Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Tyr Thr Asp Asp Asp Gly Asp
    130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
            180                 185                 190

Val Gly Arg Arg His Phe Arg Phe Phe Gln Gly Asn Asp Ser Ile
        195                 200                 205

Met Arg Leu Asn Tyr Tyr Pro Pro Cys Gln Arg Pro Tyr Asp Thr Leu
    210                 215                 220

Gly Thr Gly Pro His Cys Asp Pro Thr Ser Leu Thr Ile Leu His Gln
225                 230                 235                 240

Asp Asp Val Gly Gly Leu Gln Val Phe Asp Ala Ala Thr Leu Ala Trp
                245                 250                 255
```

```
Arg Ser Ile Arg Pro Arg Pro Gly Ala Phe Val Val Asn Ile Gly Asp
            260                 265                 270

Thr Phe Met Ala Leu Ser Asn Gly Arg Tyr Arg Ser Cys Leu His Arg
        275                 280                 285

Ala Val Val Asn Ser Arg Val Ala Arg Arg Ser Leu Ala Phe Phe Leu
    290                 295                 300

Cys Pro Glu Met Asp Lys Val Val Arg Pro Lys Glu Leu Val Asp
305                 310                 315                 320

Asp Ala Asn Pro Arg Ala Tyr Pro Asp Phe Thr Trp Arg Thr Leu Leu
                325                 330                 335

Asp Phe Thr Met Arg His Tyr Arg Ser Asp Met Arg Thr Leu Glu Ala
            340                 345                 350

Phe Ser Asn Trp Leu Ser Thr Ser Ser Asn Gly Gly Gln His Leu Leu
        355                 360                 365

Glu Lys Lys
    370

<210> SEQ ID NO 4
<211> LENGTH: 1517
<212> TYPE: DNA
<213> ORGANISM: Zea mays

<400> SEQUENCE: 4
caggaataaa ataagcctcc gcccggcttc gttgcatcca cgcacgcagc aagcgatcgg      60
atttcgccag catggcggcg gcggccgtgg tgttcgacgc cgaggcgctg agccgggagg     120
agcacatccc ggcgcagttc gtgtggccca ccgaggagcg ggcgccggcg gcggcgtgg      180 aggaggtcgc catccccgtg gtcgacctcg gcgagttcct ccgccgcggg gtgctcccgc     240
gcggcgtggc ggaggcgtgc gagcgccacg cgtcttcca ggtggtgaac cacggcgtgg      300
gcgccgcgct gctcgccgag gcctaccgct gttgcgacgc cttttacgcg ctcccgctcg     360
cggacaagca gcgcgcgcag cgccggcacg gggagaacca cggctacgcc agcagcttca     420
cgggccgctt ccactgctgc ctgccgtgga aggagacgct gtccttcaac tgccccgccg     480
gtgccgggac tgcgcgcgcc gtcgtcggct acttcgtcga cgtcctcggc gaggactacc     540
gccacatggg ggaggtgtac caggagtact gcgacgcgat gacgcgtctg gcgctggacg     600
tgacggaggt gctggcggca gcgctggggc tggaccgcgg cgcactgcgc ggcttcttcg     660
agggcggcga ctccgtcatg cggctgaacc actacccggc gtgccggcag ccgcacctga     720
cgctggggac gggcccgcac cgggacccga cgtcgctgac gctgctgcac caggacgacg     780
tgggcgggct gcaggtgcgc gccggcggcg ggccgtggcg cgcggtgcgg ccccgcgcgg     840
acgcgttcgt ggtcaacatt ggcgacacct tcgccgcgct caccgacggg cgtcacacca     900
gctgcctgca ccgcgccgtg gtgaccggcg gcggctcccg ccggtcgctc gccttcttcc     960
tcaacccgcc gctggaccgc gtcgtccgcc cgccgggcgc gctcctccag gagaacaagc    1020
aggcgggccg cccgcgcgcg ttcccggact tcacgtggcg cgagttcctc gagttcacgc    1080
agaagcacta ccggtcggac gcgggcacca tggacgcctt cgtgtcgtgg atcgcgggag    1140
gccgccgcca ccatggcgga caggaggagg gcaactgaga tcgatgcatc tctagctgta    1200
ggcagcagcg cagcagctac caagaataat ggccggcgac ggagatgcag ctacgacgca    1260
caaataaatt gagtgtttgt ggtacaataa ggacgaggac gatcaatggc gacctgtaac    1320
cggtgcagtt ttagttaatc tttcatggcg atatggcatt aaccaatcgt tggtgtaaaa    1380
tgcgtgcatg ctttgcatgc caatgttggc catgtgatgg cacagcgtga gtgtagctca    1440
```

```
cccaccgtga caacgtgcta atttcgtgtg gtcctagata ccaaggtcgt ctaatgaact   1500
tgatggattg atgattt                                                  1517

<210> SEQ ID NO 5
<211> LENGTH: 1107
<212> TYPE: DNA
<213> ORGANISM: Zea mays

<400> SEQUENCE: 5
atggcggcgg cggccgtggt gttcgacgcc gaggcgctga gccggagga gcacatcccg     60 gcgcagttcg tgtggcccac cgaggagcgg gcgccggcgg gcggcgtgga ggaggtcgcc   120
atccccgtgg tcgacctcgg cgagttcctc cgccgcgggg tgctcccgcg cggcgtggcg   180
gaggcgtgcg agcgccacgg cgtcttccag gtggtgaacc acggcgtggg cgccgcgctg   240
ctcgccgagg cctaccgctg ttgcgacgcc ttttacgcgc tcccgctcgc ggacaagcag   300
cgcgcgcagc gccggcacgg ggagaaccac ggctacgcca gcagcttcac gggccgcttc   360
cactgctgcc tgccgtggaa ggagacgctg tccttcaact gccccgccgg tgccgggact   420
gcgcgcgccc tcgtcggcta cttcgtcgac gtcctcggcg aggactaccg ccacatgggg   480
gaggtgtacc aggagtactg cgacgcgatg acgcgtctgg cgctggacgt gacggaggtg   540
ctggcggcag cgctggggct ggaccgcggc gcactgcgcg gcttcttcga gggcggcgac   600
tccgtcatgc ggctgaacca ctacccggcg tgccggcagc cgcacctgac gctggggacg   660
ggcccgcacc gggaccccga cgtcgctgacg ctgctgcacc aggacgacgt gggcgggctg   720
caggtgcgcg ccggcggcgg gccgtggcgc gcggtgcggc cccgcgcgga cgcgttcgtg   780
gtcaacattg gcgacacctt cgccgcgctc accgacgggc gtcacaccag ctgcctgcac   840
cgcgccgtgg tgaccggcgg cggctcccgc cggtcgctcg ccttcttcct caacccgccg   900
ctggaccgcg tcgtccgccc gccgggcgcg ctcctccagg agaacaagca ggcgggccgc   960
ccgcgcgcgt tcccggactt cacgtggcgc gagttcctcg agttcacgca gaagcactac  1020
cggtcggacg cgggcaccat ggacgccttc gtgtcgtgga tcgcgggagg ccgccgccac  1080
catggcggac aggaggaggg caactga                                      1107

<210> SEQ ID NO 6
<211> LENGTH: 368
<212> TYPE: PRT
<213> ORGANISM: Zea mays

<400> SEQUENCE: 6

Met Ala Ala Ala Ala Val Val Phe Asp Ala Glu Ala Leu Ser Arg Glu
1               5                   10                  15

Glu His Ile Pro Ala Gln Phe Val Trp Pro Thr Glu Glu Arg Ala Pro
                20                  25                  30

Ala Gly Gly Val Glu Glu Val Ala Ile Pro Val Val Asp Leu Gly Glu
            35                  40                  45

Phe Leu Arg Arg Gly Val Leu Pro Arg Gly Val Ala Glu Ala Cys Glu
        50                  55                  60

Arg His Gly Val Phe Gln Val Val Asn His Gly Val Gly Ala Ala Leu
    65                  70                  75                  80

Leu Ala Glu Ala Tyr Arg Cys Cys Asp Ala Phe Tyr Ala Leu Pro Leu
                85                  90                  95

Ala Asp Lys Gln Arg Ala Gln Arg Arg His Gly Glu Asn His Gly Tyr
                100                 105                 110
```

Ala Ser Ser Phe Thr Gly Arg Phe His Cys Cys Leu Pro Trp Lys Glu
        115                 120                 125

Thr Leu Ser Phe Asn Cys Pro Ala Gly Ala Gly Thr Ala Arg Ala Val
    130                 135                 140

Val Gly Tyr Phe Val Asp Val Leu Gly Glu Asp Tyr Arg His Met Gly
145                 150                 155                 160

Glu Val Tyr Gln Glu Tyr Cys Asp Ala Met Thr Arg Leu Ala Leu Asp
                165                 170                 175

Val Thr Glu Val Leu Ala Ala Leu Gly Leu Asp Arg Gly Ala Leu
            180                 185                 190

Arg Gly Phe Phe Glu Gly Gly Asp Ser Val Met Arg Leu Asn His Tyr
            195                 200                 205

Pro Ala Cys Arg Gln Pro His Leu Thr Leu Gly Thr Gly Pro His Arg
    210                 215                 220

Asp Pro Thr Ser Leu Thr Leu Leu His Gln Asp Val Gly Gly Leu
225                 230                 235                 240

Gln Val Arg Ala Gly Gly Pro Trp Arg Ala Val Arg Pro Arg Ala
                245                 250                 255

Asp Ala Phe Val Val Asn Ile Gly Asp Thr Phe Ala Ala Leu Thr Asp
            260                 265                 270

Gly Arg His Thr Ser Cys Leu His Arg Ala Val Val Thr Gly Gly Gly
            275                 280                 285

Ser Arg Arg Ser Leu Ala Phe Phe Leu Asn Pro Pro Leu Asp Arg Val
    290                 295                 300

Val Arg Pro Pro Gly Ala Leu Leu Gln Glu Asn Lys Gln Ala Gly Arg
305                 310                 315                 320

Pro Arg Ala Phe Pro Asp Phe Thr Trp Arg Glu Phe Leu Glu Phe Thr
                325                 330                 335

Gln Lys His Tyr Arg Ser Asp Ala Gly Thr Met Asp Ala Phe Val Ser
            340                 345                 350

Trp Ile Ala Gly Gly Arg Arg His Gly Gly Gln Glu Glu Gly Asn
        355                 360                 365

<210> SEQ ID NO 7
<211> LENGTH: 1522
<212> TYPE: DNA
<213> ORGANISM: Zea mays

<400> SEQUENCE: 7
gcacactcgc agctcgcaca tctcatggtg tcctaagaac ggcaagagcc agctctgcct    60
agcagcagcg cacagccaca tccatggacg ccagcccgac ccaccgctc ccctccgcg    120 ccccaactcc cagcattgac ctccccgctg caaggacag ggccgacgcg gcggctaaca    180
aggccgcggc tgtgttcgac ctgcgccggg agcccaagat cccggagcca ttcctgtggc    240
cgcacgaaga ggcgcggccg acctcggccc ggagctgga ggtgccggtg gtggacgtgg    300
gcgtgctgcg caatggcgac ggcgcggggc tccgccgcgc cgcggcgcaa gtggcggcgg    360
cgtgcgcgac gcacgggttc ttccaggtgt gcgggcacgg cgtggacgcg cgctgggc    420 gcgccgcgct ggacggcgcc agcgacttct tccggctgcc gctggctgag aagcagcggg    480
cccggcgcgt cccggcacc gtgtccgggt acacgagcgc gcacgccgac cggttcgcgt    540
ccaagctccc ctggaaggag accctgtcct tcggcttcca cgacggcgcc gcggcgcccg    600
tcgtcgtgga ctacttcacc ggcacccctcg gccaagattt cgagccagtg gggcgggtgt    660

| | |
|---|---|
| accagaggta ctgcgaggag atgaaggagc tgtcgctgac gatcatggag ctgctggagc | 720 |
| tgagcctggg cgtggagcgc ggctactacc gggagttctt cgaggacagc cgctccatca | 780 |
| tgcggtgcaa ctactacccg ccgtgcccgg tgccggagcg cacgctgggc acgggcccgc | 840 |
| actgcgaccc cacggcgctg accatcctcc tgcaggacga cgtcggcggg ctggaggtcc | 900 |
| tggtggacgg cgagtggcgc cccgtccggc ccgtcccagg cgccatggtc atcaacatcg | 960 |
| gcgacacctt catggcgctg tccaacgggc ggtacaagag ctgcctgcac cgcgcggtgg | 1020 |
| tgaaccggcg gcaggagcgg caatcgctgg ccttcttcct gtgcccgcgc gaggaccggg | 1080 |
| tggtgcgccc gccggccagc gccgcgccgc ggcagtaccc ggacttcacc tgggccgacc | 1140 |
| tcatgcgctt cacgcagcgc cactaccgcg ccgacacccg cacgctggac gccttcaccc | 1200 |
| gctggctctc ccacgcccg gcggcggcgg ctccctgcac ctaacgagcc ggccgtctct | 1260 |
| ttcgccgggg cccgcgcggg gttcgcccac gtggtgatca ggtggcagac atgtggccca | 1320 |
| cgggccccgc gccgccttcc ccattttggg acgaccctac tgctactact actagtgtac | 1380 |
| atatgcaaaa aaatacatat atatataggt actttctcta atattttat ataaagcaa | 1440 |
| ggcggcctgg tgttcttttc tttgttttgt cgacaactgt ttgatcccat cctatggacg | 1500 |
| atggatagtt caatgtttgt ac | 1522 |

<210> SEQ ID NO 8
<211> LENGTH: 1161
<212> TYPE: DNA
<213> ORGANISM: Zea mays

<400> SEQUENCE: 8

| | |
|---|---|
| atggacgcca gcccgacccc accgctcccc ctccgcgccc caactcccag cattgacctc | 60 |
| cccgctggca aggacagggc cgacgcgcg gctaacaagg ccgcggctgt gttcgacctg | 120 |
| cgccgggagc ccaagatccc ggagccattc ctgtggccgc acgaagaggc gcggccgacc | 180 |
| tcggccgcgg agctggaggt gccggtggtg gacgtgggcg tgctgcgcaa tggcgacggc | 240 |
| gcggggctcc gccgcgccgc ggcgcaagtg gcggcggcgt gcgcgacgca cgggttcttc | 300 |
| caggtgtgcg gcacggcgt ggacgcggcg ctggggcgcg ccgcgctgga cggcgccagc | 360 |
| gacttcttcc ggctgccgct ggctgagaag cagcgggccc ggcgcgtccc cggcaccgtg | 420 |
| tccgggtaca cgagcgcgca cgccgaccgg ttcgcgtcca agctcccctg gaaggagacc | 480 |
| ctgtccttcg gcttccacga cggcgccgcg gcgcccgtcg tcgtggacta cttcaccggc | 540 |
| accctcggcc aagatttcga gccagtgggg cgggtgtacc agaggtactg cgaggagatg | 600 |
| aaggagctgt cgctgacgat catggagctg ctggagctga gcctgggcgt ggagcgcggc | 660 |
| tactaccggg agttcttcga ggacagccgc tccatcatgc ggtgcaacta ctacccgccg | 720 |
| tgcccggtgc cggagcgcac gctgggcacg ggcccgcact gcgaccccac ggcgctgacc | 780 |
| atcctcctgc aggacgacgt cggcgggctg gaggtcctgg tggacggcga gtggcgcccc | 840 |
| gtccggcccg tccaggcgc catggtcatc aacatcggcg acaccttcat ggcgctgtcc | 900 |
| aacgggcggt acaagagctg cctgcaccgc gcggtggtga accggcggca ggagcggcaa | 960 |
| tcgctggcct tcttcctgtg cccgcgcgag gaccgggtgg tgcgcccgcc ggccagcgcc | 1020 |
| gcgccgcggc agtacccgga cttcacctgg gccgacctca tgcgcttcac gcagcgccac | 1080 |
| taccgcgcca cacccgcac gctggacgcc ttcacccgct ggctctccca cggcccggcg | 1140 |
| gcggcggctc cctgcaccta a | 1161 |

```
<210> SEQ ID NO 9
<211> LENGTH: 386
<212> TYPE: PRT
<213> ORGANISM: Zea mays

<400> SEQUENCE: 9
```

| | | | | | | | | | | | | | | |
|---|---|---|---|---|---|---|---|---|---|---|---|---|---|---|
| Met | Asp | Ala | Ser | Pro | Thr | Pro | Pro | Leu | Pro | Leu | Arg | Ala | Pro | Thr | Pro |
| 1 | | | | 5 | | | | | 10 | | | | | 15 | |
| Ser | Ile | Asp | Leu | Pro | Ala | Gly | Lys | Asp | Arg | Ala | Asp | Ala | Ala | Ala | Asn |
| | | | 20 | | | | | 25 | | | | | 30 | | |
| Lys | Ala | Ala | Ala | Val | Phe | Asp | Leu | Arg | Arg | Glu | Pro | Lys | Ile | Pro | Glu |
| | | 35 | | | | | 40 | | | | | 45 | | | |
| Pro | Phe | Leu | Trp | Pro | His | Glu | Glu | Ala | Arg | Pro | Thr | Ser | Ala | Ala | Glu |
| | 50 | | | | | 55 | | | | | 60 | | | | |
| Leu | Glu | Val | Pro | Val | Val | Asp | Val | Gly | Val | Leu | Arg | Asn | Gly | Asp | Gly |
| 65 | | | | | 70 | | | | | 75 | | | | | 80 |
| Ala | Gly | Leu | Arg | Arg | Ala | Ala | Ala | Gln | Val | Ala | Ala | Ala | Cys | Ala | Thr |
| | | | | 85 | | | | | 90 | | | | | 95 | |
| His | Gly | Phe | Phe | Gln | Val | Cys | Gly | His | Gly | Val | Asp | Ala | Ala | Leu | Gly |
| | | | 100 | | | | | 105 | | | | | 110 | | |
| Arg | Ala | Ala | Leu | Asp | Gly | Ala | Ser | Asp | Phe | Phe | Arg | Leu | Pro | Leu | Ala |
| | | 115 | | | | | 120 | | | | | 125 | | | |
| Glu | Lys | Gln | Arg | Ala | Arg | Arg | Val | Pro | Gly | Thr | Val | Ser | Gly | Tyr | Thr |
| | 130 | | | | | 135 | | | | | 140 | | | | |
| Ser | Ala | His | Ala | Asp | Arg | Phe | Ala | Ser | Lys | Leu | Pro | Trp | Lys | Glu | Thr |
| 145 | | | | | 150 | | | | | 155 | | | | | 160 |
| Leu | Ser | Phe | Gly | Phe | His | Asp | Gly | Ala | Ala | Pro | Val | Val | Val | Asp |
| | | | | 165 | | | | | 170 | | | | | 175 | |
| Tyr | Phe | Thr | Gly | Thr | Leu | Gly | Gln | Asp | Phe | Glu | Pro | Val | Gly | Arg | Val |
| | | | 180 | | | | | 185 | | | | | 190 | | |
| Tyr | Gln | Arg | Tyr | Cys | Glu | Glu | Met | Lys | Glu | Leu | Ser | Leu | Thr | Ile | Met |
| | | 195 | | | | | 200 | | | | | 205 | | | |
| Glu | Leu | Leu | Glu | Leu | Ser | Leu | Gly | Val | Glu | Arg | Gly | Tyr | Tyr | Arg | Glu |
| | 210 | | | | | 215 | | | | | 220 | | | | |
| Phe | Phe | Glu | Asp | Ser | Arg | Ser | Ile | Met | Arg | Cys | Asn | Tyr | Tyr | Pro | Pro |
| 225 | | | | | 230 | | | | | 235 | | | | | 240 |
| Cys | Pro | Val | Pro | Glu | Arg | Thr | Leu | Gly | Thr | Gly | Pro | His | Cys | Asp | Pro |
| | | | | 245 | | | | | 250 | | | | | 255 | |
| Thr | Ala | Leu | Thr | Ile | Leu | Leu | Gln | Asp | Asp | Val | Gly | Gly | Leu | Glu | Val |
| | | | 260 | | | | | 265 | | | | | 270 | | |
| Leu | Val | Asp | Gly | Glu | Trp | Arg | Pro | Val | Arg | Pro | Val | Pro | Gly | Ala | Met |
| | | 275 | | | | | 280 | | | | | 285 | | | |
| Val | Ile | Asn | Ile | Gly | Asp | Thr | Phe | Met | Ala | Leu | Ser | Asn | Gly | Arg | Tyr |
| | 290 | | | | | 295 | | | | | 300 | | | | |
| Lys | Ser | Cys | Leu | His | Arg | Ala | Val | Val | Asn | Arg | Gln | Glu | Arg | Gln |
| 305 | | | | | 310 | | | | | 315 | | | | | 320 |
| Ser | Leu | Ala | Phe | Phe | Leu | Cys | Pro | Arg | Glu | Asp | Arg | Val | Val | Arg | Pro |
| | | | | 325 | | | | | 330 | | | | | 335 | |
| Pro | Ala | Ser | Ala | Ala | Pro | Arg | Gln | Tyr | Pro | Asp | Phe | Thr | Trp | Ala | Asp |
| | | | 340 | | | | | 345 | | | | | 350 | | |
| Leu | Met | Arg | Phe | Thr | Gln | Arg | His | Tyr | Arg | Ala | Asp | Thr | Arg | Thr | Leu |
| | | 355 | | | | | 360 | | | | | 365 | | | |
| Asp | Ala | Phe | Thr | Arg | Trp | Leu | Ser | His | Gly | Pro | Ala | Ala | Ala | Pro |
| | 370 | | | | | 375 | | | | | 380 | | | | |

Cys Thr
385

<210> SEQ ID NO 10
<211> LENGTH: 1457
<212> TYPE: DNA
<213> ORGANISM: Zea mays

<400> SEQUENCE: 10

```
taatcacctc atcacaggtc cccccagcct cactctcgcg ccggctcaag gtacattgcg      60
tgtcctagcc aagacacgca gctcatctca gcctcacacg cacagcaaga gcgaggcgtg     120
attcgccatg gcggcctca ctatggacca ggccttcgtg caggccccg agcaccgccc       180
caagcccatc gtcaccgagg ccaccggcat ccctctcatc gacctctcgc tctggccgc      240
cagcggcggc gccgtggacg cgctggccgc cgaggtgggc gcggcgagcc gggactgggg     300
cttcttcgtg gtcgtgggcc acggcgtgcc cgcagagacc gtgcgcgcg cgacggaggc      360
gcagcgagcg ttcttcgcgc tgccggcaga gcggaaggcc gccgtgcgga ggaacgaggc     420
ggagccgctc gggtactacg agtcggagca caccaagaac gtgagggact ggaaggaggt     480
gtacgacctc gtgccgcgcg agccgccgcc gccggcagcc gtggccgacg cgagcttgt     540
gttcgataac aagtggcccc aggatctacc gggcttcaga gaggcgctgg aggagtacgc     600
gaaagcgatg gaagagctgg cgttcaagct gctggagctg atcgcccgga gcctgaagct     660
gaggcccgac cggctgcacg gcttcttcaa ggaccagacg accttcatcc ggctgaacca     720
ctaccctcct tgcccgagcc ccgacctggc cctcggcgtg gggcggcaca aggacgccgg     780
cgccctgacc atcctgtacc aggacgacgt cgggggggctc gacgtccggc ggcgctccga     840
cggcgagtgg gtccgcgtca ggcccgtgcc cgactcgttc atcatcaacg tcggcgacct     900
catccaggta cgagagcgcg gagcaccggg tgtcggtgaa ctcggcgagg gagaggttct     960
ccatgcccta cttcttcaac ccggcgacct acaccatggt ggagccggtg gaggagctgg    1020
tgagcaagga cgatccgccc aggtacgacg cctacaactg gggcgacttc ttcagcacca    1080
ggaagaacag caacttcaag aagctcaacg tggagaacat tcagatcgcg catttcaaga    1140
agagcctcgt cctcgcctaa ctactgctac tgctaggatc catgccattg ccatgtcgtc    1200
ttcagattca gagcacgcca tgtcgtcgct agcttcgtgg tagaacaaat aatgatgtgc    1260
gtgctgtgtg taagcatgga tatggatgtg aatatgtaat atgatgagca ctcctacttt    1320
ggtatgtttg gaataacag acttgtgttg gtctggttca ttatttgtaa gaaaatcaaa    1380
aagagttagt agggcaggag gctaaccaca gtcatgctgc accacatccc tggtggaaag    1440
ctggccgggt tacgcta                                                    1457
```

<210> SEQ ID NO 11
<211> LENGTH: 1116
<212> TYPE: DNA
<213> ORGANISM: Zea mays

<400> SEQUENCE: 11

```
atgggcggcc tcactatgga ccaggccttc gtgcaggccc ccgagcaccg ccccaagccc      60
atcgtcaccg aggccaccgg catccctctc atcgacctct cgcctctggc cgccagcggc     120
ggcgccgtgg acgcgctggc cgccgaggtg ggcgcggcga gcgggactg gggcttcttc      180
gtggtcgtgg gccacggcgt gcccgcagag accgtgcgcg cgcgacgga ggcgcagcga      240
gcgttcttcg cgctgccggc agagcggaag gccgccgtgc ggaggaacga ggcggagccg     300
```

-continued

```
ctcgggtact acgagtcgga gcacaccaag aacgtgaggg actggaagga ggtgtacgac      360
ctcgtgccgc gcgagccgcc gccgccggca gccgtggccg acggcgagct tgtgttcgat      420
aacaagtggc cccaggatct accgggcttc agagaggcgc tggaggagta cgcgaaagcg      480
atggaagagc tggcgttcaa gctgctggag ctgatcgccc ggagcctgaa gctgaggccc      540
gaccggctgc acggcttctt caaggaccag acgaccttca tccggctgaa ccactaccct      600
ccttgcccga gccccgacct ggccctcggc gtggggcggc acaaggacgc cggcgccctg      660
accatcctgt accaggacga cgtcgggggg ctcgacgtcc ggcggcgctc cgacggcgag      720
tgggtccgcg tcaggcccgt gcccgactcg ttcatcatca acgtcggcga cctcatccag      780
gtacgagagc gcggagcacc gggtgtcggt gaactcggcg agggagaggt tctccatgcc      840
ctacttcttc aacccggcga cctacaccat ggtggagccg gtggaggagc tggtgagcaa      900
ggacgatccg cccaggtacg acgcctacaa ctggggcgac ttcttcagca ccaggaagaa      960
cagcaacttc aagaagctca acgtggagaa cattcagatc gcgcatttca agaagagcct     1020
cgtcctcgcc taactactgc tactgctagg atccatgcca ttgccatgtc gtcttcagat     1080
tcagagcacg ccatgtcgtc gctagcttcg tggtag                               1116
```

<210> SEQ ID NO 12
<211> LENGTH: 371
<212> TYPE: PRT
<213> ORGANISM: Zea mays

<400> SEQUENCE: 12

```
Met Gly Gly Leu Thr Met Asp Gln Ala Phe Val Gln Ala Pro Glu His
1               5                   10                  15

Arg Pro Lys Pro Ile Val Thr Glu Ala Thr Gly Ile Pro Leu Ile Asp
            20                  25                  30

Leu Ser Pro Leu Ala Ala Ser Gly Ala Val Asp Ala Leu Ala Ala
        35                  40                  45

Glu Val Gly Ala Ala Ser Arg Asp Trp Gly Phe Phe Val Val Gly
    50                  55                  60

His Gly Val Pro Ala Glu Thr Val Ala Arg Ala Thr Glu Ala Gln Arg
65                  70                  75                  80

Ala Phe Phe Ala Leu Pro Ala Glu Arg Lys Ala Val Arg Arg Asn
                85                  90                  95

Glu Ala Glu Pro Leu Gly Tyr Tyr Glu Ser Glu His Thr Lys Asn Val
            100                 105                 110

Arg Asp Trp Lys Glu Val Tyr Asp Leu Val Pro Arg Glu Pro Pro Pro
        115                 120                 125

Pro Ala Val Ala Asp Gly Glu Leu Val Phe Asp Asn Lys Trp Pro
    130                 135                 140

Gln Asp Leu Pro Gly Phe Arg Glu Ala Leu Glu Glu Tyr Ala Lys Ala
145                 150                 155                 160

Met Glu Glu Leu Ala Phe Lys Leu Leu Glu Leu Ile Ala Arg Ser Leu
                165                 170                 175

Lys Leu Arg Pro Asp Arg Leu His Gly Phe Phe Lys Asp Gln Thr Thr
            180                 185                 190

Phe Ile Arg Leu Asn His Tyr Pro Pro Cys Pro Ser Pro Asp Leu Ala
        195                 200                 205

Leu Gly Val Gly Arg His Lys Asp Ala Gly Ala Leu Thr Ile Leu Tyr
    210                 215                 220

Gln Asp Asp Val Gly Gly Leu Asp Val Arg Arg Arg Ser Asp Gly Glu
```

```
                225                 230                 235                 240
Trp Val Arg Val Arg Pro Val Pro Asp Ser Phe Ile Ile Asn Val Gly
                    245                 250                 255

Asp Leu Ile Gln Val Arg Glu Arg Gly Ala Pro Gly Val Gly Glu Leu
                260                 265                 270

Gly Glu Gly Glu Val Leu His Ala Leu Leu Gln Pro Gly Asp Leu
            275                 280                 285

His His Gly Gly Ala Gly Gly Ala Gly Glu Gln Gly Arg Ser Ala
        290                 295                 300

Gln Val Arg Arg Leu Gln Leu Gly Arg Leu Leu Gln His Gln Glu Glu
305                 310                 315                 320

Gln Gln Leu Gln Glu Ala Gln Arg Gly Glu His Ser Asp Arg Ala Phe
                325                 330                 335

Gln Glu Glu Pro Arg Pro Arg Leu Thr Thr Ala Thr Arg Ile His
                340                 345                 350

Ala Ile Ala Met Ser Ser Ser Asp Ser Glu His Ala Met Ser Ser Leu
                355                 360                 365

Ala Ser Trp
    370

<210> SEQ ID NO 13
<211> LENGTH: 1733
<212> TYPE: DNA
<213> ORGANISM: Zea mays

<400> SEQUENCE: 13
atgaggccgc gcctccctcc aaatgttccc tccctgcctt cgtctttgtc gttgctcgca     60
aactccctgt cctcccctgt tacaaatacc cccacccgcc cggacagctt ccctgcatac    120
ttgcagctcg cacatctcat ggtgtcgcag gaacgacaag agccagctgt gcctagcagc    180
agcagcagca gcgccaagcg cgcagccacg tccatggacg ccagcccggc cccgccgctc    240
ctcctccgcg cccccactcc cagccccagc attgacctcc ccgctggcaa ggacaaggcc    300
gacgcggcgg ccagcaaggc cggcgcggcc gtgttcgacc tgccgccggga gcccaagatc    360 cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
gcggcgcagg tggccgcggc gtgcgcgacg cacgggttct ccaggtgtg cgggcacggc    540 gtggacgcgg cgctggggcg cgccgcgctg acggcgcca gcgacttctt ccggctgccg    600
ctcgccgaga agcagcgcgc ccggcgcgtc cccggcaccg tgtccgggta cacgagcgcg    660
cacgccgacc ggttcgcggc caagctcccc tggaaggaga ccctgtcgtt cggctaccac    720
gacggcgccg cgtcgcctgt cgtcgtggac tacttcgtcg gcaccctcgg ccaggatttc    780
gagccaatgg ggtgggtgta ccagaggtac tgcgaggaga tgaaggagct gtcgctgacg    840
atcatggagc tgctggagct gagcctgggc gtggagctgc gcggctacta ccggagttc    900 ttcgaggaca gccggtccat catgcggtgc aactactacc gccgtgccc ggagccggag    960 cgcacgctgg cacgggccc gcactgcgac cccacggcgc tcaccatcct cctgcaggac   1020
gacgtgggcg gctggaggt gctggtgga ggtgagtgg ccccgtccg gcccgtcccg   1080 ggcgccatgg tcatcaacat cggcgacacc ttcatggcgc tgtcgaacgg gaggtacaag   1140
agctgcctgc accgcgcggt ggtgaaccag cggcgggcgc ggcggtcgct ggccttcttc   1200
ctgtgcccgc gcgaggaccg ggtggtgcgc ccgccggcca gtgctgcgcc gcggcgctac   1260
```

```
ccggacttca cctgggccga cctcatgcgc ttcacgcagc gccactaccg cgccgacacc    1320
cgcacgctgg acgccttcac ccgctggctc tcccacggcc cggcccaggc ggcggcgcct    1380
ccctgcacct agcgagccgg gccaaggccg tctctttcgc cccacgtgcg cgcccagctg    1440
ggcaggtggc cagacacgcg gcccgcgggc ccgcgccgc cttgccattt tttgacgctg     1500
gccctactgc tgtgctacta gtgtacatat gcaagagtac atatatatat atatatatac    1560
gtattttcta tatattatat ataaaagcaa ggcggcccgg tgcccttctc ttgttttgtc    1620
cacaactgtt tgatcccatt attctatgga ccatggatac ttcaatgttt gtactaagac    1680
cgtgaacgtg ggattctttt ccttcctctg tgttttttct gagaaaaatt aaa           1733

<210> SEQ ID NO 14
<211> LENGTH: 1392
<212> TYPE: DNA
<213> ORGANISM: Zea mays

<400> SEQUENCE: 14
atgaggccgc gcctccctcc aaatgttccc tccctgcctt cgtctttgtc gttgctcgca     60
aactccctgt cctcccctgt tacaaatacc cccacccgcc cggacagctt ccctgcatac    120
ttgcagctcg cacatctcat ggtgtcgcag gaacgacaag agccagctgt gcctagcagc    180
agcagcagca gcgccaagcg cgcagccacg tccatggacg ccagcccggc cccgccgctc    240
ctcctccgcg cccccactcc cagccccagc attgacctcc ccgctggcaa ggacaaggcc    300
gacgcggcgg ccagcaaggc cggcgcggcc gtgttcgacc tgcgccggga gcccaagatc    360
cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
gcggcgcagg tggccgcggc gtgcgcgacg cacgggttct tccaggtgtg cgggcacggc    540
gtggacgcgg cgctggggcg cgccgcgctg gacggcgcca gcgacttctt ccggctgccg    600
ctcgccgaga gcagcgcgc ccggcgcgtc cccggcaccg tgtccgggta cacgagcgcg    660
cacgccgacc ggttcgcggc caagctcccc tggaaggaga ccctgtcgtt cggctaccac    720
gacggcgccg cgtcgcctgt cgtcgtggac tacttcgtcg gcaccctcgg ccaggatttc    780
gagccaatgg ggtgggtgta ccagaggtac tgcgaggaga tgaaggagct gtcgctgacg    840
atcatggagc tgctggagct gagcctgggc gtggagctgc gcggctacta ccggagttc    900 ttcgaggaca gccggtccat catgcggtgc aactactacc cgccgtgccc ggagccggag    960
cgcacgctgg cacgggccc gcactgcgac cccacgcgc tcaccatcct cctgcaggac     1020
gacgtgggcg ggctggaggt gctggtggac ggtgagtggc gccccgtccg gcccgtcccg    1080
ggcgccatgg tcatcaacat cggcgacacc ttcatggcgc tgtcgaacgg gaggtacaag    1140
agctgcctgc accgcgcggt ggtgaaccag cggcgggcgc ggcggtcgct ggccttcttc    1200
ctgtgcccgc gcgaggaccg ggtggtgcgc ccgccggcca gtgctgcgcc gcggcgctac    1260
ccggacttca cctgggccga cctcatgcgc ttcacgcagc gccactaccg cgccgacacc    1320
cgcacgctgg acgccttcac ccgctggctc tcccacggcc cggcccaggc ggcggcgcct    1380
ccctgcacct ag                                                        1392

<210> SEQ ID NO 15
<211> LENGTH: 463
<212> TYPE: PRT
<213> ORGANISM: Zea mays

<400> SEQUENCE: 15
```

```
Met Arg Pro Arg Leu Pro Pro Asn Val Pro Ser Leu Pro Ser Ser Leu
1               5                   10                  15

Ser Leu Leu Ala Asn Ser Leu Ser Ser Pro Val Thr Asn Thr Pro Thr
            20                  25                  30

Arg Pro Asp Ser Phe Pro Ala Tyr Leu Gln Leu Ala His Leu Met Val
        35                  40                  45

Ser Gln Glu Arg Gln Glu Pro Ala Val Pro Ser Ser Ser Ser Ser Ser
    50                  55                  60

Ala Lys Arg Ala Ala Thr Ser Met Asp Ala Ser Pro Ala Pro Pro Leu
65                  70                  75                  80

Leu Leu Arg Ala Pro Thr Pro Ser Pro Ser Ile Asp Leu Pro Ala Gly
                85                  90                  95

Lys Asp Lys Ala Asp Ala Ala Ser Lys Ala Gly Ala Ala Val Phe
            100                 105                 110

Asp Leu Arg Arg Glu Pro Lys Ile Pro Ala Pro Phe Leu Trp Pro Gln
        115                 120                 125

Glu Glu Ala Arg Pro Ser Ser Ala Ala Glu Leu Glu Val Pro Met Val
    130                 135                 140

Asp Val Gly Val Leu Arg Asn Gly Asp Arg Ala Gly Leu Arg Arg Ala
145                 150                 155                 160

Ala Ala Gln Val Ala Ala Cys Ala Thr His Gly Phe Phe Gln Val
            165                 170                 175

Cys Gly His Gly Val Asp Ala Ala Leu Gly Arg Ala Ala Leu Asp Gly
            180                 185                 190

Ala Ser Asp Phe Phe Arg Leu Pro Leu Ala Glu Lys Gln Arg Ala Arg
        195                 200                 205

Arg Val Pro Gly Thr Val Ser Gly Tyr Thr Ser Ala His Ala Asp Arg
        210                 215                 220

Phe Ala Ala Lys Leu Pro Trp Lys Glu Thr Leu Ser Phe Gly Tyr His
225                 230                 235                 240

Asp Gly Ala Ala Ser Pro Val Val Asp Tyr Phe Val Gly Thr Leu
            245                 250                 255

Gly Gln Asp Phe Glu Pro Met Gly Trp Val Tyr Gln Arg Tyr Cys Glu
        260                 265                 270

Glu Met Lys Glu Leu Ser Leu Thr Ile Met Glu Leu Leu Glu Leu Ser
        275                 280                 285

Leu Gly Val Glu Leu Arg Gly Tyr Tyr Arg Glu Phe Phe Glu Asp Ser
    290                 295                 300

Arg Ser Ile Met Arg Cys Asn Tyr Tyr Pro Pro Cys Pro Glu Pro Glu
305                 310                 315                 320

Arg Thr Leu Gly Thr Gly Pro His Cys Asp Pro Thr Ala Leu Thr Ile
            325                 330                 335

Leu Leu Gln Asp Asp Val Gly Gly Leu Glu Val Leu Val Asp Gly Glu
        340                 345                 350

Trp Arg Pro Val Arg Pro Val Pro Gly Ala Met Val Ile Asn Ile Gly
    355                 360                 365

Asp Thr Phe Met Ala Leu Ser Asn Gly Arg Tyr Lys Ser Cys Leu His
    370                 375                 380

Arg Ala Val Val Asn Gln Arg Arg Ala Arg Ser Leu Ala Phe Phe
385                 390                 395                 400

Leu Cys Pro Arg Glu Asp Arg Val Val Arg Pro Pro Ala Ser Ala Ala
            405                 410                 415
```

Pro Arg Arg Tyr Pro Asp Phe Thr Trp Ala Asp Leu Met Arg Phe Thr
            420                 425                 430

Gln Arg His Tyr Arg Ala Asp Thr Arg Thr Leu Asp Ala Phe Thr Arg
        435                 440                 445

Trp Leu Ser His Gly Pro Ala Gln Ala Ala Ala Pro Pro Cys Thr
    450                 455                 460

<210> SEQ ID NO 16
<211> LENGTH: 1510
<212> TYPE: DNA
<213> ORGANISM: Zea mays

<400> SEQUENCE: 16

```
aaagagcgcg cgacggcggc ccctgggaga gccatgcgag actggaggcg aaccgcgca      60
cgacaccaag ctgccgcgcc ggactgctgc acgcaagcgc agcgcaggac cgaccgacct    120
ccgtaggcac gcacggcgcc ggcggcatgg cggagcacct cctgtcgacg gccgtgcacg    180
acacgctgcc ggggagctac gtgcggccgg agcggagcg cccgcgcctc gcggaggtcg     240
tgaccggcgc gcgcatcccc gtcgtggacc tgggcagccc cgaccgcggc gcggtcgtgg    300
ccgccgtcgg cgacgcctgc cgctcgcacg gcttcttcca ggtcgtcaac cacgggatac    360
acgccgccct ggtcgcggcg gtgatggccg cggggcgcgg cttcttccgg ctgcccccccg   420
aggagaaggc caagctctac tccgacgacc ccgccaggaa gatccggctg tccaccagct    480
tcaacgtgcg caaggagacg gtgcacaact ggcgcgacta cctccgcctg cactgccatc    540
ccctcgacga gttcctgccc gattggccgt ccaacccgcc cgatttcaag agaccatgg     600
gcacctactg caaggaggtc cgggagctcg ggttcaggct gtacgccgcg atctcggaga    660
gcctgggcct agaggcgagc tacatgaagg aagcgctggg ggagcaggag cagcacatgg    720
cggtcaactt ctacccgccg tgcccggagc cggagctcac ctacggcctc ccggcgcaca    780
ccgaccccaa cgcgctcacc atcctgctca tggacccgga cgtcgccggc ctgcaggtgc    840
tccacgccgg ccagtgggtc gccgtcaacc cgcagcccgg cgcgctcatc atcaacatcg    900
gcgaccagct gcaggcgctg agcaacgggc agtaccggag cgtgtggcac cgcgcggtgg    960
tgaactcgga ccgggagcgc atgtccgtgg cgtcgttcct gtgcccgtgc aaccacgtcg   1020
tgctcggccc cgcgcggaag ctcgtcaccg aggacacccc ggccgtgtac aggaactaca   1080
cgtacgacaa gtactacgcc aagttctgga gcaggaacct ggaccaggag cactgcctcg   1140
agctcttcag aacctagcga atcggatacg gatggatgga tacattacat acgcgccctc   1200
tgtttttctc catgacgtta aagaacacg ttctgcaatg tttgtccatt caaggtggta    1260
tcaatcaagg ctgtggtcgt tgcaattctt ccgctccata tacatgatta aatgctttga   1320
aagaaaaga aaaaaagaa acacaagtat tatggcacta ctagtgtttt taggaacaag    1380
gaaagagggg ttgcccctgc tggctatata tattaaatat aaataaaggt aaggctgtag   1440
acattggtga ataagagaaa gtatttgagt ttctctattg tcactccaga acagactcct   1500
ttgcctcgat                                                          1510
```

<210> SEQ ID NO 17
<211> LENGTH: 1011
<212> TYPE: DNA
<213> ORGANISM: Zea mays

<400> SEQUENCE: 17

```
atggcggagc acctcctgtc gacggccgtg cacgacacgc tgccggggag ctacgtgcgg      60
```

```
ccggagccgg agcgcccgcg cctcgcggag gtcgtgaccg gcgcgcgcat ccccgtcgtg      120
gacctgggca gccccgaccg cggcgcggtc gtggccgccg tcggcgacgc ctgccgctcg      180
cacggcttct tccaggtcgt caaccacggg atacacgccg ccctggtcgc ggcggtgatg      240
gccgcggggc gcggcttctt ccggctgccc cccgaggaga aggccaagct ctactccgac      300
gaccccgcca ggaagatccg gctgtccacc agcttcaacg tgcgcaagga gacggtgcac      360
aactggcgcg actacctccg cctgcactgc catcccctcg acgagttcct gcccgattgg      420
ccgtccaacc cgcccgattt caaggagacc atgggcacct actgcaagga ggtccgggag      480
ctcgggttca ggctgtacgc cgcgatctcg gagagcctgg gcctagaggc gagctacatg      540
aaggaagcgc tgggggagca ggagcagcac atggcggtca acttctaccc gccgtgcccg      600
gagccggagc tcacctacgg cctcccggcg cacaccgacc caacgcgct caccatcctg       660
ctcatggacc cggacgtcgc cggcctgcag gtgctccacg ccggccagtg ggtcgccgtc      720
aacccgcagc ccggcgcgct catcatcaac atcggcgacc agctgcaggc gctgagcaac      780
gggcagtacc ggagcgtgtg gcaccgcgcg gtggtgaact cggaccggga gcgcatgtcc      840
gtggcgtcgt tcctgtgccc gtgcaaccac gtcgtgctcg gccccgcgcg gaagctcgtc      900
accgaggaca ccccggccgt gtacaggaac tacacgtacg acaagtacta cgccaagttc      960
tggagcagga acctggacca ggagcactgc ctcgagctct tcagaaccta g              1011

<210> SEQ ID NO 18
<211> LENGTH: 336
<212> TYPE: PRT
<213> ORGANISM: Zea mays

<400> SEQUENCE: 18

Met Ala Glu His Leu Leu Ser Thr Ala Val His Asp Thr Leu Pro Gly
1               5                   10                  15

Ser Tyr Val Arg Pro Glu Pro Glu Arg Pro Arg Leu Ala Glu Val Val
                20                  25                  30

Thr Gly Ala Arg Ile Pro Val Asp Leu Gly Ser Pro Asp Arg Gly
            35                  40                  45

Ala Val Val Ala Val Gly Asp Ala Cys Arg Ser His Gly Phe Phe
        50                  55                  60

Gln Val Val Asn His Gly Ile His Ala Ala Leu Val Ala Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
                100                 105                 110

Asn Val Arg Lys Glu Thr Val His Asn Trp Arg Asp Tyr Leu Arg Leu
            115                 120                 125

His Cys His Pro Leu Asp Glu Phe Leu Pro Asp Trp Pro Ser Asn Pro
        130                 135                 140

Pro Asp Phe Lys Glu Thr Met Gly Thr Tyr Cys Lys Glu Val Arg Glu
145                 150                 155                 160

Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
                180                 185                 190

Val Asn Phe Tyr Pro Pro Cys Pro Glu Pro Glu Leu Thr Tyr Gly Leu
            195                 200                 205
```

```
Pro Ala His Thr Asp Pro Asn Ala Leu Thr Ile Leu Leu Met Asp Pro
    210                 215                 220
Asp Val Ala Gly Leu Gln Val Leu His Ala Gly Gln Trp Val Ala Val
225                 230                 235                 240
Asn Pro Gln Pro Gly Ala Leu Ile Ile Asn Ile Gly Asp Gln Leu Gln
                245                 250                 255
Ala Leu Ser Asn Gly Gln Tyr Arg Ser Val Trp His Arg Ala Val Val
            260                 265                 270
Asn Ser Asp Arg Glu Arg Met Ser Val Ala Ser Phe Leu Cys Pro Cys
        275                 280                 285
Asn His Val Val Leu Gly Pro Ala Arg Lys Leu Val Thr Glu Asp Thr
    290                 295                 300
Pro Ala Val Tyr Arg Asn Tyr Thr Tyr Asp Lys Tyr Tyr Ala Lys Phe
305                 310                 315                 320
Trp Ser Arg Asn Leu Asp Gln Glu His Cys Leu Glu Leu Phe Arg Thr
                325                 330                 335

<210> SEQ ID NO 19
<211> LENGTH: 1387
<212> TYPE: DNA
<213> ORGANISM: Zea mays

<400> SEQUENCE: 19
gttttctttt tgaacgtaac tgacagaagc tatctgccta gctacggcgt gtcggttgct      60
tgtctcacca agcagcgac atggaagcct gacagctcgt cgcgtcgcgc catttccacc     120
caacaaagcg gcggcgccag cacgcactgc ttctgcttgt gcgtgctcct ccgttccggg    180
cacgcctcta aagtctatac agcctcgaat ccatcccggc cgccgctcct ggggatact    240 acagcgagcc gaagcgggga tggcggagat ccctgtgatc gacctgcgcg tcgccggctc    300
ggcggccgag gagtccgcgc ggctgcgggc cgcgtgcgag cgcctgggct gcttccgggt    360
gaccggccac ggcgtgccct cggtgctcct ggcagagatg aaggccgccg tgcgcgcgct    420
cttcgacctc cccgacgacg ccaagcgccg caacgccgac gtcatcaccg gcagcggcta    480
cgtcgccccc agcccgacca cccgctcta cgaggccttc gggctcctcg acgccgccgt     540
gcccaccgac gtcgacgcct tttgcgcgct cctcgacgcg ccgcccaaca tcagggagac    600
cgtcaaggcc tacgcggaga agatgcacga tgtgatcgtt ggcgtcgccc gcgagctggc    660
gtctagcctg gggctagtcg aggagcactc gttccaggac tggccgtgcc agttccgcat    720
caacaggtac aactacacgc gggagacggt gggctcctcc ggcgtgcaga cccacacgga    780
ctcgggcttc ctcaccgtgc tccatgagga cgagtgtgtc ggcggcctcg aggtcctgga    840
cccgggcacc ggcgagttcg tgcccgtgga ccccgtcgcg ggctcctttc tcgtaaacat    900
cggcgacgtc ggcacggcgt ggagcaacgg gaggctgcac aacgtgaagc accgggtgcg    960
gtgcgtcgca cccgtgccgc gcatctccat cgccatgttc ctgctcgcac ccaaggacga   1020
cagcgtgagc gcaccggcgg cgttcgtgga cgcggaccac ccgcgcaggt acaaggtgtt   1080
caactacaac gactatcgga ggctcagact gtccaccggc gagcacgcag gcgaggcgct   1140
cgcacggatg gcggcgtgac gtggctggag ctgcaaattg gattggaagc cgagacaagc   1200
cgttagttat ttaccatgcc cgtgcgttca ccgcacacaa tcatattcaa aagccataaa   1260
ataaaaaata atttaatat cagtcaacat atggtttaaa tatcatatgg agtacaatat    1320
tccgaatttt ttttgtaat ttagtctgtc ttttgaaaaa aatgcacatc tagacctccg    1380
gatgact                                                             1387
```

<210> SEQ ID NO 20
<211> LENGTH: 900
<212> TYPE: DNA
<213> ORGANISM: Zea mays

<400> SEQUENCE: 20

```
atggcggaga tccctgtgat cgacctgcgc gtcgccggct cggcggccga ggagtccgcg      60
cggctgcggg ccgcgtgcga gcgcctgggc tgcttccggg tgaccggcca cggcgtgccc     120
tcggtgctcc tggcagagat gaaggccgcc gtgcgcgcgc tcttcgacct ccccgacgac     180
gccaagcgcc gcaacgccga cgtcatcacc ggcagcggct acgtcgcccc cagcccgacc     240
aacccgctct acgaggcctt cgggctcctc gacgccgccg tgcccaccga cgtcgacgcc     300
ttttgcgcgc tcctcgacgc gccgcccaac atcagggaga ccgtcaaggc ctacgcggag     360
aagatgcacg atgtgatcgt tggcgtcgcc cgcgagctgg cgtctagcct ggggctagtc     420
gaggagcact cgttccagga ctggccgtgc cagttccgca tcaacaggta caactacacg     480
cgggagacgg tgggctcctc cggcgtgcag acccacacgg actcgggctt cctcaccgtg     540
ctccatgagg acgagtgtgt cggcggcctc gaggtcctgg acccgggcac cggcgagttc     600
gtgcccgtgg accccgtcgc gggctccttt ctcgtaaaca tcggcgacgt cggcacggcg     660
tggagcaacg ggaggctgca caacgtgaag caccgggtgc ggtgcgtcgc acccgtgccg     720
cgcatctcca tcgccatgtt cctgctcgca cccaaggacg acagcgtgag cgcaccggcg     780
gcgttcgtgg acgcggacca cccgcgcagg tacaaggtgt tcaactacaa cgactatcgg     840
aggctcagac tgtccaccgg cgagcacgca ggcgaggcgc tcgcacggat ggcggcgtga     900
```

<210> SEQ ID NO 21
<211> LENGTH: 299
<212> TYPE: PRT
<213> ORGANISM: Zea mays

<400> SEQUENCE: 21

```
Met Ala Glu Ile Pro Val Ile Asp Leu Arg Val Ala Gly Ser Ala Ala
1               5                  10                  15

Glu Glu Ser Ala Arg Leu Arg Ala Ala Cys Glu Arg Leu Gly Cys Phe
            20                  25                  30

Arg Val Thr Gly His Gly Val Pro Ser Val Leu Leu Ala Glu Met Lys
        35                  40                  45

Ala Ala Val Arg Ala Leu Phe Asp Leu Pro Asp Asp Ala Lys Arg Arg
    50                  55                  60

Asn Ala Asp Val Ile Thr Gly Ser Gly Tyr Val Ala Pro Ser Pro Thr
65                  70                  75                  80

Asn Pro Leu Tyr Glu Ala Phe Gly Leu Leu Asp Ala Ala Val Pro Thr
                85                  90                  95

Asp Val Asp Ala Phe Cys Ala Leu Leu Asp Ala Pro Asn Ile Arg
                    100                 105                 110

Glu Thr Val Lys Ala Tyr Ala Glu Lys Met His Asp Val Ile Val Gly
            115                 120                 125

Val Ala Arg Glu Leu Ala Ser Ser Leu Gly Leu Val Glu Glu His Ser
        130                 135                 140

Phe Gln Asp Trp Pro Cys Gln Phe Arg Ile Asn Arg Tyr Asn Tyr Thr
145                 150                 155                 160

Arg Glu Thr Val Gly Ser Ser Gly Val Gln Thr His Thr Asp Ser Gly
                165                 170                 175
```

```
Phe Leu Thr Val Leu His Glu Asp Glu Cys Val Gly Gly Leu Glu Val
            180                 185                 190

Leu Asp Pro Gly Thr Gly Glu Phe Val Pro Val Asp Pro Val Ala Gly
        195                 200                 205

Ser Phe Leu Val Asn Ile Gly Asp Val Gly Thr Ala Trp Ser Asn Gly
    210                 215                 220

Arg Leu His Asn Val Lys His Arg Val Arg Cys Val Ala Pro Val Pro
225                 230                 235                 240

Arg Ile Ser Ile Ala Met Phe Leu Leu Ala Pro Lys Asp Asp Ser Val
                245                 250                 255

Ser Ala Pro Ala Ala Phe Val Asp Ala Asp His Pro Arg Arg Tyr Lys
            260                 265                 270

Val Phe Asn Tyr Asn Asp Tyr Arg Arg Leu Arg Leu Ser Thr Gly Glu
        275                 280                 285

His Ala Gly Glu Ala Leu Ala Arg Met Ala Ala
    290                 295

<210> SEQ ID NO 22
<211> LENGTH: 1496
<212> TYPE: DNA
<213> ORGANISM: Zea mays

<400> SEQUENCE: 22
gtcggtctct tgtctcacca aaccggcgac atggtacatg gaggccagcc cgtcgcttgg      60
cgccacaagt ctcggtgccg tccgtccgac aagcggcgcc agcgcacgct ggctgctcgt     120
gcacgcctct aaatacggcc ccggacccgc caccaagcga aggccaatcc cgtccgccgc     180
cccccaccaa ccacgaacca cgcaagcgaa cccggccggc gcggggcagc ggcgatggcg     240
gagatcccgg tgatcgacct cgcctcgcc ggctcgtcgc ccgacgagtc ggcgcggctg      300
cgcgacgcgt gcgagcgcct gggctgcttt cgggtgaccg gccacggcgc gcccgcgggg     360
ctcctggccg acatgaaggc cgccgtgcgc gcgctcttcg acctccccga cgacgccaag     420
cgccgcaacg ccgacgtcat ccccggcagc ggctacgtcg cgccctgccc cgccaacccg     480
ctctacgagg ccttcgggct cctcgacgcc gccgcgcccg ccgacgtcga cgccttctgc     540
gcgcgcctcg acgcgccgcc caaagtcagg gagaccgtca agacctacgc ggagaagatg     600
cacgacgtga tcgtcggcgt cgccggcgag ctggccacca gcctgggcgc tgggcctggag    660 gagcactcgt tccaggactg gccgtgccag ttccgcatca acaggtacaa ctacacgcag     720
gagacggtgg gctcctccgg cgtgcagacc cacacggact cgggcttcct caccgtgctc     780
caggaggacg agtgcgtcgg cggcctcgag gtgctggacc ccgccgccgg tgagttcgtg     840
cccgtggacc ccgtcgccgg ctccttcctc gtcaacatcg cgacgtcgg cacggcgtgg     900 agcaacggga ggctccacaa cgtgaagcac cgggtgcggt gcgtcgcgcc cgtgccgcgc     960
atctccatcg ccatgttcct gctggcgccc aaggacgacc gcgtgagcgc ccggaggcg     1020 ttggtcgacg cgggccaccc cgtcggtac aagccgttca actacgacga ctaccggagg      1080
ctccggctgt ccaccggcga gcgcgcaggc gaggcgctcg cgcggatggc ggcgtgatgt     1140
cgtcacgcac gtgcaagccg ttaattatag gctcgcgcat gcatacgcct acacgagagg     1200
ttgtctcgtt aagccgttct attaaaatgt gtgggggaga agatgactac ccgtggtgcc     1260
atgtggattg ctatcgggtc tgatcaataa aatcttgcaa cacttgcacg tgcgattcca     1320
tatcctagca cgggtgggcg ccacgctagt aggtagagac cggagcggcc aaaaaatggc     1380
```

```
tacagcacca gtaggtgaac tctcaagcaa cactggctat cccacttctg acgttgtctc   1440
tctcatcact atgtatgacc agcgaatgaa gtgtttaaaa atctgacgcc gtgaaa       1496
```

<210> SEQ ID NO 23
<211> LENGTH: 903
<212> TYPE: DNA
<213> ORGANISM: Zea mays

<400> SEQUENCE: 23

```
atggcggaga tcccggtgat cgacctgcgc ctcgccggct cgtcgcccga cgagtcggcg     60
cggctgcgcg acgcgtgcga gcgcctgggc tgctttcggg tgaccggcca cggcgcgccc    120
gcggggctcc tggccgacat gaaggccgcc gtgcgcgcgc tcttcgacct ccccgacgac    180
gccaagcgcc gcaacgccga cgtcatcccc ggcagcggct acgtcgcgcc ctgccccgcc    240
aacccgctct acgaggcctt cgggctcctc gacgccgccg cgcccgccga cgtcgacgcc    300
ttctgcgcgc gcctcgacgc gccgcccaaa gtcaggagaa ccgtcaagac ctacgcggag    360
aagatgcacg acgtgatcgt cggcgtcgcc ggcgagctgg ccaccagcct ggggctgggc    420
ctggaggagc actcgttcca ggactggccg tgccagttcc gcatcaacag gtacaactac    480
acgcaggaga cggtgggctc ctccggcgtg cagacccaca cggactcggg cttcctcacc    540
gtgctccagg aggacgagtg cgtcggcggc ctcgaggtgc tggaccccgc gccggtgag     600 ttcgtgcccg tggaccccgt cgccggctcc ttcctcgtca acatcggcga cgtcggcacg    660
gcgtggagca acgggaggct ccacaacgtg aagcaccggg tgcggtgcgt cgcgcccgtg    720
ccgcgcatct ccatcgccat gttcctgctg gcgcccaagg acgaccgcgt gagcgccccg    780
gaggcgttgg tcgacgcggg ccaccccgcgt cggtacaagc cgttcaacta cgacgactac    840
cggaggctcc ggctgtccac cggcgagcgc gcaggcgagg cgctcgcgcg gatggcggcg    900
tga                                                                   903
```

<210> SEQ ID NO 24
<211> LENGTH: 300
<212> TYPE: PRT
<213> ORGANISM: Zea mays

<400> SEQUENCE: 24

```
Met Ala Glu Ile Pro Val Ile Asp Leu Arg Leu Ala Gly Ser Ser Pro
1               5                   10                  15

Asp Glu Ser Ala Arg Leu Arg Asp Ala Cys Glu Arg Leu Gly Cys Phe
            20                  25                  30

Arg Val Thr Gly His Gly Ala Pro Ala Gly Leu Leu Ala Asp Met Lys
        35                  40                  45

Ala Ala Val Arg Ala Leu Phe Asp Leu Pro Asp Asp Ala Lys Arg Arg
    50                  55                  60

Asn Ala Asp Val Ile Pro Gly Ser Gly Tyr Val Ala Pro Cys Pro Ala
65                  70                  75                  80

Asn Pro Leu Tyr Glu Ala Phe Gly Leu Leu Asp Ala Ala Ala Pro Ala
                85                  90                  95

Asp Val Asp Ala Phe Cys Ala Arg Leu Asp Ala Pro Lys Val Arg
            100                 105                 110

Glu Thr Val Lys Thr Tyr Ala Glu Lys Met His Asp Val Ile Val Gly
        115                 120                 125

Val Ala Gly Glu Leu Ala Thr Ser Leu Gly Leu Gly Leu Glu Glu His
    130                 135                 140
```

```
Ser Phe Gln Asp Trp Pro Cys Gln Phe Arg Ile Asn Arg Tyr Asn Tyr
145                 150                 155                 160

Thr Gln Glu Thr Val Gly Ser Ser Gly Val Gln Thr His Thr Asp Ser
            165                 170                 175

Gly Phe Leu Thr Val Leu Gln Glu Asp Glu Cys Val Gly Gly Leu Glu
        180                 185                 190

Val Leu Asp Pro Ala Ala Gly Glu Phe Val Pro Val Asp Pro Val Ala
        195                 200                 205

Gly Ser Phe Leu Val Asn Ile Gly Asp Val Gly Thr Ala Trp Ser Asn
        210                 215                 220

Gly Arg Leu His Asn Val Lys His Arg Val Arg Cys Val Ala Pro Val
225                 230                 235                 240

Pro Arg Ile Ser Ile Ala Met Phe Leu Leu Ala Pro Lys Asp Asp Arg
            245                 250                 255

Val Ser Ala Pro Glu Ala Leu Val Asp Ala Gly His Pro Arg Arg Tyr
            260                 265                 270

Lys Pro Phe Asn Tyr Asp Asp Tyr Arg Arg Leu Arg Leu Ser Thr Gly
            275                 280                 285

Glu Arg Ala Gly Glu Ala Leu Ala Arg Met Ala Ala
290                 295                 300

<210> SEQ ID NO 25
<211> LENGTH: 1614
<212> TYPE: DNA
<213> ORGANISM: Zea mays

<400> SEQUENCE: 25
accacacgaa ttgcacatct ccacagctca cgattccaac actagctaca tatatatgta    60
gctttctagg ctactatata cactcaccac caagtgtgaa gtgtgtatat atagtgacag   120
ctactgcaat atatacatac gcgtcaccta tatattagcc aagctagcta tatgagcttg   180
gttgcggcgc caatggcgat cgtcgacgtg gccaacgccc agctgcagca agcagcagca   240
gcagctgcca agaaagacga ggacggccat gagcagcagg agtcgtccta cgactacggc   300
gcgctgatga aaggcgtgag gcacctgtcg gacagcggac ttaccaggct gcccgacagg   360
tacgtcctgc ccgcgtccga ccgccccggc gtccttgccg tctcgtcgtc cgtggcgggc   420
agcggcaggt tcaagctccc tgtcgtcaac ctcgccggcc tccgcgaccc ctgccagcgc   480
gccgccgtgc tggccacgct cgacgccgcg tgccgggagt acggcttctt tcaggtggta   540
aaccacgggt tcgggagcga cgtgagcggc gggatgctgg acgtggcgca gcgcttcttc   600
gagctgccgc tggccgagcg agcgcggcac atgtcggcgg acgtgcgggc gccggtgcgc   660
tacggcacca gcttcaacca ggccaaggac gacgtgctct gctggcgcga cttcctcaag   720
ctcgtctgcc agccgctgca ggcggtgctc ccgtactggc cccagcagcc ggcggacctc   780
agggacgtgg ccaccaggta cgccacggcg agccaccggc tgttcatgga ggtcatggag   840
gcggcgctgg aggccctggg catccccacg gccggcgggg tgctcgggga gctggcagcg   900
tcgtcgtcgc acatgatgac ggtgaactgc taccggcgt gcccgcagcc tgagctcacg   960
ctggggatgc cctcgcactc ggactacggc ctcttcacgt tcgtcctgca ggaccacgtc  1020
gagggcctcc aggtcatgca cgacggccgc tggctcacca tcgaccccat cccgggatcg  1080
ttcgtcgtca cgtcggcga ccacctagag atctacagca acgggcggta caagagcgcg  1140
ctgcaccggg tgcacgtgaa ctccacgcgg ccgcgcatct cggtggcgtc gttccacagc  1200
ctgccggcgg agcgagtgat cgggccggcg ccggagctgg tggacgacga ggccggcaac  1260
```

```
ccgcggcggt acatggacac cgacttcgct accttcctcg cctacctcgc atccgcggac   1320
ggcaagaaca agaccttcct ccagtcaagg aagctgcctg ctgctgctcc tccatgcctc   1380
tagctaacta gatagctgct tattaatctg acagaataaa attaatcagt tcagcgcaca   1440
attccacaag cgaaaacaaa cctggatttg ttttaattag ctctgccctt cattattaca   1500
ttcaagctag ctcttggtca acgcatgcac acaagcttga gcattgactg gtcccttttc   1560
aatcggttgc attgtactcc ctccgtacca aaattggttg tcgctatagt attt          1614

<210> SEQ ID NO 26
<211> LENGTH: 1212
<212> TYPE: DNA
<213> ORGANISM: Zea mays

<400> SEQUENCE: 26
atgagcttgg ttgcggcgcc aatggcgatc gtcgacgtgg ccaacgccca gctgcagcaa     60
gcagcagcag cagctgccaa gaaagacgag gacggccatg agcagcagga gtcgtcctac    120
gactacggcg cgctgatgaa aggcgtgagg cacctgtcgg acagcggcat taccaggctg    180
cccgacaggt acgtcctgcc cgcgtccgac cgccccggcg tccttgccgt ctcgtcgtcc    240
gtggcgggca gcggcagggt caagctccct gtcgtcaacc tcgccggcct ccgcgacccc    300
tgccagcgcg ccgccgtgct ggccacgctc gacgccgcgt gccgggagta cggcttcttt    360
caggtggtaa accacgggtt cgggagcgac gtgagcggcg ggatgctgga cgtggcgcag    420
cgcttcttcg agctgccgct ggccgagcga gcgcggcaca tgtcggcgga cgtgcgggcg    480
ccggtgcgct acggcaccag cttcaaccag gccaaggacg acgtgctctg ctggcgcgac    540
ttcctcaagc tcgtctgcca gccgctgcag gcggtgctcc cgtactggcc ccagcagccg    600
gcggacctca gggacgtggc caccaggtac gccacggcga ccaccggct gttcatggag    660 gtcatggagg cggcgctgga ggccctgggc atccccacgg ccggcggcgt gctcggggag    720
ctggcagcgt cgtcgtcgca catgatgacg gtgaactgct accggcgtg cccgcagcct    780 gagctcacgc tggggatgcc ctcgcactcg gactacggcc tcttcacgtt cgtcctgcag    840
gaccacgtcg agggcctcca ggtcatgcac gacgccgcgt ggctcaccat cgaccccatc    900
ccgggatcgt tcgtcgtcaa cgtcggcgac cacctagaga tctacagcaa cgggcggtac    960
aagagcgcgc tgcaccgggt gcacgtgaac tccacgcggc cgcgcatctc ggtggcgtcg   1020
ttccacagcc tgccggcgga gcgagtgatc gggccggcgc cggagctggt ggacgacgag   1080
gccggcaacc cgcggcggta catggacacc gacttcgcta ccttcctcgc ctacctcgca   1140
tccgcggacg gcaagaacaa gaccttcctc cagtcaagga agctgcctgc tgctgctcct   1200
ccatgcctct ag                                                       1212

<210> SEQ ID NO 27
<211> LENGTH: 403
<212> TYPE: PRT
<213> ORGANISM: Zea mays

<400> SEQUENCE: 27

Met Ser Leu Val Ala Ala Pro Met Ala Ile Val Asp Val Ala Asn Ala
1               5                   10                  15

Gln Leu Gln Gln Ala Ala Ala Ala Ala Lys Lys Asp Glu Asp Gly
            20                  25                  30

His Glu Gln Gln Glu Ser Ser Tyr Asp Tyr Gly Ala Leu Met Lys Gly
        35                  40                  45
```

```
Val Arg His Leu Ser Asp Ser Gly Ile Thr Arg Leu Pro Asp Arg Tyr
 50                  55                  60

Val Leu Pro Ala Ser Asp Arg Pro Gly Val Leu Ala Val Ser Ser Ser
 65                  70                  75                  80

Val Ala Gly Ser Gly Arg Val Lys Leu Pro Val Val Asn Leu Ala Gly
                 85                  90                  95

Leu Arg Asp Pro Cys Gln Arg Ala Ala Val Leu Ala Thr Leu Asp Ala
             100                 105                 110

Ala Cys Arg Glu Tyr Gly Phe Phe Gln Val Val Asn His Gly Phe Gly
         115                 120                 125

Ser Asp Val Ser Gly Gly Met Leu Asp Val Ala Gln Arg Phe Phe Glu
130                 135                 140

Leu Pro Leu Ala Glu Arg Ala Arg His Met Ser Ala Asp Val Arg Ala
145                 150                 155                 160

Pro Val Arg Tyr Gly Thr Ser Phe Asn Gln Ala Lys Asp Asp Val Leu
                165                 170                 175

Cys Trp Arg Asp Phe Leu Lys Leu Val Cys Gln Pro Leu Gln Ala Val
            180                 185                 190

Leu Pro Tyr Trp Pro Gln Gln Pro Ala Asp Leu Arg Asp Val Ala Thr
        195                 200                 205

Arg Tyr Ala Thr Ala Ser His Arg Leu Phe Met Glu Val Met Glu Ala
210                 215                 220

Ala Leu Glu Ala Leu Gly Ile Pro Thr Ala Gly Gly Val Leu Gly Glu
225                 230                 235                 240

Leu Ala Ala Ser Ser Ser His Met Met Thr Val Asn Cys Tyr Pro Ala
                245                 250                 255

Cys Pro Gln Pro Glu Leu Thr Leu Gly Met Pro Ser His Ser Asp Tyr
            260                 265                 270

Gly Leu Phe Thr Phe Val Leu Gln Asp His Val Glu Gly Leu Gln Val
        275                 280                 285

Met His Asp Gly Arg Trp Leu Thr Ile Asp Pro Ile Pro Gly Ser Phe
290                 295                 300

Val Val Asn Val Gly Asp His Leu Glu Ile Tyr Ser Asn Gly Arg Tyr
305                 310                 315                 320

Lys Ser Ala Leu His Arg Val His Val Asn Ser Thr Arg Pro Arg Ile
                325                 330                 335

Ser Val Ala Ser Phe His Ser Leu Pro Ala Glu Arg Val Ile Gly Pro
            340                 345                 350

Ala Pro Glu Leu Val Asp Asp Glu Ala Gly Asn Pro Arg Arg Tyr Met
        355                 360                 365

Asp Thr Asp Phe Ala Thr Phe Leu Ala Tyr Leu Ala Ser Ala Asp Gly
370                 375                 380

Lys Asn Lys Thr Phe Leu Gln Ser Arg Lys Leu Pro Ala Ala Ala Pro
385                 390                 395                 400

Pro Cys Leu

<210> SEQ ID NO 28
<211> LENGTH: 1863
<212> TYPE: DNA
<213> ORGANISM: Zea mays

<400> SEQUENCE: 28
tgccaccata ccactagtgc aaggtcctag atttacactt ggtgctacac cttgcttcgc      60
```

| | |
|---|---|
| cccccttcctt ccttccttcc ttccttccct ccttccttgg tctctaggca gctagcagtg | 120 |
| tggtgctgct gccggccgcc tattggccgc ctgggactgg gatccattaa ttactgcgcg | 180 |
| cgcgcggcta accaaccaat cccagcgtgc gtaatctatt gcccacatgc cgacgccgtc | 240 |
| gcacctcaac aagaacccgc gctacctgga cttccgggcg cgcgcggcgg tgccggagtc | 300 |
| gcacgcctgg ccgggcctgc acgaccaccc cgtcgtggac ggcggcgcgc cgggccccga | 360 |
| cgccgtgccg gtggtggacc tgggcgccgc ggacccggcg ccggcgccgg cggcggcggt | 420 |
| ggcccgcgcc gccgagcaat ggggcgcgtt cctgctcacg ggccacggcg tccccgcgga | 480 |
| cctgctggcg cgcgtggagg accggatcgc caccatgttc gcgctgccgg ccgacgacaa | 540 |
| gatgcgcgcc gtgcgcgggc ccggcgacgc ctgcggctac ggctcccgc ccatctcctc | 600 |
| cttcttctcc aagtgcatgt ggtccgaggg ctacaccttc tcgccggcct ccctccgcgc | 660 |
| cgacctccgc aagctctggc ccaaggccgg cgacgactac accagcttct gtgatgtgat | 720 |
| ggaggagttc cacaagcaca tgcgcgccct cgcggacaag ctgctggagc tgttcctcat | 780 |
| ggcgctgggg ctcaccgacg agcaggccag cgccgtcgag gccgagccgga ggatcgccga | 840 |
| gacgatgacc gccaccatgc atctcaactg gtacccgagg tgcccggacc cgcggcgcgc | 900 |
| gctgggggctg atcgcgcaca ccgactcggg cttcttcacc ttcgtgatgc agagcctcgt | 960 |
| gcccgggctg cagctcttcc gccacgcccc ggaccggtgg gtggcggtgc cggccgtgcc | 1020 |
| gggcgccttc gtcgtcaacg tgggcgacct cttccacatc ctcaccaacg gccggttcca | 1080 |
| cagcgtgtac caccgcgccg tcgtgaaccg ggacctcgac aggatctcgc tcggctactt | 1140 |
| cctcggcccg ccgccgcacg ccaaggtggc gccgctgcgc gaggccgtgc cgcccggccg | 1200 |
| ggcccccgcg taccgcgccg tcacgtggcc cgagtacatg ggcgtccgca agaaggcctt | 1260 |
| caccaccggc gcctccgcgc tcaagatggt cgccctcgcc gccgccgccg acctcgacga | 1320 |
| cgacggcgac gccgccgtcg tccatcagca gcagcagcta gtcgtctcgt cgtagccgag | 1380 |
| accgatcgcc ggagactgat gctgatgatg atgcatatat acatgagaga aatcgtcgag | 1440 |
| tagactagcc gattgcaaaa gcaaccccag ctgccgaaac ctggcatatc gatcccattc | 1500 |
| tctgctgcgc acatgtatgc atgcatgcgc ttcgtccgtt cgactcgtgt gtgcttgctt | 1560 |
| gcttgcgcgt gcagcagaac taattccgtt ccgcagctag ctgctctgct ctgctctgct | 1620 |
| ggaatgtaat taagtagtag tatatggtag tagagaaaag attagctagg cgatcgatat | 1680 |
| agatgacggg ccggggaaga agacgaatta attaagatcg atcgacgacg acgagctgtg | 1740 |
| cgtggctggc tgtgttcttc tctagcctag ttacagaggc cggctgctgc tgcttccaat | 1800 |
| cgggctgctt gtcgctactg acgatcgtta gtggatccat taactaatct ggaattctgg | 1860 |
| att | 1863 |

<210> SEQ ID NO 29
<211> LENGTH: 1149
<212> TYPE: DNA
<213> ORGANISM: Zea mays

<400> SEQUENCE: 29

| | |
|---|---|
| atgccgacgc cgtcgcacct caacaagaac ccgcgctacc tggacttccg ggcggcgcgg | 60 |
| cgggtgccgg agtcgcacgc ctggccgggc ctgcacgacc accccgtcgt ggacggcggc | 120 |
| ggcgccgggcc ccgacgccgt gccggtggtg gacctgggcg ccgcggaccc ggcgccggcg | 180 |
| ccggcggcgg cggtggcccg cgccgccgag caatggggcg cgttcctgct cacgggccac | 240 |
| ggcgtccccg cggacctgct ggcgcgcgtg gaggaccgga tcgccaccat gttcgcgctg | 300 |

-continued

```
ccggccgacg acaagatgcg cgccgtgcgc gggcccggcg acgcctgcgg ctacggctcc    360
ccgcccatct cctccttctt ctccaagtgc atgtggtccg agggctacac cttctcgccg    420
gcctccctcc gcgccgacct ccgcaagctc tggcccaagg ccggcgacga ctacaccagc    480
ttctgtgatg tgatggagga gttccacaag cacatgcgcg ccctcgcgga caagctgctg    540
gagctgttcc tcatggcgct ggggctcacc gacgagcagg ccagcgccgt cgaggccgag    600
cggaggatcg ccgagacgat gaccgccacc atgcatctca actggtaccc gaggtgcccg    660
gacccgcggc gcgcgctggg gctgatcgcg cacaccgact cgggcttctt caccttcgtg    720
atgcagagcc tcgtgcccgg gctgcagctc ttccgccacg ccccggaccg gtgggtggcg    780
gtgccggccg tgccgggcgc cttcgtcgtc aacgtgggcg acctcttcca catcctcacc    840
aacggccggt ccacagcgt gtaccaccgc gccgtcgtga accgggacct cgacaggatc    900
tcgctcggct acttcctcgg cccgccgccg cacgccaagg tggcgccgct gcgcgaggcc    960
gtgccgcccg ccgggccccc gcgtaccgc gccgtcacgt ggcccgagta catgggcgtc   1020
cgcaagaagg ccttcaccac cggcgcctcc gcgctcaaga tggtcgccct cgccgccgcc   1080
gccgacctcg acgacgacgg cgacgccgcc gtcgtccatc agcagcagca gctagtcgtc   1140
tcgtcgtag                                                          1149
```

<210> SEQ ID NO 30
<211> LENGTH: 382
<212> TYPE: PRT
<213> ORGANISM: Zea mays

<400> SEQUENCE: 30

```
Met Pro Thr Pro Ser His Leu Asn Lys Asn Pro Arg Tyr Leu Asp Phe
1               5                   10                  15

Arg Ala Ala Arg Arg Val Pro Glu Ser His Ala Trp Pro Gly Leu His
                20                  25                  30

Asp His Pro Val Val Asp Gly Gly Ala Pro Gly Pro Asp Ala Val Pro
            35                  40                  45

Val Val Asp Leu Gly Ala Ala Asp Pro Ala Pro Ala Pro Ala Ala Ala
        50                  55                  60

Val Ala Arg Ala Ala Glu Gln Trp Gly Ala Phe Leu Leu Thr Gly His
65                  70                  75                  80

Gly Val Pro Ala Asp Leu Leu Ala Arg Val Glu Asp Arg Ile Ala Thr
                85                  90                  95

Met Phe Ala Leu Pro Ala Asp Asp Lys Met Arg Ala Val Arg Gly Pro
            100                 105                 110

Gly Asp Ala Cys Gly Tyr Gly Ser Pro Pro Ile Ser Ser Phe Phe Ser
        115                 120                 125

Lys Cys Met Trp Ser Glu Gly Tyr Thr Phe Ser Pro Ala Ser Leu Arg
130                 135                 140

Ala Asp Leu Arg Lys Leu Trp Pro Lys Ala Gly Asp Asp Tyr Thr Ser
145                 150                 155                 160

Phe Cys Asp Val Met Glu Glu Phe His Lys His Met Arg Ala Leu Ala
                165                 170                 175

Asp Lys Leu Leu Glu Leu Phe Leu Met Ala Leu Gly Leu Thr Asp Glu
            180                 185                 190

Gln Ala Ser Ala Val Glu Ala Glu Arg Arg Ile Ala Glu Thr Met Thr
        195                 200                 205

Ala Thr Met His Leu Asn Trp Tyr Pro Arg Cys Pro Asp Pro Arg Arg
```

```
        210                 215                 220
Ala Leu Gly Leu Ile Ala His Thr Asp Ser Gly Phe Phe Thr Phe Val
225                 230                 235                 240

Met Gln Ser Leu Val Pro Gly Leu Gln Leu Phe Arg His Ala Pro Asp
                245                 250                 255

Arg Trp Val Ala Val Pro Ala Val Pro Gly Ala Phe Val Val Asn Val
                260                 265                 270

Gly Asp Leu Phe His Ile Leu Thr Asn Gly Arg Phe His Ser Val Tyr
                275                 280                 285

His Arg Ala Val Val Asn Arg Asp Leu Asp Arg Ile Ser Leu Gly Tyr
                290                 295                 300

Phe Leu Gly Pro Pro His Ala Lys Val Ala Pro Leu Arg Glu Ala
305                 310                 315                 320

Val Pro Pro Gly Arg Ala Pro Ala Tyr Arg Ala Val Thr Trp Pro Glu
                325                 330                 335

Tyr Met Gly Val Arg Lys Lys Ala Phe Thr Thr Gly Ala Ser Ala Leu
                340                 345                 350

Lys Met Val Ala Leu Ala Ala Ala Asp Leu Asp Asp Asp Gly Asp
                355                 360                 365

Ala Ala Val Val His Gln Gln Gln Leu Val Val Ser Ser
                370                 375                 380
```

<210> SEQ ID NO 31
<211> LENGTH: 1439
<212> TYPE: DNA
<213> ORGANISM: Zea mays

<400> SEQUENCE: 31

```
gacctccatt ttgattatct ctatcctgta cgtgccgaga gtccttcaaa gccgacgacg      60
agacgacgat gcagtcgtcg tcgtcatcag cctcgacgcc ggctgccgct ccggcctcg     120
tcttcgatct cgggtctgcg gcgggcgtgc cggagacaca cgcgtggccg ggggtgaacg    180
agtacccgtc ggtggagtcc gctggccgcg acgtggtccc ggtggtggac atggggtgg    240
cctgcccgga cgcgacgcgg gcgttggcgc gcgccgcaga cgagtggggc gtgtttctgc    300
tcgtcggcca cggcgtgccc cgggaagtgg cggcgcgtgc cgaggagcag gtcgcgcgcc    360
tgttcgtgct cccggctcct gacaaggccc gcgcggggcg ccgccccggg gagcccacgg    420
ccaccggcta cggcaggccg ccctggcac tccgcttctc caagctcatg tggtccgagg     480
ggtacacgtt ccgcgccgcc accgtccgcg aagagttccg ccgcgtctgg cccgacggcg    540
gcgacgacta cctccgcttc tgcgacgtga tggaggagta cgacagagag atgagggctc    600
tcggtggcag gctgctcgac ctcttcttca tggcgctcgg cctcaccgac gtccagttcg    660
ccaccggcga gacggagcgg aggatccgcg agacctggac ggcgacgatg cacccaatcc    720
tgtgtccgga accggagcgc gccatcgggc tgacggcgca cacggactcg ggcttcatca    780
cgctcatcat gcagagcccc gtgccccggc tgcagctgct ccgccgcggg ccggaccggt    840
gggtgacggt gccggcgccg ccgggcgcgc tcatcgtcat gctcggcgac ctgttccagg    900
tgctcacgaa cggccgcttc cggagcccta tccaccgcgc cgtcgtaagc cgagagcgcg    960
agcggatctc cgtgccctac ttcctctgcc cgccggagga catgacggtg cgccgctcg   1020
cgtccgctct gctgccgggg aggaaggccg tgttccgggc cgtgacgtgg ccagagtaca   1080
tggaggtcaa gcacaaggtg ttcggcacgg atgcgccggc cctggagatg ctgcagctgc   1140
aggtggatga ggaagaacaa ggtgaaaggg ccgccaccac ctaagcccta aggaactact   1200
```

```
agctgaatcc ataaactaat aaagaattcg tgaataaggg cgttggaaga ctggacacaa    1260
cacaagagag ttgctatata tcgtatttct gaaatttaag gcaaatatct tagttaaaaa    1320
actggtatat ttaaatagac aatatatatc taaaataaag atagttcacc atttttacgg    1380
tcgaacaatg ataaagttat atattgtctg aatagtaaca aattaaagat ttccaggag     1439
```

<210> SEQ ID NO 32
<211> LENGTH: 1116
<212> TYPE: DNA
<213> ORGANISM: Zea mays

<400> SEQUENCE: 32

```
atgcagtcgt cgtcgtcatc agcctcgacg ccggctgccg cttccggcct cgtcttcgat     60
ctcgggtctg cggcgggcgt gccggagaca cacgcgtggc cggggtgaa cgagtacccg     120 tcggtggagt ccgctggccg cgacgtggtc ccggtggtgg acatgggggt ggcctgcccg    180
gacgcgacgc gggcgttggc gcgcgccgca gacgagtggg gcgtgtttct gctcgtcggc    240
cacggcgtgc cccgggaagt ggcggcgcgt gccgaggagc aggtcgcgcg cctgttcgtg    300 ctccggctc ctgacaaggc ccgcgcgggg cgccgcccg gggagcccac ggccaccggc      360
tacggcaggc cgcccctggc actccgcttc tccaagctca tgtggtccga ggggtacacg    420
ttccgcgccg ccaccgtccg cgaagagttc cgccgcgtct ggcccgacgg cggcgacgac    480
tacctccgct tctgcgacgt gatggaggag tacgacagag agatgagggc tctcggtggc    540
aggctgctcg acctcttctt catggcgctc ggcctcaccg acgtccagtt cgccaccggc    600
gagacggagc ggaggatccg cgagacctgg acggcgacga tgcacccaat cctgtgtccg    660
gaaccggagc gcgccatcgg gctgacggcg cacacggact cgggcttcat cacgctcatc    720
atgcagagcc ccgtgcccgg gctgcagctg ctccgccgcg gccggaccg gtgggtgacg    780 gtgccggcgc cgccgggcgc gctcatcgtc atgctcggcg acctgttcca ggtgctcacg    840
aacggccgct tccggagccc tatccaccgc gccgtcgtaa gccgagagcg cgagcggatc    900
tccgtgccct acttcctctg cccgccggag gacatgacgg tggcgccgct cgcgtccgct    960
ctgctgccgg ggaggaaggc cgtgttccgg gccgtgacgt ggccagagta catggaggtc    1020
aagcacaagg tgttcggcac ggatgcgccg gccctggaga tgctgcagct gcaggtggat    1080
gaggaagaac aaggtgaaag ggccgccacc acctaa                              1116
```

<210> SEQ ID NO 33
<211> LENGTH: 371
<212> TYPE: PRT
<213> ORGANISM: Zea mays

<400> SEQUENCE: 33

```
Met Gln Ser Ser Ser Ser Ala Ser Thr Pro Ala Ala Ala Ser Gly
1               5                   10                  15

Leu Val Phe Asp Leu Gly Ser Ala Ala Gly Val Pro Glu Thr His Ala
            20                  25                  30

Trp Pro Gly Val Asn Glu Tyr Pro Ser Val Glu Ser Ala Gly Arg Asp
        35                  40                  45

Val Val Pro Val Val Asp Met Gly Val Ala Cys Pro Asp Ala Thr Arg
    50                  55                  60

Ala Leu Ala Arg Ala Ala Asp Glu Trp Gly Val Phe Leu Leu Val Gly
65                  70                  75                  80

His Gly Val Pro Arg Glu Val Ala Ala Arg Ala Glu Glu Gln Val Ala
```

```
                  85                  90                  95
Arg Leu Phe Val Leu Pro Ala Pro Asp Lys Ala Arg Ala Gly Arg Arg
                100                 105                 110

Pro Gly Glu Pro Thr Ala Thr Gly Tyr Gly Arg Pro Pro Leu Ala Leu
            115                 120                 125

Arg Phe Ser Lys Leu Met Trp Ser Glu Gly Tyr Thr Phe Arg Ala Ala
        130                 135                 140

Thr Val Arg Glu Glu Phe Arg Arg Val Trp Pro Asp Gly Gly Asp Asp
145                 150                 155                 160

Tyr Leu Arg Phe Cys Asp Val Met Glu Glu Tyr Asp Arg Glu Met Arg
                165                 170                 175

Ala Leu Gly Gly Arg Leu Leu Asp Leu Phe Phe Met Ala Leu Gly Leu
                180                 185                 190

Thr Asp Val Gln Phe Ala Thr Gly Glu Thr Glu Arg Arg Ile Arg Glu
            195                 200                 205

Thr Trp Thr Ala Thr Met His Pro Ile Leu Cys Pro Glu Pro Glu Arg
        210                 215                 220

Ala Ile Gly Leu Thr Ala His Thr Asp Ser Gly Phe Ile Thr Leu Ile
225                 230                 235                 240

Met Gln Ser Pro Val Pro Gly Leu Gln Leu Leu Arg Arg Gly Pro Asp
                245                 250                 255

Arg Trp Val Thr Val Pro Ala Pro Pro Gly Ala Leu Ile Val Met Leu
                260                 265                 270

Gly Asp Leu Phe Gln Val Leu Thr Asn Gly Arg Phe Arg Ser Pro Ile
            275                 280                 285

His Arg Ala Val Val Ser Arg Glu Arg Glu Arg Ile Ser Val Pro Tyr
        290                 295                 300

Phe Leu Cys Pro Pro Glu Asp Met Thr Val Ala Pro Leu Ala Ser Ala
305                 310                 315                 320

Leu Leu Pro Gly Arg Lys Ala Val Phe Arg Ala Val Thr Trp Pro Glu
                325                 330                 335

Tyr Met Glu Val Lys His Lys Val Phe Gly Thr Asp Ala Pro Ala Leu
                340                 345                 350

Glu Met Leu Gln Leu Gln Val Asp Glu Glu Gln Gly Glu Arg Ala
            355                 360                 365

Ala Thr Thr
    370

<210> SEQ ID NO 34
<211> LENGTH: 4095
<212> TYPE: DNA
<213> ORGANISM: Zea mays

<400> SEQUENCE: 34
taaatttgtg atccttgtga agttgttata tcatgaattg tgaacttgtt gcatttgtga      60
tcttttgtca actttgttgt attgtgaagt ttgatatgtt taccgatcgt attttagatt     120
tcgatcgtta ccggtgtatt ttccgcacca aacttttgtt tccgatgttt tcgaaatacc     180
gatatcgttt ccgtttctat agttacccct ttcaatttta tttccgatta aaaatatgaa     240
aacggtaatg gttttagtgt ttatcgaccg ttttcatctc taatcatccc tgccggtgaa     300
gtttaatttt tcccttggct aaagagatgc aagctgctgt aaaatacgtt aaaacaggca     360
aggcagcccc agcagccagc atcgcgtgcc cgtctatgta catcagtgga tacgtagcat     420
ctctagtgag taatataacg attgcatttg gctggaggac gtatgttata taagtatgtc     480
```

```
atttaccagt tgcattagta tcttccctaa ctcctataat aactctcttc gtggaatgga    540
cgtagacgta tgctatataa gtattaaaaa atagttttt aagctggtgt cctcaatttt     600
gctattgttc tcgtttttat ctttagttgt gtcacaaatt taatccgtac aacaaatcaa    660
aaataccata cccttcttat attaattttc taacataaca tttgtttaga tattttcagt    720
cgtgaaaata caattctaat tctaacgtcg tagtatcaaa tcaaccatc cagaatttga    780 ccaagcttaa ttataaaaaa tataaaattt atgatactga atagatagca ttagatttgt    840
tatataatat attttttataa aataccattt ttatggtata aatattggta ctcctttact   900
ttaaactata gatagttttg actaaggatg caactgaaat tgcatcctct tttcactgca    960
ccttcattag ttttaatatt tatttagatg ggcccttgca aactgtagat atcatctctt   1020
gcaacattct ttctatagca ccacgaaaat gtattgcggc tttgaaatta taattgaatt   1080
agttgtatca tttctttcac cgatgcgtta aattcaaaat taagtgttat atttcttcat   1140
aatttgttaa atatatagac cctataatcc accattattt actataatag catacattaa   1200
cattggtttt agcctacact acgacactcg aggcattgaa ttttcctcta tcaaagaatt   1260
atatgtgtag tagtattgtt cttgacaaaa aggggggatta aaattaaact accaatattg   1320
atacttatct tatcacatcc atgaatacaa tcaacactct tacaaaagat aagatacaag   1380
attaaaaagt accatgataa tacattaaga ttattagcaa tgcattaaat taaataaatg   1440
tgcaagtgaa tcatgatttt agttttatct attttacttt taaaatatga tattctctga   1500
ctacttctaa gcataaatgt gattctaagt catgaccgat cgtgcttatt cagaaaaatg   1560
aaggagacac agatttctat aaaaaaaggt tgtcatggga ctattgggtc aaccatctta   1620
ttcatttggg aaaataagtt tagaacacat caacccattt tagatgttga gtttggccct   1680
aatggtccat tgaccttact tttgtgggtt gacatagacc atctatccca agttattgtt   1740
gtgtcacatt ccctgatatc atgaatctat attttagctt tccgttttca tatttttagt   1800
cgttacatat tttttatccg cgtactagat taaaactcta gttgttgcaa tacattttgt   1860 tcatttttt ctatttcttc tttactaaca acatattcta gttcctagct acattcttaa    1920
gtaccatagt gctataaaca ttttttatcc tacattattc cacttaagaa attgaatttt   1980
ctgcataaaa aaattatatg tccagtagtg ttgtcttata aaagcataaa gtgattaaaa   2040
ttaaaaccat tattgatatc ttattttca aaaaaaaata taagcttata gaaagtgaat   2100
taatttcatg gtaaattaat atagtttaaa ttgaattatt agtgttatta ctatgtttat   2160
tatcaatgaa acatttttca tggttgatat aacttagtgt tacttatttt agtattttt    2220 atataattct agttaacttt tagttttga tttaaaaaaa cgagaattgt gtccttttgt    2280
ggagtgagta taagaaagt aatatctgtt catcataatt tggttttta aggtacgtga    2340 aacttgcttt atatttggac tcaagctatg tctaaataca tagtaaaaaa gcaatatttc   2400
tagaaaagac aaaacatctt ataatttaga atcaaggaaa tatatagatt ttatgtgcag   2460
tgagaagcca tttacaatgg aacgttcaac gttgggccaa tagatatttt gcgatatgat   2520
gatgggcata tttttgcatg gttgtccctc cactagctat agtttgatga tacgatacgc   2580
tgcacacacc attgggttgt accatgttag tgtagcaaca gtagaaaccc aattgtggcc   2640
gtgaaccatg ataatactag gtagagtgct agctagaggt ttcaggctat tgatgcgtga   2700
attaaacttt ctgttgtgtt gcgaggaaac gagtattgtg aaatatttga aacggttttt   2760
tttgtgaaag atttgaaacg gtattttgt tgtgaaataa agatcaaggc taaataaatt   2820
```

| | |
|---|---|
| caaactaata aaacatatta attgacggcc tgaagccccc gcccccatgg ccccatgcca | 2880 |
| tagcatcagg tcccacatga catgaggccg cgcctccctc tatgttggct ccctgccttc | 2940 |
| gccgttgtcg tcgctcccga actccctctc ctccctgtt acaaatacc ccacccgccc | 3000 |
| ggacagcttc cctgcacact cgcagctcgc acatctcatg gtgtcctaag aacggcaaga | 3060 |
| gccagctctg cctagcagca gcgcacagcc acatccatgg acgccagccc gacccaccg | 3120 |
| ctccccctcc gcgccccaac tcccagcatt gacctcccg ctggcaagga cagggccgac | 3180 |
| gcggcggcta acaaggccgc ggctgtgttc gacctgcgcc gggagcccaa gatcccggag | 3240 |
| ccattcctgt ggccgcacga agaggcgcgg ccgacctcgg ccgcggagct ggaggtgccg | 3300 |
| gtggtggacg tgggcgtgct gcgcaatggc gacggcgcgg ggctccgccg cgccgcggcg | 3360 |
| caagtggcgg cggcgtgcgc gacgcacggg ttcttccagg tgtgcgggca cggcgtggac | 3420 |
| gcggcgctgg ggcgcgccgc gctggacggc gccagcgact tcttccggct gccgctggct | 3480 |
| gagaagcagc gggcccggcg cgtccccggc accgtgtccg ggtacacgag cgcgcacgcc | 3540 |
| gaccggttcg cgtccaagct cccctggaag agaccctgt ccttcggctt ccacgacggc | 3600 |
| gccgcggcgc ccgtcgtcgt ggactacttc accggcaccc tcggccaaga tttcgagcca | 3660 |
| gtggggtgag taaagaagaa gatggcgccg aatttacatt tataagtagg accagcagaa | 3720 |
| gcccctgccc ctgggggcct tagcattgca ttcgactgat gaatacgcat ggcaggcggg | 3780 |
| tgtaccagag gtactgcgag gagatgaagg agctgtcgct gacgatcatg gagctgctgg | 3840 |
| agctgagcct gggcgtggag cgcggctact accgggagtt cttcgaggac agccgctcca | 3900 |
| tcatgcggtg caactactac ccgccgtgcc cggtgccgga gcgcacgctg gcacgggcc | 3960 |
| cgcactgcga ccccacggcg ctgaccatcc tcctgcagga cgacgtcggc gggctggagg | 4020 |
| tcctggtgga cggcgagtgg cgccccgtcc ggcccgtccc aggcgccatg gtcatcaaca | 4080 |
| tcggcgacac cttca | 4095 |

<210> SEQ ID NO 35
<211> LENGTH: 7404
<212> TYPE: DNA
<213> ORGANISM: Zea mays

<400> SEQUENCE: 35

| | |
|---|---|
| cctattttgt gtctaatact cttcttatat taattgtttg gtcaaacttt agataaattt | 60 |
| gactaatgat gcaattaaaa ctgcatcacc tttactaagg tactgcttta tatgtttcga | 120 |
| caaaattttc aattattctc tatgtgtttt aatctttgcg ctacacctcc attgatttaa | 180 |
| atactcattt attttaaacc ataacttaaa ttatatcgga tctttgcatc ctttctatgg | 240 |
| caccatacat gaatcgatat tttggctgca aattttaat catgttagtt ttagcatttt | 300 |
| ttcatatcca tgtgttaagt ttgaatcatg tgttgttttt atataattta ttgaaaatat | 360 |
| agatcctaaa cttcactaat acttacaaca atagcatcat catgtgtttt aatccacgcc | 420 |
| acaacactca aggcattgaa ttttcttcta ccaaagagtt gtatgtgtgt attgttcttt | 480 |
| aaaaaataga gtgattataa ttaaactacc agtattcata tgtaaaatgt atagacatct | 540 |
| aaaataaaat ttgcaaaaaa cattgttgca gactttcaat ataattaaga atgggtttta | 600 |
| gggtcatgat atatggtttg ttaaagaaac ttgttttttt ttgcaattga taaactataa | 660 |
| aatacatttt cactattgtg tgcatatgta cttggtatac atagtggcat atatcatttt | 720 |
| tgtttacttt gaggtttgaa ttatctatgt taaaattgga taacatagat acattggtgt | 780 |
| gcgtcctttg gcccatttac ttgactgagg agcaatacta taaagtaaaa catatttgga | 840 |

```
tattttatct taaactccta gcataatatt gatttaatta tgaacaaata tatgtttagg      900
tgatagtttc atgggtggta aactatataa gaaggcttac catgatcttt gcaaactcta      960
ggctatgaaa gagttccatg atttgtctta gaagcataga caaaacagtg ataatgatct     1020
aaatcacact tatggcactg atgaccatat atgcaaagct aaatgcatgt taagttgtat     1080
tatatcatat gtttacaatg actatcgcat ataacgagga atacattgtc tatatagata     1140
gctattactg tagtagtgcc aaatgttgga caacatgaat cataatcttc aaacctagag     1200
aaattgtagt cagtcgtaca catatcgtct agtaagttgt ctatactttt tatttattgt     1260
atcaaatttt attgttatct tgcttgcttg tttgtttgta ccatagacac aatatggtca     1320
aaaagtggtc aatcgattcg aagaagattg caattgacga gtgctaacag ttgatccttt     1380
tgttgtgcac gctagcggag tagcatgaaa agagtaaaat atgaaattag cgttctaaac     1440
tgtttgtgct ataggtactt cgtatttaat ggagtgacta actataggaa ggtgagagct     1500
cagaagtcag caccctcaca cagagttcta gagttagtgg tcatcgaacc acgacaaact     1560
acatgatgag cagaagaggc aacatcaaga ctatgatcaa tagtttcggg tcaatgaatg     1620
acatcgtgat gagtatttat ctaactatat agaacaacaa cacatgatgt tttaagtaag     1680
ttcaactgat cttctattgc tatctttaag tatttaacgt agcgaataat gttttatcta     1740
tttcattcat aaataatgtt gtgacaaaag gggataacca tcactttttac catgttctag     1800 ataccacaac catctccacc atcataatgg gttcttcatt ggtgcttgga cctcaaataa     1860
tcatatctat agccaactta gctcaattct aataaaatta ggcaacttgg cttcattgta     1920
gcaaaaatag ccaacttagc tcaattttat ctaaacttag ctaatctagc acaacttaga     1980
tcaatattag gaaaaactaa tcaatctaat ctagctcaac tatagcgaaa gatagatatt     2040
gtagcataac ttagtagatc tatctcaaat tttagcaaaa actaatcaat ttagataaac     2100
tctataaaat tttaatcatt atgacttatt tccaactaat tgtaacttgc atgattttta     2160
tgttccttct ttataattag caacacctaa agacacgaat gatgaggggt ctaacgcatt     2220
cattaaccag ttgttaaata atactctagg tagatgataa gaactctaat tattctatga     2280
atctaagcta aaagatgttt aatatttaag tattggtgtt tattatgtta tttagaacga     2340
ttcatgttac ttaaagattt gttatgattt taaatatga ttatgataat ttatgtggtg      2400
tggattaact tgtgaacata tgtgatgtag atgaatatgt atgttgtgga tggaaccata     2460
tgaatatata tacacactca tatactattc gttggtgtag gtaaagcttc atccatcggt     2520
aattactaaa tggtcttcag tcattaccac taggtgaagc ttcacacgac cgataattat     2580
tgaagaacgc tcattaattt ccggtaatgg cttattggcc ttcactagtc ggtgaaaatt     2640
agctattttt ataccaataa aaattagcta atatatgtaa accaggtcta atttttatgg     2700
gcctcttacc gaccaaaatt gattagatta ttgttacaat agttttagtc aaaagctagc     2760
tatgctataa aaattttgaa ttaaagtgag tttcgtaata aaaattgcat acttttaaaa     2820
taaaataatt aaaaaacagt ttttagaaat acaatcaaac accttatgct ataaaaaaat     2880
tgtaatgtac ctacaaatat ataatacttt actttaaaat aggcctgtgc cttctcggct     2940
ctatatgggc tgcctccaac gaagcgccat ggccatgggc tccactgtgt cgggtcccac     3000
atgaggccgc gcctccctcc aaatgttccc tccctgcctt cgtctttgtc gttgctcgca     3060
aactccctgt cctcccctgt tacaaatacc cccacccgcc cggacagctt ccctgcatac     3120
ttgcagctcg cacatctcat ggtgtcgcag gaacgacaag agccagctgt gcctagcagc     3180
```

```
agcagcagca gcgccaagcg cgcagccacg tccatggacg ccagcccggc cccgccgctc    3240
ctcctccgcg cccccactcc cagccccagc attgacctcc ccgctggcaa ggacaaggcc    3300
gacgcggcgg ccagcaaggc cggcgcggcc gtgttcgacc tgcgccggga gcccaagatc    3360
cccgcgccat tcctgtggcc gcaggaagag gcgcggccgt cctcggccgc ggagctggag    3420
gtgccgatgg tggacgtggg cgtgctgcgc aatggcgacc gcgcggggct gcggcgcgcc    3480
gcggcgcagg tggccgcggc gtgcgcgacg cacgggttct tccaggtgtg cgggcacggc    3540
gtggacgcgg cgctggggcg cgccgcgctg gacgcgccca gcgacttctt ccggctgccg    3600
ctcgccgaga agcagcgcgc ccggcgcgtc cccggcaccg tgtccgggta cacgagcgcg    3660
cacgccgacc ggttcgcggc caagctcccc tggaaggaga ccctgtcgtt cggctaccac    3720
gacgcgccg cgtcgcctgt cgtcgtggac tacttcgtcg gcaccctcgg ccaggatttc    3780
gagccaatgg ggtaagtaag gtagtaagaa ggagcgccgg tttacattta ccgcacgtcg    3840
gcgtgcggtc gagtcgggac tcgggagacg tatgaacccc cgtcccgtcc catgcatgtg    3900
tggcaggtgg gtgtaccaga ggtactgcga ggagatgaag gagctgtcgc tgacgatcat    3960
ggagctgctg gagctgagcc tgggcgtgga gctgcgcggc tactaccggg agttcttcga    4020
ggacagccgt ccatcatgc ggtgcaacta ctacccgccg tgcccggagc cggagcgcac    4080
gctgggcacg ggcccgcact gcgaccccac ggcgctcacc atcctcctgc aggacgacgt    4140
gggcgggctg gaggtgctgg tggacggtga gtggcgcccc gtccggcccg tcccgggcgc    4200
catggtcatc aacatcggcg acaccttcat ggtaacgaaa cgaaagcgct cgctcctctg    4260
ttttccttgg ccgctcttgt cctgtgtgta tattcagttg agctctctct gtgctgttat    4320
ttcccgaatc ctagtggacc taaacgggca ggttattaca gcacgcacac gtaggcatgt    4380
catgtagcta gtacatacat agcgatgccg atgcaaatgc aatagagaca tgcgttcgag    4440
ttggttccta tctcggcggg ctacggcagg tacacgcggc cgcggcgcgc tctctctagt    4500
ctatccgcgg ccgcgcccag gccgatcgag gcttccgggg gagagttgcg acaagagaac    4560
ggaccgaggg ggtcggctag cggtagcaag ttccctgttg gtttgtggcg ttggagcgtt    4620
gcggagaggc ttgcgcggcg gcggggacgt cgacggggac gtggcgggga gacgatacga    4680
tgggtgccgg gcaggtttcc gaattccaaa cgttttgtg gcgtgcgtcc atggggcgcc    4740
cccaaacttc ggacgtttcc ggcgctccaa caaatcttct cgcttcacac gtcaccgtcg    4800
tcccggattc atttgcctcg tcgctccacc attcgctgct ctcctctcca cgtactctta    4860
ccctgacctt tgggaaagaa ctgaacattc gagatgcaca acagttcaaa tataacatat    4920
gcagcacaag atcgttcgac tgctatccga caagccaaca acgtgcccag tagaactgaa    4980
tgtacctgtg atttccagca ctaacttaca gcaacgttgt gaaaaaacaa aaacgaaaac    5040
aaacggcaga aaaaacagat gtattgttct acagttacac caaatatttt ctggtccttt    5100
cagcaccaac aagagccata cgcatatcta gaagacaaaa ttcctctaat ttcaccccta    5160
cgtggtagca gttcctcctc aacacagttc acgtgctagc gtcgagttct ttgggccgcc    5220
acatcgactt ctcgacgcag agcaggccct cgctgccctt ggtgtaggtc atccgcacct    5280
cccactgcac ggacttggcc atgctctcca gctcatttat cgtgtccgcg gtgtccctca    5340
cgatcagctt gccctgtggc ctcagtacac ggtcgacctc ggcgaaaact gcagccagtt    5400
tgcatctgta aacaggcaac acagattttt agtatctaaa acactgcagg caaacgccac    5460
aggttttagt cgcaagaagc aataaaagca tgcaaacaat gctacgtgta cgtatcaaag    5520
gaacatgtca aaactcgttg catgaacgat cattgatgtt tccttgctga actagtcaca    5580
```

-continued

```
tcagtctgct tcaacttctg ggtttcacta gtagatatac cagaagggta gaataatgtg      5640
aagagcaaga aatacagacc tctttctgag ctttgagaac agatggtccg cgtgcagaag      5700
gtcatacgtt cttgggtaag tgctgaaaga ctcgcaccag tcatggtaca tgccaaacaa      5760
accgcgctcg tagatgatgg gcagcgtgtc tggtgaatcg atcggcacga tattcatgac      5820
ccagaccttt tggtccctca gagctgcagc aaaactgcca tgcaacaatg taaagcatta      5880
gtcaagaaga aggtgtacag tgcatttctc cttgtcaaca gtcttcagta acaaaaaaaa      5940
agtgttatgc ttgactgaat ctttcaaaga aatatgcttg atgacttatg gtggacaagt      6000
tgcctgttat agtgttatgt tttaattaac tatgtgccag cttgggtaac tagtagttat      6060
gtagtgtgat ctgaattacc aaaatataaa taaataaata acatgccca agaaactacg       6120 aaaaccattt acttaccctc catagacagc tctcatgtcc atgacatttc tcactttgga      6180
ccagtcaatt cccatgccat tcacatacga tttacttaca acccgtttcc agtgggcatt      6240
atctgcctca aaatcttcat ttgcaggctt tccatagaca ccaaccttgg aaccatcaat      6300
ccagaaaggg gtcttctcaa gcctttgcgg ccataactct ggccattttg atcctcggac      6360
ttttgagcca ccaggcagtt tgtgcatgca tgcttccaac ggtacattcc tgcaaatcaa      6420
aaggctgtgt aagcaaagca gagaagcact tttctccatt gaaaatatac tcttctcaaa      6480
gaaccgaaac cataccaagc agcatctgca tcatcagatt ccttgcacaa tggcgggctg      6540
ttttcagatc tttctcata gcaaatattg tccattggtt tctgatatat gaccatacca       6600
acttggttta acttatcctt agtcttgttg accatcttcc agcacatgga ctttgtcaaa      6660
gtagacatgg ctgaaaaggg tatgtggcca catgttatgt tagaaataaa attcaatttt      6720
gaacagttgg tccatagcat gtattttgaa caaatgcaat ccttctccat ccatgaaaga      6780
agttgaccct tcatacttag gattattcag tactttcact catgtctgct gaatttgttc      6840
tcttggtagt tgctatacaa gaaaggggga agtacagagt agctaaactt atacaagcta      6900
tagtctgata tttgtatgaa acataaattt tggtatggat gtcttattaa aatgggaggt      6960
tgtataatat ttttctagcc tacctcaact tgcttgagac taaaaggctt tgttgttgtt      7020
gttgaggctg tatggtgctt tgactttaca aatcaagtta tcagctaccc tacttatgga      7080
tatacacctc tcataaaatg atggtaagaa gtttcgatat gtcacattaa cataagaact      7140
tcattcagtt agggtacaac gaagttaagt agttacggaa ataccattcc aaatctcaac      7200
atcctctggg agcttttggt aaacaggagt ggcagaccag acaaagtaac caccagggcg      7260
taacaagcgg ttcaattcca gcaaaagcat gccacctaaa agtagcgagc cagcaataag      7320
attcagttct atagcaaatc aataaatgaa aggaggacat gtcaatatgt aaccagcagg      7380
acaaaccttc gatgtgccaa ggga                                             7404
```

<210> SEQ ID NO 36
<211> LENGTH: 1788
<212> TYPE: DNA
<213> ORGANISM: Zea mays

<400> SEQUENCE: 36

```
aatcccagcg tgcgtaatct attgcccaca tgccgacgcc gtcgcacctc aacaagaacc        60
cgcgctacct ggacttccgg gcggcgcggc gggtgccgga gtcgcacgcc tggccgggcc       120
tgcacgacca ccccgtcgtg gacgcgcgcg cgccggggccc cgacgccgtg ccggtggtgg      180
acctgggcgc cgcggacccg gcgccggcgc cggcggcggc ggtggcccgc gccgccgagc      240
```

| | |
|---|---|
| aatgggcgc gttcctgctc acgggccacg gcgtccccgc ggacctgctg gcgcgcgtgg | 300 |
| aggaccggat cgccaccatg ttcgcgctgc cggccgacga caagatgcgc gccgtgcgcg | 360 |
| ggcccggcga cgcctgcggc tacggctccc cgcccatctc ctccttcttc tccaagtgca | 420 |
| tgtggtccga gggctacacc ttctcgccgg cctcccctcg cgccgacctc cgcaagctct | 480 |
| ggcccaaggc cggcgacgac tacaccagct tctggtacgt tgcgttgcgt gcttgtgtgc | 540 |
| gcgcacacct gccgaccgcg gccacaccgt acgcaaccca cgcgtacgta cgtgcgctag | 600 |
| ctacctgctt cgctcgcttc gctcctctcg cctcgccatg catatgcacg tacggccgta | 660 |
| caggtacagc agcaggtcac acgcacgaac gcacgcacgc accagcaccg atatgataca | 720 |
| tcatcgacgt gtcgtccccc cgtctaaggc catgcatgca tgcaagcacg cctagctagc | 780 |
| cctttggct tgctagctga cgaggggagc taggacgagc atacttactg tgcgcgtcat | 840 |
| gctcaattgc tcacactata ctactacttg ttactacagt gatgtgatgg aggagttcca | 900 |
| caagcacatg cgcgcccctcg cggacaagct gctggagctg ttcctcatgg cgctggggct | 960 |
| caccgacgag caggccagcg ccgtcgaggc cgagcggagg atcgccgaga cgatgaccgc | 1020 |
| caccatgcat ctcaactggt gggtatatat tattgtctgt catgttgtcg tcgtcgtacg | 1080 |
| cgttgcggtt gggtgtacat gtatataaca caaacaacaa aaaactaacg ccgtgccgac | 1140 |
| gacgacgacg atcatcaggt acccgaggtg cccggacccg cggcgcgcgc tggggctgat | 1200 |
| cgcgcacacc gactcgggct tcttcacctt cgtgatgcag agcctcgtgc ccgggctgca | 1260 |
| gctcttccgc cacgccccgg accggtgggt ggcggtgccg gccgtgccgg gcgccttcgt | 1320 |
| cgtcaacgtg ggcgacctct tccacatcct caccaacggc cggttccaca gcgtgtacca | 1380 |
| ccgcgccgtc gtgaaccggg acctcgacag gatctcgctc ggctacttcc tcggcccgcc | 1440 |
| gccgcacgcc aaggtggcgc cgctgcgcga ggccgtgccg cccggccggg ccccgcgta | 1500 |
| ccgcgccgtc acgtggcccg agtacatggg cgtccgcaag aaggccttca ccaccggcgc | 1560 |
| ctccgcgctc aagatggtcg ccctcgccgc cgccgccgac ctcgacgacg acggcgacgc | 1620 |
| cgccgtcgtc catcagcagc agcagctagt cgtctcgtcg tagccgagac cgatcgccgg | 1680 |
| agactgatgc tgatgatgat gcatatatac atgagagaaa tcgtcgagta gactagccga | 1740 |
| ttgcaaaagc aaccccagct gccgaaacct ggcatatcga tcccattc | 1788 |

<210> SEQ ID NO 37
<211> LENGTH: 1698
<212> TYPE: DNA
<213> ORGANISM: Zea mays

<400> SEQUENCE: 37

| | |
|---|---|
| cgtgccgaga gtccttcaaa gccgacgacg agacgacgat gcagtcgtcg tcgtcatcag | 60 |
| cctcgacgcc ggctgccgct tccggcctcg tcttcgatct cgggtctgcg gcgggcgtgc | 120 |
| cggagacaca cgcgtggccg ggggtgaacg agtacccgtc ggtggagtcc gctgccgcg | 180 |
| acgtggtccc ggtggtggac atgggggtgg cctcccggga cgcgacgcgg gcgttggcgc | 240 |
| gcgccgcaga cgagtggggc gtgtttctgc tcgtcggcca cggcgtgccc cgggaagtgg | 300 |
| cggcgcgtgc cgaggagcag gtcgcgcgcc tgttcgtgct cccggctcct gacaaggccc | 360 |
| gcgcggggcg ccgcccccggg gagcccacgg ccaccggcta cggcaggccg cccctggcac | 420 |
| tccgcttctc caagctcatg tggtccgagg ggtacacgtt ccgcgccgcc accgtccgcg | 480 |
| aagagttccg ccgcgtctgg cccgacgcg gcgacgacta cctccgcttc tggtacgtac | 540 |
| gagcgccatg tcacgtgctt gtgctttcat gcctcgtacc gtcgtcgtgc tgtacgtgtt | 600 |

```
atgtttatcg gccggtacgt cacgcgtgct cactggtta acgacgtgag cgtgcccacg     660
ttgactgcat gcatgtgcat gcgcgcgccc agcgacgtga tggaggagta cgacagagag    720
atgagggctc tcggtggcag gctgctcgac ctcttcttca tggcgctcgg cctcaccgac    780
gtccagttcg ccaccggcga gacggagcgg aggatccgcg agacctggac ggcgacgatg    840
cacccaatcc tgtacgtacg tcaaaaacga atatctgacc aatgcaaacg tttttctgca    900
atgccagtca tccactcatc ctgtacgtac ctctggactc tgcttgtcca tctactgatg    960
acacgtatgg taggtacccc aggtgtccgg aaccggagcg cgccatcggg ctgacggcgc   1020
acacggactc gggcttcatc acgctcatca tgcagagccc cgtgcccggg ctgcagctgc   1080
tccgccgcgg gccggaccgg tgggtgacgg tgccggcgcc gccgggcgcg ctcatcgtca   1140
tgctcggcga cctgttccag gtgctcacga acggccgctt ccggagccct atccaccgcg   1200
ccgtcgtaag ccgagagcgc gagcggatct ccgtgcccta cttcctctgc ccgccggagg   1260
acatgacggt ggcgccgctc gcgtccgctc tgctgccggg gaggaaggcc gtgttccggg   1320
ccgtgacgtg gccagagtac atggaggtca agcacaaggt gttcggcacg gatgcgccgg   1380
ccctggagat gctgcagctg caggtggatg aggaagaaca aggtgaaagg gccgccacca   1440
cctaagccct aaggaactac tagctgaatc cataaactaa taaagaattc gtgaataagg   1500
gcgttggaag actggacaca acacaagaga gttgctatat atcgtatttc tgaaatttaa   1560
ggcaaatatc ttagttaaaa aactggtata tttaaataga caatatatat ctaaaataaa   1620
gatagttcac cattttacg gtcgaacaat gataaagtta tatattgtct gaatagtaac    1680
aaattaaaga tttccagg                                                 1698
```

<210> SEQ ID NO 38
<211> LENGTH: 4095
<212> TYPE: DNA
<213> ORGANISM: Zea mays

<400> SEQUENCE: 38

```
cggtctaagt gaccgtttga gagaggaaaa gggttgaaag agacccggtc tttgtgacca     60
cctcaacggg gagtaggttt ataagaaccg aacctcggta aaacgaatca ccgtgtcatc    120
cgccttattt gcttgtgatt tgttttcgcc ctctctttcg gactcgttta tatttctaac    180
gctaaccccg acttgtagtt gtgcttaaag tttgtaaatt tcagattcgc cctattcacc    240
ccctctaggc gactttcata taaatattgg gagaaatatg aaaaacaaat gaaggtcgaa    300
cgagtcagag acaccataaa aaagaggtcg tcttaactag ggtgctaaac ctcaacattg    360
tagtagatct tagtactgag tttgacatct ttgacaccaa caagatggtg atacgttact    420
ttctacgtta acttgggtag gtatatcgac tatagtggcc tataacacta ggctatgtaa    480
tatgatattg tgttgagtct ttataaacat gatttttttt aaaaaaaaga gctaaaataa    540
aaaatagaaa tcgacggtac gatgcaagtt cttctcaaga caaccaaacg cacccttgcc    600
ccttttattga aattgaagta tgtgctttat caaatgttta aatactaatt ataagtatta   660
aatataattt aattataata ctaattatat agataaagac taaataacaa gacaaattta   720
ttaaatataa ttaattcatt attaacaaat acttaatgta gcacgatcga atcatggact   780
aattagtctt gatagactcg tcttaccatt taatcataat tagttttgta tactgtttat   840
aatatttcta actagctagt attaaacttt tgatgtaacc taactaaagt ttagtcacgc   900
caatacataa ggactcggat cgttcgatca cccatgacat cacgtatact aagagcatct   960
```

```
ccaaaagctc tccagaagtc tcccctaaat ctatttttt gggaaaaaca caaaaacatg    1020
tctccaacag ttcccttaaa gcgccccaa ctttttcata gcccttaaaa ctccctcatt    1080
tgtagctaca aatgaggggt ttttttgggct ccccagaaac aaactgttga tttaagggat    1140
ctgttggaga aaggattaaa atttaccctc acttattatt tagatgtccc ttaaaactga    1200
ttttgaggag tcgttttatg tagagctctt ggagatgctc taacacaccg agcacaaccg    1260
catcatcaat caaaacaacc caaagtttgt tcggtacaag tcatcagcct gtgtacacac    1320
atcagcctcg gccccgggag aagcgctagc aaacaaggtt cacctaaaaa tccatccaga    1380
ttcattgaat ccaaccagca caaacgtccc atttattaat cacctcatca caggtccccc    1440
cagcctcact ctcgcgccgg ctcaaggtac attgcgtgtc ctagccaaga cacgcagctc    1500
atctcagcct cacacgcaca gcaagagcga ggcgtgattc gccatgggcg gcctcactat    1560
ggaccaggcc ttcgtgcagg cccccgagca ccgccccaag cccatcgtca ccgaggccac    1620
cggcatccct ctcatcgacc tctcgcctct ggccgccagc ggcggcgccg tggacgcgct    1680
ggccgccgag gtgggcgcgg cgagccggga ctggggcttc ttcgtggtcg tgggccacgg    1740
cgtgcccgca gagaccgtgg cgcgcgcgac ggaggcgcag cgagcgttct tcgcgctgcc    1800
ggcagagcgg aaggccgccg tgcggaggaa cgaggcggag ccgctcgggt actacgagtc    1860
ggagcacacc aagaacgtga gggactggaa ggaggtgtac gacctcgtgc gcgcgcgagcc    1920 gccgccgccg gcagccgtgg ccgacggcga gcttgtgttc gataacaagt ggccccagga    1980
tctaccgggc ttcaggtgac gaaattaact atatatccct ttcgatcata gttgcgttaa    2040
taaattaagg gaatcgtgag cgtacgtacg taagtttccg cagagaggcg ctggaggagt    2100
acgcgaaagc gatggaagag ctggcgttca agctgctgga gctgatcgcc cggagcctga    2160
agctgaggcc cgaccggctg cacgcttct tcaaggacca gacgaccttc atccggctga    2220
accactaccc tccttgcccg agccccgacc tggccctcgg cgtggggcgg cacaaggacg    2280
ccggcgccct gaccatcctg taccaggacg acgtcggggg gctcgacgtc cggcggcgct    2340
ccgacggcga gtgggtccgc gtcaggcccg tgcccgactc gttcatcatc aacgtcggcg    2400
acctcatcca ggtacgtgcc cacctgatga actgagctga acgtaggttg catgcactgc    2460
atgtgtatag gcttctcaga tcgcttcgtg tggcgtaagg tgtggagcaa cgacaggtac    2520
gagagcgcgg agcaccgggt gtcggtgaac tcggcgaggg agaggttctc catgccctac    2580
ttcttcaacc cggcgaccta caccatggtg agccggtgg aggagctggt gagcaaggac    2640
gatccgccca gtacgacgc ctacaactgg ggcgacttct tcagcaccag gaagaacagc    2700
aacttcaaga agctcaacgt ggagaacatt cagatcgcgc atttcaagaa gagcctcgtc    2760
ctcgcctaac tactgctact gctaggatcc atgccattgc catgtcgtct tcagattcag    2820
agcacgccat gtcgtcgcta gcttcgtggt agaacaaata atgatgtgcg tgctgtgtgt    2880
aagcatggat atggatgtga atatgtaata tgatgagcac tcctactttg gtatgtttgg    2940
gaataacaga cttgtgttgg tctggttcat tatttgtaag aaaatcaaaa agagttagta    3000
gggcaggagg ctaaccacag tcatgctgca ccacatccct ggtggaaagc tggccgggtt    3060
acgctacgct cgtgcagcca gattactgca gggccgggat atgcttccgg tggaaggaag    3120
gggacggtgg ctgaggacca tggggctgga gcctgggaga gaggtcgagc tagaagaaag    3180
ggggagagag aagacgcaca acgaagatgg gtcagccagg gatttcgacc caaggggag    3240 ctagtggatt ttgggagaaa acagaaaaga gaaaagagaa aagaagaaaa atttgttggt    3300
gtgaacacaa ggttgatttg tctttttctta tttggattga tgatgagtcg tggactaacc    3360
```

```
gacccgtgag ctattgtgtc gtataatcat gtctctcggt ttctggtgtg caggtttgaa    3420
gcacagagac ggtggtcgac gcaaaggtga acgtcatgca ggttcgtgcc gatggaccgg    3480
gagcagtgaa agacgagcgt tgggacttga acaagggacc agagtcgccg gatgactagc    3540
cgcagtggct gacgcctgga acacgcatag acgtgaggac gtggtagagc aggtgaaaat    3600
cgcctagagg ggggggggt gaatagacaa aacctaaaaa ttataaactt tgaacacaaa    3660
ctttacctga ggttaccgtt agaacgagta ttaatgaaat cggagtgcgg aaggcaagtt    3720
cttcttgcta cgagttgctt aatcaatatt gataactttg ggagtcaact caaaatgatc    3780
acaagcaaaa gaactagaga gagaggagag gaagaatcaa ctcgcaaagt aatgatcaac    3840
acaaatgaac acaatgattt atttctcgag gtttggttcc gaagaaccta ctccccgttc    3900
aggagtccac ataggacatg tctctttcaa ccctttctct ctctcaaatg gtcacataga    3960
ctggttcagt tgagagcacc tagagggggg tgaataggtg atcttgtaaa atcaaacact    4020
aatagccaca aaacttagtt taaagtgtta gtacggctaa gtagctttga agcgagttat    4080
tgtgaacaca acaat                                                    4095

<210> SEQ ID NO 39
<211> LENGTH: 21
<212> TYPE: DNA
<213> ORGANISM: Artificial Sequence
<220> FEATURE:
<223> OTHER INFORMATION: suppression oligo

<400> SEQUENCE: 39
ctccatcatg cggtgcaact a                                             21

<210> SEQ ID NO 40
<211> LENGTH: 21
<212> TYPE: RNA
<213> ORGANISM: Artificial Sequence
<220> FEATURE:
<223> OTHER INFORMATION: suppression oligo

<400> SEQUENCE: 40
uaguugcacc gcaugaugga g                                             21

<210> SEQ ID NO 41
<211> LENGTH: 19
<212> TYPE: DNA
<213> ORGANISM: Artificial Sequence
<220> FEATURE:
<223> OTHER INFORMATION: suppression oligo

<400> SEQUENCE: 41
ggtactgcga ggagatgaa                                                19

<210> SEQ ID NO 42
<211> LENGTH: 21
<212> TYPE: RNA
<213> ORGANISM: Artificial Sequence
<220> FEATURE:
<223> OTHER INFORMATION: suppression oligo

<400> SEQUENCE: 42
uucaucuccu cgcaguaccu a                                             21

<210> SEQ ID NO 43
<211> LENGTH: 19
<212> TYPE: DNA
```

```
<213> ORGANISM: Artificial Sequence
<220> FEATURE:
<223> OTHER INFORMATION: suppression oligo

<400> SEQUENCE: 43
caggcgccat ggtcatcaa                                                    19

<210> SEQ ID NO 44
<211> LENGTH: 21
<212> TYPE: RNA
<213> ORGANISM: Artificial Sequence
<220> FEATURE:
<223> OTHER INFORMATION: suppression oligo

<400> SEQUENCE: 44
uugaugacca uggcgccugg a                                                 21

<210> SEQ ID NO 45
<211> LENGTH: 19
<212> TYPE: DNA
<213> ORGANISM: Artificial Sequence
<220> FEATURE:
<223> OTHER INFORMATION: suppression oligo

<400> SEQUENCE: 45
tcatgcggtg caactacta                                                    19

<210> SEQ ID NO 46
<211> LENGTH: 21
<212> TYPE: RNA
<213> ORGANISM: Artificial Sequence
<220> FEATURE:
<223> OTHER INFORMATION: suppression oligo

<400> SEQUENCE: 46
uaguaguugc accgcaugau a                                                 21

<210> SEQ ID NO 47
<211> LENGTH: 19
<212> TYPE: DNA
<213> ORGANISM: Artificial Sequence
<220> FEATURE:
<223> OTHER INFORMATION: suppression oligo

<400> SEQUENCE: 47
tcgctcgcct tcttcctca                                                    19

<210> SEQ ID NO 48
<211> LENGTH: 21
<212> TYPE: RNA
<213> ORGANISM: Artificial Sequence
<220> FEATURE:
<223> OTHER INFORMATION: suppression oligo

<400> SEQUENCE: 48
ugaggaagaa ggcgagcgac a                                                 21

<210> SEQ ID NO 49
<211> LENGTH: 19
<212> TYPE: DNA
<213> ORGANISM: Artificial Sequence
<220> FEATURE:
<223> OTHER INFORMATION: suppression oligo

<400> SEQUENCE: 49
tccaacgggc ggtacaaga                                                    19
```

<210> SEQ ID NO 50
<211> LENGTH: 21
<212> TYPE: RNA
<213> ORGANISM: Artificial Sequence
<220> FEATURE:
<223> OTHER INFORMATION: suppression oligo

<400> SEQUENCE: 50
ucuuguaccg cccguuggac c                                              21

<210> SEQ ID NO 51
<211> LENGTH: 19
<212> TYPE: DNA
<213> ORGANISM: Artificial Sequence
<220> FEATURE:
<223> OTHER INFORMATION: suppression oligo

<400> SEQUENCE: 51
gcatcaacag gtacaacta                                                 19

<210> SEQ ID NO 52
<211> LENGTH: 21
<212> TYPE: RNA
<213> ORGANISM: Artificial Sequence
<220> FEATURE:
<223> OTHER INFORMATION: suppression oligo

<400> SEQUENCE: 52
uaguuguacc uguugaugcg a                                              21

<210> SEQ ID NO 53
<211> LENGTH: 19
<212> TYPE: DNA
<213> ORGANISM: Artificial Sequence
<220> FEATURE:
<223> OTHER INFORMATION: suppression oligo

<400> SEQUENCE: 53
tggacgatgg atagttcaa                                                 19

<210> SEQ ID NO 54
<211> LENGTH: 21
<212> TYPE: RNA
<213> ORGANISM: Artificial Sequence
<220> FEATURE:
<223> OTHER INFORMATION: suppression oligo

<400> SEQUENCE: 54
uugaacuauc caucguccau c                                              21

<210> SEQ ID NO 55
<211> LENGTH: 19
<212> TYPE: DNA
<213> ORGANISM: Artificial Sequence
<220> FEATURE:
<223> OTHER INFORMATION: suppression oligo

<400> SEQUENCE: 55
tggaccatgg atacttcaa                                                 19

<210> SEQ ID NO 56
<211> LENGTH: 21
<212> TYPE: RNA
<213> ORGANISM: Artificial Sequence
<220> FEATURE:

<223> OTHER INFORMATION: suppression oligo

<400> SEQUENCE: 56
uugaaguauc caugguccau c                                               21

<210> SEQ ID NO 57
<211> LENGTH: 19
<212> TYPE: DNA
<213> ORGANISM: Artificial Sequence
<220> FEATURE:
<223> OTHER INFORMATION: suppression oligo

<400> SEQUENCE: 57
gcaaggtcct agatttaca                                                  19

<210> SEQ ID NO 58
<211> LENGTH: 21
<212> TYPE: RNA
<213> ORGANISM: Artificial Sequence
<220> FEATURE:
<223> OTHER INFORMATION: suppression oligo

<400> SEQUENCE: 58
uguaaaucua ggaccuugca a                                               21

<210> SEQ ID NO 59
<211> LENGTH: 19
<212> TYPE: DNA
<213> ORGANISM: Artificial Sequence
<220> FEATURE:
<223> OTHER INFORMATION: suppression oligo

<400> SEQUENCE: 59
cagagtacat ggaggtcaa                                                  19

<210> SEQ ID NO 60
<211> LENGTH: 21
<212> TYPE: RNA
<213> ORGANISM: Artificial Sequence
<220> FEATURE:
<223> OTHER INFORMATION: suppression oligo

<400> SEQUENCE: 60
uugaccucca uguacucugg a                                               21

<210> SEQ ID NO 61
<211> LENGTH: 19
<212> TYPE: DNA
<213> ORGANISM: Artificial Sequence
<220> FEATURE:
<223> OTHER INFORMATION: suppression oligo

<400> SEQUENCE: 61
ccatgcccta cttcttcaa                                                  19

<210> SEQ ID NO 62
<211> LENGTH: 21
<212> TYPE: RNA
<213> ORGANISM: Artificial Sequence
<220> FEATURE:
<223> OTHER INFORMATION: suppression oligo

<400> SEQUENCE: 62
uugaagaagu agggcaugga a                                               21

```
<210> SEQ ID NO 63
<211> LENGTH: 19
<212> TYPE: DNA
<213> ORGANISM: Artificial Sequence
<220> FEATURE:
<223> OTHER INFORMATION: suppression oligo

<400> SEQUENCE: 63
acatggcggt caacttcta                                                    19

<210> SEQ ID NO 64
<211> LENGTH: 21
<212> TYPE: RNA
<213> ORGANISM: Artificial Sequence
<220> FEATURE:
<223> OTHER INFORMATION: suppression oligo

<400> SEQUENCE: 64
uagaaguuga ccgccaugug a                                                 21

<210> SEQ ID NO 65
<211> LENGTH: 726
<212> TYPE: DNA
<213> ORGANISM: Rice tungro bacilliform virus

<400> SEQUENCE: 65
tcctacaaaa gggagtagta atatttaatg agcttgaagg aggatatcaa ctctctccaa        60
ggtttattgg agacctttat gctcatggtt ttattaaaca aataaacttc acaaccaagg       120
ttcctgaagg gctaccgcca atcatagcgg aaaaacttca agactataag ttccctggat       180
caaataccgt cttaatagaa cgagagattc ctcgctggaa cttcaatgaa atgaaaagag       240
aaacacagat gaggaccaac ttatatatct tcaagaatta tcgctgtttc tatggctatt       300
caccattaag gccatacgaa cctataactc ctgaagaatt tgggtttgat tactacagtt       360
gggaaaatat ggttgatgaa gacgaaggag aagttgtata catctccaag tatactaaga       420
ttatcaaagt cactaaagag catgcatggg cttggccaga acatgatgga gacacaatgt       480
cctgcaccac atcaatagaa gatgaatgga tccatcgtat ggacaatgct taaagaagct       540
ttatcaaaag caactttaag tacgaatcaa taaagaagga ccagaagata taaagcggga       600
acatcttcac atgctaccac atggctagca tctttacttt agcatctcta ttattgtaag       660
agtgtataat gaccagtgtg ccctggact ccagtatata aggagcacca gagtagtgta       720
atagat                                                                 726

<210> SEQ ID NO 66
<211> LENGTH: 165
<212> TYPE: DNA
<213> ORGANISM: Rice tungro bacilliform virus

<400> SEQUENCE: 66
acgaatcaat aaagaaggac cagaagatat aaagctggaa catcttcaca tgctaccaca        60
tggctagcat ctttacttta gcatctctat tattgtaaga gtgtataatg accagtgtgc       120
ccctggactc cagtatataa ggagcaccag agtagtgtaa tagat                      165

<210> SEQ ID NO 67
<211> LENGTH: 2000
<212> TYPE: DNA
<213> ORGANISM: Zea mays

<400> SEQUENCE: 67
```

-continued

```
ctgcaatata tacaccaaaa gtattataaa ctgtcatata tatgaccaaa accttttat      60 tttagaaaag tatattaatc atggtatatt aatcaaagtt gttgttgggg ctgcaaaaat    120
catacccttc ttccacaagc tgttccttga actgcaggta ctcaggaact ctcagctcct    180
caacagcgag ctcactgacg ttgaccctca catactccca dacaccaggc ctagggcgga    240
tggcaagtgc aacccatggg gggatgacaa tcgcctcctg taagataata gagctagaat    300
gattaaagaa ggtgcacact acaaaaggaa cagtgctgtc cagcgagatc tgaatctgat    360
gcaaacctga gctgccctca ggacatcctc aaaagcacca tccttgagct tctcgcgctc    420
agcctcaggg atcgcattgt tgtactcggc aatgatctgg tggggctgca gcatacccttt   480 tccaaggttt ttcagcctgc gcaaaacgat gtgccaaata acatcagact atgccagatc   540
tataaactca tcaaacatat acaatttcaa gaaatagttt agacgtatga tcagcagtca   600
gtagcgtggg aacatatgca acatagcgaa gaggcacaac agcaaattca ttcgaaaaaa   660
tgaaaacaaa gattcctctc ttttaactga acttctcgaa accccttca tgcctacaca    720 tccgatctag tcagatgcct atgcgttcat gctgaacaga acgtgtcaga actaagcata   780
aactggttag caagcattat cgtattcgat agacccttta gtaacaagct atacattggg   840
taagttcaga ctccaatcat tctgttcaga acatcgtat tgaatataaa actaaagaac    900
acacatgcag gtgcagccag atctaacagc agtttacagt cggtactaaa aaaagcatgg   960
tgtatgtatg tatcatcagt atccagtact aggtttcgac aaaatcctgg atgctaatta  1020
aatactcatc ttattaggga acacaggaac attatgtcta cagcattgaa tgatggccac  1080
atcatgctag atctaacaat acataatatg atggaactgg tcttaaaaag tcgcattcgc  1140
tcaaataata cccgtagcaa ataaaatgta aacttgcaga cgaagcgggg gaaatgaggg  1200
cagacctggt gaagacggcg acaagctcat tggggtgggc agagagtgag tcgccaatgc  1260
gctccctgac gctgtggagg cggctcagga cacggtcacc tgcaccttcc cccattgctg  1320
tcctcttcct ggatcctcag gcctgcacag cgaaaccgaa acggaagcgg aagcttcagt  1380
cagcagagaa aactgaaacc gaaaaacggt tcagatccgt tgacataaaa gctgcgatga  1440
catcctaaaa ctaaaacccc tccagcaaga cataaaccca actgccaaca accagtcttt  1500
taagtctcga cacacccttg acgctgcgcc acgaaactat attgcaggca agaaaccaac  1560
agaacctaac tctggaaggg gggaaagaaa cggcagacag gagcaagacc caaaaaaaaa  1620
cgactcagat cctggtacta tagtcctagt acctagacca gaaagaagaa acaaccaata  1680
caacaagagg catacaagaa ctgaatcgat gaactgaaac gcttcagagg accgaggaat  1740
ggcggagaag ggaggcgcct atttatacag atctgacgag agaaccgaac aaaaacacat  1800
cgatgggaac catggagaag aaaagggctg gccgcatggc accaatggcc tcggcctcca  1860
aaaagccgtt gaatccaaag caggcgagga cgaagcgtga cgcggcaggg tacttctcta  1920
gaaaagcacg gcatcagcaa ggtgggggg ctggggttcc ttattgcagg caatcacgag  1980
gtgattagca caaacggaag                                              2000
```

<210> SEQ ID NO 68
<211> LENGTH: 2000
<212> TYPE: DNA
<213> ORGANISM: Oryza sativa

<400> SEQUENCE: 68

```
ctgaaatata catcagagat attacaatga catatatatc gataaaagaa aaataataaa     60
attaagtttt aaattttaag aatatatgtt tttagtatcc caattatgca gatttcatac    120
```

```
ccttcttcca caagctgttc cttgaactgc aagtactcgg ggactgtcag caactcaaca    180
gcgagctcgc tcacattgac cctcacatac tcccagacac cgggcctcgg gcggatggca    240
agggcaaccc atggggagat aacaatcccc tcctgcatga taaaaaacaa ttacaagtta    300
agttagagca agcggtagag taagatgga tctctgtgat gcaatgaaat ctgaatctga    360
ttcaaacctg tgcactcctc aggacatcct caaaagcacc gtccttcagc ttctcacgat    420
cagcctcaga gattgcgttg ttgtactcag caatgatctg gtgggcctga agcattccct    480
ttccgaggtt aaccagcctg cgcaaataac agtgtcaaca aaaatatcag gccagatcta    540
tcaactcagc ctataaatat ctcaataaga taattttagc acttgagcat ttgcgcataa    600
taagaaaatt tgctattagc cacttaaaaa gaccatatat gatctgtttg cattgagatg    660
aattaaaaat tcattgtag atatgaaatg attagttttg accatttaat tggacttaat    720
gaaatatgcg cgataatcag atctacgcgc tcgcgccaat agatctagta agatgtaggt    780 ttttattt ttttgtgaaa ctttgctacc acaacaagca tctgtaccag tgcagaattc    840
attacttgta ttcagtttgt aaaccgtata tataatataa ataacatgca catgcagtca    900
gatctagcac taccagtcca cagtaatcca aaactacatt tgtatatttc atcattattc    960
agtagtacta ggtttgtaca aaatcttggc tgcagaaggc cgcacttaaa tattcattct    1020
aatcagaaac ttaaaaaaaa agtgactaca aaatgattgc atccaattca gtaaatgta    1080 gccattcctg gccagatcta acaatctcaa caacaaagat cctatatgaa catctccttc    1140
taaaagaaaa tacagtaaca tctgaaggca gtagactaga aaccaacaaa atctaatgct    1200
gggaaatcac taaatcagca cgaacctggt gaagacggcg acgagctcat tggggtgggc    1260
ggagagggag tcgccgatgc gctccctgac gctgtggagg cggctcagga cgcggtcgcc    1320
ggcagcttcc cccattgctc tcctcttcct cttggctcct caagcctgcg tgcacaacca    1380
accaccatca tcagatacat ccagacccag tcaacacaat cactccagga aaaaaaaag    1440 tcaagccata acccccaacc aaaaaccacg cctttgacaa acactggaag aaaaagaaaa    1500
tcgcagcttt ttcacaagca atctagaaga aagaaaaag aaaagactac atagcagcta    1560
taattgactg agaagcatac aggaatcaaa caatggagaa ggggagggag gaagaacaat    1620
gatgctccag gctgaggacc gaggaactgg gtgaagcggg gtaggcgcgt atttatgcag    1680
atctgaggag agaaaccacc aaaacaatcc gatggtttca acgaaaaaga tcgtcgcttc    1740
ttgctgcacc agctcaccca tagccgttga gatcgaagct aagctagcag cagcaaagct    1800
ggaacgaaga gtgacgcatt caagctcctc tcctctcctc tcctctcctc cggagcacga    1860
ggccagcatg ggatggattg gggtttcttg ttggccatgg caaaggagga ggtcattaac    1920
gttgacacgg cgtaatttaa ttaaatctta tcttaaaata tgatttaagt ggtagtaaca    1980
aggaagatta atactatgaa                                                 2000
```

<210> SEQ ID NO 69
<211> LENGTH: 2000
<212> TYPE: DNA
<213> ORGANISM: Oryza sativa

<400> SEQUENCE: 69

```
gctgtttaag aaaaacagaa gtaaaattca gtcactgtta ttttgcttca gttataatct    60
gcaaatcgtc gttctggtac ttactgtcca tcaacaagct gttccttgaa tgccaagtac   120
tcagaaacac tcagctcttc cactgccaac tcacttacat tcacccgaat gtagtcccag   180
```

| | |
|---|---|
| acaccaggcc ttggcctgat ggccagtgca acccagggcg gcagcacaat ggcttcctac | 240 |
| atacagtcaa ggaagtaagt tagaaagact ggtatttgac tttgagttga ctatcataac | 300 |
| catcctggct cattgccaaa tttacctgag cagcccggag aatgtcttca agggagcat | 360 |
| atttctcttt gtcagcttcg atcaaggcat cgaactccgc aagcagctgg tgacgctgga | 420 |
| gcattccctt tccctggtta acatacctgc atagagtgat atttaagaaa tagaaccaat | 480 |
| gcttagatct cacatccttt ctgcggctga actatgttaa tggcactacc acataaacct | 540 |
| gatttttact tcttattttt aagaccacat gatctgtact taatctagct atgaacaaac | 600 |
| aatatttcaa catcatctaa gattcatgac tcaagacaaa aatgttagag ctcatcacag | 660 |
| attattatag ataccatcat taaaactaaa gagatgcata accttgtcag ctaagaattt | 720 |
| gtaacatact aacatgttat cgtttcacat ctgggttgac taagaactaa ccaactgtat | 780 |
| ggataaaatc attgaaaact caaaacaatt agtagcaggt tccaagaaga cacaagatat | 840 |
| tatattgaga tcttcaccta gagaagagtg caatcaactc attgggatga gacgagaagg | 900 |
| tggcaccgag gcgttcgcgg agactgtgga ggcgagctag cttggcagcc atgactcaat | 960 |
| ttcaggaact gcaaagaaag gttacactta gcaacacgta ccaaaaccac tcacttgcac | 1020 |
| aagaataatt agtcaacagc catcactaag cattgcaaga ctatctctga acaggaaagc | 1080 |
| catgctaaat caacactaat aacatcacac aaaagcattg aagatcaaa acataactaa | 1140 |
| aaacagctgt ttcatctaca caactgaaag catctatggt ttacgaagca gagtgcgagt | 1200 |
| actgattcaa aataaatcaa cctgaaccaa tatactctga caatgttttc aaagggataa | 1260 |
| aagaaccagc tttatcaaat ggatttgttg ggttttagta agtatcattg agataccgat | 1320 |
| ggcatatctc aaactttgca aaattataat ggcatggttc caaattaccc tttagtatta | 1380 |
| gcaccagtta gatcctaatt cctaaatccg ataggacaga gcgaaagatc cctggagata | 1440 |
| tgaagatttg gctacagatt aagcagagcc aacatgaagt tccgaatatt atgaatccgc | 1500 |
| aagcggggag atcaaagaga agaatacgga aggtcgcgac tccatgaaag aatccaacca | 1560 |
| aaaacccaaa gattttctc agttcaaaaa aaaaaaccc ttcattttg gttcgccatc | 1620 |
| caccgacagg caccaagaca ttcctcagga agcaaaaaag attaagcaga acaagtgata | 1680 |
| agcaagacac agtatcaacg gactacgagt cgagaaaatc actgaggcgc gattcttact | 1740 |
| gcaccaagta aaaaaaaatt tgggggcaaa aagaactctg caatgggcg gagcaacgtg | 1800 |
| gcagcaaaac taaggtcga ggatttgagg tttttgccg gttttcctcg aaaccccgaa | 1860 |
| tccgctcata gtaaacccac taaactgcag cagaaacccc cctcttggtt cagatttacc | 1920 |
| gaaagcagta aacccaagaa catgtcagca aaaactcctg caagattcag ctgacgaccc | 1980 |
| accaaagaat cgcaagaaat | 2000 |

<210> SEQ ID NO 70
<211> LENGTH: 2000
<212> TYPE: DNA
<213> ORGANISM: Oryza sativa

<400> SEQUENCE: 70

| | |
|---|---|
| tggcggacgc gccacgcaca aacacaaacc tgcacacccc tgtgtcagag gaggagaggc | 60 |
| caagaaagga aatcgagtgg aggaagtgag gagcggcgga gacgtaggag gaggaggggg | 120 |
| agatggaaat ggaaagccgc gcgagagagg aggcgcgtgc tggatgggag gaggaggagg | 180 |
| aggtggtggg tttgtgtttg gagagacgag cgagagaggc gaagcattta agggaggaa | 240 |
| gagggggaga gagagagaga gagagagaga gagagagaga gagagagaaa ggaggaatat | 300 |

| | | | | | |
|---|---|---|---|---|---|
| aataaagggt | ggtgcacctg | ccaactgcta | tgctcaccaa | cactttgtac | acacccagtt | 360 |
| acacccccct | gcctttatta | tttccagtgc | agtaataact | tcaacaatta | ttgaaatgaa | 420 |
| aatggaatta | atggagttag | tatcggatta | gcgacacgct | tgccgagctt | ctagacggtg | 480 |
| cgattatttc | agcgggaacg | actttctgta | ggtgaattta | atagaggagt | gttttaaatc | 540 |
| cactcgacgt | tgtaatagct | ggtttaattc | gtttgtactg | tcgagtagtt | atccaaaatc | 600 |
| aattttggat | atttaaaaga | aaaaaaaaca | gatccgaagt | attggaccta | ctggcaaata | 660 |
| ggaattttgc | tatatatagg | tgtgcgttca | tttataatgg | agtagcatgg | agttttatta | 720 |
| atccagtaaa | tgttttcatt | gatttaatta | atataacgaa | tttcgcttga | ggccatattt | 780 |
| gttaaacgct | tttatctcta | tcatcattca | tcctaccagt | aaagagcacc | ggagatcgca | 840 |
| cttcatttaa | atatatgtcc | atgttggata | aaccatagtt | tattatagtg | ttcttttata | 900 |
| tgttttgtgg | ggaatttaga | ttgtttaata | tggcatacat | atccatccat | cattattata | 960 |
| ttctaacaca | actggataag | tgttctaaac | tattgtagaa | taactttgta | gtatgatcga | 1020 |
| tcttgtggaa | taaaaaaagt | ctgacaataa | cctttcataa | aggaatatga | atacccgtaa | 1080 |
| tcaacgcatc | aaatcattca | cggtgtacgc | ctagcgaatt | cgttggcgag | tgctcgtgcg | 1140 |
| gccgtgggct | cgctgtgatg | catgcatggc | tctctggcta | cgtcgagata | gcgattagta | 1200 |
| gcaaaattaa | gcaagccact | tattaattaa | tctttggaga | tatcatatga | ttaaggcatt | 1260 |
| aattcgtacg | tactcgtcgt | cagcgttttc | tgcaaagtcc | actacagttt | tttctttctt | 1320 |
| tgctgaaaat | gctgatgtgt | tggagatgga | gtgacgtgca | caacctgccg | ccacgtggat | 1380 |
| ggttgctgga | gcctacgtgt | catcttaatt | tgaacaaaaa | aaaagagga | ataatacatc | 1440 |
| aatacatttt | cgaatttcag | ttctgccatt | gaccagtaat | acacatgtcg | gcctcacatt | 1500 |
| ttaccctgat | cttagtaacg | ggtggtcgcc | tggtcggtca | ctgaaaaaag | ttcaggaaat | 1560 |
| tatagtcaaa | ctgaaacgaa | catattcact | ccttaaaaaa | actaaatctt | tttatatatt | 1620 |
| tgtgatattg | taaaatagct | acgggataat | gatatagata | tatatagtga | taagggatag | 1680 |
| atggatcgag | atatggagtt | gtgctttctt | taatttccac | tacttgggct | accatatttat | 1740 |
| ggtagttggt | atgaaaagat | acacagcagt | atagtgatgt | gatcaatgac | atgtatatct | 1800 |
| cacatgctcc | catgttggag | tcaaattttg | ctagactaaa | atccaattcc | aagcagtccc | 1860 |
| tagccaagaa | caaacaaaat | tcagtgaggt | cactgctgca | ccaaggactg | catgcatgca | 1920 |
| ggagaagggc | attttctctt | ttttcttttg | gagactcgat | tcaattcggt | cggtcggtcg | 1980 |
| caatggtcag | cttaattaaa | | | | | 2000 |

<210> SEQ ID NO 71
<211> LENGTH: 2000
<212> TYPE: DNA
<213> ORGANISM: Oryza sativa

<400> SEQUENCE: 71

| | | | | | |
|---|---|---|---|---|---|
| tgtgaaaggt | ggcggcacca | gcttagccgc | agcttctctc | gtcgtctccc | tgaaacgaga | 60 |
| gggaggaagt | tggtagcgtg | atatatttag | gcatgtcatc | tcttgtataa | gaagtcttat | 120 |
| ctgtgctaat | tcacacggtt | ctctaatctc | tctccattct | gttttgtaa | attggttcag | 180 |
| tagatagcgt | agggttatgc | ttatatatac | tccgtgaagt | atatatttaa | aaattagtca | 240 |
| cacgtaaagt | actatacatg | ttttatcgtc | taataacaat | aaaaacacta | atcataaaat | 300 |
| ttttttaaat | aatacgaatg | gttaaacgtt | gaatatgaac | cgtgcaaaac | tatatttatt | 360 |

```
ttgtaacaga gaaatatttt cacattaatt agattgttgt tttatggaag gttggagagc      420
tgcgccgccg ttgcgcagac ctaggaggct gcttataagt tataatcaat caattcacgg      480
atgccggctg ggacgcggcc catcgtccgg gaagacgaca actcaacgca aaaagccgat      540
atgcctccaa attgccattg ccacctctac ggctgtttat actgctccaa atcaaaagcg      600
tccatggaag aatctagtat ttcccgcaaa gacgatgatg atatgcagga ttggatatat      660 aggggggttgt tgcatgattg ctagaactcc cgtttccgaa gttgttcgtc catttttaaa     720
gctgccaaat aggaatttat tttgttttca agtgtaatag agttctgtcc agatgagtga     780
attataattt ggttcacatt ttatttgcta agtttcagtt tgaacattct caaataactt     840
ttttcttcac ttttttaaccg agtaacttag ttatttttc cgtttggacc acccaacaat      900
ttgttgctaa gtgcatctca cccgtcaaat aattccttttg aatccaaatt caattatatc    960
ccaaaaataa aaaacttctg aattccacat caattcaaac cccaaccatt ttaatttctc     1020
tccatatttt ccattctctct atttttaccct ttctctttt tccatctatt tatttttttc   1080
cttttctatt tctttctttc tccttcctt tctctgtttcc ttcttcttct cctcggctag    1140
gcccgagcca gcccgtgccg cctcgcgcca accctgtgcc gccttacgcc gcgcttgcgt    1200
gcgctcgcgc ccacctcgtg cccaacccgc gcacgccaca cgcacacacg aggacgatcg    1260
acggacgaat gcaatcatat ccccttcctt actcagctag aaggctcaag aaccgcaact    1320
ttgatctctt ccaccctctc aaatccgccc caaccctgc tgactcaatc gccattaccg      1380
gaggaaaaat ccccgaaacc ctattaccgg cgccactaac agagctccaa aattcgtcgc    1440
ataattcgaa atattctga aattgaaggt aaaaatggaa tctacatgcg aagtactccc      1500
tttcccctcc aatccgtcac tggaacgccg ccggcgccgc ctcccgctgc cactgccctg    1560
tttggccgcc gacagccgca cggcgcgccg ctgctccagg ccgccctagc ttcaaccacc    1620
gccacctttg gctccgcctc cctcctctta tgctcaccaa gcccgcctcc ctcgccggag    1680
atcgccggaa ccaccgccgc catggccgcc accgcctcct gcttctggcc gccgccgcca    1740
gcctcgccac cggcgcctat gccaccgccg accacggaaa cggagtccct acaccttggg    1800
gaccacaaaa ccggcggcat ccctcccaaa accggcctcc tccaccgccg gcgttcgtgg    1860
gattccggcc agttctgtgc agagcgagag aagaagagga aaaatagatt ttcctattga    1920
aagataaatc agaaaattcc ttttcttt cctatcaagt tgaccatccg tttgaccctca      1980 aaatcaaaat ctgagaccta                                                2000

<210> SEQ ID NO 72
<211> LENGTH: 786
<212> TYPE: DNA
<213> ORGANISM: Zea mays

<400> SEQUENCE: 72
gacatggagg tggaaggcct gacgtagata gagaagatgc tcttagcttt cattgtcttt      60
cttttgtagt catctgattt acctctctcg tttatacaac tggttttta aacactcctg      120 aacttttcaa attgtctctt tctttaccct agactagata attttaatgg tgattttgct     180
aatgtggcgc catgttagat agaggtaaaa tgaactagtt aaaagctcag agtgataaat     240
caggctctca aaaattcata aactgttttt taaatatcca aatattttta catggaaaat     300
aataaaattt agtttagtat taaaaaattc agttgaatat agttttgtct tcaaaaatta     360
tgaaactgat cttaattatt tttccttaaa accgtgctct atctttgatg tctagtttga     420
gacgattata taatttttttt tgtgcttaac tacgacgagc tgaagtacgt agaaatacta     480
```

| | | |
|---|---|---|
| gtggagtcgt gccgcgtgtg cctgtagcca ctcgtacgct acagcccaag cgctagagcc | 540 | |
| caagaggccg gaggtggaag gcgtcgcggc actatagcca ctcgccgcaa gagcccaaga | 600 | |
| gaccggagct ggaaggatga gggtctgggt gttcacgaat tgcctggagg caggaggctc | 660 | |
| gtcgtccgga gccacaggcg tggagacgtc cgggataagg tgagcagccg ctgcgatagg | 720 | |
| ggcgcgtgtg aaccccgtcg cgccccacgg atggtataag aataaaggca ttccgcgtgc | 780 | |
| aggatt | 786 | |

<210> SEQ ID NO 73
<211> LENGTH: 1160
<212> TYPE: DNA
<213> ORGANISM: Zea mays

<400> SEQUENCE: 73

| | | |
|---|---|---|
| atgtgctggt gccccataag gtaggcacct aggtctgtgt ttgaagcatc gacagatttg | 60 | |
| taaacatgtt cctatgaacc tatttctgat tgataatttg tcaaaactca tcatttgtct | 120 | |
| tcatccttgc ctgcttgcgt tcacgtgaca agtacgtgt atgtcttcgg cctttgctgt | 180 | |
| gtatgtttcg cattgcttag atgtggtgaa agaacatcag aagatgcatt gatggcgtgc | 240 | |
| ttaaaccagt gatgtgctcc aggtgttcct gcagtctgca gagatattta ctcttgtagt | 300 | |
| cttgttgaca gcacagttgt atgtgatttc ttggatgtaa tgtaaaccaa atgaaagata | 360 | |
| ggaacagttc gtcctcttcc gtatacgaag gtcactgtat catttgtcgt ggcacaagat | 420 | |
| gatctgcagg caggactgca acatggtttc ttggactgtc ctgaatgccc gttcttgttc | 480 | |
| tttagttgag ccagagcagc agcctggtgt cggtgcctga gacctgacga agcacacggc | 540 | |
| aaacaaacaa gtcgcagcag ctagcagggg cgttgccatc gccacaagcc cccaagagac | 600 | |
| ccgccgagga aagaaaaaa aaactacggc cgccgttgcc aagccgagcg tgcgaaccga | 660 | |
| tccacggatg ggagatcaga gatcacccac cgcaggcggg cggcagtggc tggcgaggtg | 720 | |
| cgtccacaga acctgctgca ggtccctgtc cgtcccggcg accccttttc taggcgagca | 780 | |
| actccccatg gcagagctgc acgcagcagg gcccgtcgtt ggttgcagct ttaaccctt | 840 | |
| ttgtttaac catacaatgc agagtcgcag aggtgaaaca ggacggaaat tacagaaaag | 900 | |
| atggtggtgt gccagcagcc ccagcatgaa gaagatcagg acaaaagaaa agcttgtgat | 960 | |
| tggtgacagc aacaggattg gattggagcc aagctaggca gtgagaggca ggcagcaaga | 1020 | |
| cgcgtcagcc actgaaatcc agagggcaac ctcggcctca caactcatat ccccttgtgc | 1080 | |
| tgttgcgcgc cgtggttagc caggtgtgct gcaggcctcc tccttgttta tatatgggag | 1140 | |
| atgctctcac cctctaaggt | 1160 | |

<210> SEQ ID NO 74
<211> LENGTH: 1532
<212> TYPE: DNA
<213> ORGANISM: Oryza sativa

<400> SEQUENCE: 74

| | | |
|---|---|---|
| tagtcctcta atatatgaaa ttttgatata ggtaaagaag ggtattgcaa ggataagaat | 60 | |
| gtaaaagaa ataagagtaa tccttaccga taatagtatt ccttctctac cgttaaaagt | 120 | |
| taaacctgtg cgtgtagcat tttaatccag gatctatcga atccgtccct cgttggcgtg | 180 | |
| ggcgacgaac acgtgcagaa gaagcttttcc ccagaaagca cctcaccgcc tcgccgtctg | 240 | |
| gcagactggc acgcggggcc ctaccctcgc tgcgcctggg cccgtccgcc ttctgcacac | 300 | |

```
tgtcacgccc ccaccegctc geegectege gectetetet cegectecge egeggeegec      360
cgacgtgata gcgacacgta ggactcgcca acacaaaaa atccatcgcg attttttggaa     420
ttttgttaca aaccaaatcc cgcattagag atttaatttg atttaattta attacgtagg     480
agtaccagat aaggagatcg agttaaaaaa gctaacggcg cggcgtggtt atctccgaat     540
cggctgtggc tccccgcgtc ggcgtcggcg cggcggcggc gcgccggccg aaccctggcc     600
gtcggatcgg gcgtcgtcct gggcccacg cgccacgggc ggctgtcgtt tgctcctcgg      660
agcggggtgg gcccaccatg gccaccacca caggtcgcgg tcgcggctga cctggcggtg     720
gtcccgtgct cgcggtgttt tttttttttc actctctttc tctcggtgga cagtagcggg     780
ggccgcggcc cgcgggggca gagattgcaa aaacagcgga aacggaagat tgcaaaattg     840
caactgcttt cctgttttta attcgggatc aaaaagattc tttcgtcggg gtccccgtgc     900
cattgttgta ttgcgcgtag gtccttgctt gtaaaagata atctccttaa ttttttctttt    960
gtactactag tgtatatgca gtaagaatat accatgagta aaatgaacca caaaactaat    1020
tacgatatac cattctcatg tagacgttct cttttctttt gctagtcata cgtgcatata    1080
taaccaaaca aaaaaatgtt tgaagtactc ctatccaatt tattactcca gtagacaaca    1140
aaagaaaatg tttgaagtaa taactgatcc atggtacagt agggttgtcg tcaatcttgt    1200
gtttctttca ttccattgta cttacaatcg tactccagct agcacagcac aatgggctta    1260
agctttggac cccaaattct gatcttgtcg gggacccgta cgaaaatact cccgtagaga    1320
tgcagatacc gtcacaacct acaaccaacg aatgttaaga aaacaaggg aaaaaaaaag    1380
aggcgaattc ggaggagaaa aaacggtggc taaaatatag tgcgggtgtg gggacgcgac    1440
gcgagcgacg aaagaggaga gaggatgggt tggcctgccc ccccctcccc tgtctataaa    1500
tgcagaggcg ccgagtgccc tagtcgccgc tc                                   1532
```

<210> SEQ ID NO 75
<211> LENGTH: 841
<212> TYPE: DNA
<213> ORGANISM: Oryza sativa

<400> SEQUENCE: 75

```
tcgaggtcat tcatatgctt gagaagagag tcgggatagt ccaaaataaa acaaaggtaa      60
gattacctgg tcaaaagtga aaacatcagt taaaaggtgg tataaagtaa aatatcggta     120
ataaaaggtg gcccaaagtg aaatttactc ttttctacta ttataaaaat tgaggatgtt     180
tttgtcggta ctttgatacg tcattttgt atgaattggt tttaagttt attcgctttt       240
ggaaatgcat atctgtattt gagtcgggtt ttaagttcgt ttgcttttgt aaatacagag     300
ggatttgtat aagaaatatc tttagaaaaa cccatatgct aatttgacat aattttttgag   360
aaaaatatat attcaggcga attctcacaa tgaacaataa taagattaaa atagctttcc     420
cccgttgcag cgcatgggta ttttttctag taaaaataaa agataaactt agactcaaaa    480
catttacaaa aacaacccct aaagttccta agcccaaag tgctatccac gatccatagc      540
aagcccagcc caacccaacc caacccaacc cacccccagtc cagccaactg acaatagtc     600
tccacacccc ccactatca ccgtgagttg tccgcacgca ccgcacgtct cgcagccaaa     660
aaaaaaaaga aagaaaaaaa agaaaaagaa aaaacagcag gtgggtccgg gtcgtggggg   720
ccggaaacgc gaggaggatc gcgagccagc gacgaggccg gccctccctc cgcttccaaa    780
gaaacgcccc ccatcgccac tatatacata ccccccctc cctcccatc cccccaaccc     840
t                                                                    841
```

<210> SEQ ID NO 76
<211> LENGTH: 1392
<212> TYPE: DNA
<213> ORGANISM: Oryza sativa

<400> SEQUENCE: 76

| | | | | | |
|---|---|---|---|---|---|
| ctcgaggtca | ttcatatgct | tgagaagaga | gtcgggatag | tccaaaataa | aacaaaggta | 60 |
| agattacctg | gtcaaaagtg | aaaacatcag | ttaaaaggtg | gtataagtaa | aatatcggta | 120 |
| ataaaaggtg | gcccaaagtg | aaatttactc | ttttctacta | ttataaaaat | tgaggatgtt | 180 |
| ttgtcggtac | tttgatacgt | cattttttgta | tgaattggtt | tttaagtttta | ttcgcgattt | 240 |
| tggaaatgca | tatctgtatt | tgagtcgggt | tttaagttcg | tttgcttttg | taaatacaga | 300 |
| gggatttgta | taagaaatat | ctttaaaaaa | acccatatgc | taatttgaca | taattttga | 360 |
| gaaaaatata | tattcaggcg | aattctcaca | atgaacaata | ataagattaa | aatagcttgc | 420 |
| ccccgttgca | gcgatgggta | ttttttctag | taaaataaaa | gataaactta | gactcaaaac | 480 |
| atttacaaaa | acaaccccta | aagtcctaaa | gcccaaagtg | ctatgcacga | tccatagcaa | 540 |
| gcccagccca | acccaaccca | acccaaccca | ccccagtgca | gccaactggc | aaatagtctc | 600 |
| cacacccccgg | cactatcacc | gtgagttgtc | cgcaccaccg | cacgtctcgc | agccaaaaaa | 660 |
| aaaaaaagaa | agaaaaaaaa | gaaaaagaaa | aaacagcagg | tgggtccggg | tcgtgggggc | 720 |
| cggaaaagcg | aggaggatcg | cgagcagcga | cgaggccggc | cctccctccg | cttccaaaga | 780 |
| aacgccccccc | atcgccacta | tatacatacc | ccccctctc | ctcccatccc | ccaacccta | 840 |
| ccaccaccac | caccaccacc | tcctcccccc | tcgctgccgg | acgacgagct | cctccccct | 900 |
| cccctccgc | cgccgccggt | aaccacccg | cgtccctctc | ctctttcttt | ctccgtttt | 960 |
| tttttccgtc | tcgtctcgat | ctttggcctt | ggtagtttgg | gggcgagagg | cggcttcgtc | 1020 |
| gcccagatcg | gtgcgcggga | ggggcgggat | ctcgcggctg | ggtctcggcg | tgcggccgga | 1080 |
| tcctcgcggg | gaatggggct | ctcggatgta | gatctgatcc | gccgttgttg | gggagatga | 1140 |
| tggggcgttt | aaaatttcgc | catgctaaac | aagatcagga | agaggggaaa | agggcactat | 1200 |
| ggtttatatt | tttatatatt | tctgctgctg | ctcgtcaggc | ttagatgtgc | tagatcttc | 1260 |
| tttcttcttt | ttgtgggtag | aatttgaatc | cctcagcatt | gttcatcggt | agttttttctt | 1320 |
| ttcatgattt | gtgacaaatg | cagcctcgtg | cggagcttt | ttgtaggtag | aagatggctg | 1380 |
| acgccgagga | ta | | | | | 1392 |

<210> SEQ ID NO 77
<211> LENGTH: 743
<212> TYPE: DNA
<213> ORGANISM: Oryza sativa

<400> SEQUENCE: 77

| | | | | | |
|---|---|---|---|---|---|
| gaattcccgg | acctccatgc | ctacatcaac | taatttgatt | ccttgagttt | acgtttagtg | 60 |
| atatgtctat | ttttagagct | tgttggggct | tcggcctcag | ctctagccag | ccaaacatgt | 120 |
| tctaccaagt | accctatgtt | ggcatgatat | agtgatgcat | tataacaata | aatgagcgag | 180 |
| ggattgctgg | ctgaaaaagc | tatactagct | gcatttggtt | atagttaacc | gaactattaa | 240 |
| ttgcgtgtac | aacaaaataa | aaaaaatgca | tgttgcacat | tctttcatta | acattatgtt | 300 |
| ttggtagtgt | gaattagaaa | tttgattgac | agtagatcga | caaacatagt | ttcaatatgc | 360 |
| ttaagttagt | tatgactttta | acatatcagt | ctccttgata | ttttcgtttt | agattcgtct | 420 |

```
ctctactagt gtgtatgtcc accttccata gcagtgaagg gttccattcc atccctggta    480
aaaaaaaatc aaccactact atttatttcc taaaaagcaa aatgataaaa tatcattttt    540
ttaataaaaa taaaaaaatt ttggggtaca taattgatgt tgccccttgg gattaacctt    600
aaaaaagggc gaattttcta gggtttggcc aagttttgca atgcaccaaa ttattcccct    660
tgggccggcc gccacccccaa aaaaaacccc aaccccccaac tttccattga aggccgggcc    720
cccttaaatc ctcatccccc caa                                            743

<210> SEQ ID NO 78
<211> LENGTH: 144
<212> TYPE: DNA
<213> ORGANISM: Oryza sativa

<400> SEQUENCE: 78
taaaaagggg cgaattttct agggtttggc caagttttgc aatgcaccaa attattcccc     60
ttgggccggc cgccaccccaa aaaaaaccc caaccccccaa ctttccattg aaggccgggc    120
ccccttaaat cctcatccccc ccaa                                          144

<210> SEQ ID NO 79
<211> LENGTH: 612
<212> TYPE: DNA
<213> ORGANISM: Cauliflower mosaic virus

<400> SEQUENCE: 79
ggtccgattg agactttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg aaaaagaag acgttccaac cacgtcttca    240
aagcaagtgg attgatgtga tggtccgatt gagactttttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gaccccttcct ctatataagg aagttcattt    600
catttggaga gg                                                        612

<210> SEQ ID NO 80
<211> LENGTH: 837
<212> TYPE: DNA
<213> ORGANISM: Coix lacryma-jobi

<400> SEQUENCE: 80
agcagactcg cattatcgat ggagctctac caaactggcc ctaggcatta acctaccatg     60
gatcacatcg taaaaaaaaa acccctaccat ggatcctatc tgtttctctt ttgccctgaa    120
agagtgaagt catcatcata tttaccatgg cgcgcgtagg agcgcttcgt cgaagaccca    180
taggggggcg gtactcgcac cgtggttgtt tcctgttatg taatatcgga tgggggagca    240
gtcggctagg ttggtcccat cggtactggt cgtcccctag tgcgctagat gcgcgatgtt    300
tgtcctcaaa aactctttttc ttcttaataa caatcatacg caaatttttt gcgtattcga    360
gaaaaaaaga agattctatc tgtttttttt ttgaaatggc tccaatttat aggaggagcc    420
cgtttaacgg cgtcgacaaa tctaacggac accaaccagc gaatgagcga acccaccagc    480
```

```
gccaagctag ccaagcgaag cagacggccg agacgctgac acccttgcct tggcgcggca    540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc caccccctccc agcttccttc gccacat      837

<210> SEQ ID NO 81
<211> LENGTH: 947
<212> TYPE: DNA
<213> ORGANISM: Oryza sativa

<400> SEQUENCE: 81
aatccgaaaa gtttctgcac cgttttcacg tcctaactaa caatataggg aacgtgtgct     60
aaatataaaa tgagacctta tatgtagc gctgataact agaactatgt aagaaaaact      120
catccaccta ctttagtggc aatcgggcta ataaaaaag agtcgctaca ctagtttcgt     180
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagat atttttttt aaaaaaaat     360
agaatgaaga tattctgaac gtatcggcaa agatttaaac atataattat ataattttat    420
agtttgtgca ttcgttatat cgcacgtcat taaggacatg tcttactcca tctcaatttt    480
tatttagtaa ttaaagacaa ttgacttatt tttattattt atctttttc gattagatgc    540
aaggtactta cgcacacact ttgtgctcat gtgcatgtgt gagtgcacct cctcaataca    600
cgttcaacta gcgacacatc tccaatatca ctcgcctatt taatacattt aggtagcaat    660
atctgaattc aagcactcca ccatcaccag accactttta ataatatcta aaatacaaaa    720
aataatttta cagaatagca tgaaaagtat gaaacgaact atttaggttt ttcacataca    780
aaaaaaaaaa gaattttgct cgtgcgcgag cgccaatctc ccatattggg cacacaggca    840
acaacagagt ggctgcccac agaacaaccc acaaaaaacg atgatctaac ggaggacagc    900
aagtccgcaa caaccttta acagcaggct ttgcggccag gagagag                  947

<210> SEQ ID NO 82
<211> LENGTH: 721
<212> TYPE: DNA
<213> ORGANISM: Mirabilis mosaic caulimovirus

<400> SEQUENCE: 82
tggagattca gaaaatctc catcaacaaa taatccaagt aaggattaat ggattgatca      60
acatccttac cgctatgggt aagattgatg aaaagtcaaa acaaaaatc aattatgcac     120
accagcatgt gttgatcacc agctattgtg ggacaccaat ttcgtccaca gacatcaaca    180
tcttatcgtc ctttgaagat aagataataa tgttgaagat aagagtggga gccaccacta    240
aaacattgct ttgtcaaaag ctaaaaaaga tgatgcccga cagccacttg tgtgaagcat    300
gtgaagccgg tccctccact aagaaaatta gtgaagcatc ttccagtggt ccctccactc    360
acagctcaat cagtgagcaa caggacgaag gaaatgacgt aagccatgac gtctaatccc    420
acaagaattt cctatataa ggaacacaaa tcagaaggaa gagatcaatc gaaatcaaaa    480
tcggaatcga aatcaaaatc ggaatcgaaa tctctcatct ctctctacct tctctctaaa    540
```

```
aaacacttag atgtgtgagt aatcacccac ttggggttgt aatatgtagt agtaaataag      600
ggaaccttag ggtataccat tgttgtaata ttattttcag tatcaataaa ataatctttc      660
agtttatctt atattcattt gtgtgacacc gtattcccat aaaaccgatc ctaatctctc      720
c                                                                      721

<210> SEQ ID NO 83
<211> LENGTH: 352
<212> TYPE: DNA
<213> ORGANISM: Peanut chlorotic streak caulimovirus

<400> SEQUENCE: 83
acagagggat ttctctgaag atcatgtttg ccagctatgc gaacaatcat cgggagatct       60
tgagccaatc aaagaggagt gatgtagacc taaagcaata atggagccat gacgtaaggg      120
cttacgccat tacgaaataa ttaaaggctg atgtgacctg tcggtctctc agaaccttta      180
ctttttatat ttggcgtgta ttttaaatt tccacggcaa tgacgatgtg acctgtgcat       240
ccgctttgcc tataaataag ttttagtttg tattgatcga cacgatcgag aagacacggc      300
catttggacg atcatttgag agtctaaaag aacgagtctt gtaatatgtt tt              352

<210> SEQ ID NO 84
<211> LENGTH: 1648
<212> TYPE: DNA
<213> ORGANISM: Sorghum bicolor

<400> SEQUENCE: 84
cactcgcaca tctcatggtg tcccaagaac ggcaagagcc agcactgcct ctgcctagca       60
acagcagcag cgccaagcga gcagccgcgt ccatggacgc cagcagcccg gccccgccgc      120
tcctcctccg cgcccccact cccagtccca gcattgacct ccccgctgcc gctggcaagg      180
ccgcggccgt gttcgacctg cggcgggagc ccaagatccc ggcgccattc ctgtggccgc      240
acgaggaggc gcgcccgacc tcggccgcgg agctggaggt tccggtggtg gacgtgggcg      300
tgctgcgcaa tggcgaccgc gcggggctgc ggcgcgccgc ggcgcaggtg gcctcggcgt      360
gcgcgacgca cggttcttc caggtgtgcg ggcacgcgct ggacgcggcc ctggggcgcg       420
ccgcgctgga cggcgccagc gacttcttcc ggctgccgct ggccgacaag cagcgcgccc      480
ggcgcgtccc cggcaccgtg tccgggtaca cgagcgcgca cgccgaccgg ttcgcgtcca      540
agctcccctg gaaggagacc ctgtccttcg gcttccacga cggcgccgcg tcgcccgtcg      600
tcgtggacta cttcaccggc accctcggcc aagatttcga gccaatgggg cgggtgtacc      660
agaggtactg cgagaagatg aaggagctgt cgctgacgat catggagctg ctggagctga      720
gcctgggcgt ggagcgcggc tactaccggg agttcttcga ggacagccgc tccatcatgc      780
ggtgcaacta ctacccgccg tgcccggagc cggagcgcac gctgggcacg ggcccgcact      840
gcgaccctac ggcgctgacc atcctcctgc aggacgacgt cggcgggctg gaggtgctgg      900
tggacggcga gtggcgcccc gtccggcccg tcccaggcgc catggtcatc aacatcggcg      960
acaccttcat ggcgctgtcg aacgggcggt acaagagctg cctgcaccgc gcggtggtga     1020
accagcggca ggagcggcgg tcgctggcct tcttcctgtg cccgcgcgag accgggtgg      1080 tgcggccgcc ggcagcagc gccacgccgc ggcagtaccc ggacttcacc tgggccgacc     1140
tcatgcgctt cacgcagcgc cactaccgcg ccgacacccg cacgctggac gccttcaccc     1200
gctggctctc ccacgcccca gtcccagccc aggaggcggc ggctccctgc acctagcgag     1260
cgagcgagcc gggccaaaca aacaaggggc aaaggccatc tctttcgccg ggcccgcgc      1320
```

```
gcggggttcg cccacgtgcg cgcccaggtg ggcgctggcc cgggcaggt ggcggacatg      1380 tggcctgcgg gccccgcgcc gccttcccat ttttggacgc tgccgcgcat gccgcatgcg      1440
tgcgtcgacg gccctactac ttctactact gctactgcga ctactagtgt acatacgcaa      1500
aaatacatat atacgtattt tctatatata tatatataag caaggcggcc ccccggtgac      1560
cttttctttg tttttgtcga caactgtgtt ttgatcccat tctagctgtt ctatggacca      1620
tggatggttc gttcaatgtt tgtacgta                                        1648

<210> SEQ ID NO 85
<211> LENGTH: 1242
<212> TYPE: DNA
<213> ORGANISM: Sorghum bicolor

<400> SEQUENCE: 85
atggtgtccc aagaacggca agagccagca ctgcctctgc ctagcaacag cagcagcgcc       60
aagcgagcag ccgcgtccat ggacgccagc agcccggccc cgccgctcct cctccgcgcc      120
cccactccca gtcccagcat tgacctcccc gctgccgctg caaggccgc ggccgtgttc      180 gacctgcggc gggagcccaa gatcccggcg ccattcctgt ggccgcacga ggaggcgcgc      240
ccgacctcgg ccgcggagct ggaggttccg gtggtggacg tgggcgtgct gcgcaatggc      300
gaccgcgcgg ggctgcggcg cgccgcggcg caggtggcct cggcgtgcgc gacgcacggg      360
ttcttccagg tgtgcgggca cggcgtggac gcggccctgg ggcgcgccgc gctggacggc      420
gccagcgact tcttccggct gccgctggcc gacaagcagc gcgcccggcg cgtccccggc      480
accgtgtccg ggtacacgag cgcgcacgcc gaccggttcg cgtccaagct ccccctggaag     540 gagacccctgt ccttcggctt ccacgacggc gccgcgtcgc ccgtcgtcgt ggactacttc      600
accggcaccc tcggccaaga tttcgagcca atggggcggg tgtaccagag gtactgcgag      660
aagatgaagg agctgtcgct gacgatcatg gagctgctgg agctgagcct gggcgtggag      720
cgcggctact accgggagtt cttcgaggac agccgctcca tcatgcggtg caactactac      780
ccgccgtgcc cggagccgga gcgcacgctg gcacgggcc cgcactgcga cctacggcg      840 ctgaccatcc tcctgcagga cgacgtcggc gggctggagg tgctggtgga cggcgagtgg      900
cgccccgtcc ggcccgtccc aggcgccatg gtcatcaaca tcggcgacac cttcatggcg      960
ctgtcgaacg gcggtacaa gagctgcctg caccgcgcgg tggtgaacca gcggcaggag     1020
cggcggtcgc tggccttctt cctgtgcccg cgcgaggacc gggtggtgcg gccgccggcc     1080
agcagcgcca cgccgcggca gtaccccgac ttcacctggg ccgacctcat cgccttcacg     1140
cagcgccact accgcgccga cacccgcacg ctggacgcct tcaccgctg gctctcccac     1200 ggcccagtcc cagcccagga ggcggcggct ccctgcacct ag                        1242

<210> SEQ ID NO 86
<211> LENGTH: 413
<212> TYPE: PRT
<213> ORGANISM: Sorghum bicolor

<400> SEQUENCE: 86

Met Val Ser Gln Glu Arg Gln Glu Pro Ala Leu Pro Leu Pro Ser Asn
1               5                   10                  15

Ser Ser Ser Ala Lys Arg Ala Ala Ala Ser Met Asp Ala Ser Ser Pro
            20                  25                  30

Ala Pro Pro Leu Leu Leu Arg Ala Pro Thr Pro Ser Pro Ser Ile Asp
        35                  40                  45
```

Leu Pro Ala Ala Gly Lys Ala Ala Val Phe Asp Leu Arg Arg
 50                  55                  60

Glu Pro Lys Ile Pro Ala Pro Phe Leu Trp Pro His Glu Glu Ala Arg
 65                  70                  75                  80

Pro Thr Ser Ala Ala Glu Leu Glu Val Pro Val Asp Val Gly Val
                 85                  90                  95

Leu Arg Asn Gly Asp Arg Ala Gly Leu Arg Arg Ala Ala Gln Val
                100                 105                 110

Ala Ser Ala Cys Ala Thr His Gly Phe Phe Gln Val Cys Gly His Gly
             115                 120                 125

Val Asp Ala Ala Leu Gly Arg Ala Ala Leu Asp Gly Ala Ser Asp Phe
130                 135                 140

Phe Arg Leu Pro Leu Ala Asp Lys Gln Arg Ala Arg Val Pro Gly
145                 150                 155                 160

Thr Val Ser Gly Tyr Thr Ser Ala His Ala Asp Arg Phe Ala Ser Lys
                165                 170                 175

Leu Pro Trp Lys Glu Thr Leu Ser Phe Gly Phe His Asp Gly Ala Ala
                180                 185                 190

Ser Pro Val Val Val Asp Tyr Phe Thr Gly Thr Leu Gly Gln Asp Phe
                195                 200                 205

Glu Pro Met Gly Arg Val Tyr Gln Arg Tyr Cys Glu Lys Met Lys Glu
210                 215                 220

Leu Ser Leu Thr Ile Met Glu Leu Leu Glu Leu Ser Leu Gly Val Glu
225                 230                 235                 240

Arg Gly Tyr Tyr Arg Glu Phe Phe Glu Asp Ser Arg Ser Ile Met Arg
                245                 250                 255

Cys Asn Tyr Tyr Pro Pro Cys Pro Glu Pro Glu Arg Thr Leu Gly Thr
                260                 265                 270

Gly Pro His Cys Asp Pro Thr Ala Leu Thr Ile Leu Leu Gln Asp Asp
            275                 280                 285

Val Gly Gly Leu Glu Val Leu Val Asp Gly Glu Trp Arg Pro Val Arg
290                 295                 300

Pro Val Pro Gly Ala Met Val Ile Asn Ile Gly Asp Thr Phe Met Ala
305                 310                 315                 320

Leu Ser Asn Gly Arg Tyr Lys Ser Cys Leu His Arg Ala Val Val Asn
                325                 330                 335

Gln Arg Gln Glu Arg Arg Ser Leu Ala Phe Phe Leu Cys Pro Arg Glu
                340                 345                 350

Asp Arg Val Val Arg Pro Pro Ala Ser Ser Ala Thr Pro Arg Gln Tyr
                355                 360                 365

Pro Asp Phe Thr Trp Ala Asp Leu Met Arg Phe Thr Gln Arg His Tyr
                370                 375                 380

Arg Ala Asp Thr Arg Thr Leu Asp Ala Phe Thr Arg Trp Leu Ser His
385                 390                 395                 400

Gly Pro Val Pro Ala Gln Glu Ala Ala Ala Pro Cys Thr
                405                 410

<210> SEQ ID NO 87
<211> LENGTH: 12906
<212> TYPE: DNA
<213> ORGANISM: Sorghum bicolor

<400> SEQUENCE: 87
cactcgcaca tctcatggtg tcccaagaac ggcaagagcc agcactgcct ctgcctagca    60

-continued

```
acagcagcag cgccaagcga gcagccgcgt ccatggacgc cagcagcccg gccccgccgc    120
tcctcctccg cgcccccact cccagtccca gcattgacct ccccgctgcc gctggcaagg    180
ccgcggccgt gttcgacctg cggcgggagc ccaagatccc ggcgccattc ctgtggccgc    240
acgaggaggc gcgcccgacc tcggccgcgg agctggaggt tccggtggtg acgtgggcg    300 tgctgcgcaa tggcgaccgc gcggggctgc ggcgcgccgc ggcgcaggtg gcctcggcgt    360
gcgcgacgca cgggttcttc caggtgtgcg ggcacgcgcg ggacgcggcc ctggggcgcg    420
ccgcgctgga cggcgccagc gacttcttcc ggctgccgct ggccgacaag cagcgcgccc    480
ggcgcgtccc cggcaccgtg tccgggtaca cgagcgcgca cgccgaccgg ttcgcgtcca    540
agctcccctg gaaggagacc ctgtccttcg gcttccacga cggcgccgcg tcgcccgtcg    600
tcgtggacta cttcaccggc accctcggcc aagatttcga gccaatgggg taagcgaagc    660
accgatttac atttaccgcg cgtcggcccc tgaggcctgg gtcttagtct tagcactgca    720
tatacggtcg gtagctctgg atatgatacg tatatatgaa accccgttcc aatcccatgc    780
acggtgtaca caggcgggtg taccagaggt actgcgagaa gatgaaggag ctgtcgctga    840
cgatcatgga gctgctggag ctgagcctgg gcgtggagcg cggctactac cgggagttct    900
tcgaggacag ccgctccatc atgcggtgca actactaccc gccgtgcccg gagccggagc    960
gcacgctggg cacgggcccg cactgcgacc ctacggcgct gaccatcctc ctgcaggacg    1020
acgtcggcgg gctggaggtg ctggtggacg gcgagtggcg ccccgtccgg cccgtcccag    1080
gcgccatggt catcaacatc ggcgacacct tcatggtaac ccctgctctg ttttttcttg    1140
tcctcctctt gtcctgtgtg tgtgtatatt cacttctctc tgtttttttg ccccgaatcc    1200
tagtggacct aactgacgg attacagcac gcacacgtag gcatgtcatg tagcagcagt    1260
ctgcagcact gtagtactta gcgatgcaat agagacatgc gttccagtcg gttccatctc    1320
ggtgggctac agctacagtc ctacacggac gcggctcgta gtcgtaggga cgggcgcgtt    1380
ctctgtatcc acacacggct gcgcccaggc cgaggcttcc gccgcgggaa agttgcgaca    1440
acagaacggg gttttgtgccg ttggagcgtt gcggagaggc agaggcttgg ggggacgggg    1500
gcgcgatacg ctgcgatggg tgggtgaccg aaggcgacgct ttcggcgggg gccccgggcct    1560 gcccaggtgc gcgcggcctc gtcgccttcc cctgtttttt tgatgccgcc gctcggtcct    1620
cggtgttctg gctccgcccg cccgctcgct gggtgcccat cccatctgat ccgatccgct    1680
ccgctccgcg gtggcggtcc tatgcgatgc cgccgcacga gcgcgggggg ccgcccgtgg    1740
aggagtagaa agtggtacaa ggttggttgg aacttggaat tgtgggggt tactgctgct    1800 ggtggctgct gctttgcaac ttgccaggct gctgctgtt gcccccgcg ttttctagcc    1860 gtttccgctc gcgatccggc acgcggcgcc cacaccgggg ctccagctcg gcccccttggc    1920 cgtgtaggta gcaggcactt gcatctgtcc gttcgacacg atgattcttg tgcactgtgt    1980
acgtatgtac taacccttttc tggtatgatg tacgcatggc atgcaggcgc tgtcgaacgg    2040
gcggtacaag agctgcctgc accgcgcggt ggtgaaccag cggcaggagc ggcggtcgct    2100
ggccttcttc ctgtgcccgc gcgaggacccg ggtggtgcgg ccgccggcca gcagcgccac    2160
gccgcggcag tacccggact tcacctgggc cgacctcatg cgcttcacgc agcgccacta    2220
ccgcgccgac acccgcacgc tggacgcctt cacccgctgg ctctcccacg gcccagtccc    2280
agcccaggag gcggcggctc cctgcaccta gcgagcgagc gagccgggcc aaacaaacaa    2340
ggggcaaagg ccatctcttt cgccggggcc cgcgcgcggg gttcgcccac gtgcgcgccc    2400
```

```
aggtgggcgc tggccgcggg caggtggcgg acatgtggcc tgcgggcccc gcgccgcctt     2460 cccattttg gacgctgccg cgcatgccgc atgcgtgcgt cgacggccct actacttcta      2520
ctactgctac tgcgactact agtgtacata cgcaaaaata catatatacg tattttctat     2580
atatatatat ataagcaagg cggcccccg gtgaccttt ctttgttttt gtcgacaact       2640
gtgttttgat cccattctag ctgttctatg gaccatggat ggttcgttca atgtttgtac    2700
gtactccacg taaccaaact actctagtgg actagtagat cgggctcatg tgatgaaact   2760
ggaccgacgc ggacgtcacg tgcgtcaccc gcgtctggta gcggtagcgc acgagcgccg   2820
aatgtttcct gggcccgcaa gagaatcgct tctcatctcc tctcaccatg aatggggaaa   2880
aatgctgcgt cgaaagttcc agacgtttcc aaattccaaa cggttttgtg gcgtccgatc   2940 catgggcgc cccaaacttc caagacgttt tcaggttcca aatcttcgtg ctccacatca    3000
ccttcttccc agattcattt gcctcgtcgc ttgctctcct gtgttattca cgggtcccac   3060
tgttgccccg tctgcgagaa agaaatttat tagagttgaa gcattcgaca tttcgactga   3120
ctgattgtta gtatcactaa atttttgtgca catgtttctt tggtcattca tctctggata   3180 tttttttag ataatggata taaatatcgg gcctctacat ctgaggaagt acacagccaa    3240
ttattttcat ctctggacat gggacgatgg aagaggcaga tagatttagg agacccttca   3300
attcagaatt tcaggtgcac aaggcctgcc tggcttgccc ggattcttgt ttcggacatg   3360
accaactagg ccgcactact tgcactgata gctggagaaa aaacaaaact ttgcaaacag   3420
caggattatc tacaagggaa actccatcca cgtgaaccag catttcaggg agagatgcga   3480 caaaaaaaa gaggcggcaa caaaaaaatc ttactgcaat tttatctctg cattgaacct   3540
cttccaacca tgccgcatcc tgtactgttt tgtatctttc ccggtggtcc gttgcgttct   3600
cacgcagttg ataacatgca gtcacgcacc accgaatcca gtgtactagg ggtagtgact   3660
tgtcacgcgg aacaacaggt cggtagcacc aagcaagtcg ctgtagactt gggcgtttaa   3720
caacgacttg cacaacagtt caaatatagc atatgcaatt atgcacaaga ttgttcgact   3780
gctatccgac aaactgaaga agctgcccaa ttgaacagaa tgtaccagtg atttccagca   3840
cactatctta cagcagcgtt gagaatgaaa caacaaatgg gggaaaacag atgtgtatta   3900
ttctacagtt acaccaaaga gtttgtcctt tcagcatcaa caagaatcat atgcatatct   3960
agtgacaaaa attcctctaa ttttacccta cttggtaaca gttctcttca acacatatat   4020
ttcacgtgct tgcatcgagt tccttgggcc gccacatcga cttctcgacg caaagcaagc   4080
cctcgttgcc cttggtgtag gtcattcgca cctcccactg cagggacttg gccatgcttt   4140
ccagttcgtt tattgtgtcc gcagtgtccc tcacaatcag tttgccttgg ggcctcagta   4200
cacgatcaac ctcggcaaaa actgccatca atttgcatct gtaaacaagc aacacagatt   4260
tagcatctgt aaacaccaca ggtttcattg caagaagcat aaagcatgca aacatgctac   4320
ttgtacatgt caaagaaaca tgtcaaactc aaacacatga aaatcattat tattgttttc   4380
ttgctgaact gatcacatta gttggtttca atttctgagt tccactagta atctatacca   4440
gaaggataga ataatgtcaa gaacaagaga tacaaacctc tttgtgagct ttgagaatag   4500
atggtccgcg tgcagaaggt cataagttct tgggtaagtg ctcaaagact cgcaccagtc   4560
atggtacata ccaaacaaac cacgctcgta aatgatgggc agtgtgtctg gtgaatcaat   4620
cggcacaata ttcatgaccc agaccttttg gtccctcaga gctgcagcaa aactgccatg   4680
caacgatgta aagcattagt aaaaatattg gttttttaa accaaaacca agaaagataa    4740
ttcctccagc ttaactgaaa gaagaaaga aaaaaactgc ttaatgactt atggtggaca    4800
```

```
agttgcctgt tatgttttat gatagctatg tgccagcttg gctaactggt agttatgtag    4860
tgtgatctga attaccaaaa aagagaagaa aaaaaaatca tgcccaagaa actgagaaag    4920
acacccattt acttaccctc catacacagc tctcatgtcc attacatttc tcactttgga    4980
ccagtcaatt cccatgccat tcacatacga tttacttaca acccttttcc agtgagcatt    5040
atctgcctcg aaatcttcat ttgcaggctt tccatagacc ccaaccttgg aaccatcaat    5100
ccagaaagga gtcttctcaa gcctttgtgg ccaaaactct ggccattttg accctcgaac    5160
tttcgagcca acaggcagtt tgtgcatgca tgcttccaaa ggtacattcc tgcaaatcaa    5220
aagattgtgt aagcaaagca gaggaagcac ttcgccgcat tgaaaatacg ttcttctcaa    5280
agaaacaaaa ccataccaag ctgcatctgc atcatcagat tccttgcaca atggtgggtt    5340
gttttcggat ctttttctcat agcaaatgtt gtccattggt ttctgaaata tgaccatacc    5400
aacttgattt aacttatcct tagtcttgtt gaccatcttc cagcacatgg actttgtcaa    5460
agtggacatc gctgaaaaga ttaaggggtc atatgttatg atagaaataa aattcaattt    5520
tgcactgttg gtacatagca tctgttttga acaaatgcaa tccttcctta tccatgaaag    5580
aagttaaccc ctgatactta ggattattca gtactttcac tcatgaactg ctgaatttgt    5640
tctgccagta gttgctatac tagaaatgtt cagtgtacca aacataaatt tggtacgggt    5700
tccttattaa agatgggagg ctgtatggta tttcgacgta acaaatcaag ttagcagcta    5760
ccctacttat ggatatacac ttctcaaaat gaatatacat agttttgata ggtgacatta    5820
attaatataa gaacttcatg cagttagggt gaaactaaac taagcagtta cggaaatacc    5880
attccaaatc tcaacatcct ctgggagctt ttggtaaaca ggagtggcag accagacaaa    5940
gtaaccacca gggcgtaaca agcggttcaa ttccagcaaa agcatgccac ctaaaaggag    6000
tcagtaataa gattcagttc tatagcaaat caataaatga aaggaagaca tgtcaccaac    6060
aagacaaacc ttcaatgtgc caagggaccc tgcagcgagc gcaatgaatg acatcaaaga    6120
ctctgctggg gtatggaagt ctcttggtgc ccatcacagc tgatattgct ggaattcccc    6180
tttctaatgc aaattgtact tgagcttcat gctcatcttt cggagcaaaa gacatggtaa    6240
gcacatctct atcaaacatg tagcctccaa agctggcaac tccacaaccg acatctagaa    6300
tgacgcggct tcgtttgccc catgcaatat caggcagtgc ctgtaatga cagtttaatc    6360 agcatatgat gaaagcaagt gtgataatat caagttcaaa gatgcaacat gaaacttca    6420 taatcatgga cagtactaag cttgcttgat agattaatgt atggatgaga ctaaaaaaaa    6480
ggaaagttgt atccatcaga acgagaggct gaaaacacat ggctggctgt gaaagcctga    6540
tgtcgtttag tctagcataa acaaactgtc ctcagcatgt agatttccat agggtggcat    6600
ttgacaaatt atgattgtgg actagcgaat caatcactga ttctcaaaag tgtgagacag    6660
atgagttcaa gtctaagggg tgactaatat gggatgctgg gatgatgatg atgatatata    6720
cctgctgaat agtatcaata tagtggaggg caccattctt gaactgagtc ccaccccag    6780 ggaacaggag gtagtcacct gatactttaa cccaattttg atgtcccttg tactctgcga    6840
gcctagtgtg aggaacattg ctgtaccata cctgcaaaaa gcagcacaag atggtaataa    6900
gtaaacagag atcttggtca gctaaagatg attcagtgtc gtacaattta gaatagcag    6960 aatcaccttg tccctgctcc ttggccactc aattgggcgt ttatatcctt ctgggagtgg    7020
aacaaggcag gtaggaggct cctcagggca atgcctctca cgatgttcat aatgtttagt    7080
agttcgaagc ttcttgatag ccttctcgtt gtcaaggcaa ggtatgtaat ctgtcgaggc    7140
```

```
actgctatta catagtttcc aggaatagct agtcgcatca cctgaagact ttgatgacgc    7200
ttggacttcc ttttcattct tggactctgc agcctgtgtg gggaatgaac cattctgggt    7260
atttgactcc ttcagaagct ctgattgggc cccatcagga aatacctcgt tggagtttga    7320
gctctgatcc ttctctccat tttcttccac cttctcttct atctgaggtt gctcctcctg    7380
agtggcatca ccttcaggct tctcttcttg atcatccttg ctctctccat caggttttc    7440
atcaccactc tcatttgtga tttcatcatc tttcttctcc ccactcttct ccccgtcacc    7500
atcgttcttc atgtcatctg accgcccttc tgattttcca tttgcatcat caaacatatc    7560
cttggtctca gctttctctg tcggcacttc cggctccttc tcttcaggct tctcctctgg    7620
cttctcagtg aacttctctt ccatcgtggc atccttgtta ttcggctcct ccggcatcgt    7680
ggcatcattg ttgtcggtgt cctcaaattt ctcagaacct tcaccagcat tgtcctgtga    7740
ggccccaaaa ttgacaggcg caggctgctg cttcaccacc ggcttcttat tcgaggagat    7800
ctccagcggg aagacagtgg acgaggtcat catccacgcg ccgaccaggc agagcgccac    7860
aaagacgacg accgtggtgg tcgtgcagaa cgacgacgac gtcgaggacg gccggcggcc    7920
gtccatcttc ccacctcggc caaatgccat tagtgcctgg cgaacatgta ccagagcacc    7980
gaccttcacg cgatttatct ccaccaacta ctgctggacc aagaaccccc aaaaaaatcg    8040
caccttttgtc tgctttgtgc tgctacagcc gcgcggcacc tgaagcaaac cacaaaaaaa    8100
acttaaatcg ccgcggacat aaatcaaggt gctggatcta agaacaaac gctggatcta    8160
ctcaagcaac aacggaagga agatccgcta ttggtgctag tattagcttc ttgtttccta    8220
gtactacagc ggctctttcc cagtataaga acacggaaa acgcggagaa atccccttc     8280
gtggccaaac atggaaagaa aattagtaaa gcgtgtgctt taaaaccccc tcgttctgtt    8340
ccttccgcgg agagctaccg catcttccaa ttgagctggt tctcagctgg gcgcaaaacg    8400
cgcactaatc aatgtccgat tccatccaca agaaaaaaa agacgggaac agctaatcca    8460
gcagctcgct cgctagctag ctagctcatc ggcggaagga cggaaccagc tttgctggat    8520
ccaggacagc aagagtgtgc aaggagaaag aacggagcag caatgcggat tgcggaggcg    8580
gtggattggt acctcgccgg aaccgaccgg agtggtcgcg gtggccctcc gcgcggatct    8640
cgaagaggag cgaggaaggg gaaggcggat gcgcgtcctt gggttctctg ccaccgcact    8700
gggcctcgcc gcgttataaa ggcggccggg cgggcgggca gcgcagtgtg agtggagtgc    8760
aatctgttgt gtagtgtgtg aagaggcgga agcggaagcg gaggagatgg gttcgcatta    8820
gacgaccgta cgtaattata cgctatacta gtacttgggt tagattactc gggagatctt    8880
ggccaaaatg tccggtctga gtgtttggta gttttatgga tttgcccttt aagatgttg    8940
gtatttctcc gggagcttag aaagaagaaa tggcgatgct ttaggccttg tttagatgcg    9000
aaaaaatttt ggatttcgct actgtggcat ttttatttgt ttgtagcaaa tattgtccaa    9060
acacggacta actaagattc atctcgcgat ttacagttaa actgtacaat tagtttttat    9120
tttcatttat atttaatgtt tcatggatgt gtcgaaagat acgatatgat agaaaatttt    9180
gaaacttttt tagttattga ggttaactaa acaatgcctt aattgagaat ttactcgagc    9240
aaaaagagtt aggtcagtct cagtggagag tttcatggtg ttgttccaa gactgccata     9300
tcatgtgaaa tgaaatgaaa cttggttgaa acactcactc tcaatggaga gtttcatttt    9360
atagtttcat gggcatttaa tttcaatact catagagagt tgatatcgtg ccaactcatt    9420
tcttctctct cttcttaaat acacagtcat atcatcaaaa aaaatccat gtagcaacat    9480
atttaatgca aataaaactc atatggtgga ctgtaggagt agcattaggc caagggcaca    9540
```

```
cacacggtca cggtgtgagt gcgacggtgc gagtgggccc gcggcggtag taagtgcgtg    9600
cgcgcccggc gccccctcc  gcggcgacga cgcagcggca gcgcgtcgtc cagtgcaccg    9660
tctgctgttc ggcgctgcgg gtcctccgcg ccacggcgca gtgaaccggg cgcgtgcatc    9720
ccgggagcgg cggcttggca ctcccctgct tgtcggtggc ggccgtcggc atcgctcggc    9780
cccggagcgt cacgaggctg ctgattggga gcgagagcga gtagtggggc tggttgggga    9840
caatcccatt cccacccggc ccaccaggct gggactggcc cactagtcac tagtgggtgg    9900
ctcatgggtg tgggtgggct ggctaatgcc gcctgcccaa caaccaaccc aaccCctgtg    9960
gacgctggta ccgtagttg  ccgcgccatg gtggactgct gccgcctgat gcctttgcct   10020
gccacgctcc acgagttgag gcgcaccaaa ctgtgctgtg ctcctgattt gtgctaatcg   10080
gccgacgcgt accattcttt ctttctttcg tctacgcgca gagaggccgg ttgactgttt   10140
cttcgttgga gggccatgtt gactcgtact aataataaaa ataataatac taggttgact   10200
ttttcaattc caacgcagca gtgcaaagct gcccacctat gagcacaggt ccttttttaa   10260
ctccgttttt gtacgtacac acgtactgtc cagcctgtgt ctaataatct taccaaaaac   10320
ctgtcatctc actatcaacc aatcaggctc tccgcctgtt cgtcgaggaa cagcagttgt   10380
tttccctact ccaacataga gtacactatg gacgcacatt accatgccag cttgagctta   10440
gcattgccca ccgttggata actgccatgc cattctcagg ccctgtttag ttcccatcta   10500
aaaattttc  atccattcca tcgaatcttt ggacacatgc atggaacatt aaatgtagat   10560
aaaaaaataa actaattaca cagtttagtt gagaatcgcg agacgaatct tttaagtcta   10620
gttactccat aattagcctt aagtgctaca gtaatccaca tatactaatg acagattaat   10680
tatgcttaat aaatttgtct tacagtttcc tgacgagcta tgtaatttgt ttttttatta   10740
gtttctaaaa acccctcccg acatccttcc gacatatccg atgtgacaac caaaaaattt   10800
tcatcttcaa tctaaacagg ccctcactct catcatctca tgccggggca gcaggtccgt   10860
cgtcaggtct gtcgtcccgt cccgtgccgt ctgaagcaac aggcgagaga acgccgttc    10920
catcggtttg ccgagcgtgc agaggataga gctatactcg atccgagag  gattgtgaaa   10980
cgaagcacgg ttaagcagtg ccgcgcacgt gctgctctgc tcctggatcc gatccagatc   11040
gactcggggc gtctcggcct cagcggcgat ggcaatcatc gcgcgcgctg ctggagctgg   11100
acgttttcgt cttgcattgc aggaggcgga acagaacgga gaaagccacg gcgcgctttg   11160
ccgacgccac gcgctgacac gagggacccg ttcagcggcc agcacgcagc ctaatcatgc   11220
ctgtcggggg gagctcatcc gttcctgaat ttgggtcatg ctccagtatc aggtattcag   11280
gtactagtac tcctgagcca tgtgctgcga caaaaaagcg aggctcctgt agtagagcct   11340
tgtttactta caaatttttt tacattctca gttatattaa atcttgtgac acatgcataa   11400
agcattaaat atacataaaa gaaataatta tttacacagt tacttataat ttgcgaaacg   11460
aatcttttaa gactggttag tttatgatta gataatattt attaaataca aatgaaagta   11520
atattattta tattttgcaa aaagtaaata agacctaggt agctaggcca acgtgagcat   11580
gtcggacccg gaccggttcg ttctacggcg cgtcccgcaa acctgcagcc aggtagtagt   11640
agtacaccgt gcacgggaga ggtgcgccat gcatgctcgg gcaaaagatc atagagaaag   11700
gtgcagcgtt tcagttgcac acctgaccga gtgacgcctc gccttgtttg gctttgttcc   11760
caaaattttt taaaattcct catcacatta aatctttgaa cgaatatatg gagcattaaa   11820
tataaataaa agaaataatt aatcatacaa tttgtctgta atttgcgaga cgaatctttt   11880
```

| | |
|---|---|
| gagcctagtt agtttataat taaataatat ttgttaaata caaacgaaaa tgctacgtta | 11940 |
| gccaaaacta aaatttttct ccaaacgtga cccagcacct tccgatcaat catcactcag | 12000 |
| cgggtcacgt cagaagatca gatggacctt gccgtccggg cctgtctctc ggcctcctcc | 12060 |
| ccatctggaa cgaacagagg tccagtcctg tttcgagtcg agctgagtcg atcagatggg | 12120 |
| cctaaatagg ccgaagacgt aggcaaaggg cccgctgatt tatctgattc ttctaggacc | 12180 |
| gtgcatgcgc ggatgggcct aggtggaaac ccaacagatg tgaggcttca aagaggaaga | 12240 |
| agtccgttac acatggagag ttagtctata atgggataat atttaccaca aacaaataaa | 12300 |
| aatactacag tagcgaaatc caaaatttt cacatctaaa caaggcccta gatgttttgt | 12360 |
| cagtgccaga ccagagaaaa tctcgtcttc tgctgtcaat agctttgatg attcctggcg | 12420 |
| gcagaggtaa agcttgcctg ggccttgttt agttccgaaa agtgaaaagt tttcggtact | 12480 |
| gtagcacttt tgtttgttcg tgacaaatat catccaatta tggactaact agaattaaaa | 12540 |
| gattcgtctc gtgatctaca gctaaactgt gtaattagtt tttgttttcg tctatattta | 12600 |
| atgtttcatg catgtgccac aagattcgat gtgacgaga attttgaaaa ttttttggtt | 12660 |
| ttcagagtga actaaacaag gcccagatgt aattgaccat gccatcgagc gcgagttgac | 12720 |
| tagagtgagt cggccctgat ggttaagtag tgcagactgc caagtggaca accgtctatc | 12780 |
| aactttgcag agtggggcga atgcactgag gatgttggag aggggcaagc caaggtaaac | 12840 |
| ttgaggaaag atgcttgttg acactgtagt atgtgaacaa tcctgtttaa ttttgtgtcc | 12900 |
| tcgacg | 12906 |

<210> SEQ ID NO 88
<211> LENGTH: 1790
<212> TYPE: DNA
<213> ORGANISM: Setaria italica

<400> SEQUENCE: 88

| | |
|---|---|
| tctcatggtg tcccaagcac agcaagagcc agctctgcct cacagcagca gcaccgccaa | 60 |
| gcgcgcagcc gcgtcactca tggacgcccg cccggcccag cctctcctcc tccgcgcccc | 120 |
| gactcccagc attgacctcc ccgcgtccaa gccggacagg gccgccgcgg cggcggcaa | 180 |
| ggccgccgcc gcctccgtgt cgacctgcg gcgggagccc aagatcccgg cgccattcgt | 240 |
| gtggccgcac gacgacgcgc ggccggcgtc ggcggcggag ctggacgtgc cgttggtgga | 300 |
| cgtgggcgtg ctgcgcaatg cgaccgcgc ggggctgcgg cgcgctgcgg cgcaggtggc | 360 |
| cgcggcgtgc gcgacgcacg ggttcttcca ggtgtgcggg cacggcgtgg gcgcggacct | 420 |
| ggcgcgcgcg gcgctggacg gcgccagtga cttcttccgg ctgccgctgg cggagaagca | 480 |
| gcgcgcccgg cgcgtcccgg ggaccgtgtc cgggtacacg agcgcgcacg ccgaccggtt | 540 |
| cgcgtccaag ctcccctgga aggagaccct ctccttcggg ttccacgacg gcgccgcgtc | 600 |
| gcccgtcgtc gtcgactact cgccggcac cctcggcag gacttcgagg cagtggggcg | 660 |
| ggtgtaccag aggtactgcg aggagatgaa ggctctgtcg ctgacgatca tggagctcct | 720 |
| ggagctgagc ctgggcgtgg agcgcggcta ctaccgcgac ttcttcgagg acagccgctc | 780 |
| catcatgcgg tgcaactact acccgccgtg cccggagccg gagcgcacgc tgggcacggg | 840 |
| cccgcactgc gaccccaccg cgctgaccat cctcctccag gacgacgtcg gcgggctcga | 900 |
| ggtcctcgtc gacggcgact ggccccgt ccgcccgtc ccggcgcca tggtcatcaa | 960 |
| catcggcgac accttcatgg ctctgtccaa cgggcggtac aagagctgcc tgcaccgggc | 1020 |
| ggtggtgaac cagcggcagg agcggcggtc gctggccttc ttcctgtgcc cgcgcgagga | 1080 |

```
ccgggtggtg cgcccgccgg ccagcggcgc cgtcggcgag gcgccccgcc gctacccgga    1140
cttcacctgg gccgacctca tgcgcttcac gcagcgccac taccgcgccg acacccgcac    1200
gctggacgcc ttcacacgct ggctctccca cggcccggcc caggacgcgc cagtggcggc    1260
ggcggcttcc acctagctag cggcgcggat ccgaccgagc ccattgacga cgccgtccct    1320
ttccgccgcc gccggggccc gcgcgggggt tcaccccacg tgcgcgccca ggtgggcgag    1380
gtggcggcct cgtggcccgc gggccccgcg ccgccttccc attttgggc gctgccgccc     1440 cgcgcgcatg ccggatgcgt gcgtccacgg cctactgctg ctactagtgt acatatacaa    1500
acatacatat atacgtagta taaatatata agcaagcggc ccgtgcccc ttttcgtttt     1560 cttgttttgt cgatcacaat ctctggattc gatggatgga taaatgtttg tacgcatgca    1620
tgtagatggg ctcatgaaat ttcagaatct ggaacgacg aggagctcac gtgcctcttc     1680
cgtgtctggt agcggtagct gcgtgccaaa tgtctggtgg gcccaaagaa attctagtgc    1740
cacccgtccg gatccggcat ccgaaagttc ccgacggttc gacacccgaa               1790

<210> SEQ ID NO 89
<211> LENGTH: 1272
<212> TYPE: DNA
<213> ORGANISM: Setaria italica

<400> SEQUENCE: 89
atggtgtccc aagcacagca agagccagct ctgcctcaca gcagcagcac cgccaagcgc     60
gcagccgcgt cactcatgga cgcccgcccg gcccagcctc tcctcctccg cgccccgact    120
cccagcattg acctccccgc gtccaagccg gacagggccg ccgcggcggc cggcaaggcc    180
gccgccgcct ccgtgttcga cctgcggcgg gagcccaaga tcccggcgcc attcgtgtgg    240
ccgcacgacg acgcgcggcc ggcgtcggcg gcggagctgg acgtgccgtt ggtggacgtg    300
ggcgtgctgc gcaatggcga ccgcgcgggg ctgcggcgcg ctgcggcgca ggtggccgcg    360
gcgtgcgcga cgcacggggtt cttccaggtg tgcgggcacg gcgtgggcgc ggacctggcg    420
cgcgcggcgc tggacggcgc cagtgacttc ttccggctgc cgctggcgga gaagcagcgc    480
gcccggcgcg tcccggggac cgtgtccggg tacgagcg cgcacgccga ccggttcgcg      540
tccaagctcc cctggaagga gaccctctcc ttcgggttcc acgacggcgc cgcgtcgccc    600
gtcgtcgtcg actacttcgc cggcaccctc gggcaggact tcgaggcagt ggggcgggtg    660
taccagaggt actgcgagga gatgaaggct ctgtcgctga cgatcatgga gctcctggag    720
ctgagcctgg gcgtggagcg cggctactac cgcgacttct tcgaggacag ccgctccatc    780
atgcggtgca actactaccc gccgtgcccg gagccggagc gcacgctggg cacgggcccg    840
cactgcgacc ccaccgcgct gaccatcctc tccaggacg acgtcggcgg gctcgaggtc    900
ctcgtcgacg gcgactggcg ccccgtccgc cccgtccccg gcgccatggt catcaacatc    960
ggcgacacct tcatggctct gtccaacggg cggtacaaga gctgcctgca ccgggcggtg   1020
gtgaaccagc ggcaggagcg gcggtcgctg gccttcttcc tgtgccccgcg cgaggaccgg   1080 gtggtgcgcc cgccggccag cggcgccgtc ggcgaggcgc cccgccgcta cccggacttc   1140
acctgggccg acctcatgcg cttcacgcag cgccactacc gcgccgacac ccgcacgctg   1200
gacgccttca cacgctggct ctcccacggc ccggcccagg acgcgccagt ggcggcggcg   1260
gcttccacct ag                                                       1272

<210> SEQ ID NO 90
```

```
<211> LENGTH: 423
<212> TYPE: PRT
<213> ORGANISM: Setaria italica

<400> SEQUENCE: 90

Met Val Ser Gln Ala Gln Gln Glu Pro Ala Leu Pro His Ser Ser Ser
1               5                   10                  15

Thr Ala Lys Arg Ala Ala Ala Ser Leu Met Asp Ala Arg Pro Ala Gln
            20                  25                  30

Pro Leu Leu Leu Arg Ala Pro Thr Pro Ser Ile Asp Leu Pro Ala Ser
        35                  40                  45

Lys Pro Asp Arg Ala Ala Ala Ala Gly Lys Ala Ala Ala Ala Ala Ser
50                  55                  60

Val Phe Asp Leu Arg Arg Glu Pro Lys Ile Pro Ala Pro Phe Val Trp
65                  70                  75                  80

Pro His Asp Asp Ala Arg Pro Ala Ser Ala Ala Glu Leu Asp Val Pro
                85                  90                  95

Leu Val Asp Val Gly Val Leu Arg Asn Gly Asp Arg Ala Gly Leu Arg
            100                 105                 110

Arg Ala Ala Ala Gln Val Ala Ala Ala Cys Ala Thr His Gly Phe Phe
        115                 120                 125

Gln Val Cys Gly His Gly Val Gly Ala Asp Leu Ala Arg Ala Ala Leu
130                 135                 140

Asp Gly Ala Ser Asp Phe Phe Arg Leu Pro Leu Ala Glu Lys Gln Arg
145                 150                 155                 160

Ala Arg Arg Val Pro Gly Thr Val Ser Gly Tyr Thr Ser Ala His Ala
                165                 170                 175

Asp Arg Phe Ala Ser Lys Leu Pro Trp Lys Glu Thr Leu Ser Phe Gly
            180                 185                 190

Phe His Asp Gly Ala Ala Ser Pro Val Val Asp Tyr Phe Ala Gly
        195                 200                 205

Thr Leu Gly Gln Asp Phe Glu Ala Val Gly Arg Val Tyr Gln Arg Tyr
210                 215                 220

Cys Glu Glu Met Lys Ala Leu Ser Leu Thr Ile Met Glu Leu Leu Glu
225                 230                 235                 240

Leu Ser Leu Gly Val Glu Arg Gly Tyr Tyr Arg Asp Phe Phe Glu Asp
                245                 250                 255

Ser Arg Ser Ile Met Arg Cys Asn Tyr Tyr Pro Cys Pro Glu Pro
            260                 265                 270

Glu Arg Thr Leu Gly Thr Gly Pro His Cys Asp Pro Thr Ala Leu Thr
        275                 280                 285

Ile Leu Leu Gln Asp Asp Val Gly Gly Leu Glu Val Leu Val Asp Gly
290                 295                 300

Asp Trp Arg Pro Val Arg Pro Val Pro Gly Ala Met Val Ile Asn Ile
305                 310                 315                 320

Gly Asp Thr Phe Met Ala Leu Ser Asn Gly Arg Tyr Lys Ser Cys Leu
                325                 330                 335

His Arg Ala Val Val Asn Gln Arg Gln Glu Arg Ser Leu Ala Phe
            340                 345                 350

Phe Leu Cys Pro Arg Glu Asp Arg Val Val Arg Pro Ala Ser Gly
        355                 360                 365

Ala Val Gly Glu Ala Pro Arg Arg Tyr Pro Asp Phe Thr Trp Ala Asp
370                 375                 380

Leu Met Arg Phe Thr Gln Arg His Tyr Arg Ala Asp Thr Arg Thr Leu
```

385             390             395             400
Asp Ala Phe Thr Arg Trp Leu Ser His Gly Pro Ala Gln Asp Ala Pro
                405                 410                 415
Val Ala Ala Ala Ala Ser Thr
            420

<210> SEQ ID NO 91
<211> LENGTH: 2888
<212> TYPE: DNA
<213> ORGANISM: Setaria italica

<400> SEQUENCE: 91

| | | | | | |
|---|---|---|---|---|---|
| tctcatggtg | tcccaagcac | agcaagagcc | agctctgcct | cacagcagca | gcaccgccaa | 60 |
| gcgcgcagcc | gcgtcactca | tggacgcccg | cccggcccag | cctctcctcc | tccgcgcccc | 120 |
| gactcccagc | attgacctcc | ccgcgtccaa | gccgacagg | gccgccgcgg | cggccggcaa | 180 |
| ggccgccgcc | gcctcgtgt | tcgacctgcg | gcgggagccc | aagatcccgg | cgccattcgt | 240 |
| gtggccgcac | gacgacgcgc | ggccggcgtc | ggcggcggag | ctggacgtgc | cgttggtgga | 300 |
| cgtgggcgtg | ctgcgcaatg | cgaccgcgc | ggggctgcgg | cgcgctgcgg | cgcaggtggc | 360 |
| cgcggcgtgc | gcgacgcacg | ggttcttcca | ggtgtgcggg | cacggcgtgg | gcgcggacct | 420 |
| ggcgcgcgcg | cgctggacg | cgccagtga | cttcttccgg | ctgccgctgg | cggagaagca | 480 |
| gcgcgcccgg | cgcgtcccgg | ggaccgtgtc | cgggtacacg | agcgcgcacg | ccgaccggtt | 540 |
| cgcgtccaag | ctcccctgga | aggagaccct | ctccttcggg | ttccacgacg | cgccgcgtc | 600 |
| gcccgtcgtc | gtcgactact | tcgccggcac | cctcgggcag | gacttcgagg | cagtgggta | 660 |
| agtatgtagg | aatgaacttg | gcacgcattg | catccacatg | gcgtgctgat | cgaacgagct | 720 |
| gagccaaccg | gcatgcacac | atggcgtggc | aggcgggtgt | accagaggta | ctgcgaggag | 780 |
| atgaaggctc | tgtcgctgac | gatcatggag | ctcctggagc | tgagcctggg | cgtggagcgc | 840 |
| ggctactacc | gcgacttctt | cgaggacagc | cgctccatca | tgcggtgcaa | ctactacccg | 900 |
| ccgtgcccgg | agccggagcg | cacgctgggc | acgggcccgc | actgcgaccc | caccgcgctg | 960 |
| accatcctcc | tccaggacga | cgtcggcggg | ctcgaggtcc | tcgtcgacgg | cgactggcgc | 1020 |
| cccgtccgcc | ccgtccccgg | cgccatggtc | atcaacatcg | gcgacacctt | catggtacgg | 1080 |
| ccgccgctaa | tccatccttt | tgttgctctt | atctcctctg | gcgagtgcga | gtaacgaaag | 1140 |
| cgctagctcc | cctgctcctt | gtcctgctct | gtttcccaag | tcctaatgga | gctaaccggg | 1200 |
| cagactgcaa | cacgcacgcg | taggcatgtc | acgtagccac | cacttgcact | gtgctgcgca | 1260 |
| gcgacgacgc | aacgcggacg | tgcgttcgag | tcggttccat | ctcggcgccg | ctacacgcgg | 1320 |
| ccgcggctcc | tagcctccta | gggctccctg | atccctatcc | ccgagccctt | ccgcgggaaa | 1380 |
| agttcgttgg | cgacggcaga | ggagagccga | cgggtccgtg | ccgttggagc | gtggcggcag | 1440 |
| gagaggccgg | gagggtgttt | tgttgcgttg | cgcggcggcg | cggaggatgc | gatggcgcgg | 1500 |
| gcgggcggcg | ctttcggcgg | tggccccgc | gacccacgtg | cgcgcgcggt | ctcgtcgcct | 1560 |
| tccctgtttt | ggtgccacct | ctctgtgtcc | gggaatgggt | tggcttagcg | gcgaccgaga | 1620 |
| ccgggcggtg | gtctggcctg | ctccggcgc | ccatcccgcc | tggtctctca | tcctgctcct | 1680 |
| cctatgcgcg | agggggcctg | tagcggctgg | agtacaagca | gattggttgg | gttgggttgc | 1740 |
| tgctgcttgg | ctgttgcccg | ccgcttttct | agccgtttcc | gctcgccatc | ggcacgcgg | 1800 |
| cgcccacgcc | ggggctccag | ctcggcccct | ttggccgtgt | gggtggcagg | cacccctgca | 1860 |
| tcgtctcgtg | cgtccggttt | ccgcgcctgg | ccccccgcct | tgaggtttcc | ctgtgctttt | 1920 |

| | |
|---|---:|
| gacaagactt tcgtagatat atgtgtgtgt atgtgtgtgt gtgcgtgcgc gcgtgtgtgt | 1980 |
| atatatatat ataaataaat aacatctgtg aatgatggat tacacgtgta gctgaccggc | 2040 |
| tgattgtgtt cgcgtgtgtg tcttcgatgc attgcaggct ctgtccaacg ggcggtacaa | 2100 |
| gagctgcctg caccgggcgg tggtgaacca gcggcaggag cggcggtcgc tggccttctt | 2160 |
| cctgtgcccg cgcgaggacc gggtggtgcg cccgccggcc agcggcgccg tcggcgaggc | 2220 |
| gccccgccgc tacccggact tcacctgggc cgacctcatg cgcttcacgc agcgccacta | 2280 |
| ccgcgccgac acccgcacgc tggacgcctt cacacgctgg ctctcccacg gcccggccca | 2340 |
| ggacgcgcca gtggcggcgg cggcttccac ctagctagcg gcgcggatcc gaccgagccc | 2400 |
| attgacgacg ccgtcccttt ccgccgccgc cggggcccgc gcggggttc accccacgtg | 2460 |
| cgcgcccagg tgggcgaggt ggcggcctcg tggcccgcgg gccccgcgcc gccttcccat | 2520 |
| ttttgggcgc tgccgccccg cgcgcatgcc ggatgcgtgc gtccacggcc tactgctgct | 2580 |
| actagtgtac atatacaaac atacatatat acgtagtata aatatataag caagcggccc | 2640 |
| ggtgccccctt ttcgttttct tgttttgtcg atcacaatct ctggattcga tggatggata | 2700 |
| aatgtttgta cgcatgcatg tagatgggct catgaaattt cagaatctgg aacgacgag | 2760 |
| gagctcacgt gcctcttccg tgtctggtag cggtagctgc gtgccaaatg tctggtgggc | 2820 |
| ccaaagaaat tctagtgcca cccgtccgga tccggcatcc gaaagttccc gacggttcga | 2880 |
| cacccgaa | 2888 |

<210> SEQ ID NO 92
<211> LENGTH: 1567
<212> TYPE: DNA
<213> ORGANISM: Oryza sativa

<400> SEQUENCE: 92

| | |
|---|---:|
| tgcccagaca gctcgccctg cacacacaca cacactcaca ctcacacacg ctctcaactc | 60 |
| actcccgctc aacacagcgc tcacttctca tctccaatct catggtggcc gagcacccca | 120 |
| cgccaccaca gccgcaccaa ccaccgccca tggactccac cgccggctct ggcattgccg | 180 |
| cccccggcgg cggcggcggtg tgcgacctga ggatggagcc caagatcccg gagccattcg | 240 |
| tgtggccgaa cggcgacgcg aggccggcgt cggcggcgga gctggacatg cccgtggtcg | 300 |
| acgtgggcgt gctccgcgac ggcgacgccg aggggctgcg ccgcgccgcg cgcaggtgg | 360 |
| ccgccgcgtg cgccacgcac gggttcttcc aggtgtccga gcacggcgtc gacgccgctc | 420 |
| tggcgcgcgc cgcgctcgac ggcgccagcg acttcttccg cctcccgctc gccgagaagc | 480 |
| gccgcgcgcg ccgcgtcccg ggcaccgtgt ccggctacac cagcgcccac gccgaccgct | 540 |
| tcgcctccaa gctcccatgg aaggagaccc tctccttcgg cttccacgac cgcgccgccg | 600 |
| cccccgtcgt cgccgactac ttctccagca ccctcggccc cgacttcgcg ccaatgggga | 660 |
| gggtgtacca gaagtactgc gaggagatga aggagctgtc gctgacgatc atggaactcc | 720 |
| tggagctgag cctgggcgtg gagcgaggct actacaggga gttcttcgcg gacagcagct | 780 |
| caatcatgcg gtgcaactac tacccgccat gccggagcc ggagcggacg ctcggcacgg | 840 |
| gcccgcactg cgaccccacc gccctcacca tcctcctcca ggacgacgtc ggcggcctcg | 900 |
| aggtcctcgt cgacggcgaa tggcgccccg tcagcccgt cccggcgcc atggtcatca | 960 |
| acatcggcga caccttcatg gcgctgtcga acgggaggta taagagctgc ctgcacaggg | 1020 |
| cggtggtgaa ccagcggcgg gagcggcggt cgctggcgtt cttcctgtgc ccgcgggagg | 1080 |

| | |
|---|---|
| acagggtggt gcggccgccg ccgagcgccg ccacgccgca gcactacccg gacttcacct | 1140 |
| gggccgacct catgcgcttc acgcagcgcc actaccgcgc cgacacccgc acgctcgacg | 1200 |
| ccttcacgcg ctggctcgcg ccgccggccg ccgacgccgc cgcgacggcg caggtcgagg | 1260 |
| cggccagctg atcgccgaac ggaacgaaac ggaacgaaca gaagccgatt tttggcgggg | 1320 |
| cccacgccca cgtgaggccc cacgtggaca gtgggcccgg gcggaggtgg cacccacgtg | 1380 |
| gaccgcgggc cccgcgccgc cttccaattt tggaccctac cgctgtacat attcatatat | 1440 |
| tgcaagaaga agcaaaacgt acgtgtgggt tgggttgggc ttctctctat tactaaaaaa | 1500 |
| aatataatgg aacgacggat gaatggatgc ttatttattt atctaaattg aattcgaatt | 1560 |
| cggctca | 1567 |

<210> SEQ ID NO 93
<211> LENGTH: 1170
<212> TYPE: DNA
<213> ORGANISM: Oryza sativa

<400> SEQUENCE: 93

| | |
|---|---|
| atggtggccg agcaccccac gccaccacag ccgcaccaac caccgccat ggactccacc | 60 |
| gccggctctg gcattgccgc cccggcggcg gcggcggtgt gcgacctgag gatggagccc | 120 |
| aagatcccgg agccattcgt gtggccgaac ggcgacgcga ggccggcgtc ggcggcggag | 180 |
| ctggacatgc ccgtggtcga cgtgggcgtg ctccgcgacg cgacgccga ggggctgcgc | 240 |
| cgcgccgcgg cgcaggtggc cgccgcgtgc gccacgcacg ggttcttcca ggtgtccgag | 300 |
| cacggcgtcg acgccgctct ggcgcgcgcc gcgctcgacg gcgccagcga cttcttccgc | 360 |
| ctcccgctcg ccgagaagcg ccgcgcgcgc gcgtcccgg gcaccgtgtc cggctacacc | 420 |
| agcgcccacg ccgaccgctt cgcctccaag ctcccatgga aggagaccct ctccttcggc | 480 |
| ttccacgacc gcgccgccgc ccccgtcgtc gccgactact tctccagcac cctcggcccc | 540 |
| gacttcgcgc caatggggag ggtgtaccag aagtactgcg aggagatgaa ggagctgtcg | 600 |
| ctgacgatca tggaactcct ggagctgagc ctgggcgtgg agcgaggcta ctacagggag | 660 |
| ttcttcgcgc acagcagctc aatcatgcgg tgcaactact acccgccatg cccggagccg | 720 |
| gagcggacgc tcggcacggg cccgcactgc gaccccaccg ccctcaccat cctcctccag | 780 |
| gacgacgtcg gcggcctcga ggtcctcgtc gacggcgaat ggcgcccgt cagccccgtc | 840 |
| cccggcgcca tggtcatcaa catcggcgac accttcatgg cgctgtcgaa cgggaggtat | 900 |
| aagagctgcc tgcacagggc ggtggtgaac cagcggcggg agcggcggtc gctggcgttc | 960 |
| ttcctgtgcc cgcgggagga cagggtggtg cggccgccgc cgagcgccgc cacgccgcag | 1020 |
| cactacccgg acttcacctg gccgacctca tgcgcttca cgcagcgcca ctaccgcgcc | 1080 |
| gacacccgca cgctcgacgc cttcacgcgc tggctcgcg cgccggccgc cgacgccgcc | 1140 |
| gcgacggcgc aggtcgaggc ggccagctga | 1170 |

<210> SEQ ID NO 94
<211> LENGTH: 389
<212> TYPE: PRT
<213> ORGANISM: Oryza sativa

<400> SEQUENCE: 94

Met Val Ala Glu His Pro Thr Pro Pro Gln Pro His Gln Pro Pro Pro
1               5                   10                  15

Met Asp Ser Thr Ala Gly Ser Gly Ile Ala Ala Pro Ala Ala Ala Ala
            20                  25                  30

Val Cys Asp Leu Arg Met Glu Pro Lys Ile Pro Pro Phe Val Trp
     35                  40                  45

Pro Asn Gly Asp Ala Arg Pro Ala Ser Ala Ala Glu Leu Asp Met Pro
 50                  55                  60

Val Val Asp Val Gly Val Leu Arg Asp Gly Asp Ala Glu Gly Leu Arg
 65                  70                  75                  80

Arg Ala Ala Ala Gln Val Ala Ala Ala Cys Ala Thr His Gly Phe Phe
                 85                  90                  95

Gln Val Ser Glu His Gly Val Asp Ala Ala Leu Ala Arg Ala Ala Leu
                 100                 105                 110

Asp Gly Ala Ser Asp Phe Phe Arg Leu Pro Leu Ala Glu Lys Arg Arg
                 115                 120                 125

Ala Arg Arg Val Pro Gly Thr Val Ser Gly Tyr Thr Ser Ala His Ala
             130                 135                 140

Asp Arg Phe Ala Ser Lys Leu Pro Trp Lys Glu Thr Leu Ser Phe Gly
145                 150                 155                 160

Phe His Asp Arg Ala Ala Pro Val Val Ala Asp Tyr Phe Ser Ser
                 165                 170                 175

Thr Leu Gly Pro Asp Phe Ala Pro Met Gly Arg Val Tyr Gln Lys Tyr
             180                 185                 190

Cys Glu Glu Met Lys Glu Leu Ser Leu Thr Ile Met Glu Leu Leu Glu
             195                 200                 205

Leu Ser Leu Gly Val Glu Arg Gly Tyr Tyr Arg Glu Phe Phe Ala Asp
     210                 215                 220

Ser Ser Ser Ile Met Arg Cys Asn Tyr Tyr Pro Cys Pro Glu Pro
225                 230                 235                 240

Glu Arg Thr Leu Gly Thr Gly Pro His Cys Asp Pro Thr Ala Leu Thr
                 245                 250                 255

Ile Leu Leu Gln Asp Asp Val Gly Gly Leu Glu Val Leu Val Asp Gly
             260                 265                 270

Glu Trp Arg Pro Val Ser Pro Val Pro Gly Ala Met Val Ile Asn Ile
     275                 280                 285

Gly Asp Thr Phe Met Ala Leu Ser Asn Gly Arg Tyr Lys Ser Cys Leu
 290                 295                 300

His Arg Ala Val Val Asn Gln Arg Arg Glu Arg Arg Ser Leu Ala Phe
305                 310                 315                 320

Phe Leu Cys Pro Arg Glu Asp Arg Val Val Arg Pro Pro Ser Ala
                 325                 330                 335

Ala Thr Pro Gln His Tyr Pro Asp Phe Thr Trp Ala Asp Leu Met Arg
                 340                 345                 350

Phe Thr Gln Arg His Tyr Arg Ala Asp Thr Arg Thr Leu Asp Ala Phe
                 355                 360                 365

Thr Arg Trp Leu Ala Pro Pro Ala Ala Asp Ala Ala Thr Ala Gln
     370                 375                 380

Val Glu Ala Ala Ser
385

<210> SEQ ID NO 95
<211> LENGTH: 3140
<212> TYPE: DNA
<213> ORGANISM: Oryza sativa

<400> SEQUENCE: 95
tgcccagaca gctcgccctg cacacacaca cacactcaca ctcacacacg ctctcaactc    60

-continued

```
actcccgctc aacacagcgc tcacttctca tctccaatct catggtggcc gagcacccca    120
cgccaccaca gccgcaccaa ccaccgccca tggactccac cgccggctct ggcattgccg    180
ccccggcggc ggcggcggtg tgcgacctga ggatggagcc caagatcccg gagccattcg    240
tgtggccgaa cggcgacgcg aggccggcgt cggcggcgga gctggacatg cccgtggtcg    300
acgtgggcgt gctccgcgac ggcgacgccg aggggctgcg ccgcgccgcg cgcaggtgg     360 ccgccgcgtg cgccacgcac gggttcttcc aggtgtccga gcacggcgtc gacgccgctc    420
tggcgcgcgc cgcgctcgac ggcgccagcg acttcttccg cctcccgctc gccgagaagc    480
gccgcgcgcg ccgcgtcccg ggcaccgtgt ccggctacac cagcgcccac gccgaccgct    540
tcgcctccaa gctcccatgg aaggagaccc tctccttcgg cttccacgac cgcgccgccg    600
cccccgtcgt cgccgactac ttctccagca ccctcggccc cgacttcgcg ccaatggggt    660
aattaaaacg atggtggacg acattgcatt tcaaattcaa aacaaattca aaacacaccg    720
accgagatta tgctgaattc aaacgcgttt gtgcgcgcag gagggtgtac cagaagtact    780
gcgaggagat gaaggagctg tcgctgacga tcatggaact cctggagctg agcctgggcg    840
tggagcgagg ctactacagg gagttcttcg cggacagcag ctcaatcatg cggtgcaact    900 actaccccgcc atgcccggag ccggagcgga cgctcggcac gggcccgcac tgcgacccca    960
ccgccctcac catcctcctc caggacgacg tcggcggcct cgaggtcctc gtcgacggcg   1020
aatggcgccc cgtcagcccc gtcccggcg ccatggtcat caacatcggc gacaccttca    1080
tggtaaacca tctcctattc tcctctcctc tgttctcctc tgcttcgaag caacagaaca    1140
agtaattcaa gcttttttttt ctctctcgcg cgaaattgac gagaaaaata agatcgtggt   1200
aggggcgggg ctttcagctg aaagcgggaa gaaaccgacc tgacgtgatt tctctgttcc   1260
aatcacaaac aatggaatgc cccactcctc catgtgttat gatttatctc acatcttata   1320
gttaatagga gtaagtaaca agctactttt ttcatattat agttcgtttg atttttttt    1380 tttaaagttt ttttagtttt atccaaattt attgaaaaac ttagcaacgt ttataatacc   1440
aaattagtct catttagttt aatattgtat atattttgat aatatattta tgttatatta   1500
aaaatattac tatattttc tataaacatt attaaaagcc atttataata taaaatggaa    1560
ggagtaatta atatggatct cccccgacat gagaatattt tccgatggtg tgacgacgcc   1620
atgtaagctt cggtgggcct ggacggcag aggtgccaac agccacgtcc aacaccccct    1680 gggtccccc ctaacactcc aaacagtagt gagtagtgtc tcgtcgcgtt ttagtatttg    1740
atgacaaaca aagtgtgagt tgagttagcc accaccaact tgcacacgag cacatacatt    1800
tgtgtccatt ctcgccagtc acttccatct ctagtcctaa ctcctatcta gcgatgtaag    1860
cggataattt catcatccgt atataaacct gtttgttata gttaatttcc tatataatac    1920
tataacagta tacattttaa aagaaaacaa aattaggata aacaggccct gctcctatcc    1980
atccatggca cttggaagga ccagactcgg tcatgccatg ccaagccaag atatgggtta    2040
tggaagagta gagaagagga gagatgagag ataagcatgc gttctcctcc tcgttggatg    2100
tgtattttgg agggatttgt gtagtagtag cagcggcgcc gcggggacgg atgcggatgg    2160
tggcgctttc ggtggcgttt tcccgggggg gttttggttt ggcgcttggg ggggatggca    2220
tggcgcggcg tgcggctgca cgccacacac acgcgcgcgc acgcacgtac gtcgtcgtcg    2280 ccgcgggcg acggtagctt agggtggtgt gttccgcgcg cgggcgcgga ttgttccatg    2340
ccgatcgatt tggcgccacc ctcgccgcgg ctcttgtcgc gtcgtgcgcc tctctcgcgc    2400
```

```
ggtttgtcct tgtcgcgttg ctcagccggc gacgggggca cggacattgg cgatgtagcc    2460
ctgcacgtgt cggcctctcc gttgatgaat gatgatgtat gtatgtattt ttttttgtct    2520
gaaggaattt gtggggaatt gttgtgtgtg caggcgctgt cgaacgggag gtataagagc    2580
tgcctgcaca gggcggtggt gaaccagcgg cgggagcggc ggtcgctggc gttcttcctg    2640
tgcccgcggg aggacagggt ggtgcggccg ccgccgagcg ccgccacgcc gcagcactac    2700
ccggacttca cctgggccga cctcatcgcg ttcacgcagc gccactaccg cgccgacacc    2760
cgcacgctcg acgccttcac gcgctggctc gcgccgccgg ccgccgacgc gccgcgacg    2820 gcgcaggtcg aggcggccag ctgatcgccg aacggaacga aacggaacga acagaagccg    2880 attttttggcg gggcccacgc ccacgtgagg ccccacgtgg acagtgggcc cgggcggagg    2940
tggcacccac gtggaccgcg ggccccgcgc cgccttccaa ttttggaccc taccgctgta    3000
catattcata tattgcaaga agaagcaaaa cgtacgtgtg ggttgggttg ggcttctctc    3060
tattactaaa aaaaatataa tggaacgacg gatgaatgga tgcttattta tttatctaaa    3120
ttgaattcga attcggctca                                                 3140

<210> SEQ ID NO 96
<211> LENGTH: 1170
<212> TYPE: DNA
<213> ORGANISM: Triticum aestivum

<400> SEQUENCE: 96
atggacacca gccctgcaac tcccctgctc ctccagcctc ctgctcccag cattgacccg      60
ttcgccgcca aggcggccgt caacaagggc ggcggcgcgg caaccgcggt gtacgacctc     120
cggagggagc cgaagatccc cgccccgttc gtgtggccgc acgccgaggt gcgccccacc     180
acggcccagg agctggccgt gccggtggtg gacgtgggcg tgctgcgcaa tggcgacgcc     240
gcggggctcc gccgcgccgt ggcgcaggtg gccgcggcgt gccacgca cgggttcttc       300 caggtgtccg gcacggcgt ggacgaggcc ctggcgcgcg cggcgctgga cggcgcgagc      360
ggcttcttcc ggctgccgct ggccgagaag cagcgcgcgc ggcgcgtccc ggggaccgtg     420
tccgggtaca cgagcgcgca cgccgaccgg ttcgcctcca gctccctg gaaggagacc       480 ctctccttcg gcttccacga ccgcgccggc gccgcgcccg tcgtggtgga ctacttcacc     540
agcaccctcg gccggactac gagccaatg ggagggtgt accaggagta ctgcgggaag       600
atgaaggagc tgtcgctgag gatcatggag ctgctggagc tgagccaggg cgtggagaag     660
cgcgggtact accgggagtt cttcgcggac agcagctcca tcatgcggtg caactactac     720
ccgccgtgcc cggagccgga gcacgctg gcacgggcc cgcactgcga ccccacggcg        780
ctcaccatcc tactgcagga cgacgtgggc gggctgagg tcctcgtcga cggcgactgg      840
cgccccgtcc gccccgtccc cggcgccatg gtcatcaaca tcggcgacac cttcatggcg    900
ctgtcgaacg gcggtacaa gagctgcctg caccgcgcgg tggtgaaccg gcggcaggag     960
cggcggtcgc tggccttctt cctgtgcccg cgcgaggacc gcgtggtgcg gccgccgccg   1020
ggcctgagga gcccgcggcg gtaccccggac ttcacctggg ctgacctcat gcgcttcacg   1080
cagcgccact accgcgccga cacgcgcacc ctcgacgcct tcacccagtg gttctcctcc   1140
tcctcctcct cggcccagga ggcggcctga                                     1170

<210> SEQ ID NO 97
<211> LENGTH: 389
<212> TYPE: PRT
<213> ORGANISM: Triticum aestivum
```

<400> SEQUENCE: 97

```
Met Asp Thr Ser Pro Ala Thr Pro Leu Leu Leu Gln Pro Pro Ala Pro
1               5                   10                  15

Ser Ile Asp Pro Phe Ala Ala Lys Ala Ala Val Asn Lys Gly Gly Gly
                20                  25                  30

Ala Ala Thr Ala Val Tyr Asp Leu Arg Arg Glu Pro Lys Ile Pro Ala
            35                  40                  45

Pro Phe Val Trp Pro His Ala Glu Val Arg Pro Thr Thr Ala Gln Glu
    50                  55                  60

Leu Ala Val Pro Val Val Asp Val Gly Val Leu Arg Asn Gly Asp Ala
65                  70                  75                  80

Ala Gly Leu Arg Arg Ala Val Ala Gln Val Ala Ala Cys Ala Thr
                85                  90                  95

His Gly Phe Phe Gln Val Ser Gly His Gly Val Asp Glu Ala Leu Ala
                100                 105                 110

Arg Ala Ala Leu Asp Gly Ala Ser Gly Phe Phe Arg Leu Pro Leu Ala
            115                 120                 125

Glu Lys Gln Arg Ala Arg Arg Val Pro Gly Thr Val Ser Gly Tyr Thr
130                 135                 140

Ser Ala His Ala Asp Arg Phe Ala Ser Lys Leu Pro Trp Lys Glu Thr
145                 150                 155                 160

Leu Ser Phe Gly Phe His Asp Arg Ala Gly Ala Pro Val Val Val
                165                 170                 175

Asp Tyr Phe Thr Ser Thr Leu Gly Pro Asp Tyr Glu Pro Met Gly Arg
            180                 185                 190

Val Tyr Gln Glu Tyr Cys Gly Lys Met Lys Glu Leu Ser Leu Arg Ile
            195                 200                 205

Met Glu Leu Leu Glu Leu Ser Gln Gly Val Glu Lys Arg Gly Tyr Tyr
210                 215                 220

Arg Glu Phe Phe Ala Asp Ser Ser Ile Met Arg Cys Asn Tyr Tyr
225                 230                 235                 240

Pro Pro Cys Pro Glu Pro Glu Arg Thr Leu Gly Thr Gly Pro His Cys
            245                 250                 255

Asp Pro Thr Ala Leu Thr Ile Leu Leu Gln Asp Asp Val Gly Gly Leu
            260                 265                 270

Glu Val Leu Val Asp Gly Asp Trp Arg Pro Val Arg Pro Val Pro Gly
            275                 280                 285

Ala Met Val Ile Asn Ile Gly Asp Thr Phe Met Ala Leu Ser Asn Gly
            290                 295                 300

Arg Tyr Lys Ser Cys Leu His Arg Ala Val Val Asn Arg Arg Gln Glu
305                 310                 315                 320

Arg Arg Ser Leu Ala Phe Phe Leu Cys Pro Arg Glu Asp Arg Val Val
            325                 330                 335

Arg Pro Pro Pro Gly Leu Arg Ser Pro Arg Arg Tyr Pro Asp Phe Thr
            340                 345                 350

Trp Ala Asp Leu Met Arg Phe Thr Gln Arg His Tyr Arg Ala Asp Thr
            355                 360                 365

Arg Thr Leu Asp Ala Phe Thr Gln Trp Phe Ser Ser Ser Ser Ser Ser
            370                 375                 380

Ala Gln Glu Ala Ala
385
```

<210> SEQ ID NO 98
<211> LENGTH: 3050
<212> TYPE: DNA
<213> ORGANISM: Triticum aestivum

<400> SEQUENCE: 98

```
ctcatggtgc tccagaccgc tcagcaagaa ccatccctga cgcgtccgcc tcactgcagc      60
gtcgccagcg cgcgctcgcc ggcggccatg gacaccagcc ctgcaactcc cctgctcctc     120
cagcctcctg ctcccagcat tgacccgttc gccgccaagg cggccgtcaa caagggcggc     180
ggcgcggcaa ccgcggtgta cgacctccgg agggagccga agatccccgc cccgttcgtg     240
tggccgcacg ccgaggtgcg ccccaccacg gcccaggagc tggccgtgcc ggtggtggac     300
gtgggcgtgc tgcgcaatgg cgacgccgcg gggctccgcc gcgccgtggc gcaggtggcc     360
gcggcgtgcg ccacgcacgg gttcttccag gtgtccgggc acggcgtgga cgaggccctg     420
gcgcgcgcgg cgctggacgg cgcgagcggc ttcttccggc tgccgctggc cgagaagcag     480
cgcgcgcggc gcgtcccggg gaccgtgtcc gggtacacga gcgcgcacgc cgaccggttc     540
gcctccaagc tcccctggaa ggagaccctc tccttcggct ccacgaccg cgccggcgcc      600 gcgcccgtcg tggtggacta cttcaccagc accctcgggc cggactacga gccaatgggg     660
taatatatcc acccgcccac acccctatcc ggccagcacg aatccatccc cgccactgca     720 ttttttttcct tttgtttccg cgcgaccgta cgttcgatcg gcgcccacgt acgtacgtgc     780
gtacgcagta gcagtacttg aagccgccgt actacgtgct gagtagtgac aactgaacac     840
gtgcaggagg gtgtaccagg agtactgcgg gaagatgaag gagctgtcgc tgaggatcat     900
ggagctgctg gagctgagcc agggcgtgga gaagcgcggg tactaccggg agttcttcgc     960
ggacagcagc tccatcatgc ggtgcaacta ctacccgccg tgcccggagc cggagcgcac    1020
gctgggcacg ggcccgcact cgacccccac ggcgctcacc atcctactgc aggacgacgt    1080
gggcgggctg gaggtcctcg tcgacggcga ctggcgcccc gtccgccccg tccccggcgc    1140
catggtcatc aacatcggcg acaccttcat ggtaattact cctctctcag cgttgctttc    1200
gctgattaat tgcagaaaca gtagtcaact acccatgctc tgttccgctg tgctctgctt    1260
cccaacgagc gaaccggccc ataaaaactg ccttgctgtc ttggaaccaa gaggaaaggg    1320
accgtgggag cctaccgaca cgacgtgatt gcactctgct tcctaacaag cgagccgccg    1380
gtagggctat caccgtaagg gctccttga ttcaaaggaa tttcttagga tttctgaagg      1440
attgaaatcc ttaggatttt ttcctatgtt ggtacttcga ttcataggat tgaatcccat    1500 aggattttt tcctatgaaa tcttctgtac tacatttcat aggaaatcta acatccactc      1560 caacctttt tatatttcc tttgtttttc atgtgccatc aaacactcct tgttaatcct      1620
ataggattca agtgggcatg ccactccaat cctatacttt tcccattcct acgttttcaa    1680
aatcctacga atcaaagagg ccctaaagct gctgacatga cgtgatttt ttttctttt      1740 cttctttct ttctcagctc caatcaacgc tggttattag atcattagag tggacaggtt     1800
gaattaacat gcagtagtta gtagttagca gccacaaacg ggtccgttc tctgaagtct     1860 gaactgacat aagtcctgat catcgaccat tctttgcttc ctaggacgat gcctgttgga    1920
acttgcgtcc aatgcccgtt agggagtggt aattgtcatc acttttagac tcgtcgattc    1980
cactgatgaa gacgtagcac atggatgagc caacgtatcc gtttctagtg gtctcgaaaa    2040
gtagggtttc attcattcta tctatctatc cgtccgtcca aaaggctgc gatgcgagca     2100 cttgagtcgg agccaatcag agcgcgagaa aagatagggg gggtagcaag ccatgtcgga    2160
```

| | |
|---|---|
| ggggcgtttg cttccggcag gtttggattc ttgtggtagg cgggcggctc tgtacagtag | 2220 |
| cggcggtgac ggtgaggtgg cggcgctttc ggtggcgggc caacccaggt gcatgcacgc | 2280 |
| gcgctcgtcg ttttcccgcc tgaatctgcc gctgcgccca tggcaagggg gtgggtgctg | 2340 |
| ccgccgggcg atggagtaga tcacggtcgc cgtcgggctc ggccagttga tcacggttcg | 2400 |
| ttcgtgcggt actaggttcc cccacggcac tgtgactgca tcgttccggc cctcgccatt | 2460 |
| ggcgatcggg caatctcctg ttcatccgtc gctgttgatt cctcggccac gatagaccat | 2520 |
| gcgcgtgccg gtcgtcgccc cgtcgcgctc gcttcacgtg ctcgtcgcgt ggctcccgtc | 2580 |
| ccacacgagg ccgccgcttt ctgacccagt ggagcgcgtg atttacagtt tatatatgtc | 2640 |
| gctgcatttt tcttttttgtg tgctgctcat tttgcttgga cggagaccgg gaacgattag | 2700 |
| ccacggatct aacgcgttgt tgcttgtttt caatgcatgc atgcaggcgc tgtcgaacgg | 2760 |
| gcggtacaag agctgcctgc accgcgcggt ggtgaaccgg cggcaggagc ggcggtcgct | 2820 |
| ggccttcttc ctgtgcccgc gcgaggaccg cgtggtgcgg ccgccgccgg gcctgaggag | 2880 |
| cccgcggcgg tacccggact tcacctgggc tgacctcatg cgcttcacgc agcgccacta | 2940 |
| ccgcgccgac acgcgcaccc tcgacgcctt cacccagtgg ttctcctcct cctcctcctc | 3000 |
| ggcccaggag gcggcctgat tctgctctgc cacgaaacga tcggtccaca | 3050 |

<210> SEQ ID NO 99
<211> LENGTH: 1486
<212> TYPE: DNA
<213> ORGANISM: Hordeum vulgare

<400> SEQUENCE: 99

| | |
|---|---|
| gaccagtagc atatagtttt tcttgtgttt gccatggtgg acgtgtcgaa ctttgtagaa | 60 |
| gccaatggca atgcagcagt atcgattcct gccatggaag ttgctgggag tcctcacgtc | 120 |
| ccgttcgttc ctcgggacgc gaacgcgaca gacagcaaga atgccaagga cgtcctcgac | 180 |
| ctctggcgga agcagaaaca aatcccggct cccttcatct ggccccacgc cgacgcgcgg | 240 |
| ccgtcgtcga tcttggagct ggacgtgccc gtggtcgaca tcggcgcggc cctgcacagc | 300 |
| gccgccggga tggcccgcgc gcgcggcgcag gtggccgagg catgcgcgag ccacggcttc | 360 |
| ttccaggtga ccgggcacgg cgtcgacccc cgcgctggccc aagcagcgct cgacggcgca | 420 |
| gcggacttct tccgcctgcc gctcgccacc aagcagcgcg cccgccgatc cccggggacc | 480 |
| gtcaaagggt acgcctccgc ccacgccgac cgcttcgccg ccaagcttcc ctggaaggag | 540 |
| actctctcct tcatccacaa ccacgtccac gaggacgtcg cgcgcccgcg caagcagtcac | 600 |
| gtcgtcgact acttcacctc cgcccttggc gacgacttca tgcacctagg ggaggtgtac | 660 |
| caggagtact gtgaggcgat ggaggacgcg tcgctggcga taatggaggt gctgggggtg | 720 |
| agcctggggc tggggagagg gtactacagg gacttcttcg ccgacggcag ctccatcatg | 780 |
| aggtgcaact actacccgcg cgtgcccgag ccggaccgga cgctggggac ggggccgcac | 840 |
| tgcgacccgt cggcgctgac catcctgctg caggacggca aggtgacgg gctccaggtg | 900 |
| ctcgtcgacg gcgcatggcg ctccgtgcgg cccaagcccg gcgagctcgt cgtaaacatc | 960 |
| ggcgacacct tcatggcgct gtcgaacggc cggtacaaga gctgcctcca ccgcgcggtg | 1020 |
| gtgcaccggg agaaggagcg ccggtcgctg gcctacttcc tcgccccgcg ggaggaccgg | 1080 |
| gtggttcgcc cgccgccttc gccggcgccg gcgccgcggc tctacccgga cttcacctgg | 1140 |
| gcggagctca tgcgattcac gcagcgccac taccgcgccg acgcccgcac gctcgacgcc | 1200 |
| ttcgcgtgct ggctcgacct gcccagctgc cccaccacgc cccaggccca agggactgtc | 1260 |

```
tagtgtctgt gatgtatcat ctgtctcagc tgttgtatac gaccacttgt gtctgctagc    1320
tctgcgcttg tgtttcttat gtgagctaac taactaaata gtgtgtatat ttcttgccgc    1380
gccttatgca agccctagtc tagaacatgt aataattaac ttaagcatat acgttgatct    1440
ttggtgtatt tttcatattt ccttcataat gaataatcta ttatgc                  1486
```

<210> SEQ ID NO 100
<211> LENGTH: 1230
<212> TYPE: DNA
<213> ORGANISM: Hordeum vulgare

<400> SEQUENCE: 100

```
atggtggacg tgtcgaactt tgtagaagcc aatggcaatg cagcagtatc gattcctgcc      60
atggaagttg ctgggagtcc tcacgtcccg ttcgttcctc gggacgcgaa cgcgacagac     120
agcaagaatg ccaaggacgt cctcgacctc tggcggcagc agaaacaaat cccggctccc     180
ttcatctggc cccacgccga cgcgcggccg tcgtcgatct tggagctgga cgtgcccgtg     240
gtcgacatcg gcgcggccct gcacagcgcc gccgggatgg cccgcgccgc ggcgcaggtg     300
gccgaggcat gcgcgagcca cggcttcttc caggtgaccg gcacggcgt cgaccccgcg     360 ctggcccaag cagcgctcga cggcgcagcg gacttcttcc gcctgccgct cgccaccaag     420
cagcgcgccc gccgatcccc ggggaccgtc aaagggtacg cctccgccca cgccgaccgc     480
ttcgccgcca gcttccctg aaggagact ctctccttca tccacaacca cgtccacgag      540
gacgtcggcg cccgcgcaag cagtcacgtc gtcgactact tcacctccgc ccttggcgac     600
gacttcatgc acctagggga ggtgtaccag gagtactgtg aggcgatgga ggacgcgtcg     660
ctggcgataa tggaggtgct gggggtgagc ctggggctgg ggagagggta ctacagggac     720
ttcttcgccg acggcagctc catcatgagg tgcaactact acccgcggtg cccggagccg     780
gaccggacgc tggggacggg gccgcactgc gaccgtcgg cgctgaccat cctgctgcag      840
gacggcgagg tggacgggct ccaggtgctc gtcgacggcg catggcgctc cgtgcggccc     900
aagcccggcg agctcgtcgt aaacatcggc gacaccttca tggcgctgtc gaacggccgg     960
tacaagagct gcctccaccg cgcggtggtg caccgggaga aggagcgccg gtcgctggcc    1020
tacttcctcg ccccgcggga ggaccggggtg gttcgcccgc cgccttcgcc ggcgccggcg    1080
ccgcggctct accggactt cacctgggcg agctcatgc gattcacgca gcgccactac      1140
cgcgccgacg cccgcacgct cgacgccttc gcgtgctggc tcgacctgcc cagctgcccc    1200
accacgcccc aggcccaagg gactgtctag                                      1230
```

<210> SEQ ID NO 101
<211> LENGTH: 409
<212> TYPE: PRT
<213> ORGANISM: Hordeum vulgare

<400> SEQUENCE: 101

```
Met Val Asp Val Ser Asn Phe Val Glu Ala Asn Gly Asn Ala Ala Val
1               5                   10                  15

Ser Ile Pro Ala Met Glu Val Ala Gly Ser Pro His Val Pro Phe Val
            20                  25                  30

Pro Arg Asp Ala Asn Ala Thr Asp Ser Lys Asn Ala Lys Asp Val Leu
        35                  40                  45

Asp Leu Trp Arg Gln Gln Lys Gln Ile Pro Ala Pro Phe Ile Trp Pro
    50                  55                  60
```

```
His Ala Asp Ala Arg Pro Ser Ser Ile Leu Glu Leu Asp Val Pro Val
 65                  70                  75                  80

Val Asp Ile Gly Ala Ala Leu His Ser Ala Gly Met Ala Arg Ala
             85                  90                  95

Ala Ala Gln Val Ala Glu Ala Cys Ala Ser His Gly Phe Phe Gln Val
            100                 105                 110

Thr Gly His Gly Val Asp Pro Ala Leu Ala Gln Ala Ala Leu Asp Gly
        115                 120                 125

Ala Ala Asp Phe Phe Arg Leu Pro Leu Ala Thr Lys Gln Arg Ala Arg
    130                 135                 140

Arg Ser Pro Gly Thr Val Lys Gly Tyr Ala Ser Ala His Ala Asp Arg
145                 150                 155                 160

Phe Ala Ala Lys Leu Pro Trp Lys Glu Thr Leu Ser Phe Ile His Asn
                165                 170                 175

His Val His Glu Asp Val Gly Ala Arg Ala Ser Ser His Val Val Asp
            180                 185                 190

Tyr Phe Thr Ser Ala Leu Gly Asp Asp Phe Met His Leu Gly Glu Val
        195                 200                 205

Tyr Gln Glu Tyr Cys Glu Ala Met Glu Asp Ala Ser Leu Ala Ile Met
    210                 215                 220

Glu Val Leu Gly Val Ser Leu Gly Leu Gly Arg Gly Tyr Tyr Arg Asp
225                 230                 235                 240

Phe Phe Ala Asp Gly Ser Ser Ile Met Arg Cys Asn Tyr Tyr Pro Arg
                245                 250                 255

Cys Pro Glu Pro Asp Arg Thr Leu Gly Thr Gly Pro His Cys Asp Pro
            260                 265                 270

Ser Ala Leu Thr Ile Leu Leu Gln Asp Gly Glu Val Asp Gly Leu Gln
        275                 280                 285

Val Leu Val Asp Gly Ala Trp Arg Ser Val Arg Pro Lys Pro Gly Glu
    290                 295                 300

Leu Val Val Asn Ile Gly Asp Thr Phe Met Ala Leu Ser Asn Gly Arg
305                 310                 315                 320

Tyr Lys Ser Cys Leu His Arg Ala Val Val His Arg Glu Lys Glu Arg
                325                 330                 335

Arg Ser Leu Ala Tyr Phe Leu Ala Pro Arg Glu Asp Arg Val Val Arg
            340                 345                 350

Pro Pro Pro Ser Pro Ala Pro Ala Pro Arg Leu Tyr Pro Asp Phe Thr
        355                 360                 365

Trp Ala Glu Leu Met Arg Phe Thr Gln Arg His Tyr Arg Ala Asp Ala
    370                 375                 380

Arg Thr Leu Asp Ala Phe Ala Cys Trp Leu Asp Leu Pro Ser Cys Pro
385                 390                 395                 400

Thr Thr Pro Gln Ala Gln Gly Thr Val
                405

<210> SEQ ID NO 102
<211> LENGTH: 1423
<212> TYPE: DNA
<213> ORGANISM: Sorghum bicolor

<400> SEQUENCE: 102
cctctcatca caggccccag cctcactctt ctcacagcaa gacatcgcag cctcacaacc      60
acacagcaac gtgatcgcca tgggcgggct caccatggag caggccttcg tgcaggcccc     120
cgagcaccgc cccaagccca ccgtcaccga ggccaccggc atcctggtca tcgacctctc     180
```

-continued

| | |
|---|---|
| gcctctcacc gccagcgaca ccgacgcggc gcggtggac gcgctggccg ccgaggtggg | 240 |
| cgcggcgagc cgggactggg gcttcttcgt ggtggttggc cacggcgtgc ccgcggagac | 300 |
| cgtggcgcgc gcgacggcgg cgcagcgcgc gttcttcgcg ctgccggcgg agcggaaggc | 360 |
| cgccgtgcgc aggagcgagg cggagccgct cgggtactac gagtcggagc acaccaagaa | 420 |
| cgtcagggac tggaaggagg tgttcgacct cgtcccgcgc gatccgccgc cgccagcagc | 480 |
| cgtggccgac ggcgagctcg tcttcaagaa caagtggccc caggatctgc cgggcttcag | 540 |
| agaggcgctg gaggagtacg cggcagcgat ggaggagctg tcgttcaagc tgctggagct | 600 |
| gatcgcccga agcttgaagc tgaggcccga ccggctgcac ggcttcttca aggaccagac | 660 |
| gacgttcatc cggctgaacc actaccctcc atgcccgagc ccggacctgg cgctgggagt | 720 |
| ggggcggcac aaggacgcgg gggcgctgac catcctgtac caggacgaag tgggcgggct | 780 |
| ggacgtccgg cggcgctcct ccgacggcgg cggcggcgag tgggtgcggg tgaggcccgt | 840 |
| gccggagtcg ttcgtcatca acgtcggcga cctcgtccag gtgtggagca acgacaggta | 900 |
| cgagagcgcg gagcaccggg tgtcggtgaa ctcggcgagg gagaggttct ccatgcccta | 960 |
| cttcttcaac ccggcgagct acaccatggt ggagccggtg gaggagctgg tgagcgacga | 1020 |
| cgacccgccc aggtacgacg cctacagctg gggcgagttc ttcagcacca ggaagaacag | 1080 |
| caacttcaag aagctcagcg tggagaacat tcagatcgcg catttcaaga agaccctcgt | 1140 |
| cctcgcctag ataagcagca ggatactaca ggtctacagg actaggacaa gccgatcgag | 1200 |
| gtgaccggcc gtcgtcttca gattcagtat atgcgtgtcg ccgttcgtgt tagaacaaat | 1260 |
| taataatgtg cgcgctgtgt gctgtgtgtg tggagtaaaa aaaaactaaa catggatgtg | 1320 |
| catgttcaaa aaaaaaaaca tggatgcgag tatgtttggg aataataaca ggcttgtgac | 1380 |
| ggtctggttt atttgcaaat tcaaaccgaa ttggttgatc ttc | 1423 |

<210> SEQ ID NO 103
<211> LENGTH: 1071
<212> TYPE: DNA
<213> ORGANISM: Sorghum bicolor

<400> SEQUENCE: 103

| | |
|---|---|
| atgggcgggc tcaccatgga gcaggccttc gtgcaggccc ccgagcaccg ccccaagccc | 60 |
| accgtcaccg aggccaccgg catcctggtc atcgacctct cgcctctcac cgccagcgac | 120 |
| accgacgcgg ccgcggtgga cgcgctggcc gccgaggtgg cgcggcgag ccgggactgg | 180 |
| ggcttcttcg tggtggttgg ccacggcgtg ccgcgcgaga ccgtggcgcg cgcgacggcg | 240 |
| gcgcagcgcg cgttcttcgc gctgccggcg gagcggaagg ccgccgtgcg caggagcgag | 300 |
| gcggagccgc tcgggtacta cgagtcggag cacaccaaga acgtcaggga ctggaaggag | 360 |
| gtgttcgacc tcgtcccgcg cgatccgccg ccgccagcag ccgtggccga cggcgagctc | 420 |
| gtcttcaaga acaagtggcc ccaggatctg ccgggcttca gagaggcgct ggaggagtac | 480 |
| gcggcagcga tggaggagct gtcgttcaag ctgctggagc tgatcgcccg agcttgaag | 540 |
| ctgaggcccg accggctgca cggcttcttc aaggaccaga cgacgttcat ccggctgaac | 600 |
| cactaccctc catgcccgag cccggacctg gcgctggagt ggggcggca aaggacgcg | 660 |
| ggggcgctga ccatcctgta ccaggacgaa gtgggcgggc tggacgtccg gcggcgctcc | 720 |
| tccgacggcg gcggcggcga gtgggtgcgg gtgaggcccg tgccggagtc gttcgtcatc | 780 |
| aacgtcggcg acctcgtcca ggtgtggagc aacgacaggt acgagagcgc ggagcaccgg | 840 |

```
gtgtcggtga actcggcgag ggagaggttc tccatgccct acttcttcaa cccggcgagc    900
tacaccatgg tggagccggt ggaggagctg gtgagcgacg acgacccgcc caggtacgac    960
gcctacagct ggggcgagtt cttcagcacc aggaagaaca gcaacttcaa gaagctcagc   1020
gtggagaaca ttcagatcgc gcatttcaag aagaccctcg tcctcgccta g            1071
```

<210> SEQ ID NO 104
<211> LENGTH: 356
<212> TYPE: PRT
<213> ORGANISM: Sorghum bicolor

<400> SEQUENCE: 104

```
Met Gly Gly Leu Thr Met Glu Gln Ala Phe Val Gln Ala Pro Glu His
1               5                   10                  15

Arg Pro Lys Pro Thr Val Thr Glu Ala Thr Gly Ile Leu Val Ile Asp
            20                  25                  30

Leu Ser Pro Leu Thr Ala Ser Asp Thr Asp Ala Ala Ala Val Asp Ala
        35                  40                  45

Leu Ala Ala Glu Val Gly Ala Ala Ser Arg Asp Trp Gly Phe Phe Val
    50                  55                  60

Val Val Gly His Gly Val Pro Ala Glu Thr Val Ala Arg Ala Thr Ala
65                  70                  75                  80

Ala Gln Arg Ala Phe Phe Ala Leu Pro Ala Glu Arg Lys Ala Ala Val
                85                  90                  95

Arg Arg Ser Glu Ala Glu Pro Leu Gly Tyr Tyr Glu Ser Glu His Thr
            100                 105                 110

Lys Asn Val Arg Asp Trp Lys Glu Val Phe Asp Leu Val Pro Arg Asp
        115                 120                 125

Pro Pro Pro Pro Ala Ala Val Ala Asp Gly Glu Leu Val Phe Lys Asn
    130                 135                 140

Lys Trp Pro Gln Asp Leu Pro Gly Phe Arg Glu Ala Leu Glu Glu Tyr
145                 150                 155                 160

Ala Ala Ala Met Glu Glu Leu Ser Phe Lys Leu Leu Glu Leu Ile Ala
                165                 170                 175

Arg Ser Leu Lys Leu Arg Pro Asp Arg Leu His Gly Phe Phe Lys Asp
            180                 185                 190

Gln Thr Thr Phe Ile Arg Leu Asn His Tyr Pro Pro Cys Pro Ser Pro
        195                 200                 205

Asp Leu Ala Leu Gly Val Gly Arg His Lys Asp Ala Gly Ala Leu Thr
    210                 215                 220

Ile Leu Tyr Gln Asp Glu Val Gly Gly Leu Asp Val Arg Arg Arg Ser
225                 230                 235                 240

Ser Asp Gly Gly Gly Glu Trp Val Arg Val Arg Pro Val Pro Glu
                245                 250                 255

Ser Phe Val Ile Asn Val Gly Asp Leu Val Gln Val Trp Ser Asn Asp
            260                 265                 270

Arg Tyr Glu Ser Ala Glu His Arg Val Ser Val Asn Ser Ala Arg Glu
        275                 280                 285

Arg Phe Ser Met Pro Tyr Phe Phe Asn Pro Ala Ser Tyr Thr Met Val
    290                 295                 300

Glu Pro Val Glu Glu Leu Val Ser Asp Asp Pro Pro Arg Tyr Asp
305                 310                 315                 320

Ala Tyr Ser Trp Gly Glu Phe Ser Thr Arg Lys Asn Ser Asn Phe
                325                 330                 335
```

```
        Lys Lys Leu Ser Val Glu Asn Ile Gln Ile Ala His Phe Lys Lys Thr
                340                 345                 350

Leu Val Leu Ala
        355

<210> SEQ ID NO 105
<211> LENGTH: 1499
<212> TYPE: DNA
<213> ORGANISM: Sorghum bicolor

<400> SEQUENCE: 105
cctctcatca caggccccag cctcactctt ctcacagcaa gacatcgcag cctcacaacc      60
acacagcaac gtgatcgcca tgggcgggct caccatggag caggccttcg tgcaggcccc     120
cgagcaccgc cccaagccca ccgtcaccga ggccaccggc atcctggtca tcgacctctc     180
gcctctcacc gccagcgaca ccgacgcggc cgcggtggac gcgctggccg ccgaggtggg     240
cgcggcgagc cgggactggg gcttcttcgt ggtggttggc cacggcgtgc ccgcggagac     300
cgtggcgcgc gcgacggcgg cgcagcgcgc gttcttcgcg ctgccggcgg agcggaaggc     360
cgccgtgcgg aggagcgagg cggagccgct cgggtactac gagtcggagc acaccaagaa     420
cgtcagggac tggaaggagg tgttcgacct cgtcccgcgc gatccgccgc cgccagcagc     480
cgtggccgac ggcgagctcg tcttcaagaa caagtggccc caggatctgc cgggcttcag     540
gtgacgaaat caactatct tttcgatcat attttaccat ttaatagttt aacaataatt     600 gaacttttt ttgcagagag gcgctggagg agtacgcggc agcgatggag gagctgtcgt     660
tcaagctgct ggagctgatc gcccggagct gaagctgag gccgaccgg ctgcacggct     720 tcttcaagga ccagacgacg ttcatccggc tgaaccacta ccctccatgc ccgagcccgg     780
acctggcgct gggagtgggg cggcacaagg acgcgggggc gctgaccatc ctgtaccagg     840
acgaagtggg cgggctggac gtccggcggc gctcctccga cggcggcggc ggcgagtggg     900
tgcgggtgag gcccgtgccg gagtcgttcg tcatcaacgt cggcgacctc gtccaggtgt     960
ggagcaacga caggtacgag agcgcggagc accgggtgtc ggtgaactcg gcgagggaga    1020
ggttctccat gccctacttc ttcaacccgg cgagctacac catggtgagc ccggtggagg    1080
agctggtgag cgacgacgac ccgcccaggt acgacgccta cagctggggc gagttcttca    1140
gcaccaggaa gaacagcaac ttcaagaagc tcagcgtgga gaacattcag atcgcgcatt    1200
tcaagaagac cctcgtcctc gcctagataa gcagcaggat actacaggtc tacaggacta    1260
ggacaagccg atcgaggtga ccggccgtcg tcttcagatt cagtatatgc gtgtcgccgt    1320
tcgtgttaga acaaattaat aatgtgcgcg ctgtgtgctg tgtgtgtgga gtaaaaaaaa    1380
actaaacatg gatgtgcatg ttcaaaaaaa aaaacatgga tgcgagtatg tttgggaata    1440
ataacaggct tgtgacggtc tggtttattt gcaaattcaa accgaattgg ttgatcttc    1499

<210> SEQ ID NO 106
<211> LENGTH: 1490
<212> TYPE: DNA
<213> ORGANISM: Setaria italica

<400> SEQUENCE: 106
accccacaca cacacccgca ctgcatgcgg cgtcctagct aatcagtcgc tgctggcagc      60
ctcacaagtc acacaactcc gacgcaggaa agctcgatcc atcgccatgg gcggcttctc     120
catggatcag tccttcgtgc aggccccga gcaccgcccc aagcccaccg tcaccgaggc     180
cacgggcatc ccgctcatcg acctctcgcc actcaccggc ggtggcggcg gcgacgcggc     240
```

```
cgccgtggac gcgctggccg ccgaggtggg cgcggcgagc cgggactggg gcttcttcgt    300
ggtggtgggg cacggtgtgc cggcggagac cgtggcgcgc gccacggagg cgcagcgcgc    360
gttcttcgcc ctgccggcgg agcggaaagc cgccgtgcgg aggagcgagg cggagccgct    420
cgggtactac gagtcggagc acaccaagaa cgtcaggac tggaaggagg tgtacgacct     480
cgtcccgggc gggcttcagc cgccgatagc cgtggccgac ggcgaggtcg tgttcgaaaa    540
caagtggccc gaagacctgc cgggattcag agaggcgttg gaggagtaca tgcaagcgat    600
ggaagagctg gcattcaaga tactggagct gatcgcccgg agcctgaacc tgaggcctga    660
cagactgcac ggcttcttca aggaccagac caccttcatc cggctcaacc actaccctcc    720
ctgcccgagc cccgacctcg ccctcggcgt cggccggcac aaggacgccg agcactgac    780 catcctctac caggacgacg tcggcgggct cgacgtccgg cgccgttccg acggcgattg    840
ggtccgcgtc aagcctgtcc ccgactcctt catcatcaac gtcggcgacc tcatccaggt    900
ttggagcaac gacaggtacg agagcgcgga gcaccgggtt acggtgaact cggccaagga    960
gaggttctcc aggccctact tcttcaaccc ggcgggctac accatggtgg agccggtgga   1020
ggagctggtg agcgaggagg acccgccccg gtacgacgcc tacaactggg gcaacttctt   1080
cagcaccagg aagaacagca acttcaagaa gctgagcgtg gagaacatcc agatcgcgca   1140
tttcaagagg agcgtcgccg cctaggatac gcacagaaag atcccatatg ctgacttgct   1200
gatgaggcga caggcggccg tgtcgtcttc agattcagag actgggagta acatttgtg    1260 cggtgttctg taatcgtgat gtgacgaaa ctttagatat atgtttggaa ataacagcct    1320
tgtgttggtc tggcttatcc gcaaagtcaa gattttcttc tacattttgg gattattgtt    1380
ggtaagcatt aagcaacgtc cagttcttac ttcttagctc gatcagtgga cgtaggaccg    1440
gcctctgatg acaagggtga tttatgagaa atgtcatgta tatatgttcc                1490

<210> SEQ ID NO 107
<211> LENGTH: 1059
<212> TYPE: DNA
<213> ORGANISM: Setaria italica

<400> SEQUENCE: 107
atgggcggct tctccatgga tcagtccttc gtgcaggccc ccgagcaccg ccccaagccc     60
accgtcaccg aggccacggg catcccgctc atcgacctct cgccactcac cggcggtggc    120
ggcggcgacg cggccgccgt ggacgcgctg ccgccgaggg tgggcgcggc gagccgggac    180
tggggcttct tcgtggtggt ggggcacggt gtgccggcgg agaccgtggc gcgcgccacg    240
gaggcgcagc gcgcgttctt cgccctgccg gcggagcgga agccgccgt gcggaggagc    300 gaggcggagc cgctcgggta ctacgagtcg gagcacacca agaacgtcag ggactggaag    360
gaggtgtacg acctcgtccc gggcgggctt cagccgccga tagccgtggc cgacggcgag    420
gtcgtgttcg aaaacaagtg gcccgaagac ctgccgggat tcagagaggc gttggaggag    480
tacatgcaag cgatggaaga gctggcattc aagatactgg agctgatcgc ccggagcctg    540
aacctgaggc ctgacagact gcacggcttc ttcaaggacc agaccacctt catccggctc    600
aaccactacc ctccctgccc gagccccgac ctcgccctcg cgtcggccg gcacaaggac    660 gccggagcac tgaccatcct ctaccaggac gacgtcggcg gctcgacgt ccggcgccgt    720 tccgacggcg attgggtccg cgtcaagcct gtccccgact ccttcatcat caacgtcggc    780
gacctcatcc aggtttggag caacgacagg tacgagagcg cggagcaccg ggttacggtg    840
```

```
aactcggcca aggagaggtt ctccaggccc tacttcttca acccggcggg ctacaccatg    900
gtggagccgg tggaggagct ggtgagcgag gaggacccgc cccggtacga cgcctacaac    960
tggggcaact tcttcagcac caggaagaac agcaacttca agaagctgag cgtggagaac   1020
atccagatcg cgcatttcaa gaggagcgtc gccgcctag                          1059
```

<210> SEQ ID NO 108
<211> LENGTH: 352
<212> TYPE: PRT
<213> ORGANISM: Setaria italica

<400> SEQUENCE: 108

```
Met Gly Gly Phe Ser Met Asp Gln Ser Phe Val Gln Ala Pro Glu His
1               5                   10                  15

Arg Pro Lys Pro Thr Val Thr Glu Ala Thr Gly Ile Pro Leu Ile Asp
            20                  25                  30

Leu Ser Pro Leu Thr Gly Gly Gly Gly Asp Ala Ala Val Asp
        35                  40                  45

Ala Leu Ala Ala Glu Val Gly Ala Ala Ser Arg Asp Trp Gly Phe Phe
    50                  55                  60

Val Val Val Gly His Gly Val Pro Ala Glu Thr Val Arg Ala Thr
65                  70                  75                  80

Glu Ala Gln Arg Ala Phe Phe Ala Leu Pro Ala Glu Arg Lys Ala Ala
                85                  90                  95

Val Arg Arg Ser Glu Ala Glu Pro Leu Gly Tyr Tyr Glu Ser Glu His
            100                 105                 110

Thr Lys Asn Val Arg Asp Trp Lys Glu Val Tyr Asp Leu Val Pro Gly
        115                 120                 125

Gly Leu Gln Pro Pro Ile Ala Val Ala Asp Gly Glu Val Val Phe Glu
    130                 135                 140

Asn Lys Trp Pro Glu Asp Leu Pro Gly Phe Arg Glu Ala Leu Glu Glu
145                 150                 155                 160

Tyr Met Gln Ala Met Glu Glu Leu Ala Phe Lys Ile Leu Glu Leu Ile
                165                 170                 175

Ala Arg Ser Leu Asn Leu Arg Pro Asp Arg Leu His Gly Phe Phe Lys
            180                 185                 190

Asp Gln Thr Thr Phe Ile Arg Leu Asn His Tyr Pro Pro Cys Pro Ser
        195                 200                 205

Pro Asp Leu Ala Leu Gly Val Gly Arg His Lys Asp Ala Gly Ala Leu
    210                 215                 220

Thr Ile Leu Tyr Gln Asp Asp Val Gly Gly Leu Asp Val Arg Arg Arg
225                 230                 235                 240

Ser Asp Gly Asp Trp Val Arg Val Lys Pro Val Pro Asp Ser Phe Ile
                245                 250                 255

Ile Asn Val Gly Asp Leu Ile Gln Val Trp Ser Asn Asp Arg Tyr Glu
            260                 265                 270

Ser Ala Glu His Arg Val Thr Val Asn Ser Ala Lys Glu Arg Phe Ser
        275                 280                 285

Arg Pro Tyr Phe Phe Asn Pro Ala Gly Tyr Thr Met Val Glu Pro Val
    290                 295                 300

Glu Glu Leu Val Ser Glu Glu Asp Pro Pro Arg Tyr Asp Ala Tyr Asn
305                 310                 315                 320

Trp Gly Asn Phe Phe Ser Thr Arg Lys Asn Ser Asn Phe Lys Lys Leu
                325                 330                 335
```

Ser Val Glu Asn Ile Gln Ile Ala His Phe Lys Arg Ser Val Ala Ala
        340                 345                 350

<210> SEQ ID NO 109
<211> LENGTH: 1886
<212> TYPE: DNA
<213> ORGANISM: Setaria italica

<400> SEQUENCE: 109

```
accccacaca cacacccgca ctgcatgcgg cgtcctagct aatcagtcgc tgctggcagc      60
ctcacaagtc acacaactcc gacgcaggaa agctcgatcc atcgccatgg gcggcttctc     120
catggatcag tccttcgtgc aggccccccga gcaccgcccc aagcccaccg tcaccgaggc    180
cacgggcatc ccgctcatcg acctctcgcc actcaccggc ggtggcggcg gcgacgcggc    240
cgccgtggac gcgctggccg ccgaggtggg cgcggcgagc cgggactggg gcttcttcgt    300
ggtggtgggg cacggtgtgc cggcggagac cgtggcgcgc gccacggagg cgcagcgcgc    360
gttcttcgcc ctgccggcgg agcggaaagc cgccgtgcgg aggagcgagg cggagccgct    420
cgggtactac gagtcggagc acaccaagaa cgtcagggac tggaaggagg tgtacgacct    480
cgtcccgggc gggcttcagc cgccgatagc cgtggccgac ggcgaggtcg tgttcgaaaa    540
caagtggccc gaagacctgc cgggattcag gtgaatcaac ttgcgcatat tgttgtttct    600
ggcattgcat atgatcgtcg tgccagtatg ttttgacaat attttttgttt tcatattttt    660
ggtgaagatg gaaaatctt tgttgaaata atcagggaat tttcacatct ttttttaatc     720
aaagatagaa taggttcggt tactgaattt tgatgatgga cagaaaaagc tgtgttttca    780
ctttccatct cagcgatgtt tttttgtgga tgaattctcc taaattttg tcttttcatg    840
ttaaaacttg aacgggaatt ctcgcagaga ggcgttggag gagtacatgc aagcgatgga    900
agagctggca ttcaagatac tggagctgat cgcccggagc ctgaacctga ggcctgacag    960
actgcacggc ttcttcaagg accagaccac cttcatccgg ctcaaccact accctccctg    1020
cccgagcccc gacctcgccc tcggcgtcgg ccggcacaag gacgccggag cactgaccat   1080
cctctaccag gacgacgtcg gcgggctcga cgtccggcgc cgttccgacg gcgattgggt   1140
ccgcgtcaag cctgtccccg actccttcat catcaacgtc ggcgacctca tccaggtaca   1200
acaaacaaaa acacacgtca ttctcaaatc ttttcgtgct gttaatgctc attcacgaat   1260
tgatatctta catgaacgac tgagactttt tcaggtttgg agcaacgaca ggtacgagag    1320
cgcggagcac cgggttacgg tgaactcggc caaggagagg ttctccaggc cctacttctt    1380
caacccggcg gctacacca tggtggagcc ggtggaggag ctggtgagcg aggaggaccc    1440
gccccggtac gacgcctaca ctggggcaa cttcttcagc accaggaaga acagcaactt    1500
caagaagctg agcgtggaga acatccagat cgcgcatttc aagaggagcg tcgccgccta   1560
ggatacgcac agaaagatcc catatgctga cttgctgatg aggcgacagg cggccgtgtc   1620
gtcttcagat tcagagactg ggagtaaaca tttgtgcggt gttctgtaat cgtgatgtga   1680
cgagaacttt agatatatgt ttggaaataa cagccttgtg ttggtctggc ttatccgcaa   1740
agtcaagatt ttcttctaca ttttgggatt attgttggta agcattaagc aacgtccagt   1800
tcttacttct tagctcgatc agtggacgta ggaccggcct ctgatgacaa gggtgattta   1860
tgagaaatgt catgtatata tgttcc                                         1886
```

<210> SEQ ID NO 110
<211> LENGTH: 1379
<212> TYPE: DNA

<213> ORGANISM: Oryza sativa

<400> SEQUENCE: 110

```
aagccacacg cacacacaca cacacgctga cacacgagac gaaacacttgt gctacagctt    60
ctcgccacca gctactgatc gaccatgggc ggcctctcca tggaccaggc gttcgtgcag   120
gcccccgagc accgccccaa ggcgtccgtc gccgaggccg acggcatccc ggtcatcgac   180
ctctcccctc tcctcgccgc cggcgatggc gacgccgacg gggtggacgc gctcgcggcg   240
gaggtcggga gggcgagccg ggactggggc ttcttcgtgg tggtgcgcca cggtgtgccc   300
gcggaggcgg tggcgcgcgc ggcggaggcg cagaggacgt tcttcgcgct gccgccggag   360
cggagggcgg ccgtggcgcg gagcgaggcg gcgccgatgg ggtactacgc gtccgagcac   420
accaagaacg tcagggactg gaaggaggtg ttcgacctcg tcccgcgcca gacgccgccg   480
ccgccgacga ccgccgtggc cgacggcgac ctggtgttcg acaacaagtg gcccgacgac   540
ctgccgggat tcagggaggc aatggaggag tacggcgaag cggtggagga gctggcgttc   600
aagctgctgg agctgatcgc caggagcctc ggcctgagac ccgaccgcct ccatggcttc   660
ttcaaggacg accagaccac cttcatccgg ctcaaccact accctccctg cccgagcccc   720
gacctcgccc tcggcgtcgg ccgccacaag gacgccggcg cgctcaccgt gctctaccag   780
gacgatgtcg gcggcctcga cgtccgccgc cgatccgacg gcgagtgggt gcgcgtcagg   840
cccgtccctc actccttcat catcaacgtc ggcgacatca tccaggtgtg gagcaatgac   900
aggtacgaga gcgcggagca ccgggtggcg gtgaacgtgg agaaggagag gttctccatc   960
cctttcttct tcaacccggc gggccacacc atggtggagc cactggagga ggtcgtgagc  1020
gacgagagcc cggccaggta caaccccctac aactggggcg aattcttcag caccaggaag  1080
aacagcaact tcaagaagct ggacgtggag aacgtccaga tcacgcattt caggaagaat  1140
taacgcgccg gctagatcat gttcagtaaa ttttcagatg atgatgcgtg gacaaccata  1200
tagcctttgc gtcataagtt aataatgtct gtgacagtat atcatgtaaa caatcgtatg  1260
atgtggcttc tctatctgcc ggtgatggta atgtgacatt gtagaagagg gtttgtgaga  1320
tacttccttc acttaacttt tacgaatgaa tatagacaac cacaacatcc ttgtcgtga   1379
```

<210> SEQ ID NO 111
<211> LENGTH: 1059
<212> TYPE: DNA
<213> ORGANISM: Oryza sativa

<400> SEQUENCE: 111

```
atgggcggcc tctccatgga ccaggcgttc gtgcaggccc ccgagcaccg ccccaaggcg    60
tccgtcgccg aggccgacgg catcccggtc atcgacctct cccctctcct cgccgccggc   120
gatggcgacg ccgacggggt ggacgcgctc gcggcggagg tcgggagggc gagccgggac   180
tggggcttct tcgtggtggt gcgccacggt gtgcccgcgg aggcggtggc gcgcggcg    240
gaggcgcaga ggacgttctt cgcgctgccg ccggagcgga gggcggccgt ggcgcggagc   300
gaggcggcgc cgatggggta ctacgcgtcc gagcacacca gaacgtcag ggactggaag   360
gaggtgttcg acctcgtccc gcgccagacg ccgccgccgc cgacgaccgc cgtggccgac   420
ggcgacctgg tgttcgacaa caagtggccc gacgacctgc cgggattcag ggaggcaatg   480
gaggagtacg gcgaagcggt ggaggagctg gcgttcaagc tgctggagct gatcgccagg   540
agcctcggcc tgagacccga ccgcctccat ggcttcttca aggacgacca gaccaccttc   600
atccggctca accactaccc tccctgcccg agccccgacc tcgccctcgg cgtcggccgc   660
```

```
cacaaggacg ccggcgcgct caccgtgctc taccaggacg atgtcggcgg cctcgacgtc    720
cgccgccgat ccgacggcga gtgggtgcgc gtcaggcccg tccctcactc cttcatcatc    780
aacgtcggcg acatcatcca ggtgtggagc aatgacaggt acgagagcgc ggagcaccgg    840
gtggcggtga acgtggagaa ggagaggttc tccatccctt tcttcttcaa cccggcgggc    900
cacaccatgg tggagccact ggaggaggtc gtgagcgacg agagcccggc caggtacaac    960
ccctacaact ggggcgaatt cttcagcacc aggaagaaca gcaacttcaa gaagctggac    1020
gtggagaacg tccagatcac gcatttcagg aagaattaa                           1059
```

<210> SEQ ID NO 112
<211> LENGTH: 352
<212> TYPE: PRT
<213> ORGANISM: Oryza sativa

<400> SEQUENCE: 112

```
Met Gly Gly Leu Ser Met Asp Gln Ala Phe Val Gln Ala Pro Glu His
1               5                   10                  15

Arg Pro Lys Ala Ser Val Ala Glu Ala Asp Gly Ile Pro Val Ile Asp
            20                  25                  30

Leu Ser Pro Leu Leu Ala Ala Gly Asp Gly Asp Ala Asp Gly Val Asp
        35                  40                  45

Ala Leu Ala Ala Glu Val Gly Arg Ala Ser Arg Asp Trp Gly Phe Phe
    50                  55                  60

Val Val Val Arg His Gly Val Pro Ala Glu Ala Val Ala Arg Ala Ala
65                  70                  75                  80

Glu Ala Gln Arg Thr Phe Phe Ala Leu Pro Pro Glu Arg Arg Ala Ala
                85                  90                  95

Val Ala Arg Ser Glu Ala Ala Pro Met Gly Tyr Tyr Ala Ser Glu His
            100                 105                 110

Thr Lys Asn Val Arg Asp Trp Lys Glu Val Phe Asp Leu Val Pro Arg
        115                 120                 125

Gln Thr Pro Pro Pro Thr Thr Ala Val Ala Asp Gly Asp Leu Val
    130                 135                 140

Phe Asp Asn Lys Trp Pro Asp Asp Leu Pro Gly Phe Arg Glu Ala Met
145                 150                 155                 160

Glu Glu Tyr Gly Glu Ala Val Glu Glu Leu Ala Phe Lys Leu Leu Glu
                165                 170                 175

Leu Ile Ala Arg Ser Leu Gly Leu Arg Pro Asp Arg Leu His Gly Phe
            180                 185                 190

Phe Lys Asp Asp Gln Thr Thr Phe Ile Arg Leu Asn His Tyr Pro Pro
        195                 200                 205

Cys Pro Ser Pro Asp Leu Ala Leu Gly Val Gly Arg His Lys Asp Ala
    210                 215                 220

Gly Ala Leu Thr Val Leu Tyr Gln Asp Asp Val Gly Gly Leu Asp Val
225                 230                 235                 240

Arg Arg Arg Ser Asp Gly Glu Trp Val Arg Val Arg Pro Val Pro His
                245                 250                 255

Ser Phe Ile Ile Asn Val Gly Asp Ile Ile Gln Val Trp Ser Asn Asp
            260                 265                 270

Arg Tyr Glu Ser Ala Glu His Arg Val Ala Val Asn Val Glu Lys Glu
        275                 280                 285

Arg Phe Ser Ile Pro Phe Phe Phe Asn Pro Ala Gly His Thr Met Val
    290                 295                 300
```

| Glu | Pro | Leu | Glu | Glu | Val | Val | Ser | Asp | Glu | Ser | Pro | Ala | Arg | Tyr | Asn |
|-----|-----|-----|-----|-----|-----|-----|-----|-----|-----|-----|-----|-----|-----|-----|-----|
| 305 |     |     |     | 310 |     |     |     | 315 |     |     |     | 320 |     |     |     |

| Pro | Tyr | Asn | Trp | Gly | Glu | Phe | Phe | Ser | Thr | Arg | Lys | Asn | Ser | Asn | Phe |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Lys | Lys | Leu | Asp | Val | Glu | Asn | Val | Gln | Ile | Thr | His | Phe | Arg | Lys | Asn |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

<210> SEQ ID NO 113
<211> LENGTH: 2027
<212> TYPE: DNA
<213> ORGANISM: Oryza sativa

<400> SEQUENCE: 113

```
aagccacacg cacacacaca cacacgctga cacacgagac gaacacttgt gctacagctt    60
ctcgccacca gctactgatc gaccatgggc ggcctctcca tggaccaggc gttcgtgcag   120
gcccccgagc accgcccaa ggcgtccgtc gccgaggccg acggcatccc ggtcatcgac   180
ctctcccctc tcctcgccgc cggcgatggc gacgccgacg gggtggacgc gctcgcggcg   240
gaggtcggga gggcgagccg ggactggggc ttcttcgtgg tggtgcgcca cggtgtgccc   300
gcggaggcg tggcgcgcgc ggcggaggcg cagaggacgt tcttcgcgct gccgccggag   360
cggagggcgg ccgtggcgcg gagcgaggcg gcgccgatgg ggtactacgc gtccgagcac   420
accaagaacg tcagggactg gaaggaggtg ttcgacctcg tcccgcgcca gacgccgccg   480
ccgccgacga ccgccgtggc cgacggcgac ctggtgttcg acaacaagtg gcccgacgac   540
ctgccgggat tcaggtcagg tcaccacatc gatcgatcgt cttcttcatc ctcgcatcaa   600
ttcagttcaa cctcatcgaa ttcttgagca gggaggcaat ggaggagtac ggcgaagcgg   660
tggaggagct ggccgttcaag ctgctggagc tgatcgccag gagcctcggc ctgagacccg   720
accgcctcca tggcttcttc aaggacgacc agaccacctt catccggctc aaccactacc   780
ctccctgccc gagccccgac ctcgccctcg gcgtcggccg ccacaaggac gccggcgcgc   840
tcaccgtgct ctaccaggac gatgtcggcg gcctcgacgt ccgccgccga tccgacggcg   900
agtgggtgcg cgtcaggccc gtccctcact ccttcatcat caacgtcggc gacatcatcc   960
aggtactttt tttttgagc agctacatat ttatcaacaa attttcttct aacaattat    1020
cggacataaa tatattacaa tgaaagaata attgtatcat aacttgtgtg tccttatatg   1080
taagttttag aaatcctata gtaacatggt attttcgcga aagcggagat tgtgagaccg   1140
tatcttttca cccatgcgcg tcatatgatt ttttttttctt gccaacttaa ataaatttca   1200
aagtaaatct aatagattaa aattatgtga aacttacata taagttttct acggtaacac   1260
gctattttca cgaaacggag gtcgttccaa gttgaatgaa tcttgaagta aatctaacga   1320
tttaaaatta tgtgcataca cgttatatta cagttatata caagttataa tataattaca   1380
ctacaattat aacggtattc atagttgaca aacttttaaa agagaattag ttaataaata   1440
tataacaaca ttgtagttta attgttacta tttgacatca tttttatttg cattttgaat   1500
ttgactgaaa aaattgagag tgcgcttgtc caggtgtgga gcaatgacag gtacgagagc   1560
gcggagcacc gggtggcggt gaacgtggag aaggagaggt ctccatccc tttcttcttc   1620
aacccggcgg gccacaccat ggtggagcca ctggaggagg tcgtgagcga cgagagcccg   1680
gccaggtaca cccctacaa ctggggcgaa ttcttcagca ccaggaagaa cagcaacttc   1740
aagaagctgg acgtggagaa cgtccagatc acgcatttca ggaagaatta acgccggc    1800
tagatcatgt tcagtaaatt ttcagatgat gatgcgtgga caaccatata gcctttgcgt   1860
```

```
cataagttaa taatgtctgt gacagtatat catgtaaaca atcgtatgat gtggcttctc   1920
tatctgccgg tgatggtaat gtgacattgt agaagagggt ttgtgagata cttccttcac   1980
ttaactttta cgaatgaata tagacaacca caacatcctt gtcgtga               2027
```

<210> SEQ ID NO 114
<211> LENGTH: 1747
<212> TYPE: DNA
<213> ORGANISM: Triticum aestivum

<400> SEQUENCE: 114

```
tcactcaagg ccacaacaca ctcgccagtc catcgccacc atacgtgaca acttgagtta     60
cttgatctgt tgctcatcga tctcgacatc gccatgggcg gcctctccat ggaccaggcc    120
ttcgtgcagg cccccgagca tcgcaccaag gcgaacctcg ccgacgcggc cggcatcccg    180
gtcatcgacc tctcccctct cgccgccggc gacaaggccg gcctggacgc cctcgcggcc    240
gaggtgggca gggcgagccg tgactggggg ttcttcgtgg tggtgcgcca cggcgtgccg    300
gcggagacgg tggcgcgggc gctggaggcg cagagggcct tcttcgcgct gcccgcggac    360
cggaaggcgg ccgtgcggag ggacgaggcg cgccgctgg ggtactacga gtcggagcac    420
accaagaacg tcagggactg gaaggaggtg ttcgacctcg tccccgcga ccgccgccg    480 cctgccgcgg ttgccgacgg cgagctcatg ttcgagaaca agtggcccga ggacctgccg    540
gggttcagag aggctctcga agagtacgag aaagcgatgg aggagctggc gttcaagctg    600
ctggagctga tcgcccggag cctgggactg agaccggacc ggctgcacgg cttcttcaag    660
gaccagacca ccttcatccg gctgaaccac tacccgccct gccccagccc cgacctcgcc    720
ctcggcgtcg gtcgccacaa ggacgccggc gcgctcacca tcctctacca ggacgacgtc    780
ggcgggctcg acgtccggcg ccgctccgac ggcgagtggg tgcgcgtcag gcctgtcccg    840
gactcctacg tcatcaacgt cggcgacatc atccaggtgt ggagcaacga caggtacgag    900
agcgcggagc acagggtgtc ggtgaactcg cacaaggaga ggttctccat gccctacttc    960
ttcgaccccg ggagcgacgc catgatcgag ccgttggagg agatggtgag cgacgaaagg   1020
ccggccaggt acgacgccta caactggggc aacttcttca gcaccaggaa gaacagcaac   1080
ttcaggaagc tcgccgtcga aaacgtccag atcgcacact tcagaaagga ccgaccttaa   1140
atgaaggatc cctcatgaat tcatgatcct tccgctctcc tcagtgatcc tagtgctaca   1200
actacaagca tctccccgtt tgtagtaatc atatataaat aagtattccc tccgtaaact   1260
aatataagag catttaaaac actactctag tgatctaaat gctcttatat tagtttacag   1320
agagagtatt gtgtattaat aatgactttc tctgtttcaa ataagtgat gacgtggttt   1380 tagttcaatt ttttttagag aggaggcatc tgacgggcct taaactgagg accttagagt   1440
acaaacaagg ttcgacgaaa gtaagtttaa gggatacaag gccgtagcca acaaaacgcg   1500
acgcagcgcg caatctaaaa tcagcgtgct gtcaaggtag ctggagacgt ccatgccgtt   1560
aatctctctc aagaagctcg ccgaagctca gtgcaccttg cgtgcactct tgtgaagagc   1620
accttcacgt gtcctttgtc ctgagatttt gtcaacagtt tccatgactg caagaaaaac   1680
actagtttgt ataatagctc agcgggatgt cgaatgaatt gcccctcaat caaagcttta   1740
tttctag                                                           1747
```

<210> SEQ ID NO 115
<211> LENGTH: 1047
<212> TYPE: DNA

<213> ORGANISM: Triticum aestivum

<400> SEQUENCE: 115

```
atgggcggcc tctccatgga ccaggccttc gtgcaggccc cgagcatcg caccaaggcg      60
aacctcgccg acgcggccgg catcccggtc atcgacctct cccctctcgc cgccggcgac    120
aaggccggcc tggacgccct cgcggccgag gtgggcaggg cgagccgtga ctggggttc     180
ttcgtggtgg tgcgccacgg cgtgccggcg agacggtgg cgcgggcgct ggaggcgcag     240
agggccttct tcgcgctgcc cgcggaccgg aaggcggccg tgcggaggga cgaggcggcg    300
ccgctggggt actacgagtc ggagcacacc aagaacgtca gggactggaa ggaggtgttc    360
gacctcgtcc ccgcgagcc gccgccgcct gccgcggttg ccgacggcga gctcatgttc    420
gagaacaagt ggcccgagga cctgccgggg ttcagagagg ctctcgaaga gtacgagaaa    480
gcgatggagg agctggcgtt caagctgctg gagctgatcg cccggagcct gggactgaga    540
ccggaccggc tgcacggctt cttcaaggac cagaccacct tcatccggct gaaccactac    600
ccgccctgcc ccagccccga cctcgccctc ggcgtcggtc gccacaagga cgccggcgcg    660
ctcaccatcc tctaccagga cgacgtcggc gggctcgacg tccggcgccg ctccgacggc    720
gagtgggtgc gcgtcaggcc tgtcccggac tcctacgtca tcaacgtcgg cgacatcatc    780
caggtgtgga gcaacgacag gtacgagagc gcggagcaca gggtgtcggt gaactcgcac    840
aaggagaggt tctccatgcc ctacttcttc gaccccggga gcgacgccat gatcgagccg    900
ttggaggaga tggtgagcga cgaaaggccg gccaggtacg acgcctacaa ctggggcaac    960
ttcttcagca ccaggaagaa cagcaacttc aggaagctcg ccgtcgaaaa cgtccagatc   1020
gcacacttca gaaaggaccg accttaa                                        1047
```

<210> SEQ ID NO 116
<211> LENGTH: 348
<212> TYPE: PRT
<213> ORGANISM: Triticum aestivum

<400> SEQUENCE: 116

```
Met Gly Gly Leu Ser Met Asp Gln Ala Phe Val Gln Ala Pro Glu His
  1               5                  10                  15

Arg Thr Lys Ala Asn Leu Ala Asp Ala Ala Gly Ile Pro Val Ile Asp
                 20                  25                  30

Leu Ser Pro Leu Ala Ala Gly Asp Lys Ala Gly Leu Asp Ala Leu Ala
             35                  40                  45

Ala Glu Val Gly Arg Ala Ser Arg Asp Trp Gly Phe Phe Val Val Val
         50                  55                  60

Arg His Gly Val Pro Ala Glu Thr Val Ala Arg Ala Leu Glu Ala Gln
 65                  70                  75                  80

Arg Ala Phe Phe Ala Leu Pro Ala Asp Arg Lys Ala Ala Val Arg Arg
                 85                  90                  95

Asp Glu Ala Ala Pro Leu Gly Tyr Tyr Glu Ser Glu His Thr Lys Asn
                100                 105                 110

Val Arg Asp Trp Lys Glu Val Phe Asp Leu Val Pro Arg Glu Pro Pro
            115                 120                 125

Pro Pro Ala Ala Val Ala Asp Gly Glu Leu Met Phe Glu Asn Lys Trp
        130                 135                 140

Pro Glu Asp Leu Pro Gly Phe Arg Glu Ala Leu Glu Glu Tyr Glu Lys
145                 150                 155                 160

Ala Met Glu Glu Leu Ala Phe Lys Leu Leu Glu Leu Ile Ala Arg Ser
```

```
                 165                 170                 175
Leu Gly Leu Arg Pro Asp Arg Leu His Gly Phe Phe Lys Asp Gln Thr
            180                 185                 190

Thr Phe Ile Arg Leu Asn His Tyr Pro Pro Cys Pro Ser Pro Asp Leu
        195                 200                 205

Ala Leu Gly Val Gly Arg His Lys Asp Ala Gly Ala Leu Thr Ile Leu
    210                 215                 220

Tyr Gln Asp Asp Val Gly Gly Leu Asp Val Arg Arg Ser Asp Gly
225                 230                 235                 240

Glu Trp Val Arg Val Arg Pro Val Pro Asp Ser Tyr Val Ile Asn Val
                245                 250                 255

Gly Asp Ile Ile Gln Val Trp Ser Asn Asp Arg Tyr Glu Ser Ala Glu
            260                 265                 270

His Arg Val Ser Val Asn Ser His Lys Glu Arg Phe Ser Met Pro Tyr
        275                 280                 285

Phe Phe Asp Pro Gly Ser Asp Ala Met Ile Glu Pro Leu Glu Glu Met
    290                 295                 300

Val Ser Asp Glu Arg Pro Ala Arg Tyr Asp Ala Tyr Asn Trp Gly Asn
305                 310                 315                 320

Phe Phe Ser Thr Arg Lys Asn Ser Asn Phe Arg Lys Leu Ala Val Glu
                325                 330                 335

Asn Val Gln Ile Ala His Phe Arg Lys Asp Arg Pro
            340                 345

<210> SEQ ID NO 117
<211> LENGTH: 1863
<212> TYPE: DNA
<213> ORGANISM: Triticum aestivum

<400> SEQUENCE: 117
tcactcaagg ccacaacaca ctcgccagtc catcgccacc atacgtgaca acttgagtta      60
cttgatctgt tgctcatcga tctcgacatc gccatgggcg gcctctccat ggaccaggcc     120
ttcgtgcagg cccccgagca tcgcaccaag gcgaacctcg ccgacgcggc cggcatcccg     180
gtcatcgacc tctcccctct cgccgccggc gacaaggccg gcctggacgc cctcgcggcc     240
gaggtgggca gggcgagccg tgactggggg ttcttcgtgg tggtgcgcca cggcgtgccg     300
gcggagacgt tggcgcgggc gctggaggcg cagagggcct tcttcgcgct gcccgcggac     360
cggaaggcgg ccgtgcggag ggacgaggcg gcgccgctgg ggtactacga gtcggagcac     420
accaagaacg tcagggactg gaaggaggtg ttcgacctcg tccccgcgca gccgccgccg     480
cctgccgcgg ttgccgacgg cgagctcatg ttcgagaaca gtggcccga ggacctgccg     540 gggttcaggt acggtcatca actcaatcaa ttctgcgacc ccgagagaaa tggttcacta     600
ttattcgtgg ttcatacgta tgattcagac gttaatctcg atgcaaattg atttgtgcat     660
gcagagaggc tctcgaagag tacgagaaag cgatggagga gctggcgttc aagctgctgg     720
agctgatcgc ccggagcctg ggactgagac cggaccggct gcacggcttc ttcaaggacc     780
agaccacctt catccggctg aaccactacc cgccctgccc cagccccgac ctcgccctcg     840
gcgtcggtcg ccacaaggac gccggcgcgc tcaccatcct ctaccaggac gacgtcggcg     900
ggctcgacgt ccggcgccgc tccgacggcg agtgggtgcg cgtcaggcct gtcccggact     960
cctacgtcat caacgtcggc gacatcatcc aggtgtggag caacgacagg tacgagagcc    1020
cggagcacag ggtgtcggtg aactcgcaca aggagaggtt ctccatgccc tacttcttcg    1080
```

```
acccccgggag cgacgccatg atcgagccgt tggaggagat ggtgagcgac gaaaggccgg    1140
ccaggtacga cgcctacaac tggggcaact tcttcagcac caggaagaac agcaacttca    1200
ggaagctcgc cgtcgaaaac gtccagatcg cacacttcag aaaggaccga ccttaaatga    1260
aggatccctc atgaattcat gatccttccg ctctcctcag tgatcctagt gctacaacta    1320
caagcatctc cccgtttgta gtaatcatat ataaataagt attccctccg taaactaata    1380
taagagcatt taaaacacta ctctagtgat ctaaatgctc ttatattagt ttacagagag    1440
agtattgtgt attaataatg actttctctg tttcaaaata agtgatgacg tggttttagt    1500 tcaattttt ttagagagga ggcatctgac gggccttaaa ctgaggacct tagagtacaa    1560
acaaggttcg acgaaagtaa gtttaaggga tacaaggccg tagccaacaa aacgcgacgc    1620
agcgcgcaat ctaaaatcag cgtgctgtca aggtagctgg agacgtccat gccgttaatc    1680
tctctcaaga agctcgccga agctcagtgc accttgcgtg cactcttgtg aagagcacct    1740
tcacgtgtcc tttgtcctga gattttgtca acagtttcca tgactgcaag aaaaacacta    1800
gtttgtataa tagctcagcg ggatgtcgaa tgaattgccc tcaatcaaa gctttatttc    1860 tag                                                                  1863
```

<210> SEQ ID NO 118
<211> LENGTH: 349
<212> TYPE: PRT
<213> ORGANISM: Hordeum vulgare

<400> SEQUENCE: 118

```
Met Gly Gly Leu Ser Met Gly Gln Ala Phe Val Gln Ala Pro Glu His
1               5                   10                  15

Arg Thr Lys Pro Thr Leu Ala Asp Ala Asp Gly Ile Pro Val Ile Asp
                20                  25                  30

Leu Ser Pro Leu Ala Ala Gly Asp Glu Ala Gly Val Asp Ala Leu Ala
            35                  40                  45

Ala Glu Val Gly Arg Ala Ser Arg Asp Trp Gly Phe Phe Val Val Val
        50                  55                  60

Arg His Gly Val Pro Ala Glu Thr Val Ala Arg Ala Leu Glu Ala Gln
65                  70                  75                  80

Arg Ala Phe Phe Ala Leu Pro Ala Glu Arg Lys Ala Ala Val Arg Arg
                85                  90                  95

Asp Glu Ala Ala Pro Leu Gly Tyr Tyr Glu Ser Glu His Thr Lys Asn
                100                 105                 110

Val Arg Asp Trp Lys Glu Val Phe Asp Phe Val Pro Arg Glu Pro Pro
            115                 120                 125

Pro Pro Ala Ala Val Ala Asp Gly Glu Leu Val Phe Glu Asn Lys Trp
        130                 135                 140

Pro Glu Asp Leu Pro Gly Phe Arg Val Ala Phe Glu Glu Tyr Ala Lys
145                 150                 155                 160

Ala Met Glu Glu Leu Ala Phe Lys Leu Leu Glu Leu Ile Ala Arg Ser
                165                 170                 175

Leu Gly Leu Thr Pro Asp Arg Leu Asn Gly Phe Phe Lys Asp His Gln
            180                 185                 190

Thr Thr Phe Ile Arg Leu Asn His Tyr Pro Pro Cys Pro Ser Pro Asp
        195                 200                 205

Leu Ala Leu Gly Val Gly Arg His Lys Asp Ala Gly Ala Leu Thr Val
    210                 215                 220

Leu Tyr Gln Asp Asp Val Gly Gly Leu Asp Val Arg His Arg Ser Asp
```

```
              225                 230                 235                 240
Gly Glu Trp Val Arg Val Arg Pro Val Pro Asp Ser Tyr Val Ile Asn
                245                 250                 255

Val Gly Asp Ile Ile Gln Val Trp Ser Asn Asp Arg Tyr Glu Ser Ala
                260                 265                 270

Glu His Arg Val Ser Val Asn Ser Asp Lys Glu Arg Phe Ser Met Pro
                275                 280                 285

Tyr Phe Phe Asn Pro Gly Ser Asp Ala Met Val Glu Pro Leu Glu Glu
                290                 295                 300

Met Val Ser Asp Glu Arg Pro Ala Arg Tyr Asp Ala Tyr Asn Trp Gly
305                 310                 315                 320

His Phe Phe Ser Thr Arg Lys Asn Ser Asn Phe Lys Lys Leu Asp Val
                325                 330                 335

Glu Asn Val Gln Ile Ala His Phe Arg Lys Leu His Leu
                340                 345

<210> SEQ ID NO 119
<211> LENGTH: 1963
<212> TYPE: DNA
<213> ORGANISM: Sorghum bicolor

<400> SEQUENCE: 119
```

| | | | | | |
|---|---|---|---|---|---|
| tataaatacc | acgccatgta | cttctctgct | tctacacttc | tccagcttct | ctcatgccat | 60 |
| accactagtg | caaggtccta | gatttacact | tggtgctaca | gcttcttcct | ccctccctcc | 120 |
| cctctctagg | cagctagcac | gcagcgcagc | acacgaaaca | tctattgacc | ggccgcctcc | 180 |
| gccggggatc | cataattact | atactaccaa | tcggccagcg | tcatgccgac | gccgtcgcac | 240 |
| ctcgcgaacc | cgcgctactt | cgacttccgt | gcggcgcggc | gggtgccgga | gacgcacgcc | 300 |
| tggccggggc | tgcacgacca | ccccgtcgtg | gacgcggcg | cgccggggcc | agacgccgtc | 360 |
| cccgtggtgg | acctcgcggg | ggcggcggac | gagccgagag | ccgcggtggt | ggcccaagtg | 420 |
| gcgcgcgccg | ccgagcaatg | gggcgcgttc | ctgctcacgg | gcacggcgt | ccccgcggag | 480 |
| ctgctggcgc | gcgtcgagga | ccggatcgcc | accatgttcg | cgctgccagc | ggacgacaag | 540 |
| atgcgcgccg | tgcgcgggcc | tggcgacgcc | tgcggctacg | gctccccgcc | catctcctcc | 600 |
| ttcttctcca | agtgcatgtg | gtcggaggga | tacaccttct | cgccggccaa | cctccgcgcc | 660 |
| gacctccgca | agctctggcc | taaggccggc | gacgactaca | ccagcttctg | tgatgtgatg | 720 |
| gaggagttcc | acaagcacat | gcgtgccctc | gcggacaagc | tgctggagct | gttcctcatg | 780 |
| gcgctggggc | tcaccgacga | gcaggtcggc | ggcgtggagg | cggagcggag | gatcgccgag | 840 |
| acgatgaccg | ccaccatgca | cctcaactgg | taccctcggt | gcccggaccc | cgccgcgcg | 900 |
| ctggggctga | tcgcgcacac | cgactcgggc | ttcttcacct | tcgtgctgca | gagcctcgtc | 960 |
| ccggggctgc | agctcttccg | ccacgccccg | gaccggtggg | tggcggtgcc | ggcggtaccg | 1020 |
| ggcgccttcg | tcgtcaacgt | gggcgacctc | ttccacatcc | tcaccaacgg | ccggttccac | 1080 |
| agcgtgtacc | accgcgccgt | cgtgaaccgg | gacctcgaca | ggatatctct | cggctacttc | 1140 |
| ctcggcccgc | cgccgcacgc | caaggtggcg | ccgctaaggg | aggccgtgcc | gcccggccgc | 1200 |
| accccgcgt | accgcgccgt | cacgtggccc | gagtacatgg | gcgtccgcaa | gaaggccttc | 1260 |
| accaccggcg | catccgcgct | caagatggtc | gccctcgccg | ccgccgccgc | cgccgccgac | 1320 |
| ctcgacgatg | acgccggtgc | tggcgccgcc | gccgaacctg | tcgtccatca | gcagctactc | 1380 |
| gtctcgtcgt | agccgatcga | tcgccggatc | ggtcgagact | gatgatgatg | atgcatatat | 1440 |

```
actcgtcgat ggagtagaca gactaatcaa gcaaccctga aactatgaat gcatgcgtgc    1500
gcttcgtgct tgcttgcgca tgcagctagc aggcttcatt ccgttccgca gctgctctgc    1560
tccaacctgc tctgctggat tgatgtatat ggtagaagaa ttaagagatc gatggatgac    1620
ggaggaagaa gaagacgaag acgacgatga ggaaaaggac acgctgtacg tagctggttc    1680
ttctagtcta gtttacagca ggccgggcgg ccggctgctg cttccaatcg agtttgtcgt    1740
tactgacgat tgttagtgga tcgattaact aatctggaat tctggattat taatataatg    1800
catgtggttt ggcatctggc gtaaagcagg taatggtacc tagccagtag ccagtagcca    1860
ggctggtcaa tgataggtct ataccctgat cctgtactgt tgtttctttc ggtctttctg    1920
agagagaaaa aaaacgaata tatggcgtac tcaattcatc aaa                      1963
```

<210> SEQ ID NO 120
<211> LENGTH: 1170
<212> TYPE: DNA
<213> ORGANISM: Sorghum bicolor

<400> SEQUENCE: 120

```
atgccgacgc cgtcgcacct cgcgaacccg cgctacttcg acttccgtgc ggcgcggcgg     60
gtgccggaga cgcacgcctg gccggggctg cacgaccacc ccgtcgtgga cggcggcgcg    120
ccggggccag acgccgtccc cgtggtggac ctcgcggggg cggcggacga gccgagagcc    180
gcggtggtgg cccaagtggc gcgcgccgcc gagcaatggg gcgcgttcct gctcacgggg    240
cacggcgtcc ccgcggagct gctggcgcgc gtcgaggacc ggatcgccac catgttcgcg    300
ctgccagcgg acgacaagat gcgcgccgtg cgcgggcctg cgacgcctg cggctacggc    360 tccccgccca tctcctcctt cttctccaag tgcatgtggt cggagggata caccttctcg    420
ccggccaacc tccgcgccga cctccgcaag ctctggccta aggccggcga cgactacacc    480
agcttctgtg atgtgatgga ggagttccac aagcacatgc gtgccctcgc ggacaagctg    540
ctggagctgt tcctcatggc gctggggctc accgacgagc aggtcggcgg cgtgaggcg    600 gagcggagga tcgccgagac gatgaccgcc accatgcacc tcaactggta ccctcggtgc    660
ccggacccgc gccgcgcgct ggggctgatc gcgcacaccg actcgggctt cttcaccttc    720
gtgctgcaga gcctcgtccc ggggctgcag ctcttccgcc acgccccgga ccggtgggtg    780
gcggtgccgg cggtaccggg cgccttcgtc gtcaacgtgg cgacctcttc cacatcctc    840 accaacggcc ggttccacag cgtgtaccac cgcgccgtcg tgaaccggga cctcgacagg    900
atatctctcg gctacttcct cggcccgccg ccgcacgcca aggtggcgcc gctaagggag    960
gccgtgccgc ccggccgcac ccccgcgtac cgcgccgtca cgtggcccga gtacatgggc   1020
gtccgcaaga aggccttcac caccggcgca tccgcgctca agatggtcgc cctcgccgcc   1080
gccgccgccg ccgccgacct cgacgatgac gccggtgctg gcgccgccgc cgaacctgtc   1140
gtccatcagc agctactcgt ctcgtcgtag                                    1170
```

<210> SEQ ID NO 121
<211> LENGTH: 389
<212> TYPE: PRT
<213> ORGANISM: Sorghum bicolor

<400> SEQUENCE: 121

```
Met Pro Thr Pro Ser His Leu Ala Asn Pro Arg Tyr Phe Asp Phe Arg
1               5                   10                  15

Ala Ala Arg Arg Val Pro Glu Thr His Ala Trp Pro Gly Leu His Asp
            20                  25                  30
```

His Pro Val Val Asp Gly Gly Ala Gly Pro Asp Ala Pro Val
        35                  40                  45

Val Asp Leu Ala Gly Ala Ala Asp Glu Pro Arg Ala Val Val Ala
 50                  55                  60

Gln Val Ala Arg Ala Ala Glu Gln Trp Gly Ala Phe Leu Leu Thr Gly
65                   70                  75                  80

His Gly Val Pro Ala Glu Leu Leu Ala Arg Val Glu Asp Arg Ile Ala
                85                  90                  95

Thr Met Phe Ala Leu Pro Ala Asp Asp Lys Met Arg Ala Val Arg Gly
                100                 105                 110

Pro Gly Asp Ala Cys Gly Tyr Gly Ser Pro Ile Ser Ser Phe Phe
                115                 120                 125

Ser Lys Cys Met Trp Ser Glu Gly Tyr Thr Phe Ser Pro Ala Asn Leu
        130                 135                 140

Arg Ala Asp Leu Arg Lys Leu Trp Pro Lys Ala Gly Asp Asp Tyr Thr
145                 150                 155                 160

Ser Phe Cys Asp Val Met Glu Glu Phe His Lys His Met Arg Ala Leu
                165                 170                 175

Ala Asp Lys Leu Leu Glu Leu Phe Leu Met Ala Leu Gly Leu Thr Asp
                180                 185                 190

Glu Gln Val Gly Gly Val Glu Ala Glu Arg Arg Ile Ala Glu Thr Met
        195                 200                 205

Thr Ala Thr Met His Leu Asn Trp Tyr Pro Arg Cys Pro Asp Pro Arg
        210                 215                 220

Arg Ala Leu Gly Leu Ile Ala His Thr Asp Ser Gly Phe Phe Thr Phe
225                 230                 235                 240

Val Leu Gln Ser Leu Val Pro Gly Leu Gln Leu Phe Arg His Ala Pro
                245                 250                 255

Asp Arg Trp Val Ala Val Pro Ala Val Pro Gly Ala Phe Val Val Asn
                260                 265                 270

Val Gly Asp Leu Phe His Ile Leu Thr Asn Gly Arg Phe His Ser Val
        275                 280                 285

Tyr His Arg Ala Val Val Asn Arg Asp Leu Asp Arg Ile Ser Leu Gly
        290                 295                 300

Tyr Phe Leu Gly Pro Pro His Ala Lys Val Ala Pro Leu Arg Glu
305                 310                 315                 320

Ala Val Pro Pro Gly Arg Thr Pro Ala Tyr Arg Ala Val Thr Trp Pro
                325                 330                 335

Glu Tyr Met Gly Val Arg Lys Lys Ala Phe Thr Thr Gly Ala Ser Ala
                340                 345                 350

Leu Lys Met Val Ala Leu Ala Ala Ala Ala Ala Asp Leu Asp
        355                 360                 365

Asp Asp Ala Gly Ala Gly Ala Ala Ala Glu Pro Val Val His Gln Gln
        370                 375                 380

Leu Leu Val Ser Ser
385

<210> SEQ ID NO 122
<211> LENGTH: 2321
<212> TYPE: DNA
<213> ORGANISM: Sorghum bicolor

<400> SEQUENCE: 122
tataaatacc acgccatgta cttctctgct tctacacttc tccagcttct ctcatgccat    60

```
accactagtg caaggtccta gatttacact tggtgctaca gcttcttcct ccctccctcc      120
cctctctagg cagctagcac gcagcgcagc acacgaaaca tctattgacc ggccgcctcc      180
gccggggatc cataattact atactaccaa tcggccagcg tcatgccgac gccgtcgcac      240
ctcgcgaacc cgcgctactt cgacttccgt gcggcgcggc gggtgccgga gacgcacgcc      300
tggccggggc tgcacgacca ccccgtcgtg gacggcggcg cgccggggcc agacgccgtc      360
cccgtggtgg acctcgcggg ggcggcggac gagccgagag ccgcggtggt ggcccaagtg      420
gcgcgcgccg ccgagcaatg gggcgcgttc ctgctcacgg ggcacggcgt cccgcggag       480 ctgctggcgc gcgtcgagga ccggatcgcc accatgttcg cgctgccagc ggacgacaag      540
atgcgcgccg tgcgcgggcc tggcgacgcc tgcggctacg gctccccgcc catctcctcc      600
ttcttctcca agtgcatgtg gtcggaggga tacaccttct cgccggccaa cctccgcgcc      660
gacctccgca agctctggcc taaggccggc gacgactaca ccagcttctg gtacgtgcac      720
ccgccggccg cgccgccgcca cacaccgtac ccacacacgt gcgcgctcgc gcctagctac      780
tagtagctgc tttgctttgc ttaccttga ttctcgcctt tgccatgcat atgcatgatg      840
cacgtacagg tactgcaggt acaacatgtc acacgcacgc acgcacgcac aacccatagt      900
ccgatacgat acatcatcga tcgacgtgtc gtcaccgtct aaggccatgc atgcatgcaa      960
gcacacgcct agaccttttt agcatgctgg ctgacgagga gtatactagc taataagcta     1020
cttgtcactg cgcgtcttgc ttaattacac tagtgcatat ttctacagtg atgtgatgga     1080
ggagttccac aagcacatgc gtgccctcgc ggacaagctg ctggagctgt tcctcatggc     1140
gctggggctc accgacgagc aggtcggcgg cgtggaggcg gagcggagga tcgccgagac     1200
gatgaccgcc accatgcacc tcaactggta ccctcggtgc ccggacccgc gccgcgcgct     1260
ggggctgatc gcgcacaccg actcgggctt cttcaccttc gtgctgcaga gcctcgtccc     1320
ggggctgcag ctcttccgcc acgccccgga ccggtgggtg gcggtgccgg cggtaccggg     1380
cgccttcgtc gtcaacgtgg gcgacctctt ccacatcctc accaacggcc ggttccacag     1440
cgtgtaccac cgcgccgtcg tgaacccgga cctcgacagg atatctctcg gctacttcct     1500
cggcccgccg ccgcacgcca aggtggcgcc gctaagggag gccgtgccgc ccggccgcac     1560
ccccgcgtac cgcgccgtca cgtggcccga gtacatgggc gtccgcaaga aggccttcac     1620
caccggcgca tccgcgctca agatggtcgc cctcgccgcc gccgccgcg ccgccgacct      1680 cgacgatgac gccggtgctg gcgccgccgc cgaacctgtc gtccatcagc agctactcgt     1740
ctcgtcgtag ccgatcgatc gccggatcgg tcgagactga tgatgatgat gcatatatac     1800
tcgtcgatgg agtagacaga ctaatcaagc aaccctgaaa ctatgaatgc atgcgtgcgc     1860
ttcgtgcttg cttgcgcatg cagctagcag gcttcattcc gttccgcagc tgctctgctc     1920
caacctgctc tgctggattg atgtatatgg tagaagaatt aagagatcga tggatgacgg     1980
aggaagaaga agacgaagac gacgatgagg aaaaggacac gctgtacgta gctggttctt     2040
ctagtctagt ttacagcagg ccgggcggcc ggctgctgct tccaatcgag tttgtcgtta     2100
ctgacgattg ttagtggatc gattaactaa tctggaattc tggattatta atataatgca     2160
tgtggtttgg catctggcgt aaagcaggta atggtaccta gccagtagcc agtagccagg     2220
ctggtcaatg ataggtctat accctgatcc tgtactgttg tttctttcgg tctttctgag     2280
agagaaaaaa aacgaatata tggcgtactc aattcatcaa a                         2321
```

<210> SEQ ID NO 123

```
<211> LENGTH: 1796
<212> TYPE: DNA
<213> ORGANISM: Setaria italica

<400> SEQUENCE: 123
actagtgcaa ggtcctagat ttacacttgg tgcttgcttg tttcttccta gttgctactg      60
gtagcacgca gtggctggct ggccgtaatc tattgtctgg gctcgatcgg tgattaggaa     120
gtagccaaag caagctaagg ccgccgccgc cgccgccatg ccgacgccgt cgcacctcaa     180
gaacccgctc tacttcgact tccgcgccgc gcggcgggtg ccggagtccc acgcctggcc     240
ggggctcgac gaccacccg tggtggacgg cggcggcgcg ccggggtccc cggacgccgt      300
gccggtggtg gacctgcgcg agccgggcgc gcgcggcggt gcccgcgtgg cgcgcgccgc     360
cgagcagtgg ggcgcgttcc tgctcaccgg ccacggcgtc cccgcggagc tcctggcgcg     420
cgtcgaggac cgcgtcgcgt gcatgttcgc gctgccggcc gccgacaaga tgcgcgccgt     480
gcgcgggccg ggggacgcct gcggctacgg ctcgccgccc atctcctcct tcttctccaa     540
gtgcatgtgg tccgagggct acaccttctc gccggcctcc ctccgccgcg acctccgcaa     600
gctctggccc aaggccggcg acgactacga cagcttctgt gacgtgatgg aggagttcca     660
caaggagatg cgcgccctcg ccgacaggct cctggagctg ttcctcaggg cgctcgggct     720
caccggcgag caggtcggcg ccgtcgaggc ggagcggagg atcggcgaga cgatgaccgc     780
caccatgcac ctcaactggt atccgaggtg ccccggacccg cggcgcgcgc tggggctgat    840
cgcgcacacg gactcgggct tcttcaccctt cgtgctgcag agcctcgtgc cggggctgca    900
gctgttccgg cacggcccca accggtgggt ggcggtgccg gccgtgccgg gcgccttcgt    960
cgtcaacgtc ggcgacctct tccacatcct cacgaacggc cgcttccaca gcgtgtacca   1020
ccgcgccgtc gtcaacccggg acctcgaccg gatatcgctc ggctacttcc tcggcccgcc    1080
gccccacgcc aaggtggcgc cgctccggga ggtcgtgccg ccgggccggg ccccgccta    1140 ccgcgccgtc acgtggcccg agtacatggg cgtccgcaag aaggccttca ccaccggcgc   1200
ctccgcgctc aagatggtcg ccgccgccgc cgccgccacc gaatccgacg acaccgacgc   1260
agccgccgcc gccgttcacc agccgccggt cgtcgtctca tcgtagccga tcgatcgccg   1320
gaaacacaga cgatgcatac cgtaccccga gcaatctaat caaaacaagg catccattct   1380
cgcgcgcatg cagcggccag ccgggcttcc gcagctgctc ggcctcctct gctggctgtg   1440
gaaatggaaa atttttaatct gagatgaaga cgaagacgaa gacgaaacgg agaggaaaag   1500
gacatgctgt agctgtttct tctagttgcg caggccgctc ccagtcgagt ttgtcgttac   1560
tgacgattat tactctgatg aaaactaatc tgaattaatg catgtagttt ggcaatttgg   1620
tactaaaggt aggcacctag ccaggctggt caatgatagg tctataacct gatcctgttc   1680
tctgttgttt tcctttgtct gagaaaaaat ggaaataatt gatccggccg gacgggtgta   1740
ctgataggtg atgctgaatt gctgatgcaa gaggttgcga gctgcagtga gcagca        1796

<210> SEQ ID NO 124
<211> LENGTH: 1149
<212> TYPE: DNA
<213> ORGANISM: Setaria italica

<400> SEQUENCE: 124
atgccgacgc cgtcgcacct caagaacccg ctctacttcg acttccgcgc cgcgcggcgg      60
gtgccggagt cccacgcctg gccggggctc gacgaccacc ccgtggtgga cggcggcggc    120
gcgccggggt ccccggacgc cgtgccggtg gtggacctgc gcagccgggg cgccgcggcg   180
```

```
gtggcccgcg tggcgcgcgc cgccgagcag tggggcgcgt tcctgctcac cggccacggc    240
gtccccgcgg agctcctggc gcgcgtcgag accgcgtcg cgtgcatgtt cgcgctgccg     300
gccgccgaca agatgcgcgc cgtgcgcggg ccgggggacg cctgcggcta cggctcgccg    360
cccatctcct ccttcttctc caagtgcatg tggtccgagg gctacacctt ctcgccggcc    420
tccctccgcc gcgacctccg caagctctgg cccaaggccg gcgacgacta cgacagcttc    480
tgtgacgtga tggaggagtt ccacaaggag atgcgcgccc tcgccgacag gctcctggag    540
ctgttcctca gggcgctcgg gctcaccggc gagcaggtcg cgccgtcga ggcggagcgg      600 aggatcggcg agacgatgac cgccaccatg cacctcaact ggtatccgag gtgcccggac    660
ccgcggcgcg cgctggggct gatcgcgcac acggactcgg gcttcttcac cttcgtgctg    720
cagagcctcg tgccggggct gcagctgttc cggcacggcc ccaaccggtg ggtggcggtg    780
ccggccgtgc cgggcgcctt cgtcgtcaac gtcggcgacc tcttccacat cctcacgaac    840
ggccgcttcc acagcgtgta ccaccgcgcc gtcgtcaacc gggacctcga ccggatatcg    900
ctcggctact cctcggccc gccgcccac gccaaggtgg cgccgctccg ggaggtcgtg      960
ccgccgggcc gggccccgc ctaccgcgcc gtcacgtggc ccgagtacat gggcgtccgc    1020
aagaaggcct tcaccaccgg cgcctccgcg ctcaagatgg tcgccgccgc cgccgccgcc    1080
accgaatccg acgacaccga cgcagccgcc gccgccgttc accagccgcc ggtcgtcgtc    1140
tcatcgtag                                                          1149
```

<210> SEQ ID NO 125
<211> LENGTH: 382
<212> TYPE: PRT
<213> ORGANISM: Setaria italica

<400> SEQUENCE: 125

```
Met Pro Thr Pro Ser His Leu Lys Asn Pro Leu Tyr Phe Asp Phe Arg
1               5                   10                  15

Ala Ala Arg Arg Val Pro Glu Ser His Ala Trp Pro Gly Leu Asp Asp
                20                  25                  30

His Pro Val Val Asp Gly Gly Gly Ala Pro Gly Ser Pro Asp Ala Val
            35                  40                  45

Pro Val Val Asp Leu Arg Glu Pro Gly Ala Ala Val Ala Arg Val
        50                  55                  60

Ala Arg Ala Ala Glu Gln Trp Gly Ala Phe Leu Leu Thr Gly His Gly
65                  70                  75                  80

Val Pro Ala Glu Leu Leu Ala Arg Val Glu Asp Arg Val Ala Cys Met
                85                  90                  95

Phe Ala Leu Pro Ala Ala Asp Lys Met Arg Ala Val Arg Gly Pro Gly
                100                 105                 110

Asp Ala Cys Gly Tyr Gly Ser Pro Pro Ile Ser Ser Phe Phe Ser Lys
            115                 120                 125

Cys Met Trp Ser Glu Gly Tyr Thr Phe Ser Pro Ala Ser Leu Arg Arg
        130                 135                 140

Asp Leu Arg Lys Leu Trp Pro Lys Ala Gly Asp Asp Tyr Asp Ser Phe
145                 150                 155                 160

Cys Asp Val Met Glu Glu Phe His Lys Glu Met Arg Ala Leu Ala Asp
                165                 170                 175

Arg Leu Leu Glu Leu Phe Leu Arg Ala Leu Gly Leu Thr Gly Glu Gln
                180                 185                 190
```

```
Val Gly Ala Val Glu Ala Glu Arg Arg Ile Gly Glu Thr Met Thr Ala
            195                 200                 205

Thr Met His Leu Asn Trp Tyr Pro Arg Cys Pro Asp Pro Arg Arg Ala
    210                 215                 220

Leu Gly Leu Ile Ala His Thr Asp Ser Gly Phe Phe Thr Phe Val Leu
225                 230                 235                 240

Gln Ser Leu Val Pro Gly Leu Gln Leu Phe Arg His Gly Pro Asn Arg
                245                 250                 255

Trp Val Ala Val Pro Ala Val Pro Gly Ala Phe Val Val Asn Val Gly
                260                 265                 270

Asp Leu Phe His Ile Leu Thr Asn Gly Arg Phe His Ser Val Tyr His
            275                 280                 285

Arg Ala Val Val Asn Arg Asp Leu Asp Arg Ile Ser Leu Gly Tyr Phe
        290                 295                 300

Leu Gly Pro Pro Pro His Ala Lys Val Ala Pro Leu Arg Glu Val Val
305                 310                 315                 320

Pro Pro Gly Arg Ala Pro Ala Tyr Arg Ala Val Thr Trp Pro Glu Tyr
                325                 330                 335

Met Gly Val Arg Lys Lys Ala Phe Thr Thr Gly Ala Ser Ala Leu Lys
            340                 345                 350

Met Val Ala Ala Ala Ala Ala Thr Glu Ser Asp Asp Thr Asp Ala
        355                 360                 365

Ala Ala Ala Val His Gln Pro Pro Val Val Val Ser Ser
    370                 375                 380

<210> SEQ ID NO 126
<211> LENGTH: 2146
<212> TYPE: DNA
<213> ORGANISM: Setaria italica

<400> SEQUENCE: 126
actagtgcaa ggtcctagat ttacacttgg tgcttgcttg tttcttccta gttgctactg      60
gtagcacgca gtggctggct ggccgtaatc tattgtctgg gctcgatcgg tgattaggaa     120
gtagccaaag caagctaagg ccgccgccgc cgccgccatg ccgacgccgt cgcacctcaa     180
gaacccgctc tacttcgact ccgcgccgc gcggcgggtg ccggagtccc acgcctggcc     240
ggggctcgac gaccaccccg tggtggacgg cggcggcgcg ccggggtccc cggacgccgt     300
gccggtggtg gacctgcgcg agccgggcgc cgcggcggtg gcccgcgtgg cgcgcgccgc     360
cgagcagtgg ggcgcgttcc tgctcaccgg ccacggcgtc cccgcggagc tcctggcgcg     420
cgtcgaggac cgcgtcgcgt gcatgttcgc gctgccggcc gccgacaaga tgcgcgccgt     480
gcgcgggccg ggggacgcct gcggctacgg ctcgccgccc atctcctcct tcttctccaa     540
gtgcatgtgg tccgagggct acaccttctc gccggcctcc ctccgccgcg acctccgcaa     600
gctctggccc aaggccggcg acgactacga cagcttctgg tacgtcgtcg tctatagcta     660
gtagctagcc gccggcacac gtgcgcctga cctgctccgc catgcatggt gcacgtatgc     720
agatcgatca cacgcaccga tcgatcgacg tgtcccggtc aaggccatgc atgcatgcaa     780
gcaaccaaca gcacgcctcc tgatactgct tgttgcttac accgttggta tgtgcctgtt     840
gcctacagtg acgtgatgga ggagttccac aaggagatgc gcgccctcgc cgacaggctc     900
ctggagctgt tcctcagggc gctcgggctc accggcgagc aggtcggcgc cgtcgaggcg     960
gagcggagga tcggcgagac gatgaccgcc accatgcacc tcaactggta tgtgccatgc    1020
catgaccacc tgcgtctatg aactaacgga agcttccatc gcgtgtccat gacgatttag    1080
```

```
aagctgtagt ccagagcttg agacaaacga aacgaagctt acatggtggc gtgacgtgtc   1140
gcgtgcaggt atccgaggtg cccggacccg cggcgcgcgc tggggctgat cgcgcacacg   1200
gactcgggct tcttcacctt cgtgctgcag agcctcgtgc cggggctgca gctgttccgg   1260
cacggcccca accggtgggt ggcggtgccg gccgtgccgg gcgccttcgt cgtcaacgtc   1320
ggcgacctct ccacatcct cacgaacggc cgcttccaca cgtgtaccca ccgcgccgtc   1380
gtcaaccggg acctcgaccg gatatcgctc ggctacttcc tcggcccgcc gccccacgcc   1440
aaggtggcgc cgctccggga ggtcgtgccg ccgggccggg cccccgccta ccgcgccgtc   1500
acgtggcccg agtacatggg cgtccgcaag aaggccttca ccaccggcgc ctccgcgctc   1560
aagatggtcg ccgccgccgc cgccgccacc gaatccgacg acaccgacgc agccgccgcc   1620
gccgttcacc agccgccggt cgtcgtctca tcgtagccga tcgatcgccg gaaacacaga   1680
cgatgcatac cgtaccccga gcaatctaat caaaacaagg catccattct cgcgcgcatg   1740
cagcggccag ccgggcttcc gcagctgctc ggcctcctct gctggctgtg gaaatggaaa   1800 atttaatct gagatgaaga cgaagacgaa gacgaaacgg agaggaaaag gacatgctgt   1860
agctgtttct tctagttgcg caggccgctc ccagtcgagt ttgtcgttac tgacgattat   1920
tactctgatg aaaactaatc tgaattaatg catgtagttt ggcaatttgg tactaaaggt   1980
aggcacctag ccaggctggt caatgatagg tctataacct gatcctgttc tctgttgttt   2040
tcctttgtct gagaaaaaat ggaataatt gatccggccg gacgggtgta ctgataggtg   2100
atgctgaatt gctgatgcaa gaggttgcga gctgcagtga gcagca               2146

<210> SEQ ID NO 127
<211> LENGTH: 1933
<212> TYPE: DNA
<213> ORGANISM: Oryza sativa

<400> SEQUENCE: 127
actactcatt ccactattgt aaagtcatag aaaaaattta tatagagaga aaaaattagt     60
gttgttattg ttactggctt tctgccagac gagacgagcg agcgcgcgag tgtgttgctc    120
tctggtcatc gtcgtcgtcg tcgcgatgcc gacgccgtcg cacttgaaga acccgctctg    180
cttcgacttc cgggcggcga ggcgggtgcc ggagacgcac gcgtggccgg ggctggacga    240
ccacccggtg gtgacggcg gcggcggcgg cggcgaggac gcggtgccgg tggtggacgt    300
cggggcgggc gacgcggcgg cgcgggtggc gcggcggcg gagcagtggg gcgcgttcct    360
tctggtcggg cacggcgtgc cggcggcgct gctgtcgcgc gtcgaggagc gcgtcgcccg    420
cgtgttctcc ctgccggcgt cggagaagat gcgcgccgtc gcggccccg gcgagccctg    480 cggctacggc tcgccgccca tctcctcctt cttctccaag ctcatgtggt ccgagggcta    540
caccttctcc ccttcctccc tccgctccga gctccgccgc ctctggccca gtccggcga    600 cgactacctc tcttctgtg acgtgatgga ggagtttcac aaggagatgc ggcggctagc    660
cgacgagttg ctgaggttgt tcttgagggc gctggggctc accggcgagg aggtcgccgg    720
agtcgaggcg gagaggagga tcggcgagag gatgacggcg acggtgcacc tcaactggta    780
cccgaggtgc ccggagccgc ggcgagcgct ggggctcatc gcgcacacgg actcgggctt    840
cttcaccttc gtgctccaga gcctcgtccc ggggctgcag ctgttccgtc gagggcccga    900
ccggtgggtg gcggtgccgg cggtggcggg gccttcgtc gtcaacgtcg gcgacctctt    960
ccacatcctc accaacggcc gcttccacag cgtctaccac cgcgccgtcg tgaaccgcga   1020
```

| | |
|---|---|
| ccgcgaccgg gtctcgctcg gctacttcct cggcccgccg ccggacgccg aggtggcgcc | 1080 |
| gctgccggag gccgtgccgg ccggccggag ccccgcctac cgcgctgtca cgtggccgga | 1140 |
| gtacatggcc gtccgcaaga aggccttcgc caccggcggc tccgccctca agatggtctc | 1200 |
| caccgacgcc gccgccgccg ccgacgaaca cgacgacgtc gccgccgccg ccgacgtcca | 1260 |
| cgcataagct atagctacta gctacctcga tctcacgcaa aaaaaaaaag aaacaattaa | 1320 |
| tagagcaaaa aaaaaaagaa gagaaaatgg tggtacttgt gtttaaggtt tcctccatgc | 1380 |
| aaaatggttt gcatgcatgc atgcaaagct agcatctgca gctgcaagaa ttacaagagc | 1440 |
| agagaagcag acagctagat ggagataatt aattaattaa ttaatctaat taagcatgca | 1500 |
| ataattaaga ttattattct gatttcagaa ctgaaaaaaa aagtgtggtt aattaattat | 1560 |
| tggttaggct taattttatc tagatgtaga aaaagaatca agatcttcaa gcaagagaa | 1620 |
| agaggatcga agaagaagga aaagaaaacg aaaaggacat gctgtgttgt ctcttctagt | 1680 |
| tgtaccctgg ctgctgatta agtgctttgt tttgttgctg caagcttgtc gttactgatt | 1740 |
| attagttagt tatgcatcta attgattaaa ctaatctgtt tggcattttg gctcgagcta | 1800 |
| agctatagcc aggctggtca atgataggaa cttgtacaat ttaagcaatt gaacctgatc | 1860 |
| ctgtactggc atgtatgtat atatgcaagt gatgagaacc actagctagt atagctagac | 1920 |
| atgtatttgt ata | 1933 |

<210> SEQ ID NO 128
<211> LENGTH: 1122
<212> TYPE: DNA
<213> ORGANISM: Oryza sativa

<400> SEQUENCE: 128

| | |
|---|---|
| atgccgacgc cgtcgcactt gaagaacccg ctctgcttcg acttccgggc ggcgaggcgg | 60 |
| gtgccggaga cgcacgcgtg gccggggctg acgaccacc cggtggtgga cggcggcggc | 120 |
| ggcggcggcg aggacgcggt gccggtggtg gacgtcgggg cgggcgacgc ggcggcgcgg | 180 |
| gtggcgcggg cggcggagca gtggggcgcg ttccttctgg tcgggcacgg cgtgccggcg | 240 |
| gcgctgctgt cgcgcgtcga ggagcgcgtc gcccgcgtgt tctccctgcc ggcgtcggag | 300 |
| aagatgcgcg ccgtccgcgg ccccggcgag ccctgcggct acggctcgcc gcccatctcc | 360 |
| tccttcttct ccaagctcat gtggtccgag ggctacacct tctcccctc ctccctccgc | 420 |
| tccgagctcc gccgcctctg gcccaagtcc ggcgacgact acctcctctt ctgtgacgtg | 480 |
| atggaggagt ttcacaagga gatgcggcgg ctagccgacg agttgctgag gttgttcttg | 540 |
| agggcgctgg ggctcaccgg cgaggaggtc gccggagtcg aggcggagag gaggatcggc | 600 |
| gagaggatga cggcgacggt gcacctcaac tggtacccga ggtgcccgga gccgcggcga | 660 |
| gcgctggggc tcatcgcgca cacggactcg ggcttcttca ccttcgtgct ccagagcctc | 720 |
| gtcccggggc tgcagctgtt ccgtcgaggg cccgaccggt gggtggcggt gccggcggtg | 780 |
| gcgggggcct tcgtcgtcaa cgtcggcgac ctcttccaca tcctcaccaa cggccgcttc | 840 |
| cacagcgtct accaccgcgc cgtcgtgaac cgcgaccgcg accgggtctc gctcggctac | 900 |
| ttcctcggcc cgccgccgga cgccgaggtg gcgccgctgc cggaggccgt gccggccggc | 960 |
| cggagccccg cctaccgcgc tgtcacgtgg ccggagtaca tggccgtccg caagaaggcc | 1020 |
| ttcgccaccg gcggctccgc cctcaagatg gtctccaccg acgccgccgc cgccgccgac | 1080 |
| gaacacgacg acgtcgccgc cgccgccgac gtccacgcat aa | 1122 |

```
<210> SEQ ID NO 129
<211> LENGTH: 373
<212> TYPE: PRT
<213> ORGANISM: Oryza sativa

<400> SEQUENCE: 129

Met Pro Thr Pro Ser His Leu Lys Asn Pro Leu Cys Phe Asp Phe Arg
1               5                   10                  15

Ala Ala Arg Arg Val Pro Glu Thr His Ala Trp Pro Gly Leu Asp Asp
            20                  25                  30

His Pro Val Val Asp Gly Gly Gly Gly Gly Glu Asp Ala Val Pro
        35                  40                  45

Val Val Asp Val Gly Ala Gly Asp Ala Ala Arg Val Ala Arg Ala
    50                  55                  60

Ala Glu Gln Trp Gly Ala Phe Leu Leu Val Gly His Gly Val Pro Ala
65                  70                  75                  80

Ala Leu Leu Ser Arg Val Glu Glu Arg Val Ala Arg Val Phe Ser Leu
                85                  90                  95

Pro Ala Ser Glu Lys Met Arg Ala Val Arg Gly Pro Gly Glu Pro Cys
            100                 105                 110

Gly Tyr Gly Ser Pro Pro Ile Ser Ser Phe Phe Ser Lys Leu Met Trp
        115                 120                 125

Ser Glu Gly Tyr Thr Phe Ser Pro Ser Ser Leu Arg Ser Glu Leu Arg
130                 135                 140

Arg Leu Trp Pro Lys Ser Gly Asp Asp Tyr Leu Leu Phe Cys Asp Val
145                 150                 155                 160

Met Glu Glu Phe His Lys Glu Met Arg Arg Leu Ala Asp Glu Leu Leu
                165                 170                 175

Arg Leu Phe Leu Arg Ala Leu Gly Leu Thr Gly Glu Glu Val Ala Gly
            180                 185                 190

Val Glu Ala Glu Arg Arg Ile Gly Glu Arg Met Thr Ala Thr Val His
        195                 200                 205

Leu Asn Trp Tyr Pro Arg Cys Pro Glu Pro Arg Arg Ala Leu Gly Leu
210                 215                 220

Ile Ala His Thr Asp Ser Gly Phe Phe Thr Phe Val Leu Gln Ser Leu
225                 230                 235                 240

Val Pro Gly Leu Gln Leu Phe Arg Arg Gly Pro Asp Arg Trp Val Ala
                245                 250                 255

Val Pro Ala Val Ala Gly Ala Phe Val Val Asn Val Gly Asp Leu Phe
            260                 265                 270

His Ile Leu Thr Asn Gly Arg Phe His Ser Val Tyr His Arg Ala Val
        275                 280                 285

Val Asn Arg Asp Arg Asp Arg Val Ser Leu Gly Tyr Phe Leu Gly Pro
    290                 295                 300

Pro Pro Asp Ala Glu Val Ala Pro Leu Pro Glu Ala Val Pro Ala Gly
305                 310                 315                 320

Arg Ser Pro Ala Tyr Arg Ala Val Thr Trp Pro Glu Tyr Met Ala Val
                325                 330                 335

Arg Lys Lys Ala Phe Ala Thr Gly Gly Ser Ala Leu Lys Met Val Ser
            340                 345                 350

Thr Asp Ala Ala Ala Ala Ala Asp Glu His Asp Asp Val Ala Ala Ala
        355                 360                 365

Ala Asp Val His Ala
    370
```

<210> SEQ ID NO 130
<211> LENGTH: 2040
<212> TYPE: DNA
<213> ORGANISM: Oryza sativa

<400> SEQUENCE: 130

```
actactcatt ccactattgt aaagtcatag aaaaaattta tatagagaga aaaaattagt      60
gttgttattg ttactggctt tctgccagac gagacgagcg agcgcgcgag tgtgttgctc     120
tctggtcatc gtcgtcgtcg tcgcgatgcc gacgccgtcg cacttgaaga acccgctctg     180
cttcgacttc cgggcggcga ggcggtgcc ggagacgcac gcgtggccgg ggctggacga      240
ccacccggtg gtggacggcg gcggcggcgg cggcgaggac gcggtgccgg tggtggacgt     300
cggggcgggc gacgcggcgg cgcgggtggc gcggcggcg gagcagtggg gcgcgttcct      360
tctggtcggg cacggcgtgc cggcggcgct gctgtcgcgc gtcgaggagc gcgtcgcccg     420
cgtgttctcc ctgccggcgt cggagaagat gcgcgccgtc cgcggccccg gcgagccctg     480
cggctacggc tcgccgccca tctcctcctt cttctccaag ctcatgtggt ccgagggcta     540
caccttctcc ccttcctccc tccgctccga gctccgccgc ctctggccca agtccggcga     600
cgactacctc ctcttctggt atatatacat atatactctc ccatgcattc catgcacata     660
cactctacgt atatatctac ctctacgtat atatctacgt attgatctac gtataatata     720
cgcagtgacg tgatggagga gtttcacaag gagatgcggc ggctagccga cgagttgctg     780
aggttgttct tgagggcgct ggggctcacc ggcgaggagg tcgccggagt cgaggcggag     840
aggaggatcg gcgagaggat gacgcgacg gtgcacctca actggtaccc gaggtgcccg      900
gagccgcggc gagcgctggg gctcatcgcg cacacggact cgggcttctt caccttcgtg     960
ctccagagcc tcgtcccggg gctgcagctg ttccgtcgag ggcccgaccg gtgggtggcg    1020
gtgccggcgg tggcggggc cttcgtcgtc aacgtcggcg acctcttcca catcctcacc    1080
aacggccgct tccacagcgt ctaccaccgc gccgtcgtga accgcgaccg cgaccgggtc    1140
tcgctcggct acttcctcgg cccgccgccg gacgccgagg tggcgccgct gccggaggcc    1200
gtgccggccg gccggagccc cgcctaccgc gctgtcacgt ggccggagta catggccgtc    1260
cgcaagaagg ccttcgccac cggcggctcc gccctcaaga tggtctccac cgacgccgcc    1320
gccgccgccg acgaacacga cgacgtcgcc gccgccgccg acgtccacgc ataagctata    1380
gctactagct acctcgatct cacgcaaaaa aaaaagaaa caattaatag agcaaaaaaa     1440
aaagaagag aaaatggtgg tacttgtgtt taaggtttcc tccatgcaaa atggtttgca    1500
tgcatgcatg caaagctagc atctgcagct gcaagaatta caagagcaga gaagcagaca    1560
gctagatgga gataattaat taattaatta atctaattaa gcatgcaata attaagatta    1620
ttattctgat ttcagaactg aaaaaaaaag tgtggttaat taattattgg ttaggcttaa    1680
ttttatctag atgtagaaaa agaatcaaga tcttcaagca agagagaaga ggatcgaaga    1740
agaaggaaaa gaaaacgaaa aggacatgct gtgttgtctc ttctagttgt accctggctg    1800
ctgattaagt gctttgtttt gttgctgcaa gcttgtcgtt actgattatt agttagttat    1860
gcatctaatt gattaaacta atctgtttgg cattttggct cgagctaagc tatagccagg    1920
ctggtcaatg ataggaactt gtacaattta agcaattgaa cctgatcctg tactggcatg    1980
tatgtatata tgcaagtgat gagaaccact agctagtata gctagacatg tatttgtata    2040
```

<210> SEQ ID NO 131
<211> LENGTH: 1332

```
<212> TYPE: DNA
<213> ORGANISM: Hordeum vulgare

<400> SEQUENCE: 131
acactcactc ctcaatccat ccgtctccac cattgctcgc tagctcgagc tctactagct      60
agcactgcaa agtcagccgg gccggagttg atttggtcct tgttagcttg accgatcgta     120
tacgtatcgc caggatgccg acgccgtcgc acctgagcaa ggacccgcac tacttcgact     180
tccgggcggc gcggcgggtg ccggagacac acgcgtggcc ggggctgcac gaccacccgg     240
tggtggacgg cggcggcgcg ggcggagggc cggacgcggt gccggtggtg gacatgcgcg     300
acccgtgcgc cgcggaggcg gtggcgctgg ccgcgcagga ctggggcgcc ttcctcttgc     360
agggccacgg cgtcccgttg gagctgctgg cccgcgtgga ggccgcgata gcgggcatgt     420
tcgcgctgcc ggcgtcggag aagatgcgcg ccgtgcggcg gcccggcgac tcgtgcggct     480
acgggtcgcc gcccatctcc tccttcttct ccaagtgcat gtggtccgag ggctacacct     540
tctcccggc caacctccgc tccgacctcc gcaagctctg gcccaaggcc ggccacgact     600
accgccactt ctgtgccgtg atggaggagt tccacaggga gatgcgcgtt ctggccgaca     660
agctgctgga gctgttcctg gtggccctcg ggctcaccgg cgagcaggtc gccgccgtcg     720
agtcggagca caagatcgcc gagaccatga ccgccacaat gcacctcaac tggtacccca     780
agtgcccgga cccgaagcga gcgctgggcc tgatcgcgca cacggactcg ggcttcttca     840
ccttcgtgct ccagagcctg gtgcccgggc tgcagctgtt ccggcacggc cccgaccgtt     900
gggtgacggt gccgccgtg ccgggcgcca tggtcgtcaa cgtcggcgac ctcttccaca     960
tcctcaccaa tggccgcttc cacagcgtct accaccgcgc cgtcgtcaac cgcgacagcg    1020
accggatatc gctggggtac ttcctcggcc cgcccgccca cgttaaggtg cgccgctca    1080
gggaggccct cgccggcacg cccgctgcct accgcgccgt cacgtggccc gagtacatgg    1140
gcgtgcgcaa gaaggccttc accaccggcg cctccgcgct caagatggtc gccatctcca    1200
ccgacgacgc cgccgacgtc ctccccgacg tcctctcgtc gtagatcggc gccggccatc    1260
acccggccgg ccaagagacc gatctataca aacaattagt gaacaaaaaa aaaaaaaaa    1320
aaaaaaaaaa aa                                                        1332

<210> SEQ ID NO 132
<211> LENGTH: 1110
<212> TYPE: DNA
<213> ORGANISM: Hordeum vulgare

<400> SEQUENCE: 132
atgccgacgc cgtcgcacct gagcaaggac ccgcactact tcgacttccg ggcggcgcgg      60
cgggtgccgg agacacacgc gtggccgggg ctgcacgacc accggtggt ggacggcggc     120
ggcgcgggcg gagggccgga cgcggtgccg gtggtggaca tgcgcgaccc gtgcgccgcg     180
gaggcggtgg cgctgccgc gcaggactgg ggcgccttcc tcttgcaggg ccacggcgtc     240
ccgttggagc tgctggcccg cgtggaggcc gcgatagcgg gcatgttcgc gctgccggcg     300
tcggagaaga tgcgcgccgt gcggcggccc ggcgactcgt gcggctacgg gtcgccgccc     360
atctcctcct tcttctccaa gtgcatgtgg tccgagggct acaccttctc ccggccaac     420
ctccgctccg acctccgcaa gctctggccc aaggccggcc acgactaccg ccacttctgt     480
gccgtgatga ggagttcca cagggagatg cgcgttctgg ccgacaagct gctggagctg     540
ttcctggtgg ccctcgggct caccggcgag caggtcgccg ccgtcgagtc ggagcacaag     600
```

-continued

```
atcgccgaga ccatgaccgc cacaatgcac ctcaactggt accccaagtg cccggacccg    660
aagcgagcgc tgggcctgat cgcgcacacg gactcgggct tcttcacctt cgtgctccag    720
agcctggtgc ccgggctgca gctgttccgg cacggcccg accgttgggt gacggtgccc     780
gccgtgccgg cgccatggt cgtcaacgtc ggcgacctct ccacatcct caccaatggc      840 cgcttccaca gcgtctacca ccgcgccgtc gtcaaccgcg acagcgaccg gatatcgctg    900
gggtacttcc tcggcccgcc cgcccacgtt aaggtggcgc cgctcaggga ggccctcgcc    960
ggcacgcccg ctgcctaccg cgccgtcacg tggcccgagt acatgggcgt gcgcaagaag   1020
gccttcacca ccggcgcctc cgcgctcaag atggtcgcca tctccaccga cgacgccgcc   1080
gacgtcctcc ccgacgtcct ctcgtcgtag                                    1110
```

<210> SEQ ID NO 133
<211> LENGTH: 369
<212> TYPE: PRT
<213> ORGANISM: Hordeum vulgare

<400> SEQUENCE: 133

```
Met Pro Thr Pro Ser His Leu Ser Lys Asp Pro His Tyr Phe Asp Phe
1               5                  10                  15

Arg Ala Ala Arg Arg Val Pro Glu Thr His Ala Trp Pro Gly Leu His
                20                  25                  30

Asp His Pro Val Val Asp Gly Gly Ala Gly Gly Pro Asp Ala
        35                  40                  45

Val Pro Val Val Asp Met Arg Asp Pro Cys Ala Ala Glu Ala Val Ala
    50                  55                  60

Leu Ala Ala Gln Asp Trp Gly Ala Phe Leu Leu Gln Gly His Gly Val
65                  70                  75                  80

Pro Leu Glu Leu Leu Ala Arg Val Glu Ala Ala Ile Ala Gly Met Phe
                85                  90                  95

Ala Leu Pro Ala Ser Glu Lys Met Arg Ala Val Arg Arg Pro Gly Asp
            100                 105                 110

Ser Cys Gly Tyr Gly Ser Pro Pro Ile Ser Ser Phe Ser Lys Cys
        115                 120                 125

Met Trp Ser Glu Gly Tyr Thr Phe Ser Pro Ala Asn Leu Arg Ser Asp
    130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Val Leu Ala Asp Lys
                165                 170                 175

Leu Leu Glu Leu Phe Leu Val Ala Leu Gly Leu Thr Gly Glu Gln Val
            180                 185                 190

Ala Ala Val Glu Ser Glu His Lys Ile Ala Glu Thr Met Thr Ala Thr
        195                 200                 205

Met His Leu Asn Trp Tyr Pro Lys Cys Pro Asp Pro Lys Arg Ala Leu
    210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
                245                 250                 255

Val Thr Val Pro Ala Val Pro Gly Ala Met Val Val Asn Val Gly Asp
            260                 265                 270

Leu Phe His Ile Leu Thr Asn Gly Arg Phe His Ser Val Tyr His Arg
        275                 280                 285
```

```
Ala Val Val Asn Arg Asp Ser Asp Arg Ile Ser Leu Gly Tyr Phe Leu
            290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
                325                 330                 335

Val Arg Lys Lys Ala Phe Thr Thr Gly Ala Ser Ala Leu Lys Met Val
            340                 345                 350

Ala Ile Ser Thr Asp Asp Ala Ala Asp Val Leu Pro Asp Val Leu Ser
                355                 360                 365

Ser

<210> SEQ ID NO 134
<211> LENGTH: 1653
<212> TYPE: DNA
<213> ORGANISM: Triticum aestivum
<220> FEATURE:
<221> NAME/KEY: misc_feature
<222> LOCATION: (1594)..(1600)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t

<400> SEQUENCE: 134
cacgagatcc atccgtctcc accattgctc gctagctcga gctcctagct agtactgcaa    60
agtcagccgg ggagttgatt tggtccttct tggcttgacc gatcgtacgt gccgccagga   120
tgccgacgcc ggcgcacctg agcaaggacc cgcgctactt cgacttccgg gcggcgcggc   180
gggtgccgga gacgcacgcg tggcccgggc tgcacgacca ccccgtggtg gacggcagcg   240
gcgcgggcgg agggccggac gcggtgccgg tggtggacat gcgcgacccg tgcgcggcgg   300
aggcggtggc gctggcggcg caggactggg gcgccttcct cctggagggc cacggcgtcc   360
cgttggagct gctggcgcgc gtggaggccg cgatcgcggg catgttcgcg ctgccggcgt   420
cggagaagat gcgcgccgtg cggcggcccg cgactcgtg cggctacggg tcgccgccca   480
tctcctcctt cttctccaag tgcatgtggt ccgagggcta caccttctcc ccggccaacc   540
tccgctccga cctccgcaag ctctggccca aggccggcca cgactaccgc cacttctgcg   600
ccgtgatgga ggagttccac agggagatgc gcgcgctggc cgacaagctg ctggagctgt   660
tcctggtggc cctcgggctc accggcgagc aggtcgccgc cgtcgagtcc gagcagaaga   720
tcgccgagac catgaccgcc acaatgcacc tcaactggta ccccaagtgc ccggacccga   780
agcgggcgct gggcctgatc gcgcacacgg actcgggctt cttcaccttc gtgctgcaga   840
gccttgtgcc cgggctgcag ctgttccggc acggccccga ccggtgggtg acggtgcccg   900
ccgtgccggg ggccatggtc gtcaacgtcg gcgacctctt ccagatcctc accaacggcc   960
gcttccacag cgtctaccac cgcgccgtcg tcaaccgcga cagcgaccgg atatcgctcg  1020
gctacttcct cggcccgccc gcccacgtca aggtggcgcc gctcagggag gccctggccg  1080
gcacgcccgc cgcctaccgc gccgtcacgt ggcccgagta catgggcgtg cgcaagaagg  1140
ccttcaccac cggcgcctcc gcgctcaaga tggtcgccat ctccactgac aacgacgccg  1200
ccaaccacac ggacgacctg atctcgtcgt agatcggcgc cggccatcac cggccggcca  1260
agggatcgat ctacacacac aattagtgaa caaaaaaatg ccagagatgg tgcatggtgg  1320
gctggtagct tagctgaggt agctaggagg aagagcgcgc gtgcggctgt cgttcgtgcg  1380
```

```
gctgttcccg caaaaaaaaa aaaggtttcc tccatatatg tctccatgca gaactgcaga   1440
tgctggtggt ggatgcgtcc atgcagcagg gaacgaacta attgtaagaa atcaagcaa    1500 acttagttct acatctgtaa ttaagtatgc atgccacttg gtttaattca attcaagtgc   1560
agaaaaaatt atgatgggaa aaaaaaagac atgnnnnnnn aaaaaaaaaa aaaaaaaaaa   1620
aaaaaaaaaa aaaaaaaaaa naaaaaaaaa aaa                                1653
```

<210> SEQ ID NO 135
<211> LENGTH: 1113
<212> TYPE: DNA
<213> ORGANISM: Triticum aestivum

<400> SEQUENCE: 135

```
atgccgacgc cggcgcacct gagcaaggac ccgcgctact tcgacttccg ggcggcgcgg    60
cgggtgccgg agacgcacgc gtggcccggg ctgcacgacc accccgtggt ggacggcagc   120
ggcgcgggcg gagggccgga cgcggtgccg gtggtggaca tgcgcgaccc gtgcgcggcg   180
gaggcggtgg cgctggcggc gcaggactgg ggcgccttcc tcctggaggg ccacggcgtc   240
ccgttggagc tgctggcgcg cgtggaggcc gcgatcgcgg gcatgttcgc gctgccggcg   300
tcggagaaga tgcgcgccgt gcggcggccc ggcgactcgt gcggctacgg gtcgccgccc   360
atctcctcct tcttctccaa gtgcatgtgg tccgagggct acaccttctc cccgccaac    420 ctccgctccg acctccgcaa gctctggccc aaggccggcc acgactaccg ccacttctgc   480
gccgtgatgg aggagttcca cagggagatg cgcgcgctgg ccgacaagct gctggagctg   540
ttcctggtgg ccctcgggct caccggcgag caggtcgccg ccgtcgagtc cgagcagaag   600
atcgccgaga ccatgaccgc cacaatgcac ctcaactggt accccaagtg cccggacccg   660
aagcgggcgc tgggcctgat cgcgcacacg gactcgggct tcttcacctt cgtgctgcag   720
agccttgtgc ccgggctgca gctgttccgg cacggccccg accggtgggt gacggtgccc   780
gccgtgccgg gggccatggt cgtcaacgtc ggcgacctct tccagatcct caccaacggc   840
cgcttccaca cgtctacca ccgcgccgtc gtcaaccgcg acagcgaccg gatatcgctc   900
ggctacttcc tcggcccgcc cgcccacgtc aaggtggcgc cgctcaggga ggccctggcc   960
ggcacgcccg ccgcctaccg cgccgtcacg tggcccgagt acatgggcgt gcgcaagaag  1020
gccttcacca ccgcgcctc cgcgctcaag atggtcgcca tctccactga caacgacgcc  1080
gccaaccaca cggacgacct gatctcgtcg tag                                1113
```

<210> SEQ ID NO 136
<211> LENGTH: 370
<212> TYPE: PRT
<213> ORGANISM: Triticum aestivum

<400> SEQUENCE: 136

```
Met Pro Thr Pro Ala His Leu Ser Lys Asp Pro Arg Tyr Phe Asp Phe
1               5                   10                  15

Arg Ala Ala Arg Arg Val Pro Glu Thr His Ala Trp Pro Gly Leu His
                20                  25                  30

Asp His Pro Val Val Asp Gly Ser Gly Ala Gly Gly Gly Pro Asp Ala
            35                  40                  45

Val Pro Val Val Asp Met Arg Asp Pro Cys Ala Ala Glu Ala Val Ala
        50                  55                  60

Leu Ala Ala Gln Asp Trp Gly Ala Phe Leu Leu Glu Gly His Gly Val
65                  70                  75                  80
```

Pro Leu Glu Leu Leu Ala Arg Val Glu Ala Ala Ile Ala Gly Met Phe
            85                  90                  95

Ala Leu Pro Ala Ser Glu Lys Met Arg Ala Val Arg Arg Pro Gly Asp
        100                 105                 110

Ser Cys Gly Tyr Gly Ser Pro Pro Ile Ser Ser Phe Phe Ser Lys Cys
        115                 120                 125

Met Trp Ser Glu Gly Tyr Thr Phe Ser Pro Ala Asn Leu Arg Ser Asp
    130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Ala Leu Ala Asp Lys
                165                 170                 175

Leu Leu Glu Leu Phe Leu Val Ala Leu Gly Leu Thr Gly Glu Gln Val
            180                 185                 190

Ala Ala Val Glu Ser Glu Gln Lys Ile Ala Glu Thr Met Thr Ala Thr
        195                 200                 205

Met His Leu Asn Trp Tyr Pro Lys Cys Pro Asp Pro Lys Arg Ala Leu
    210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
                245                 250                 255

Val Thr Val Pro Ala Val Pro Gly Ala Met Val Val Asn Val Gly Asp
            260                 265                 270

Leu Phe Gln Ile Leu Thr Asn Gly Arg Phe His Ser Val Tyr His Arg
        275                 280                 285

Ala Val Val Asn Arg Asp Ser Asp Arg Ile Ser Leu Gly Tyr Phe Leu
    290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
                325                 330                 335

Val Arg Lys Lys Ala Phe Thr Thr Gly Ala Ser Ala Leu Lys Met Val
            340                 345                 350

Ala Ile Ser Thr Asp Asn Asp Ala Ala Asn His Thr Asp Asp Leu Ile
        355                 360                 365

Ser Ser
    370

<210> SEQ ID NO 137
<211> LENGTH: 1884
<212> TYPE: DNA
<213> ORGANISM: Triticum aestivum

<400> SEQUENCE: 137
tatatataca gctccttgta cttctctcgt tcttacactc actcctcaat ccatccgtct      60
ccaccattgc tcgctagctc gagctcctag ctagtactgc aaagtcagcc ggggagttga     120
tttggtcctt cttggcttga ccatcgtac gtgccgccag gatgccgacg ccggcgcacc     180
tgagcaagga cccgcgctac ttcgacttcc gggcggcgcg gcgggtgccg agacgcacg     240 cgtggcccgg gctgcacgac caccccgtgg tggacggcag cggcgcgggc ggagggccgg     300
acgcggtgcc ggtggtggac atgcgcgacc cgtgcgcggc ggaggcggtg gcgctggcgg     360
cgcaggactg gggcgccttc ctcctggagg gccacggcgt cccgttggag ctgctggcgc     420

```
gcgtggaggc cgcgatcgcg ggcatgttcg cgctgccggc gtcggagaag atgcgcgccg    480
tgcggcggcc cggcgactcg tgcggctacg ggtcgccgcc catctcctcc ttcttctcca    540
agtgcatgtg gtccgagggc tacaccttct ccccggccaa cctccgctcc gacctccgca    600
agctctggcc caaggccggc cacgactacc gccacttctg gtacgtacgc cggccgccga    660
tgcgcatata cacgtcatag tacggcacct acctaactgg ctctggccaa ccgtccgtac    720
acacgtgaag gggcgacgtg tccgactccg accatgcatg catgcacgcg cgcgaaactt    780
gttactcctg ttctgctatg gcagcagcta gccgcgtgtg tccgttcgta ggagtagtta    840
cttacacagt tacacttacg ccgtccgtcg tgttcctcga cgtgcagcgc cgtgatggag    900
gagttccaca gggagatgcg cgcgctggcc gacaagctgc tggagctgtt cctggtggcc    960
ctcgggctca ccggcgagca ggtcgccgcc gtcgagtccg agcagaagat cgccgagacc   1020
atgaccgcca caatgcacct caactggtac gttccactac tactccagta gtacaagtac   1080
aatatataga atacaaatgg cagcagccac gacgacacgt actccaccat gcagcaaagc   1140
atatattgtc ggtgcggcgg ttgacacgga gttgtgtcgt gtcgttgatt cacaggtacc   1200
ccaagtgccc ggacccgaag cgggcgctgg gcctgatcgc gcacacggac tcgggcttct   1260
tcaccttcgt gctgcagagc cttgtgcccg ggctgcagct gttccggcac ggccccgacc   1320
ggtgggtgac ggtgcccgcc gtgccggggg ccatggtcgt caacgtcggc gacctcttcc   1380
agatcctcac caacggccgc ttccacagcg tctaccaccg cgccgtcgtc aaccgcgaca   1440
gcgaccggat atcgctcggc tacttcctcg gcccgcccgc ccacgtcaag gtggcgccgc   1500
tcagggaggc cctggccggc acgcccgccg cctaccgcgc cgtcacgtgg cccgagtaca   1560
tgggcgtgcg caagaaggcc ttcaccaccg gcgcctccgc gctcaagatg gtcgccatct   1620
ccactgacaa cgacgccgcc aaccacacgg acgacctgat ctcgtcgtag atcggcgccg   1680
gccatcaccg gccggccaag ggatcgatct acacacacaa ttagtgaaca aaaaaatgcc   1740
agagatggtg catggtgggc tggtagctta gctgaggtag ctaggaggaa gagcgcgcgt   1800
gcggctgtcg ttcgtgcggc tgttcccgca aaaaaaaaaa ggtttcctcc atatakgtcc   1860
ccakscaaaa tsgmaawgct gggg                                         1884

<210> SEQ ID NO 138
<211> LENGTH: 20
<212> TYPE: RNA
<213> ORGANISM: Artificial Sequence
<220> FEATURE:
<223> OTHER INFORMATION: suppression oligo

<400> SEQUENCE: 138
acggguucuu ccaggugugc                                                 20

<210> SEQ ID NO 139
<211> LENGTH: 20
<212> TYPE: RNA
<213> ORGANISM: Artificial Sequence
<220> FEATURE:
<223> OTHER INFORMATION: suppression oligo

<400> SEQUENCE: 139
cacggguucu uccaggugug                                                 20

<210> SEQ ID NO 140
<211> LENGTH: 20
<212> TYPE: RNA
```

```
<213> ORGANISM: Artificial Sequence
<220> FEATURE:
<223> OTHER INFORMATION: suppression oligo

<400> SEQUENCE: 140
cauugaccuc cccgcuggca                                              20

<210> SEQ ID NO 141
<211> LENGTH: 20
<212> TYPE: RNA
<213> ORGANISM: Artificial Sequence
<220> FEATURE:
<223> OTHER INFORMATION: suppression oligo

<400> SEQUENCE: 141
ccagcgggga ggucaaugcu                                              20

<210> SEQ ID NO 142
<211> LENGTH: 20
<212> TYPE: RNA
<213> ORGANISM: Artificial Sequence
<220> FEATURE:
<223> OTHER INFORMATION: suppression oligo

<400> SEQUENCE: 142
cccagcauug accuccccgc                                              20

<210> SEQ ID NO 143
<211> LENGTH: 20
<212> TYPE: RNA
<213> ORGANISM: Artificial Sequence
<220> FEATURE:
<223> OTHER INFORMATION: suppression oligo

<400> SEQUENCE: 143
cgcgcucgug uacccggaca                                              20

<210> SEQ ID NO 144
<211> LENGTH: 20
<212> TYPE: RNA
<213> ORGANISM: Artificial Sequence
<220> FEATURE:
<223> OTHER INFORMATION: suppression oligo

<400> SEQUENCE: 144 cuccccggcgc aggucgaaca                                             20

<210> SEQ ID NO 145
<211> LENGTH: 20
<212> TYPE: RNA
<213> ORGANISM: Artificial Sequence
<220> FEATURE:
<223> OTHER INFORMATION: suppression oligo

<400> SEQUENCE: 145
guguacccgg acacggugcc                                              20

<210> SEQ ID NO 146
<211> LENGTH: 20
<212> TYPE: RNA
<213> ORGANISM: Artificial Sequence
<220> FEATURE:
<223> OTHER INFORMATION: suppression oligo

<400> SEQUENCE: 146
ugcagggaag cuguccgggc                                              20
```

<210> SEQ ID NO 147
<211> LENGTH: 20
<212> TYPE: RNA
<213> ORGANISM: Artificial Sequence
<220> FEATURE:
<223> OTHER INFORMATION: suppression oligo

<400> SEQUENCE: 147
uucuuccagg ugugcgggca                                          20

<210> SEQ ID NO 148
<211> LENGTH: 20
<212> TYPE: RNA
<213> ORGANISM: Artificial Sequence
<220> FEATURE:
<223> OTHER INFORMATION: suppression oligo

<400> SEQUENCE: 148 agaucccgc gccauuccug                                           20

<210> SEQ ID NO 149
<211> LENGTH: 20
<212> TYPE: RNA
<213> ORGANISM: Artificial Sequence
<220> FEATURE:
<223> OTHER INFORMATION: suppression oligo

<400> SEQUENCE: 149
augcagggaa gcuguccggg                                          20

<210> SEQ ID NO 150
<211> LENGTH: 20
<212> TYPE: RNA
<213> ORGANISM: Artificial Sequence
<220> FEATURE:
<223> OTHER INFORMATION: suppression oligo

<400> SEQUENCE: 150
auuccugugg ccgcaggaag                                          20

<210> SEQ ID NO 151
<211> LENGTH: 20
<212> TYPE: RNA
<213> ORGANISM: Artificial Sequence
<220> FEATURE:
<223> OTHER INFORMATION: suppression oligo

<400> SEQUENCE: 151
cagcggggag gucaaugcug                                          20

<210> SEQ ID NO 152
<211> LENGTH: 20
<212> TYPE: RNA
<213> ORGANISM: Artificial Sequence
<220> FEATURE:
<223> OTHER INFORMATION: suppression oligo

<400> SEQUENCE: 152
caggaauggc gcggggaucu                                          20

<210> SEQ ID NO 153
<211> LENGTH: 20
<212> TYPE: RNA
<213> ORGANISM: Artificial Sequence
<220> FEATURE:

<223> OTHER INFORMATION: suppression oligo

<400> SEQUENCE: 153
gacuacuucg ucggcacccu                                              20

<210> SEQ ID NO 154
<211> LENGTH: 20
<212> TYPE: RNA
<213> ORGANISM: Artificial Sequence
<220> FEATURE:
<223> OTHER INFORMATION: suppression oligo

<400> SEQUENCE: 154
gccaggauuu cgagccaaug                                              20

<210> SEQ ID NO 155
<211> LENGTH: 20
<212> TYPE: RNA
<213> ORGANISM: Artificial Sequence
<220> FEATURE:
<223> OTHER INFORMATION: suppression oligo

<400> SEQUENCE: 155
ggaacauuug gagggaggcg                                              20

<210> SEQ ID NO 156
<211> LENGTH: 20
<212> TYPE: RNA
<213> ORGANISM: Artificial Sequence
<220> FEATURE:
<223> OTHER INFORMATION: suppression oligo

<400> SEQUENCE: 156
gggaggucaa ugcuggggcu                                              20

<210> SEQ ID NO 157
<211> LENGTH: 20
<212> TYPE: RNA
<213> ORGANISM: Artificial Sequence
<220> FEATURE:
<223> OTHER INFORMATION: suppression oligo

<400> SEQUENCE: 157
uuggcucgaa auccuggccg                                              20

<210> SEQ ID NO 158
<211> LENGTH: 20
<212> TYPE: RNA
<213> ORGANISM: Artificial Sequence
<220> FEATURE:
<223> OTHER INFORMATION: suppression oligo

<400> SEQUENCE: 158
acggguucuu ccaggugugc                                              20

<210> SEQ ID NO 159
<211> LENGTH: 20
<212> TYPE: RNA
<213> ORGANISM: Artificial Sequence
<220> FEATURE:
<223> OTHER INFORMATION: suppression oligo

<400> SEQUENCE: 159
cacggguucu uccaggugug                                              20

```
<210> SEQ ID NO 160
<211> LENGTH: 20
<212> TYPE: RNA
<213> ORGANISM: Artificial Sequence
<220> FEATURE:
<223> OTHER INFORMATION: suppression oligo

<400> SEQUENCE: 160
cauugaccuc cccgcuggca                                               20

<210> SEQ ID NO 161
<211> LENGTH: 20
<212> TYPE: RNA
<213> ORGANISM: Artificial Sequence
<220> FEATURE:
<223> OTHER INFORMATION: suppression oligo

<400> SEQUENCE: 161
ccagcgggga ggucaaugcu                                               20

<210> SEQ ID NO 162
<211> LENGTH: 20
<212> TYPE: RNA
<213> ORGANISM: Artificial Sequence
<220> FEATURE:
<223> OTHER INFORMATION: suppression oligo

<400> SEQUENCE: 162
cccagcauug accuccccgc                                               20

<210> SEQ ID NO 163
<211> LENGTH: 20
<212> TYPE: RNA
<213> ORGANISM: Artificial Sequence
<220> FEATURE:
<223> OTHER INFORMATION: suppression oligo

<400> SEQUENCE: 163
cgcgcucgug uacccggaca                                               20

<210> SEQ ID NO 164
<211> LENGTH: 20
<212> TYPE: RNA
<213> ORGANISM: Artificial Sequence
<220> FEATURE:
<223> OTHER INFORMATION: suppression oligo

<400> SEQUENCE: 164 cuccccggcgc aggucgaaca                                              20

<210> SEQ ID NO 165
<211> LENGTH: 20
<212> TYPE: RNA
<213> ORGANISM: Artificial Sequence
<220> FEATURE:
<223> OTHER INFORMATION: suppression oligo

<400> SEQUENCE: 165
guguacccgg acacggugcc                                               20

<210> SEQ ID NO 166
<211> LENGTH: 20
<212> TYPE: RNA
<213> ORGANISM: Artificial Sequence
<220> FEATURE:
<223> OTHER INFORMATION: suppression oligo
```

<400> SEQUENCE: 166
ugcagggaag cuguccgggc                                              20

<210> SEQ ID NO 167
<211> LENGTH: 20
<212> TYPE: RNA
<213> ORGANISM: Artificial Sequence
<220> FEATURE:
<223> OTHER INFORMATION: suppression oligo

<400> SEQUENCE: 167
uucuuccagg ugugcgggca                                              20

<210> SEQ ID NO 168
<211> LENGTH: 228
<212> TYPE: PRT
<213> ORGANISM: Zea mays

<400> SEQUENCE: 168

Met Ala Arg Glu Arg Arg Glu Ile Lys Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ser Val Leu Cys Asp Ala Asp Val Ala Leu Ile Val Phe
        35                  40                  45

Ser Ser Thr Gly Lys Leu Ser Gln Phe Ala Ser Ser Met Asn Glu
    50                  55                  60

Ile Ile Asp Lys Tyr Ser Thr His Ser Lys Asn Leu Gly Lys Ala Glu
65                  70                  75                  80

Gln Pro Ser Leu Asp Leu Asn Leu Glu His Ser Lys Tyr Ala Asn Leu
                85                  90                  95

Asn Glu Gln Leu Val Glu Ala Ser Leu Arg Leu Arg Gln Met Arg Gly
            100                 105                 110

Glu Glu Leu Glu Gly Leu Ser Val Glu Glu Leu Gln Gln Leu Glu Lys
        115                 120                 125

Asn Leu Glu Ser Gly Leu His Arg Val Leu Gln Thr Lys Asp Gln Gln
    130                 135                 140

Phe Leu Glu Gln Ile Ser Asp Leu Glu Lys Lys Ser Thr Gln Leu Ala
145                 150                 155                 160

Glu Glu Asn Arg Gln Leu Arg Asn Gln Val Ser His Ile Pro Pro Val
                165                 170                 175

Gly Lys Gln Ser Val Ala Asp Thr Glu Asn Val Ile Ala Glu Asp Gly
            180                 185                 190

Gln Ser Ser Glu Ser Val Met Thr Ala Leu His Ser Gly Ser Ser Gln
        195                 200                 205

Asp Asn Asp Asp Gly Ser Asp Val Ser Leu Lys Leu Gly Leu Pro Cys
    210                 215                 220

Val Ala Trp Lys
225

<210> SEQ ID NO 169
<211> LENGTH: 687
<212> TYPE: DNA
<213> ORGANISM: Zea mays

<400> SEQUENCE: 169
atggcgaggg agcgacggga gataagagg atagagagcg cggcggcgcg gcaggtcacg     60

| ttctccaagc | gccgccgcgg | cctcttcaag | aaggctgagg | agctctccgt | gctgtgcgat | 120 |

| gccgacgtcg | cgctcatcgt | cttctcctcc | acgggaaagc | tctcccagtt | cgccagctcc | 180 |

| agtatgaatg | agatcattga | caagtacagc | acacattcta | aaacctggg | gaaagcagaa | 240 |

| cagccttcac | ttgacttgaa | cttagaacat | agcaaatatg | caaatttgaa | tgagcaactt | 300 |

| gtggaagcaa | gccttcgact | caggcagatg | agaggtgaag | aacttgaggg | attgagtgtt | 360 |

| gaagaactcc | agcaattgga | gaagaatctg | gaatctggtc | tgcataggg | gcttcaaaca | 420 |

| aaggatcaac | aattcttgga | acagatcagc | gacctcgaaa | aaagagtac | acaactggca | 480 |

| gaggagaaca | gcaactgag | gaatcaagta | tcccacatac | ccccagttgg | caagcaatca | 540 |

| gttgctgata | ctgaaaatgt | tatcgctgaa | gatgggcaat | cctctgaatc | agtcatgact | 600 |

| gcgttgcatt | ctgggagttc | acaggataat | gatgatggtt | cggatgtctc | tctaaaatta | 660 |

| gggctgcctt | gtgttgcatg | gaagtga | | | | 687 |

<210> SEQ ID NO 170
<211> LENGTH: 1528
<212> TYPE: DNA
<213> ORGANISM: Oryza sativa

<400> SEQUENCE: 170

| ggaagctaac | tagtcacggc | gaatacatga | cgacatcggc | ctacaacgca | caacttcttg | 60 |

| gcataaaagc | ttcaatttca | atgccctat | ctggaagccc | taggcgccgc | gcaaatgtaa | 120 |

| aacattcgct | tcgcttggct | tgttatccaa | aatagagtat | ggacctccga | cagattggca | 180 |

| acccgtgggt | aatcgaaaat | ggctccatct | gccccttttgt | cgaaggaatc | aggaaacggc | 240 |

| cctcacctcc | tggcggagtg | tagatatgtg | aaagaatcta | ggcgacactt | gcagactgga | 300 |

| caacatgtga | acaaataaga | ccaacgttat | ggcaacaagc | ctcgacgcta | ctcaagtggt | 360 |

| gggaggccac | cgcatgttcc | aacgaagcgc | caaagaaagc | cttgcagact | ctaatgctat | 420 |

| tagtcgccta | ggatatttgg | aatgaaagga | accgcagagt | ttttcagcac | caagagcttc | 480 |

| cggtggctag | tctgatagcc | aaaattaagg | aggatgccaa | acatgggtc | ttggcgggcg | 540 |

| cgaaacacct | tgataggtgg | cttacctttt | aacatgttcg | ggccaaaggc | cttgagacgg | 600 |

| taaagttttc | tatttgcgct | tgcgcatgta | caattttatt | cctctattca | atgaaattgg | 660 |

| tggctcactg | gttcattaaa | aaaaaagaa | tctagcctgt | tcgggaagaa | gaggatttta | 720 |

| ttcgtgagag | agagagagag | agagagagag | agagggagag | agaaggagga | ggaggatttt | 780 |

| caggcttcgc | attgcccaac | ctctgcttct | gttggcccaa | gaagaatccc | aggcgcccat | 840 |

| gggctggcag | tttaccacgg | acctacctag | cctaccttag | ctatctaagc | gggccgacct | 900 |

| agtagctacg | tgcctagtgt | agattaaagt | tggcgggcca | gcaggaagcc | acgctgcaat | 960 |

| ggcatcttcc | cctgtccttc | gcgtacgtga | aaacaaaccc | aggtaagctt | agaatcttct | 1020 |

| tgcccgttgg | actgggacac | ccaccaatcc | caccatgccc | cgatattcct | ccggtctcgg | 1080 |

| ttcatgtgat | gtcctctctt | gtgtgatcac | ggagcaagca | ttcttaaacg | gcaaaagaaa | 1140 |

| atcaccaact | tgctcacgca | gtcacgctgc | accgcgcgaa | gcgacgcccg | ataggccaag | 1200 |

| atcgcgagat | aaaataacaa | ccaatgatca | taaggaaaca | agcccgcgat | gtgtcgtgtg | 1260 |

| cagcaatctt | ggtcatttgc | gggatcgagt | gcttcacggc | taaccaaata | ttcggccgat | 1320 |

| gatttaacac | attatcagcg | tagatgtacg | tacgatttgt | taattaatct | acgagccttg | 1380 |

| ctagggcagg | tgttctgcca | gccaatccag | atcgccctcg | tatgcacgct | cacatgatgg | 1440 |

| cagggcaggg | ttcacatgag | ctctaacggt | cgattaatta | atcccggggc | tcgactataa | 1500 |

```
atacctccct aatcccatga tcaaaacc                                      1528
```

<210> SEQ ID NO 171
<211> LENGTH: 99
<212> TYPE: DNA
<213> ORGANISM: Oryza sativa

<400> SEQUENCE: 171

```
atctcaagca gcctaatcat ctccagctga tcaagagctc ttaattagct agctagtgat    60
tagctgcgct tgtgatcgat cgatctcggg tacgtagca                          99
```

<210> SEQ ID NO 172
<211> LENGTH: 804
<212> TYPE: DNA
<213> ORGANISM: Zea mays

<400> SEQUENCE: 172

```
accgtcttcg gtacgcgctc actccgccct ctgcctttgt tactgccacg tttctctgaa    60
tgctctcttg tgtggtgatt gctgagagtg gtttagctgg atctagaatt acactctgaa   120
atcgtgttct gcctgtgctg attacttgcc gtcctttgta gcagcaaaat atagggacat   180
ggtagtacga aacgaagata gaacctacac agcaatacga gaaatgtgta atttggtgct   240
tagcggtatt tatttaagca catgttggtg ttatagggca cttggattca gaagtttgct   300
gttaatttag gcacaggctt catactacat gggtcaatag tatagggatt catattatag   360
gcgatactat aataatttgt tcgtctgcag agcttattat ttgccaaaat tagatattcc   420
tattctgttt ttgtttgtgt gctgttaaat tgttaacgcc tgaaggaata aatataaatg   480
acgaaatttt gatgtttatc tctgctcctt tattgtgacc ataagtcaag atcagatgca   540
cttgttttaa atattgttgt ctgaagaaat aagtactgac agtattttga tgcattgatc   600
tgcttgtttg ttgtaacaaa atttaaaaat aaagagtttc cttttttgttg ctctccttac   660
ctcctgatgg tatctagtat ctaccaactg acactatatt gcttctcttt acatacgtat   720
cttgctcgat gccttctccc tagtgttgac cagtgttact cacatagtct ttgctcattt   780
cattgtaatg cagataccaa gcgg                                          804
```

<210> SEQ ID NO 173
<211> LENGTH: 250
<212> TYPE: DNA
<213> ORGANISM: Oryza sativa

<400> SEQUENCE: 173

```
ggattgggaa gcaagcttgg gaattggttt gagatttgag gaggaaaagc ataatggcag    60
cttatttggg taattaattg gtgtgggttt aattttcctt tttccgtatg gattgtaaat   120
tagtcgtcgg aggccatggc caccgaacga tcgaatttag tgttttcatc ggggtttaat   180
caatcgcgaa caattgtaat caaatacact tgtttaaatc tcatcaatgt tttcatgaaa   240
atcatctcga                                                          250
```

<210> SEQ ID NO 174
<211> LENGTH: 997
<212> TYPE: DNA
<213> ORGANISM: Artificial Sequence
<220> FEATURE:
<223> OTHER INFORMATION: Promoter sequence, with original source from
      Zea mays

<400> SEQUENCE: 174

```
gctgcttccg gtagcctgaa gcagaaaaaa actgaaagaa acatgacaga taattccctc      60
ggagaaactt ggcatgtttc ccgttggtca tgtaggacga cgataatgat aaattggtaa     120
gcaaagaaaa aggctactaa gctcgagcag tagaagctac ctagctcgtc gtaacgaaga     180
aacttctcgt ccttcaggta gacccttgct tgtttgcagt actttagtta gggttcggtc     240
tttaattctt ttgctgggca gcagtaaacg gagatgagaa gcgcgagctg atcattgttg     300
ccattctgtg caacgaagct aggggaccaa tgctgactcg cacgagggca tagttgctga     360
tggtcataga cgacgcgttc acttaaaata ataagaatt ataaattgtt gtcataagtc      420
gtgcagccta atataggaga gtgcggcatt gctgtagcta attaagagag tattccggtc     480
atgcttgagc ttggagaatt tttgagggtc cgttcgcttg gagagtcgga gattttgag     540 ggcccgttcg cttgcacaat aataaacaaa gatttgttct agctcatcca aatctatata     600
aattaaagaa gtaattcggt taggaatcaa tccagagctc taattcttaa aaaccgaaca     660
gggcctgagt tgtttgtcta gacgacatta tctgattaag ttattttcat cttcaatttc     720
aaatgtgatc tagcggcata aaacttgttg tctgacagat atttgacttc cacacgggcc     780
acagctcaat tacaaacata cttcaaacat caggcagagg cagagcacta gcagcattcg     840
ctacgtggcg gtgggcagca gtggccagca cattcgacaa ctgccacgga tcccgtacta     900
cttcaaacac gtatcgcttc cagaatccag agtcacacgt gtgcagctgc atgaacccag     960
ctcactccct taagaacagc tcgacgctca cctgtct                              997
```

<210> SEQ ID NO 175
<211> LENGTH: 228
<212> TYPE: PRT
<213> ORGANISM: Zea mays

<400> SEQUENCE: 175

```
Met Ala Arg Glu Arg Glu Ile Lys Arg Ile Glu Ser Ala Ala Ala
1               5                   10                  15

Arg Gln Val Thr Phe Ser Lys Arg Arg Arg Gly Leu Phe Lys Lys Ala
                20                  25                  30

Glu Glu Leu Ser Val Leu Cys Asp Ala Asp Val Ala Leu Ile Val Phe
            35                  40                  45

Ser Ser Thr Gly Lys Leu Ser Gln Phe Ala Ser Ser Ser Met Asn Glu
        50                  55                  60

Ile Ile Asp Lys Tyr Ser Thr His Ser Lys Asn Leu Gly Lys Ala Glu
65                  70                  75                  80

Gln Pro Ser Leu Asp Leu Asn Leu Glu His Ser Lys Tyr Ala Asn Leu
                85                  90                  95

Asn Glu Gln Leu Val Glu Ala Ser Leu Arg Leu Arg Gln Met Arg Gly
            100                 105                 110

Glu Glu Leu Glu Gly Leu Ser Val Glu Glu Leu Gln Gln Leu Glu Lys
        115                 120                 125

Asn Leu Glu Ser Gly Leu His Arg Val Leu Gln Thr Lys Asp Gln Gln
    130                 135                 140

Phe Leu Glu Gln Ile Ser Asp Leu Glu Gln Lys Ser Thr Gln Leu Ala
145                 150                 155                 160

Glu Glu Asn Arg Gln Leu Arg Asn Gln Val Ser His Ile Pro Pro Val
                165                 170                 175

Gly Lys Gln Ser Val Ala Asp Thr Glu Asn Val Ile Ala Glu Asp Gly
            180                 185                 190
```

```
Gln Ser Ser Glu Ser Val Met Thr Ala Leu His Ser Gly Ser Ser Gln
            195                 200                 205

Asp Asn Asp Asp Gly Ser Asp Val Ser Leu Lys Leu Gly Leu Pro Cys
210                 215                 220

Val Ala Trp Lys
225

<210> SEQ ID NO 176
<211> LENGTH: 228
<212> TYPE: PRT
<213> ORGANISM: Zea mays

<400> SEQUENCE: 176

Met Ala Arg Glu Arg Arg Glu Ile Lys Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ser Val Leu Cys Asp Ala Asp Val Ala Leu Ile Val Phe
            35                  40                  45

Ser Ser Thr Gly Lys Leu Ser Gln Phe Ala Ser Ser Met Asn Glu
50                  55                  60

Ile Ile Asp Lys Tyr Ser Thr His Ser Lys Asn Leu Gly Lys Ala Glu
65                  70                  75                  80

Gln Pro Ser Leu Asp Leu Asn Leu Glu His Ser Lys Tyr Ala Asn Leu
                85                  90                  95

Asn Glu Gln Leu Val Glu Ala Ser Leu Arg Leu Arg Gln Met Arg Gly
            100                 105                 110

Glu Glu Leu Glu Gly Leu Ser Val Glu Glu Leu Gln Gln Leu Glu Lys
        115                 120                 125

Asn Leu Glu Ser Gly Leu His Arg Val Leu Gln Thr Lys Asp Gln Gln
    130                 135                 140

Phe Leu Glu Gln Ile Ser Asp Leu Glu Gln Lys Ser Thr Gln Leu Ala
145                 150                 155                 160

Glu Glu Asn Arg Gln Leu Arg Asn Gln Val Ser His Ile Pro Pro Val
                165                 170                 175

Gly Lys Gln Ser Val Ala Asp Ala Glu Asn Val Ile Ala Glu Asp Gly
            180                 185                 190

Gln Ser Ser Glu Ser Val Met Thr Ala Leu His Ser Gly Ser Ser Gln
        195                 200                 205

Asp Asn Asp Asp Gly Ser Asp Val Ser Leu Lys Leu Gly Leu Pro Cys
    210                 215                 220

Val Ala Trp Lys
225

<210> SEQ ID NO 177
<211> LENGTH: 228
<212> TYPE: PRT
<213> ORGANISM: Zea mays

<400> SEQUENCE: 177

Met Ala Arg Glu Arg Arg Glu Ile Lys Arg Ile Glu Ser Ala Ala Ala
1               5                   10                  15

Arg Gln Val Thr Phe Ser Lys Arg Arg Arg Gly Leu Phe Lys Lys Ala
            20                  25                  30

Gln Glu Leu Ser Val Leu Cys Asp Ala Asp Val Ala Leu Ile Val Phe
            35                  40                  45
```

```
Ser Ser Thr Gly Lys Leu Ser Gln Phe Ala Ser Ser Met Asn Glu
    50                  55                  60

Ile Ile Asp Lys Tyr Asn Thr His Ser Lys Asn Leu Gly Lys Thr Glu
65                  70                  75                  80

Gln Pro Ser Leu Asp Leu Asn Leu Glu His Ser Lys Tyr Ala Asn Leu
                85                  90                  95

Asn Glu Gln Leu Ala Glu Ala Ser Leu Arg Leu Arg Gln Met Arg Gly
            100                 105                 110

Glu Glu Leu Glu Gly Leu Asn Val Glu Leu Gln Gln Leu Glu Lys
            115                 120                 125

Asn Leu Glu Ser Gly Leu His Arg Val Leu Gln Thr Lys Asp Gln Gln
    130                 135                 140

Phe Leu Glu Gln Ile Asn Asp Leu Glu Arg Lys Ser Thr Gln Leu Ala
145                 150                 155                 160

Glu Glu Asn Met Gln Leu Arg Asn Gln Val Ser Gln Ile Pro Pro Ala
                165                 170                 175

Gly Lys Gln Ala Val Ala Asp Thr Glu Asn Val Ile Ala Glu Glu Gly
            180                 185                 190

Gln Ser Ser Glu Ser Val Met Thr Ala Leu His Ser Gly Ser Ser Gln
    195                 200                 205

Asp Asn Asp Asp Gly Ser Asp Val Ser Leu Lys Leu Gly Leu Pro Cys
    210                 215                 220

Val Ala Trp Lys
225

<210> SEQ ID NO 178
<211> LENGTH: 228
<212> TYPE: PRT
<213> ORGANISM: Zea mays

<400> SEQUENCE: 178

Met Ala Arg Glu Arg Arg Glu Ile Lys Arg Ile Glu Ser Ala Ala Ala
1               5                   10                  15

Arg Gln Val Thr Phe Ser Lys Arg Arg Gly Leu Phe Lys Lys Ala
            20                  25                  30

Gln Glu Leu Ser Val Leu Cys Asp Ala Asp Val Ala Leu Ile Val Phe
            35                  40                  45

Ser Ser Thr Gly Lys Leu Ser Gln Phe Ala Ser Ser Met Asn Glu
    50                  55                  60

Ile Ile Asp Lys Tyr Asn Thr His Ser Lys Asn Leu Gly Lys Thr Glu
65                  70                  75                  80

Gln Pro Ser Leu Asp Leu Asn Leu Glu His Ser Lys Tyr Ala Asn Leu
                85                  90                  95

Asn Glu Gln Leu Ala Glu Ala Ser Leu Arg Leu Arg Gln Met Arg Gly
            100                 105                 110

Glu Glu Leu Glu Gly Leu Asn Val Glu Leu Gln Gln Leu Glu Lys
            115                 120                 125

Asn Leu Glu Ser Gly Leu His Arg Val Leu Gln Thr Lys Asp Ser Gln
    130                 135                 140

Phe Leu Glu Gln Ile Asn Asp Leu Glu Arg Lys Ser Thr Gln Leu Ala
145                 150                 155                 160

Glu Glu Asn Met Gln Leu Arg Asn Gln Val Ser Gln Ile Pro Pro Ala
                165                 170                 175

Gly Lys Gln Ala Val Ala Asp Thr Glu Asn Val Ile Ala Glu Glu Gly
            180                 185                 190
```

```
Gln Ser Ser Glu Ser Val Met Thr Ala Leu His Ser Gly Ser Ser Gln
        195                 200                 205

Asp Asn Asp Gly Gly Ser Asp Val Ser Leu Lys Leu Gly Leu Pro Cys
    210                 215                 220

Val Ala Trp Lys
225

<210> SEQ ID NO 179
<211> LENGTH: 228
<212> TYPE: PRT
<213> ORGANISM: Lolium perenne

<400> SEQUENCE: 179

Met Ala Arg Glu Arg Arg Glu Ile Lys Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ser Val Leu Cys Asp Ala Asp Val Ala Leu Ile Val Phe
        35                  40                  45

Ser Ser Thr Gly Lys Leu Ser Gln Phe Ala Ser Ser Ser Met Asn Glu
50                  55                  60

Ile Ile Asp Lys Tyr Ser Thr His Ser Lys Asn Leu Gly Lys Ala Asp
65                  70                  75                  80

Gln Pro Ser Leu Asp Leu Asn Leu Glu His Ser Lys Tyr Ala Asn Leu
                85                  90                  95

Asn Asp Gln Leu Ala Glu Ala Ser Leu Arg Leu Arg Gln Met Arg Gly
            100                 105                 110

Glu Gly Leu Glu Gly Leu Thr Val Asp Glu Leu Gln Gln Leu Glu Lys
        115                 120                 125

Asn Leu Glu Thr Gly Leu His Arg Val Leu Gln Thr Lys Asp Gln Gln
130                 135                 140

Phe Leu Glu Gln Ile Asn Glu Leu Gln Arg Lys Ser Ser Gln Leu Ala
145                 150                 155                 160

Glu Glu Asn Met Gln Leu Arg Asn Gln Val Ser Gln Ile Pro Ile Ala
                165                 170                 175

Gly Lys Pro Val Val Ala Asp Thr Glu Asn Val Ile Ala Glu Asp Gly
            180                 185                 190

Gln Ser Ser Glu Ser Val Met Thr Ala Leu His Ser Gly Ser Ser Gln
        195                 200                 205

Asp Asn Asp Asp Gly Ser Asp Val Ser Leu Lys Leu Gly Leu Pro Cys
    210                 215                 220

Ser Ala Trp Lys
225

<210> SEQ ID NO 180
<211> LENGTH: 228
<212> TYPE: PRT
<213> ORGANISM: Triticum aestivum

<400> SEQUENCE: 180

Met Ala Arg Glu Arg Arg Glu Ile Lys Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ser Val Leu Cys Asp Ala Asp Val Ala Leu Ile Val Phe
        35                  40                  45
```

```
Ser Ser Thr Gly Lys Leu Ser Gln Phe Ala Ser Ser Thr Asn Glu
    50                  55                  60

Ile Ile Asp Lys Tyr Ser Thr His Ser Lys Asn Leu Gly Lys Thr Asp
65                  70                  75                  80

Gln Pro Ala Leu Asp Leu Asn Leu Glu His Ser Lys Tyr Ala Asn Leu
                85                  90                  95

Asn Asp Gln Leu Ala Glu Ala Ser Leu Arg Leu Arg Gln Met Arg Gly
            100                 105                 110

Glu Glu Leu Glu Gly Leu Ser Val Asp Glu Leu Gln Gln Leu Glu Lys
        115                 120                 125

Asn Leu Glu Thr Gly Leu His Arg Val Leu Gln Thr Lys Asp Gln Gln
    130                 135                 140

Phe Leu Glu Gln Ile Asn Glu Leu His Arg Lys Ser Ser Gln Leu Ala
145                 150                 155                 160

Glu Glu Asn Met Lys Leu Arg Asn Gln Val Gly Gln Ile Pro Thr Ala
                165                 170                 175

Gly Lys Leu Val Val Ala Asp Thr Glu Asn Val Val Ala Glu Asp Gly
            180                 185                 190

Gln Ser Ser Glu Ser Val Met Thr Ala Leu His Ser Gly Ser Ser Gln
        195                 200                 205

Asp Asn Asp Asp Gly Ser Asp Val Ser Leu Lys Leu Gly Leu Pro Cys
    210                 215                 220

Leu Pro Trp Lys
225

<210> SEQ ID NO 181
<211> LENGTH: 228
<212> TYPE: PRT
<213> ORGANISM: Triticum aestivum

<400> SEQUENCE: 181

Met Ala Arg Glu Arg Arg Glu Ile Lys Arg Ile Glu Ser Ala Ala Ala
1               5                   10                  15

Arg Gln Val Thr Phe Ser Lys Arg Arg Arg Gly Leu Phe Lys Lys Ala
            20                  25                  30

Glu Glu Leu Ser Val Leu Cys Asp Ala Asp Val Ala Leu Ile Val Phe
        35                  40                  45

Ser Ser Thr Gly Lys Leu Ser Gln Phe Ala Ser Ser Ser Met Asn Glu
    50                  55                  60

Ile Ile Asp Lys Tyr Ser Thr His Ser Lys Asn Leu Gly Lys Thr Asp
65                  70                  75                  80

Gln Pro Ala Leu Asp Leu Asn Leu Glu His Ser Lys Tyr Ala Asn Leu
                85                  90                  95

Asn Asp Gln Leu Ala Glu Ala Ser Leu Arg Leu Arg Gln Met Arg Gly
            100                 105                 110

Glu Glu Leu Glu Gly Leu Ser Val Asp Glu Leu Gln Leu Leu Glu Lys
        115                 120                 125

Asn Leu Glu Thr Gly Leu His Arg Val Leu Gln Thr Lys Asp Gln Gln
    130                 135                 140

Phe Leu Glu Gln Ile Asn Glu Leu His Arg Lys Ser Ser Gln Leu Ala
145                 150                 155                 160

Glu Glu Asn Met Lys Leu Arg Asn Gln Val Gly Gln Ile Pro Thr Ala
                165                 170                 175

Gly Lys Leu Val Val Ala Asp Thr Glu Asn Val Val Ala Glu Asp Gly
```

```
                180             185                 190
Gln Ser Ser Glu Ser Val Met Thr Ala Leu His Ser Gly Ser Ser Gln
            195                 200                 205
Asp Asn Asp Asp Gly Ser Asp Val Ser Leu Lys Leu Gly Leu Pro Cys
            210                 215                 220
Leu Pro Trp Lys
225

<210> SEQ ID NO 182
<211> LENGTH: 228
<212> TYPE: PRT
<213> ORGANISM: Triticum aestivum

<400> SEQUENCE: 182

Met Ala Arg Glu Arg Arg Glu Ile Lys Arg Ile Glu Ser Ala Ala Ala
1               5                   10                  15
Arg Gln Val Thr Phe Pro Lys Arg Arg Arg Gly Leu Phe Lys Lys Ala
            20                  25                  30
Glu Glu Leu Ser Val Leu Cys Asp Ala Asp Val Ala Leu Ile Val Phe
        35                  40                  45
Ser Ser Thr Gly Lys Leu Ser Gln Phe Ala Ser Ser Ser Met Asn Glu
    50                  55                  60
Ile Ile Asp Lys Tyr Ser Thr His Ser Lys Asn Leu Gly Lys Thr Asp
65                  70                  75                  80
Arg Pro Ala Leu Asp Leu Asn Leu Glu His Ser Lys Tyr Ala Asn Leu
                85                  90                  95
Asn Asp Gln Leu Ala Glu Ala Ser Leu Arg Leu Arg Gln Met Arg Gly
            100                 105                 110
Glu Glu Leu Glu Gly Leu Ser Val Asp Glu Leu Gln Gln Leu Glu Lys
        115                 120                 125
Asn Leu Glu Thr Gly Leu His Arg Val Leu Gln Thr Lys Asp Gln Gln
    130                 135                 140
Phe Leu Glu Gln Ile Asn Glu Leu His Arg Lys Ser Ser Gln Leu Ala
145                 150                 155                 160
Glu Glu Asn Met Lys Leu Arg Asn Gln Val Gly Gln Ile Pro Thr Ala
                165                 170                 175
Gly Lys Leu Val Val Ala Asp Thr Glu Asn Val Val Ala Glu Asp Gly
            180                 185                 190
Gln Ser Ser Glu Ser Val Met Thr Ala Leu His Ser Gly Ser Ser Gln
        195                 200                 205
Asp Asn Asp Asp Gly Ser Asp Val Ser Leu Lys Leu Gly Leu Pro Cys
    210                 215                 220
Leu Pro Trp Lys
225

<210> SEQ ID NO 183
<211> LENGTH: 225
<212> TYPE: PRT
<213> ORGANISM: Hordeum vulgare subsp. vulgare

<400> SEQUENCE: 183

Met Ala Arg Glu Arg Arg Glu Ile Lys Arg Ile Glu Ser Ala Ala Ala
1               5                   10                  15
Arg Gln Val Thr Phe Ser Lys Arg Arg Arg Gly Leu Phe Lys Lys Ala
            20                  25                  30
Glu Glu Leu Ser Val Leu Cys Asp Ala Asp Val Ala Leu Ile Val Phe
```

```
                35                  40                  45
Ser Ser Thr Gly Lys Leu Ser Gln Phe Ala Ser Ser Ser Met Asn Glu
 50                  55                  60

Ile Ile Asp Lys Tyr Ser Thr His Ser Lys Asn Leu Gly Lys Thr Asp
 65                  70                  75                  80

Gln Pro Thr Leu Asp Leu Asn Leu Glu His Ser Lys Tyr Ala Asn Leu
                 85                  90                  95

Asn Asp Gln Leu Ala Glu Ala Ser Leu Arg Leu Arg Gln Met Arg Gly
                100                 105                 110

Glu Glu Leu Glu Gly Leu Ser Val Asp Glu Leu Gln Gln Leu Glu Lys
                115                 120                 125

Asn Leu Glu Thr Gly Leu His Lys Val Leu Gln Thr Lys Asp Gln Gln
                130                 135                 140

Phe Leu Glu Gln Ile Asn Glu Leu His Arg Lys Ser Ser Gln Leu Ala
145                 150                 155                 160

Glu Glu Asn Lys Lys Leu Arg Asn Gln Val Ala Gln Val Pro Thr Ala
                165                 170                 175

Gly Lys Leu Val Val Val Asp Thr Glu Asn Val Ile Ala Glu Asp Gly
                180                 185                 190

Gln Ser Ser Glu Ser Val Met Thr Ala Leu His Ser Gly Ser Ser Gln
                195                 200                 205

Asp Asn Asp Asp Gly Ser Asp Val Ser Leu Lys Leu Ala Leu Pro Trp
210                 215                 220

Lys
225

<210> SEQ ID NO 184
<211> LENGTH: 229
<212> TYPE: PRT
<213> ORGANISM: Oryza sativa Indica Group

<400> SEQUENCE: 184

Met Ala Arg Glu Arg Glu Ile Lys Arg Ile Glu Ser Ala Ala Ala
 1               5                  10                  15

Arg Gln Val Thr Phe Ser Lys Arg Arg Gly Leu Phe Lys Lys Ala
                 20                  25                  30

Glu Glu Leu Ser Val Leu Cys Asp Ala Asp Val Ala Leu Ile Val Phe
                 35                  40                  45

Ser Ser Thr Gly Lys Leu Ser His Phe Ala Ser Ser Ser Met Asn Glu
 50                  55                  60

Ile Ile Asp Lys Tyr Asn Thr His Ser Asn Asn Leu Gly Lys Ala Glu
 65                  70                  75                  80

Gln Pro Ser Leu Asp Leu Asn Leu Glu His Ser Lys Tyr Ala His Leu
                 85                  90                  95

Asn Glu Gln Leu Ala Glu Ala Ser Leu Arg Leu Arg Gln Met Arg Gly
                100                 105                 110

Glu Glu Leu Glu Gly Leu Ser Ile Asp Glu Leu Gln Gln Leu Glu Lys
                115                 120                 125

Asn Leu Glu Ala Gly Leu His Arg Val Met Leu Thr Lys Asp Gln Gln
                130                 135                 140

Phe Met Glu Gln Ile Ser Glu Leu Gln Arg Lys Ser Ser Gln Leu Ala
145                 150                 155                 160

Glu Glu Asn Met Gln Leu Arg Asn Gln Val Ser Gln Ile Ser Pro Ala
                165                 170                 175
```

```
Glu Lys Gln Val Val Asp Thr Glu Asn Phe Val Thr Glu Gly Gln
            180                 185                 190

Ser Ser Glu Ser Val Met Thr Ala Leu His Ser Gly Ser Gln Ser
        195                 200                 205

Gln Asp Asn Asp Asp Gly Ser Asp Val Ser Leu Lys Leu Gly Leu Pro
    210                 215                 220

Cys Gly Ala Trp Lys
225

<210> SEQ ID NO 185
<211> LENGTH: 228
<212> TYPE: PRT
<213> ORGANISM: Oryza sativa Japonica Group

<400> SEQUENCE: 185

Met Ala Arg Glu Arg Arg Glu Ile Lys Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ser Val Leu Cys Asp Ala Asp Val Ala Leu Ile Val Phe
            35                  40                  45

Ser Ser Thr Gly Lys Leu Ser His Phe Ala Ser Ser Ser Met Asn Glu
        50                  55                  60

Ile Ile Asp Lys Tyr Asn Thr His Ser Asn Asn Leu Gly Lys Ala Glu
65              70                  75                  80

Gln Pro Ser Leu Asp Leu Asn Leu Glu His Ser Lys Tyr Ala His Leu
                85                  90                  95

Asn Glu Gln Leu Ala Glu Ala Ser Leu Arg Leu Arg Gln Met Arg Gly
            100                 105                 110

Glu Glu Leu Glu Gly Leu Ser Ile Asp Glu Leu Gln Gln Leu Glu Lys
            115                 120                 125

Asn Leu Glu Ala Gly Leu His Arg Val Met Leu Thr Lys Asp Gln Gln
        130                 135                 140

Phe Met Glu Gln Ile Ser Glu Leu Gln Arg Lys Ser Ser Gln Leu Ala
145                 150                 155                 160

Glu Glu Asn Met Gln Leu Arg Asn Gln Val Ser Gln Ile Ser Pro Ala
                165                 170                 175

Glu Lys Gln Val Val Asp Thr Glu Asn Phe Val Thr Glu Gly Gln Ser
            180                 185                 190

Ser Glu Ser Val Met Thr Ala Leu His Ser Gly Ser Ser Gln Ser Gln
        195                 200                 205

Asp Asn Asp Asp Gly Ser Asp Val Ser Leu Lys Leu Gly Leu Pro Cys
    210                 215                 220

Gly Ala Trp Lys
225

<210> SEQ ID NO 186
<211> LENGTH: 223
<212> TYPE: PRT
<213> ORGANISM: Oryza sativa Japonica Group

<400> SEQUENCE: 186

Met Ala Arg Glu Arg Arg Glu Ile Arg Arg Ile Glu Ser Ala Ala Ala
1               5                   10                  15

Arg Gln Val Thr Phe Ser Lys Arg Arg Gly Leu Phe Lys Lys Ala
            20                  25                  30
```

```
Glu Glu Leu Ala Val Leu Cys Asp Ala Asp Val Ala Leu Val Val Phe
             35                  40                  45

Ser Ser Thr Gly Lys Leu Ser Gln Phe Ala Ser Ser Asn Met Asn Glu
 50                  55                  60

Ile Ile Asp Lys Tyr Thr Thr His Ser Lys Asn Leu Gly Lys Thr Asp
 65                  70                  75                  80

Lys Gln Pro Ser Ile Asp Leu Asn Leu Glu His Ser Lys Cys Ser Ser
                 85                  90                  95

Leu Asn Glu Gln Leu Ala Glu Ala Ser Leu Gln Leu Arg Gln Met Arg
            100                 105                 110

Gly Glu Glu Leu Glu Gly Leu Ser Val Glu Glu Leu Gln Gln Met Glu
            115                 120                 125

Lys Asn Leu Glu Ala Gly Leu Gln Arg Val Leu Cys Thr Lys Asp Gln
130                 135                 140

Gln Phe Met Gln Glu Ile Ser Glu Leu Gln Arg Lys Gly Ile Gln Leu
145                 150                 155                 160

Ala Glu Glu Asn Met Arg Leu Arg Asp Gln Met Pro Gln Val Pro Thr
                165                 170                 175

Ala Gly Leu Ala Val Pro Asp Thr Glu Asn Val Leu Thr Glu Asp Gly
            180                 185                 190

Gln Ser Ser Glu Ser Val Met Thr Ala Leu Asn Ser Gly Ser Ser Gln
            195                 200                 205

Asp Asn Asp Asp Gly Ser Asp Ile Ser Leu Lys Leu Gly Leu Pro
            210                 215                 220
```

<210> SEQ ID NO 187
<211> LENGTH: 226
<212> TYPE: PRT
<213> ORGANISM: Festuca arundinacea

<400> SEQUENCE: 187

```
Met Ala Arg Glu Arg Arg Glu Ile Arg Arg Ile Glu Ser Ala Ala Ala
 1               5                  10                  15

Arg Gln Val Thr Phe Ser Lys Arg Arg Arg Gly Leu Phe Lys Lys Ala
             20                  25                  30

Glu Glu Leu Gly Val Leu Cys Asp Ala Asp Val Ala Leu Val Val Phe
             35                  40                  45

Ser Ser Thr Gly Lys Leu Ser Gln Phe Gly Ser Ser Met Asp Glu
 50                  55                  60

Ile Ile Asp Lys Tyr Ser Thr His Ser Lys Asn Leu Gly Lys Ser Gln
 65                  70                  75                  80

Glu Lys Pro Ala Leu Asp Leu Asn Val Glu His Ser Lys Tyr Asn Ser
                 85                  90                  95

Leu Asn Glu Gln Leu Ala Glu Ala Ser Leu His Leu Arg His Met Arg
            100                 105                 110

Gly Glu Glu Leu Ala Gly Leu Ser Val Gly Glu Leu Gln Gln Met Glu
            115                 120                 125

Lys Asp Leu Glu Thr Gly Leu Gln Arg Val Leu Cys Thr Lys Asp Gln
130                 135                 140

Gln Phe Met Gln Gln Ile Ser Asp Leu Gln Gln Lys Gly Thr Gln Leu
145                 150                 155                 160

Ala Glu Glu Asn Met Arg Leu Arg Asn Gln Met Pro Gln Val Pro Thr
                165                 170                 175

Ala Gly Met Met Ala Val Ala Asp Thr Glu Asn Val Val Thr Glu Asp
            180                 185                 190
```

```
Val Leu Ser Ser Glu Ser Val Met Thr Ala Val His Ser Gly Ser Ser
        195                 200                 205

Gln Asp Asn Asp Asp Gly Ser Asp Ile Ser Leu Lys Leu Ala Leu Pro
    210                 215                 220

Trp Lys
225

<210> SEQ ID NO 188
<211> LENGTH: 226
<212> TYPE: PRT
<213> ORGANISM: Triticum aestivum

<400> SEQUENCE: 188

Met Ala Arg Glu Arg Arg Ala Ile Arg Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ala Val Leu Cys Asp Ala Asp Val Ala Leu Val Val Phe
        35                  40                  45

Ser Ser Thr Gly Lys Leu Ser Gln Phe Ala Ser Ser Ser Met Asn Glu
50                  55                  60

Ile Ile Asp Lys Tyr Ser Thr His Ser Lys Asn Leu Gly Lys Ser Asp
65                  70                  75                  80

Gln Gln Pro Ala Ile Asp Leu Asn Leu Glu His Cys Lys Tyr Asp Ser
                85                  90                  95

Leu Asn Glu Gln Leu Ala Glu Ala Ser Leu Arg Leu Arg His Met Arg
            100                 105                 110

Gly Glu Glu Leu Asp Gly Leu Ser Val Gly Glu Leu Gln Gln Met Glu
        115                 120                 125

Lys Asn Leu Glu Thr Gly Leu Gln Lys Val Leu Cys Thr Lys Asp Arg
130                 135                 140

Gln Phe Met Gln Gln Ile Ser Asp Leu Gln Gln Lys Gly Thr Gln Leu
145                 150                 155                 160

Ala Glu Glu Asn Met Arg Leu Lys Asn Gln Met His Glu Val Pro Thr
                165                 170                 175

Val Ser Thr Val Ala Val Ala Glu Ala Asn Val Val Pro Glu Asp
            180                 185                 190

Ala His Ser Ser Asp Ser Val Met Thr Ala Val His Ser Gly Ser Ser
        195                 200                 205

Gln Asp Asn Asp Asp Gly Ser Asp Ile Ser Leu Lys Leu Ala Leu Pro
    210                 215                 220

Trp Lys
225

<210> SEQ ID NO 189
<211> LENGTH: 226
<212> TYPE: PRT
<213> ORGANISM: Triticum aestivum

<400> SEQUENCE: 189

Met Ala Arg Glu Arg Arg Ala Ile Arg Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ala Val Leu Cys Asp Ala Asp Val Ala Leu Val Val Phe
        35                  40                  45
```

```
Ser Ser Thr Gly Lys Leu Ser Gln Phe Ala Ser Ser Ser Met Asn Glu
    50                  55                  60

Ile Ile Asp Lys Tyr Ser Thr His Ser Lys Asn Leu Gly Lys Ser Asp
65                  70                  75                  80

Gln Gln Pro Ala Ile Asp Leu Asn Leu Glu His Cys Lys Tyr Asp Ser
                85                  90                  95

Leu Asn Glu Gln Leu Ala Glu Ala Ser Leu Arg Leu Arg His Met Arg
            100                 105                 110

Gly Glu Glu Leu Asp Gly Leu Ser Val Gly Glu Leu Gln Gln Met Glu
            115                 120                 125

Lys Asn Leu Glu Thr Gly Leu Gln Arg Val Leu Cys Thr Lys Asp Arg
130                 135                 140

Gln Phe Met Gln Gln Ile Ser Asp Leu Gln Gln Lys Gly Thr Gln Leu
145                 150                 155                 160

Ala Glu Glu Asn Met Arg Leu Lys Asn Gln Met His Glu Val Pro Thr
                165                 170                 175

Ala Ser Thr Val Ala Val Ala Glu Ala Glu Asn Val Val Pro Glu Asp
            180                 185                 190

Ala His Ser Ser Asp Ser Val Met Thr Ala Val His Ser Gly Ser Ser
            195                 200                 205

Gln Asp Asn Asp Asp Gly Ser Asp Ile Ser Leu Lys Leu Ala Leu Pro
210                 215                 220

Trp Lys
225

<210> SEQ ID NO 190
<211> LENGTH: 226
<212> TYPE: PRT
<213> ORGANISM: Triticum aestivum

<400> SEQUENCE: 190

Met Ala Arg Glu Arg Arg Ala Ile Arg Arg Ile Glu Ser Ala Ala Ala
1               5                   10                  15

Arg Gln Val Thr Phe Ser Lys Arg Arg Arg Gly Leu Phe Lys Lys Ala
                20                  25                  30

Glu Glu Leu Ala Val Leu Cys Asp Ala Asp Val Ala Leu Val Val Phe
            35                  40                  45

Ser Ser Thr Gly Lys Leu Ser Gln Phe Ala Ser Ser Ser Met Asn Glu
    50                  55                  60

Ile Ile Asp Lys Tyr Ser Thr His Ser Lys Asn Leu Gly Lys Ser Asp
65                  70                  75                  80

Gln Gln Pro Ala Ile Asp Leu Asn Leu Glu His Cys Lys Tyr Asp Ser
                85                  90                  95

Leu Asn Glu Gln Leu Ala Glu Ala Ser Leu Arg Leu Arg His Met Arg
            100                 105                 110

Gly Glu Glu Leu Asp Gly Leu Ser Val Gly Glu Leu Gln Gln Met Glu
            115                 120                 125

Lys Asn Leu Glu Thr Gly Leu Gln Arg Val Leu Cys Thr Lys Asp Arg
130                 135                 140

Gln Phe Met Gln Gln Ile Ser Asp Leu Gln His Lys Gly Thr Gln Leu
145                 150                 155                 160

Ala Glu Glu Asn Met Arg Leu Lys Asn Gln Met His Glu Val Pro Thr
                165                 170                 175

Ala Ser Thr Val Ala Val Ala Glu Ala Glu Asn Val Val Pro Glu Asp
```

```
                180              185              190
Ala His Ser Ser Asp Ser Val Met Thr Ala Val His Ser Gly Ser Ser
            195              200              205

Gln Asp Asn Asp Asp Gly Ser Asp Ile Ser Leu Lys Leu Ala Leu Pro
            210              215              220

Trp Lys
225

<210> SEQ ID NO 191
<211> LENGTH: 221
<212> TYPE: PRT
<213> ORGANISM: Oryza sativa Indica Group

<400> SEQUENCE: 191

Met Ala Arg Glu Arg Arg Glu Ile Arg Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ala Val Leu Cys Asp Ala Asp Val Ala Leu Val Val Phe
            35                  40                  45

Ser Ser Thr Gly Lys Leu Ser Gln Phe Ala Ser Ser Asn Met Asn Glu
        50                  55                  60

Ile Ile Asp Lys Tyr Thr Thr His Ser Lys Asn Leu Gly Lys Thr Asp
65                  70                  75                  80

Lys Gln Pro Ser Ile Asp Leu Asn Leu Glu His Ser Lys Cys Ser Ser
                85                  90                  95

Leu Asn Glu Gln Leu Ala Glu Ala Ser Leu Gln Leu Arg Gln Met Arg
            100                 105                 110

Gly Glu Glu Leu Glu Gly Leu Ser Val Glu Leu Gln Gln Met Glu
            115                 120                 125

Lys Asn Leu Glu Ala Gly Leu Gln Arg Val Leu Cys Thr Lys Asp Gln
130                 135                 140

Gln Phe Met Gln Glu Ile Ser Glu Leu Gln Arg Lys Gly Ile Gln Leu
145                 150                 155                 160

Ala Glu Glu Asn Met Arg Leu Arg Asp Gln Met Pro Gln Val Pro Thr
                165                 170                 175

Ala Gly Leu Ala Val Pro Asp Thr Glu Asn Val Leu Thr Glu Asp Gly
            180                 185                 190

Gln Ser Ser Glu Ser Val Met Thr Ala Leu Asn Ser Gly Ser Ser Gln
            195                 200                 205

Asp Asn Asp Asp Gly Ser Asp Ile Ser Leu Lys Leu Gly
            210                 215                 220

<210> SEQ ID NO 192
<211> LENGTH: 228
<212> TYPE: PRT
<213> ORGANISM: Triticum aestivum

<400> SEQUENCE: 192

Met Ala Arg Glu Arg Arg Ala Ile Arg Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ala Val Leu Cys Asp Ala Asp Val Ala Leu Val Val Phe
            35                  40                  45

Ser Ser Thr Gly Lys Leu Ser Gln Phe Ala Ser Ser Ser Met Asn Glu
```

```
                50                  55                  60
Ile Ile Asp Lys Tyr Ser Thr His Ser Lys Asn Leu Gly Lys Ser Asp
 65                  70                  75                  80

Gln Gln Pro Ala Ile Asp Leu Asn Leu Glu His Cys Lys Tyr Asp Ser
                 85                  90                  95

Leu Asn Glu Gln Leu Ala Glu Ala Ser Leu Arg Leu Arg Arg Met Arg
                100                 105                 110

Gly Glu Glu Leu Asp Gly Leu Ser Val Gly Glu Leu Gln Gln Met Glu
                115                 120                 125

Lys Asn Leu Glu Thr Gly Leu Gln Arg Val Leu Cys Thr Lys Asp Arg
130                 135                 140

Gln Phe Met Gln Gln Ile Asn Asp Leu Gln Gln Lys Gly Thr Gln Leu
145                 150                 155                 160

Ala Glu Glu Asn Met Arg Leu Lys Asn Gln Met His Glu Val Pro Thr
                165                 170                 175

Ala Ser Met Val Ala Val Ala Asp Ala Asp Ala Glu Asn Val Val Pro
                180                 185                 190

Asp Asp Val His Ser Ser Asp Ser Val Met Thr Ala Val His Ser Ala
                195                 200                 205

Ser Ser Gln Asp Asn Asp Asp Gly Ser Asp Ile Ser Leu Lys Leu Ala
210                 215                 220

Leu Pro Trp Lys
225

<210> SEQ ID NO 193
<211> LENGTH: 245
<212> TYPE: PRT
<213> ORGANISM: Oryza sativa Japonica Group

<400> SEQUENCE: 193

Met Ala Arg Glu Arg Glu Ile Arg Arg Ile Glu Ser Ala Ala Ala
 1               5                  10                  15

Arg Gln Val Thr Phe Ser Lys Arg Arg Arg Gly Leu Phe Lys Lys Ala
                 20                  25                  30

Glu Glu Leu Ala Val Leu Cys Asp Ala Asp Val Ala Leu Val Val Phe
                 35                  40                  45

Ser Ser Thr Gly Lys Leu Ser Gln Phe Ala Ser Ser Asn Met Asn Glu
 50                  55                  60

Ile Ile Asp Lys Tyr Thr Thr His Ser Lys Asn Leu Gly Lys Thr Asp
 65                  70                  75                  80

Lys Gln Pro Ser Ile Asp Leu Asn Phe Phe Leu Ile Ile Leu Leu Arg
                 85                  90                  95

Thr Tyr Thr Asn Ser Tyr Ala Tyr Ile His Leu Leu Gln Leu Glu
                100                 105                 110

His Ser Lys Cys Ser Ser Leu Asn Glu Gln Leu Ala Glu Ala Ser Leu
                115                 120                 125

Gln Leu Arg Gln Met Arg Gly Glu Glu Leu Glu Gly Leu Ser Val Glu
130                 135                 140

Glu Leu Gln Gln Met Glu Lys Asn Leu Glu Ala Gly Leu Gln Arg Val
145                 150                 155                 160

Leu Cys Thr Lys Asp Gln Gln Phe Met Gln Glu Ile Ser Glu Leu Gln
                165                 170                 175

Arg Lys Gly Ile Gln Leu Ala Glu Glu Asn Met Arg Leu Arg Asp Gln
                180                 185                 190
```

```
Met Pro Gln Val Pro Thr Ala Gly Leu Ala Val Pro Asp Thr Glu Asn
            195                 200                 205

Val Leu Thr Glu Asp Gly Gln Ser Ser Glu Ser Val Met Thr Ala Leu
    210                 215                 220

Asn Ser Gly Ser Ser Gln Asp Asn Asp Asp Gly Ser Asp Ile Ser Leu
225                 230                 235                 240

Lys Leu Gly Leu Pro
                245

<210> SEQ ID NO 194
<211> LENGTH: 223
<212> TYPE: PRT
<213> ORGANISM: Hordeum vulgare subsp. vulgare

<400> SEQUENCE: 194

Met Ala Arg Glu Arg Arg Ala Ile Arg Ile Glu Ser Ala Ala Ala
1               5                   10                  15

Arg Gln Val Thr Phe Ser Lys Arg Arg Arg Gly Leu Phe Lys Lys Ala
            20                  25                  30

Glu Glu Leu Ala Val Leu Cys Asp Ala Asp Val Ala Leu Val Val Phe
        35                  40                  45

Ser Ser Thr Gly Lys Leu Ser Gln Phe Ala Ser Ser Ser Met Asn Glu
    50                  55                  60

Ile Ile Asp Lys Tyr Ser Thr His Ser Lys Asn Leu Gly Lys Ser Asp
65                  70                  75                  80

Gln Gln Pro Ala Ile Asp Leu Asn Leu Glu His Cys Lys Tyr Asp Ser
                85                  90                  95

Leu Asn Glu Gln Leu Ala Glu Ala Ser Leu Arg Leu Arg His Met Arg
            100                 105                 110

Gly Glu Glu Leu Asp Gly Leu Ser Val Gly Glu Leu Gln Gln Met Glu
        115                 120                 125

Lys Asn Leu Glu Thr Gly Leu Gln Arg Val Leu Cys Thr Lys Asp Arg
    130                 135                 140

Gln Phe Met Gln Gln Ile Ser Asp Leu Gln Gln Lys Gly Thr Gln Leu
145                 150                 155                 160

Ala Glu Glu Asn Met Arg Leu Lys Asn Gln Met His Glu Val Pro Thr
                165                 170                 175

Ala Ser Met Val Ala Val Ala Asp Val Val Pro Glu Asp Val His Ser
            180                 185                 190

Ser Asp Ser Val Met Thr Ala Val His Ser Ala Ser Ser Gln Asp Asn
        195                 200                 205

Asp Asp Gly Ser Asp Ile Ser Leu Lys Leu Ala Leu Pro Trp Lys
    210                 215                 220

<210> SEQ ID NO 195
<211> LENGTH: 219
<212> TYPE: PRT
<213> ORGANISM: Lolium perenne

<400> SEQUENCE: 195

Met Ala Arg Glu Arg Arg Glu Ile Arg Arg Ile Glu Ser Ala Ala Ala
1               5                   10                  15

Arg Gln Val Thr Phe Ser Lys Arg Arg Arg Gly Leu Phe Lys Lys Ala
            20                  25                  30

Glu Glu Leu Gly Val Leu Cys Asp Ala Asp Val Ala Leu Val Val Phe
        35                  40                  45
```

```
Ser Ala Thr Gly Lys Leu Ser Gln Phe Ala Ser Ser Met Asp Glu
 50                  55                  60

Ile Ile Asp Lys Tyr Ser Ala His Ser Lys Asn Leu Gly Lys Ser Gln
 65                  70                  75                  80

Glu Lys Pro Ala Leu Asp Leu Asn Val Glu His Ser Lys Tyr Asn Ser
                 85                  90                  95

Leu Asn Glu Lys Leu Ala Glu Ala Ser Leu His Leu Arg His Met Arg
                100                 105                 110

Gly Glu Glu Leu Gly Gly Leu Ser Val Gly Glu Leu Gln Gln Met Glu
                115                 120                 125

Lys Asp Leu Glu Thr Gly Leu Gln Arg Val Leu Cys Thr Lys Asp Gln
130                 135                 140

Gln Phe Met Gln Gln Ile Ser Asp Leu Gln Gln Lys Gly Thr Gln Leu
145                 150                 155                 160

Ala Glu Glu Asn Met Arg Leu Arg Asn Gln Met Pro Gln Val Pro Thr
                    165                 170                 175

Ala Gly Met Met Ala Ile Thr Glu Asp Val Leu Ser Ser Glu Ser Val
                180                 185                 190

Met Thr Ala Val His Ser Gly Ser Ser Gln Asp Asn Asp Asp Gly Ser
                195                 200                 205

Asp Ile Ser Leu Lys Leu Ala Leu Pro Trp Lys
    210                 215

<210> SEQ ID NO 196
<211> LENGTH: 225
<212> TYPE: PRT
<213> ORGANISM: Sorghum bicolor

<400> SEQUENCE: 196

Met Ala Arg Glu Arg Arg Glu Ile Arg Arg Ile Glu Asn Ala Ala Ala
 1               5                  10                  15

Arg Gln Val Thr Tyr Ser Lys Arg Arg Arg Gly Leu Phe Lys Lys Ala
                 20                  25                  30

Glu Glu Leu Ala Val Leu Cys Asp Ala Asp Val Ala Leu Val Val Phe
             35                  40                  45

Ser Ala Thr Gly Lys Leu Ser Gln Phe Ala Ser Thr Ser Met Asn His
 50                  55                  60

Ile Ile Asp Lys Tyr Ser Thr His Ser Lys Asn Leu Gly Lys Ser His
 65                  70                  75                  80

Gln Gln Ser Pro Ile Asp Leu Asn Ile Glu Gln Ser Lys Tyr Thr Gly
                 85                  90                  95

Leu Asn Glu Gln Leu Ala Glu Ala Thr His Gly Leu Arg Gln Met Arg
                100                 105                 110

Gly Glu Asn Leu Glu Gly Leu Ser Val Glu Glu Leu His Gln Met Glu
                115                 120                 125

Arg Lys Leu Glu Ala Gly Leu His Arg Val Leu Ser Thr Lys Asp Gln
130                 135                 140

Leu Phe Thr Gln Gln Ile Ser Glu Leu Gln Gln Lys Gly Thr Gln Leu
145                 150                 155                 160

Glu Asp Glu Asn Arg Arg Leu Lys Glu Gln Met Pro Gln Val Leu Thr
                    165                 170                 175

Ala Gly Thr Met Val Val Gly Ala Gly Ala Glu Asn Ile Leu Thr Glu
                180                 185                 190

Asp Gly Gln Ser Ser Glu Ser Val Met Thr Ala Leu His Ser Gly Ser
                195                 200                 205
```

Ser Leu Asp Asn Asp Asp Gly Ser Asp Ile Cys Leu Lys Leu Ser Leu
                210                 215                 220

Pro
225

<210> SEQ ID NO 197
<211> LENGTH: 225
<212> TYPE: PRT
<213> ORGANISM: Zea mays

<400> SEQUENCE: 197

Met Ala Arg Glu Arg Arg Glu Ile Arg Ile Glu Ser Ala Ala Ala
1               5                   10                  15

Arg Gln Val Thr Phe Ser Lys Arg Arg Gly Leu Phe Lys Lys Ala
                20                  25                  30

Glu Glu Leu Ala Val Leu Cys Asp Ala Asp Val Ala Leu Val Val Phe
                35                  40                  45

Ser Ala Thr Gly Arg Leu Ser Gln Phe Ala Ser Ser Val Asn Asp
            50                  55                  60

Ile Val Asp Lys Tyr Ser Thr His Ser Lys Asn Leu Gly Lys Ser His
65                  70                  75                  80

Gln Gln Pro Ser Ile Asp Leu Asn Val Glu Gln Ser Lys Tyr Ser Gly
                85                  90                  95

Leu Asn Glu Gln Leu Ala Glu Thr Asn Gly Leu Arg Gln Met Arg
                100                 105                 110

Gly Glu Asp Leu Glu Gly Leu Ser Val Glu Glu Leu His Arg Met Glu
            115                 120                 125

Arg Lys Leu Glu Ala Gly Leu His Arg Val Ile Ser Thr Lys Asp Gln
        130                 135                 140

Leu Phe Met Gln Gln Ile Gly Glu Leu Leu Gln Lys Gly Thr Gln Leu
145                 150                 155                 160

Glu Asp Glu Asn Arg Arg Leu Lys Glu Gln Met Pro Gln Val Leu Thr
                165                 170                 175

Ala Gly Thr Met Val Val Ala Ala Ala Glu Asn Ile Leu Thr Glu
                180                 185                 190

Asp Gly Gln Ser Ser Glu Ser Val Met Thr Ala Leu His Ser Gly Ser
            195                 200                 205

Ser Leu Asp Cys Asp Asp Gly Ser Asp Ile Ser Leu Lys Leu Ser Leu
        210                 215                 220

Pro
225

<210> SEQ ID NO 198
<211> LENGTH: 225
<212> TYPE: PRT
<213> ORGANISM: Zea mays

<400> SEQUENCE: 198

Met Ala Arg Glu Arg Arg Glu Ile Arg Ile Glu Ser Ala Ala Ala
1               5                   10                  15

Arg Gln Val Thr Phe Ser Lys Arg Arg Gly Leu Phe Lys Lys Ala
                20                  25                  30

Glu Glu Leu Ala Val Leu Cys Asp Ala Asp Val Ala Leu Val Val Phe
                35                  40                  45

Ser Ala Thr Gly Arg Leu Ser Gln Phe Ala Ser Ser Val Asn Asp
            50                  55                  60

```
Ile Val Asp Lys Tyr Ser Thr His Ser Lys Asn Leu Gly Lys Ser His
 65                  70                  75                  80

Gln Gln Pro Ser Ile Asp Leu Asn Val Glu Gln Ser Lys Tyr Ser Gly
                 85                  90                  95

Leu Asn Glu Gln Leu Ala Glu Glu Thr Asn Gly Leu Arg Gln Met Arg
            100                 105                 110

Gly Glu Asp Leu Glu Gly Leu Ser Val Glu Glu Leu His Arg Met Glu
        115                 120                 125

Arg Lys Leu Glu Ala Gly Leu His Arg Val Ile Ser Thr Lys Asp Gln
130                 135                 140

Leu Phe Met Gln Gln Ile Gly Glu Leu Leu Gln Lys Gly Thr Gln Leu
145                 150                 155                 160

Glu Asp Glu Asn Arg Arg Leu Lys Glu Gln Met Pro Gln Val Leu Thr
                165                 170                 175

Gly Gly Thr Met Val Ala Ala Ala Glu Asn Ile Leu Thr Glu
            180                 185                 190

Asp Gly Gln Ser Ser Glu Ser Val Met Thr Ala Leu His Ser Gly Ser
        195                 200                 205

Ser Leu Asp Cys Asp Asp Gly Ser Asp Ile Ser Leu Lys Leu Ser Leu
    210                 215                 220

Pro
225

<210> SEQ ID NO 199
<211> LENGTH: 183
<212> TYPE: PRT
<213> ORGANISM: Zea mays

<400> SEQUENCE: 199

Met Ala Arg Glu Arg Glu Ile Arg Ile Glu Ser Ala Ala Ala
  1               5                  10                  15

Arg Gln Val Thr Phe Ser Lys Arg Arg Gly Leu Phe Lys Lys Ala
                 20                  25                  30

Glu Glu Leu Ala Val Leu Cys Asp Ala Asp Val Ala Leu Val Val Phe
             35                  40                  45

Ser Ala Thr Gly Arg Leu Ser Gln Phe Ala Ser Ser Ser Val Asn Asp
 50                  55                  60

Ile Val Asp Lys Tyr Ser Thr His Ser Lys Asn Leu Gly Lys Ser His
 65                  70                  75                  80

Gln Gln Pro Ser Ile Asp Leu Asn Val Glu Gln Ser Lys Tyr Ser Gly
                 85                  90                  95

Leu Asn Glu Gln Leu Ala Glu Glu Thr Asn Gly Leu Arg Gln Met Arg
            100                 105                 110

Gly Glu Asp Leu Glu Gly Leu Ser Val Glu Glu Leu His Arg Met Glu
        115                 120                 125

Arg Lys Leu Glu Ala Gly Leu His Arg Val Ile Ser Thr Lys Asp Gln
130                 135                 140

Leu Phe Met Gln Gln Ile Gly Glu Leu Leu Gln Lys Gly Thr Gln Leu
145                 150                 155                 160

Glu Asp Glu Asn Arg Arg Leu Lys Glu Gln Lys Ile Ser Ser Leu Lys
                165                 170                 175

Thr Gly Ser Arg Leu Asn Leu
            180
```

```
<210> SEQ ID NO 200
<211> LENGTH: 363
<212> TYPE: DNA
<213> ORGANISM: Zea mays

<400> SEQUENCE: 200
catacaaatt atatatatat attttaaata tcaaatcttt ataagaatga tgatccactg       60
tccactgctg cccacttccc acgcccaaaa caagttcacc tccgtggcgc gtgttccgaa      120
aagtcctctt gttgtgggcg ggagaatgga ggcgtaatat ttcggcgtcc ccgaaatttg      180
cttgcacctt attggccgag ccaccoctcc cacggatcgt gccctgctgg caacattgca      240
gccatcggtg ccoctctaga tccaaccatc cactgtcctc gcacgcggat ccacgggccc      300
accagcctcg gcagccgagt tgtttaaact ttataaatac ccgtcgccgc ctgctacttt      360
ccc                                                                    363

<210> SEQ ID NO 201
<211> LENGTH: 3912
<212> TYPE: DNA
<213> ORGANISM: Arabidopsis thaliana

<400> SEQUENCE: 201
acaccaataa aaatacacag caataaaatc gctacgtata tatatatata atatgtatta       60
tctattacaa gatagtaata gagtatagca agttgtatca tctaacaaac tatgcgaata      120
aaatttgaac attgtgacat gtagatgtag tgtaatttag ctaagtgctt atcatcagta      180
acatagaccg acttaacttt ttacgaaaaa aaaaagtaa catagaccga aaaaatgcat      240
atcgtaaatt taatggaaaa cacaatttac gataagtaaa aaacaaaaag aaattacgat      300
aagtcgagaa aaatgcaaca aattgagata agtattgat aaaaccatga aagtgtcggc      360
gtatgtaaat gcggtgatta atgtgatcat tagagcgtgt gtgttaaacg cggcggtttt      420
agtggagatt gatcagctga taacactctt accgggacga atctaattcc atattcatgg      480
cttgttaaaa cctaagacat acgcaatctc taatttgcta gtatagttag ttctatatta      540
tttttcgact aataatgtaa acatatgatt attaagtcgc aaaagagtg cttaacaacc      600 aaaaagtgga ttaattaact tggtgggaaa agttacaaaa cctttaatga ttactctttg      660
taccaagaat agtggcgaag cactataaga gcagagaaaa gaagctcaat aatgtactaa      720
aagttgtaga ttttttacagc ttaaatacac caaaattaat agaaaagttg gtaatttttt      780
aattcatggc tactgattta gattttagaa acaatagta gtatcattgt cacatcttaa      840
acacacaata ggtatgtttt aaatcaaagg ccgtagttaa tttgtcaaaa atgtatgcat      900
ttggtatttg gatgtctccg aaaggatgga tatatggact tgttagataa tttcatacct      960
cagtatcaat agtcatggag cccaaattgc tcaaaaacat attttttaatt ccaagacttt     1020 gatgaagacg taataatgag tccaatgggc catcagatac aatgttcgga atttaacggg     1080
tttgttagtt ataagtattg ggcttgacct atctggttca atgatatgta ggaacaaccc     1140
aatttgcaaa gctttattaa aagactcttt agttgtcgtc aaggtttaac ttgtagtagt     1200
tggtaagaaa ttctacgtga aataggcaac attacaaaaa caaaaatcaa ttcgaaatca     1260
tacaaaacga aaccaagtag taaccaacta cactattatg acattaatga ttagacattc     1320
ccaaatcata caagttcctg tcatgaagga aacaatggtc cgtatttgca aacgattaca     1380
aaaattcaaa ccaaaaatga aaaaacgagt taaattattt ggtttataaa aatagtaatg     1440
tcaacagaag actagattgg gaaacctgaa gcgaacagag ctttaaaaa cgagtttgaa     1500
```

```
cggctgggat catttggtac aatacccacc gtaagtttgt ttaccctagg gatgcaagcc    1560
aaaggcccaa atcagttact acttactgct acaaccatcg tctcagcttt ttgtctcagc    1620 ttttttactaa tgaagcatac aatttcttgg gcatgtcaca tctcgacacg tgtccactat   1680
tctcttctct tattggctac tcgttcgtag gcttctgtta atagatgatc tctctataac    1740
tctaacagtc ttttctttct ctttatttcg ttttggtatt ttaagtttca aattgaaaat    1800
aataggagga aaagtctagt tttaaatatt gttttttttac aagtgaacgt gaaccaattt   1860
acctcttttt ttttatatat cctatcggct aatctggtta gtatcggtag aaatgcaccg    1920
aggtgctaca gagattaatg ctagggatag tcagaccgct tgtatttctg actatcaagt    1980
aaatctacgc ccaactcaca tatttcccaa acaaatgtga tttttttttt tttttttttt    2040
tttttttttt ttttgtaaca aatgtgattt tgttttcaag gaaaatagaa cttacgtttg    2100
ggaatttcac ccttcactaa agcttccttc tgccattaga ccacaaaggc ttgggcaatt    2160
taccattttt gtaaaagtag aaaacaaaat gcctaaaatg ttcatacttc attacatcaa    2220
caaggttatg cccacgatat agaggcatgt aacatttata tatatagtgg aagaagccta    2280
cgagctttat taataagtat aaactctgat tattaggtaa ataaattact taaaacgatt    2340
actcaactga caaaaccgta gttgaataat aaggttacta tgaataccga ttgaatattg    2400
caaagccgga attgaaaaat atataacaga tcaaatgttc aagtgtggtc ataattctca    2460
cataggtcat atagctgaac ccatgcatct atttactagt ctatagaaag tactagagac    2520
gcatacagct gaacctactc tattcttttta ttaattttgg ttctcgtgga tacaaaattc    2580
ctccaacatt tattagaacg aataaaacca atatgatgat gattagttat tggtaaacat    2640
ataaacgttg agtaaacttc aaaatagatt gaagtactat taagacttgc attttttccc    2700
cttgggttat attcttgaat cgtttcgaag tattttaact ttcaagaata gaaggttcct    2760
caactataaa caattacatt aatcaaaacc atttctatgt aaacaacata attttgtat    2820 attttagtct tccccaaaag tttgaccgat agggcggttt agaccgtata gtacgactgt    2880
acaacaaaaa ggactctgga gacctaaaga tccaaaacta tgcaaaataa agatacggtc    2940
ggaccaattt aatctaacaa aaccaaatcc ttatactaaa ctatttaccg atacatttcc    3000
atataacaca gtacacacaa ttaaatcaaa cattattgga agaacaagat agaatattgg    3060
cttaatctcg aacgattaga gttatcctag agcctcggag cttttgtcac atataatata    3120
aactatggta tatataaaca tgactctcat ttgtatttat cgcaaggtac aattccacca    3180 attttttttcg tcccactcat acagctttaa ttgtgaaatc aatccataaa aaaccaacat   3240
gtgacatggt ctctataact ataactataa gatagtaaaa aattcacatc aacataaaag   3300
aaaaccaatc atattggcta aaaaaaacta acggtcgaaa aacgtataac cacaaaacca    3360
aaccggtcca accggtgtcc ccaatcacta tcaaagcatt aactaacttt cacaaggaaa    3420
agcatagttc agtttctcta catcgcttcc catcctctta accctgttta ctcgaatcat    3480
ccaccgttgg atcaaacacg cgctacaaat ctagcgcgtg accgaggttt ttacacagtg    3540
gaatattacc atgcattgga aagcggcgtc tacaacaaac ggcgggtcat gtcaccgtca    3600
aaatcaacct tcttaattc ctaacgccgt tacttatctc cgtttactaa aaatgttaat     3660
gcgtgtgaga gtgaagatca tatactaatt agaagtggct aatgttttaa cgtgacatta    3720
ttatcatagt taatggttcg atcagagttt taagtagtaa atgatataag tgtgtgtata    3780
taattgcata catatatact ctcacactct gacagatttg tcgtggtctt agtattctct    3840
ttcatggcta gttatatagg gctctagtac attatctctc tctcccatt tctctgtctc     3900
``` tctcttctttt aa                                                            3912

<210> SEQ ID NO 202
<211> LENGTH: 1600
<212> TYPE: DNA
<213> ORGANISM: Zea mays

<400> SEQUENCE: 202
agctcgtaga gtgaggccga ggcagtgagc caccgtgtgt acgtacgcac gcactggtgg          60
tactgaaaaa caaaaggtgc gcgcgcggcc gcgaatatta tgcaggctgc ctgccgcgcg         120
tacctagcta gctacgactt tcaccctgtc catgaaacga tcatggcgtc ccgaagaaac         180
cgtacaaagg ctactactag tactccgcct gtgtgaaaaa catggcgtac atttcgcatc         240
ctgaattcgt aacacatgtt caatttctta aataaaatga atcaacagga aataaaaaag         300
aatttgggtg tttcttcttt ctgtctgaac tagtgtattt tagatgcaag ttaatggaaa         360
cagggagttc tcgatttaa aaatattcc ctccgtttct ttttagttgt cgctggatag          420
ttcaatttta cactatccag cgacaactaa acaaaacaa agggagtact aaagcaaaaa         480
aaaaactgac atatgggta agacatctcc tgacattata ttaagaatag cttctcacat          540
aagtcgagaa aactcttgaa tcccttcctc acacatacat agcggtaccg tagctcatat         600
gagaaacgac cgagacagac cggaccatag atctacgctt tgacgtggga caaacgagga         660 gatttttaa ccacgtccta aaattcgctc ctacggagga cttaggacct aagaaatgat          720
acatagatca actaaccatc tcggttagag gaattctcga aaaaaaatac tagagcgagc         780
aatgatgcac tacctagtga tactatggac cggtgctata tggcatggtt gcatgggtag         840
ccttttgcag tttgcatcaa gcagggagac agacaggggc ttggcttggc catgctagac         900
gttgcgggtg cagttgccac aaggggagcc tgccattcca cacacctcct actctgcatg         960
cgctctctct ctctctctct ctctctcaaa ttctcaacaa gtgttgaagc ggccgaagct        1020
agagccttcg ggggtgtttg gtttgaggaa tcatttaatc caaaatgtag tgatgcatca        1080
tgggtccatt cctcaaattt ggtgggatga cctcattcct catattagta ctaactaaat        1140
aactataagg aacgaggtga tgatggatca actcaatcca ttccacaaac caaataaaaa        1200
agtgatgagt gagaagacga tggattagat cattcctcaa accaaacagc ttattcgtgt        1260
gtcaacttca cttgtctctc tccaaaagat atcgtcgtat cccatgatcc ttcctccgg         1320 cgccaaccta tatctcacca tgcacctagc acgcagctac gcgctctctc tctctctctc        1380
tctctctctc tctgcatgct agctagcttt cctctagcct ctatagctcc tatgatatgc        1440
accccggcct ccttataaac cctcctcaat gcctctccct tttccaaggc aaggccaagg        1500
cggcaaaccc ttccctcctc ctccttggcg cagaccggag agatcacagg agctcaggaa        1560
ggccggtgtg accagctgct gaggcatggc ggccaacgtg                               1600

<210> SEQ ID NO 203
<211> LENGTH: 2000
<212> TYPE: DNA
<213> ORGANISM: Zea mays

<400> SEQUENCE: 203
gttctatgag gtggaccaat gaaatggcac acaccatctg tgtcagcttc aattatatat          60
taacaatcaa ttttgctatt tgatatgata tttctttaat attttttatac ttaaatctca       120 accacgaagt ttttaattgt atttaactaa aatcagtcag taatctttcg atgatcaaag         180

```
gtaaccaact aagaaggtta cttgcaagga accatgacac ttgtaatggt ggttgtaaat    240
acagatacta catcatcatc tgcccataag gtattctaga atacttagcg cagtttacat    300
gcaacatgtg agtacatatg gtggttatgt aggagacaca actggttgct acatggcaac    360
ttcaacaatt tgttcagtta ttcatgcatc aaaaactatt gtcattccat caccgcaatt    420
tggttggcct aggtagttat tcagagcttc tagtattctc actttaaaat catcaatgaa    480
cacatacata tagcttgttg tactcataaa actatagcgt aaagcaatat atctactgct    540
cattcaagaa tatatgtggt tttataaaga tggaccaatt aaaggtgcac tcaatctatg    600
tcatctatgg tgaaaaggtg aaacttctat atatattaac aaccaatttt gctacatgat    660
acgatatctg taataataat tttatactta attatgcacc gctatatttt taaattatat    720
ctttatctaa aaccgaaagc ttttccgtga ttaatggtaa ccggtataga aggttgctta    780
aaaggaacca caacacttgg catggcagta gtaaatatag gcactatacc attgtctggc    840
cacaaaggta ctttagcaca ctccgcatat ctttcgtaca atgtgttgat acatatggtg    900
gatatctaga ggacattgct tgttgttaca tcacaacttc aacaattata gtcattcatg    960
catcagaaat cactggcatt ccttcaccac aatttgtttg gcccaagtaa cttattaata   1020
gcttttggta tcccccctct ctaaaatcac taatgataac atacacatag cttgatttac   1080
tcatgaaact atagcataaa gtaatctatc tagtgcccat tgaagaatat acgtggttct   1140
atggagatga accgatgaaa cgcgcactca agctatgtta tcttcggtgc gaaggcacaa   1200
cttctatatt gacatccaat tttgctatct gatatggtat ctctaataat attttttatac  1260 gtaaatatcc gccgttaaat ctgcaccgct atgtttttat aattatattt atttgaaacc   1320
gaaagctttt ccgtgattaa tggtaaccgg ctaaaaagat tacttataag aaagcttaag   1380
atctttaaca tgaatgaatg ccatacatca aggatactat gccatcctat atatgtccac   1440
aaatatactc tagcatgacg gtaatataat gggatatata taccctcata aatcatggat   1500
actatttgta aggactttgg tatttgtaca gtcattcatg catcagaaac tactaaaaag   1560
caaaatgaaa agttaatcta tgtagatttt gcattgcatt cccctcaacc aagcaagcat   1620
ccagaggaac gaaggacaaa tgttattcaa ttttgtattg ctttccctc aaccaagcaa   1680 gcagcccaaa gaacaacaaa tggcattccc atgagagaaa aaaaaatac ttgtaggtgg    1740 ggccaccctc ccctacctat atatacccct gttcacgccg ttcccaagac cacaccacca   1800
gtccatccat cctgcgctgc gctgcgctcg tgacaagcat cgcaagcagc tcctcctcct   1860 cccctgtag ccaacacctt cctgttccgg gcgcagtagc ggctgtcggc cctcgatctg   1920
acgagccatg acgaagcacg ccgcctactc cagcgaggac gtggtcgcgg ccgtggcggc   1980
gccggcgccg gccggccggc                                               2000
```

<210> SEQ ID NO 204
<211> LENGTH: 1860
<212> TYPE: DNA
<213> ORGANISM: Zea mays

<400> SEQUENCE: 204

```
tactccgcat ggcacaccgg acaatccggt gctacatcgg acagtccggt gaatcatagc     60
ggagaggctc cccgaaaacc cgaagctagt tagttggagt tgatccaccc tggtgcaccg    120
gacactgtcc agtggcacac tgaacagtcc ggtgcgccag accagggcag acttcggttt    180
tcattgctat tttcatttga acccttttctt ataactttgt attggtttat tgtgaacctt    240
tggcacctgt ggaacatata ttctattaca aactagttag tccaataatt tgtgttggtc    300
```

```
aattcatcca ccaacattta ggaaaatgtt tgaccctatt tcccttttcag tagtcattta      360 aacacgacaa tattttcacc acataaatgc atttaaaata tatacgccta gtatttcgaa      420
attcaaactc tctccatcgt agttctcatg gtattttttc aaaccgacgt taaattcatt      480
atctaaaagt cgtcacaaga aatttgttta gtgggtgttt ggtttatata gagaagagat      540
tgattttttg tccctcaatc ttcttcaatt ttttatcgct aaattagcaa atacggaaac      600
taaaatacat atgtttgttt ataattataa tatgtacata ttataataatt caacaaaatt    660 tgaactaaca gctagttaaa aatttattag attataatat aatctagata tattataatc      720
tcaaaccctt aagaactaaa aaaaattagt aggggtgggc acatttttac cataaaccga      780
accgaaccga accgaaattt tggttttttt ggtagttcgg ttcggtttcg gttttttgtat    840 ctaagaagtt cggttttcgg tatcgtaatc ggttttcacc gtataccgaa ccgaaaaaac      900
cgaataccaa actttatcaa ttctcaaatt tgactattcg attatgtgaa ctaattgtgt      960
gatacaatta aattgttatt cacttatttg tatgtgatgt atgatgtata tctaaatatt      1020
tgtacctata taatttttac tttttaaaat tatatgtaat ctatcatgta aacttgttgt      1080
atgtattgtc ttgattataa gtttggtatt cggttttttac cgaaaaatcg aagtaaaaaa    1140
ccgaaaccga acttctcggt ttttcatttt ctagaaaacc gaacggtttc taatgtttga    1200 aaaccgaag tttttaaaa ccgaaaaacc gaaccgaagt ttagaaaaaa accgaatgcc        1260
cagccctaaa aattagtacc ccataagaac taaaaaaaga taaaatgact aaaaattaat    1320
cagttgaaac caaacctatt ttcccccaca cctcacggta ttgtttcgca ttccaagttt    1380
gaaacacgac tggaaacaaa acccaaaacg actggaggga ccgagcttgt gctgagcagc    1440
agagatggcg ggaaatgctg cgtctcccgc ctcagtttcg gatgcccgc cctttcccaa      1500 accggccacc gccgccgccc gtgtctcccc accgacaggg gggtccaatc cttaaccacg    1560
gaccagggcc cccacctgtc aggtggacct tccgaagcaa ggatcggcca ggcgggaaaa    1620
catttcgcgg caggtggcgg ttgcgccaaa tttctccctc ccttttccgt tcggcgtccc    1680
caaacgcctc cctattaatc tccccgcgtt ccccttccct cgcgccgccg ctccccccctc    1740 ccaaagctcg ccccgctccc agctagggtt tcctcttccc atccacagcc gccggggcgc    1800
cgccgacgag gacagcgccg ccacgatgtt ggagttgcgt ctggtgcagg ggagcctcct    1860
```

<210> SEQ ID NO 205  
<211> LENGTH: 1000  
<212> TYPE: DNA  
<213> ORGANISM: Zea mays
<400> SEQUENCE: 205

```
aggcggggga acgaacgcgg gtgtgggcgg gcgaacggtg tggattcaca gaagcgaacg      60
gatggtacag attcaccgaa ggcagaacac aaaaaggcag gctactattg cttacttaat    120
aagtagtaga gatttgcgcc catcttcaat gttaaggaaa agcataacgt ttgtgctgcc      180
gcgataattg ctgtctgcgt ttgggtccca ccgccagggg gccggtcgac gtctccgtcc      240
acgggtcagg tctcctcccg ctgcccgacg caaggagcca ttgaccaccc aagggcccct    300
gcctaggacg gccccacctg tctgtcgtgc cgctgatcgc ccgtcgctga tggggcccgg    360
ccagcccacc caccccctccg cacgtcacgg cgtaacgcgc ggcgcgaccc atccgtcccc    420
tccgtgttct gtccgcatgc gcgcgccgcc cgtaatttct ttccgccgcg agtcgcggcg    480
cccgctcgtg gccggtgcgc gcgtccacaa ccgccgccac cgccttccca cttccaaata    540
```

| | |
|---|---|
| cgcctgctgc cactttcccc attcctgtct gaccatcccc acgcccccct gctgtggcct | 600 |
| ctgctctctc ctgccagttc acctgctgcc tccggtgccc gctgctgtgc ctcgctcgct | 660 |
| caccaccacc aatcgccacc ccgtgcggca gccgcgctgc catcccgcgg aggactggag | 720 |
| gagcacgcat atccgagcct tccctgccgc gtcgcatgga ctcatgctgt cgcgggccgc | 780 |
| ctcccgcatc gcctccaacc gggtgcctgc taactggcc gattttcttc ctcgcgtagc | 840 |
| cccattccgc agcacaaata gcgcgtcact ttcccaattt ctatcgcgtg cccccctccc | 900 |
| gatcctgcca tttcgtgcat cctgtagcgt ctggcagtgc gggggtcatc ggggatggag | 960 |
| tgggtggaca ggaccaaggc ctccgccgcc gccgccgcag | 1000 |

<210> SEQ ID NO 206
<211> LENGTH: 1528
<212> TYPE: DNA
<213> ORGANISM: Oryza sativa

<400> SEQUENCE: 206

| | |
|---|---|
| ggaagctaac tagtcacggc gaatacatga cgacatcggc ctacaacgca caacttcttg | 60 |
| gcataaaagc ttcaatttca atgccctat ctggaagccc taggcgccgc gcaaatgtaa | 120 |
| aacattcgct tcgcttggct tgttatccaa aatagagtat ggacctccga cagattggca | 180 |
| acccgtgggt aatcgaaaat ggctccatct gccccttgt cgaaggaatc aggaaacggc | 240 |
| cctcacctcc tggcggagtg tagatatgtg aaagaatcta ggcgacactt gcagactgga | 300 |
| caacatgtga acaaataaga ccaacgttat ggcaacaagc ctcgacgcta ctcaagtggt | 360 |
| gggaggccac cgcatgttcc aacgaagcgc caaagaaagc cttgcagact ctaatgctat | 420 |
| tagtcgccta ggatatttgg aatgaaagga accgcagagt ttttcagcac caagagcttc | 480 |
| cggtggctag tctgatagcc aaaattaagg aggatgccaa acatgggtc ttggcgggcg | 540 |
| cgaaacacct tgataggtgg cttacctttt aacatgttcg ggccaaaggc cttgagacgg | 600 |
| taaagttttc tatttgcgct tgcgcatgta caatttatt cctctattca atgaaattgg | 660 |
| tggctcactg gttcattaaa aaaaaagaa tctagcctgt tcgggaagaa gaggattta | 720 |
| ttcgtgagag agagagagag agagagagag agagggagag agaaggagga ggaggatttt | 780 |
| caggcttcgc attgcccaac ctctgcttct gttggcccaa gaagaatccc aggcgcccat | 840 |
| gggctggcag tttaccacgg acctacctag cctaccttag ctatctaagc gggccgacct | 900 |
| agtagctacg tgcctagtgt agattaaagt tggcgggcca gcaggaagcc acgctgcaat | 960 |
| ggcatcttcc cctgtccttc gcgtacgtga aaacaaaccc aggtaagctt agaatcttct | 1020 |
| tgcccgttgg actgggacac ccaccaatcc caccatgccc cgatattcct ccggtctcgg | 1080 |
| ttcatgtgat gtcctctctt gtgtgatcac ggagcaagca ttcttaaacg gcaaaagaaa | 1140 |
| atcaccaact tgctcacgca gtcacgctgc accgcgcgaa gcgacgcccg ataggccaag | 1200 |
| atcgcgagat aaaataacaa ccaatgatca taaggaaaca agcccgcgat gtgtcgtgtg | 1260 |
| cagcaatctt ggtcatttgc gggatcgagt gcttcacggc taaccaaata ttcggccgat | 1320 |
| gatttaacac attatcagcg tagatgtacg tacgatttgt taattaatct acgagccttg | 1380 |
| ctagggcagg tgttctgcca gccaatccag atcgccctcg tatgcacgct cacatgatgg | 1440 |
| cagggcaggg ttcacatgag ctctaacggt cgattaatta atcccggggc tcgactataa | 1500 |
| atacctccct aatcccatga tcaaaacc | 1528 |

<210> SEQ ID NO 207
<211> LENGTH: 1280

<212> TYPE: DNA
<213> ORGANISM: Setaria italica

<400> SEQUENCE: 207

```
tccaccgatc atcacacaca gccagtagtg ggggtgggcc aagcaatcag gcacccggca      60
atgcgagctg atgcgtgatg atggtgctac caacaaactg actataaaat ttctgatttg     120
aaagggattg gcctcgatat tttattagct ccccggcttt tgtcacgaca cgttagcatg     180
cgtgccttct agaagctagt ccgggtatta ccgctagaaa gttcccgaaa tgaagcattt     240
accacccgta aagctcattt ttctttatga tgagtagaca cggtaccaac attgaggacc     300
gattggttgg ctcccaaaat ctgccctgcc aaactagggc aagttcataa attttgacat     360
tcgcttggtt ggcaatcaat taaatcctat tctaaaattc ttgcctaggt tttgatataa     420
catgccctat attttggtct actcaaattt tggtatggta aattttgaac accaacaaat     480
caggctatta tttatcttat ctctttctca atttcattac acagcaaggc agtaattaaa     540
aggaccgtat atacaatgga tgtaagaata aaatgtataa gtagaaatat attggcatgc     600
ctcgtgctgg tgcatgtcga tatgctctca attagaagtt ggagacaggt tatgcttagg     660
atagtcccaa cctatgatat ctgtgtgtct atactgccac ataagtaaga catcacttta     720
gaaattacat tctacaacct ataatttctt agtgtggatc cttaattaat tcatcatctc     780
tcctctcaat tcctcatcaa ttatgaagac accatcttct tccaatgcaa atttaacact     840
gtctaggatc taggttcagg tgttgatact gggtcttgca tgagatccag tttcttgttc     900
ttccaattct ctctcattta atatataatc acataagcaa aagatcctat gtagctgcac     960
aattaatgct atggaaacta tcctaatcgg agggttggga ctgctcctgc ctatggcggc    1020
ttattcccca tttgcctaac ctgaaaatcg aaagggagtg catgacaggg caaacactag    1080
tgttgcctgc atcaataatc gtccatgatt atatagaggt agcatgactt ttttaggcgt    1140
cgtgtcctaa tcaatcagaa aagaaagcca acctaatcgc tatgggccgc aaccaccgat    1200
gcgactatgc gagtatatgg aacccgttgc tactcccca ctatatatcg tggagtctga    1260
tggcaatcca acggcagacg                                                1280
```

<210> SEQ ID NO 208
<211> LENGTH: 1435
<212> TYPE: DNA
<213> ORGANISM: Arabidopsis thaliana

<400> SEQUENCE: 208

```
taggaaaaaa gtttatattc ctacccaaac tttcggcacc agagacaaat taggtttgtt      60
cagaaaatca gtcgctcatc gacagactta acaccacaaa atcatcagaa tttctttggg     120
acaaaatgga aaatgttctt cacggctcca cctaccaaaa tttcgatatc aagctcaaaa     180
gcatacacaa actataacta attccatagt tacgtaatct taacttcgaa ttcaacaaca     240
catgcatgca tcgactgaat cttcaacaaa tgcaatcaaa cacacaaaat tgctaccaaa     300
aaaatatgat tttttttttta tgatttcaat tttcatccgg cacttagtcc aaaacttttt     360
ttgtgtgtca acatttttta aaaaatctt taaacggata tctgatctaa gagcatgttc      420
ataggtgata cttacaaaat atttttaaga aattttttag tattatttat aatgtttgtt     480
taataaatat atataagatt ttttgctttt atcaaatgtg accaatcaga agaaaccacg     540
tcagatgata ctgatatgac aaatatgata ctgatcaaac atattctaat tgctttacta     600
atataaaaat aattttttgga cttgtgatac tctaaaaata tcacccatat acatggtcta     660
```

| | |
|---|---|
| atatatggat cgtaaaaaac tcatatataa tattaataag tagtagaaga gcgtagacca | 720 |
| tgtcctgggt cgtcgtccaa atgaccacaa gaagatttca aaacagagga aaatatttct | 780 |
| cattaaataa gttttcctga cgcataagat aacattatta caagattcag aaaaagaaag | 840 |
| gtgaaaggat aatgtttctc ctactatata agatgtgtac atctgaaaaa atatgaatat | 900 |
| atttgtaacg tttgactgtt attacatgat taatacgata taaatattaa cattttttt | 960 |
| caaaataaaa gtaatatagt aaggaaatga aaagaggcat gaagcatgcc tctttttttg | 1020 |
| gtcggctgcc gtttacaatt gccaattgcg atagttactc ttcttgcgtg tacgactttt | 1080 |
| gttttttttt acatattcgc caataatttg acgttttcta ttagtttgtt tgatactctg | 1140 |
| ttgtcttgct aaaactcaat aaaacattaa attactttct tgaatgaagc tggaacaaat | 1200 |
| ctaacataaa tagaaaatga tgggcaagtt gatgttattc gtaaatttat ttagattata | 1260 |
| ttatataaaa agcaatccaa ttatatatct catatataca atttcttatc ttactttgtc | 1320 |
| aatgtcatat acgtaactaa aacttgcgga aatagaaaat gccacgtgta tggtggacat | 1380 |
| aatccgaatc tctctctttc ttctataaat agtggccatt cccattggtt gaaat | 1435 |

<210> SEQ ID NO 209
<211> LENGTH: 1940
<212> TYPE: DNA
<213> ORGANISM: Zea mays

<400> SEQUENCE: 209

| | |
|---|---|
| caaatatcca ctcacagcca tacccgtggt tgcaacaaat atctatccac aaccatacct | 60 |
| gcgggtaaat tcatatccat gtacgtgctc attaggtttt ggacaggttt tgtatatatg | 120 |
| tcggatatga cagagacaat cattttcaac aactcaatag cataatcaat caaaattctt | 180 |
| cccaattta cctgaacaca caattaaaaa cttaataaaa aaattatata aatcacatg | 240 |
| tcttttaaca atcaatattc tcaacacgac aacatggaag acgcgtcgga ctagaagggg | 300 |
| tggagcgctg gggaccactg gggaagcgac agtgaggctc accggcagtg tggactaaag | 360 |
| atccgagagc agttgggcgg gcgactggtg tcggattgag ggacacgaag gggcgacgat | 420 |
| agtgtggact gaataaccaa gagcagttgg cgcgagcggt tggcgtagtc ttgaggtgta | 480 |
| ggcaagaagg gacaaccacg agcgtatgag gtgcgggttg tggctagggg cactagagat | 540 |
| tagaagggg agacgtctgc caggtgcgaa cggtacaggt gttgcggccc cgtaggactt | 600 |
| ggaaggggac acatgacgta gttcaagaaa ccagcaaggc tagaagggt gaccataagt | 660 |
| gggaaattag gagttcacgg agttagggtt tgctctttgt tgtgtaatat gagcaaaaca | 720 |
| aaaataaata aactatatgc tgatttcgga tatgcaacag gtaatccgtg ggtggaaggt | 780 |
| aatattctaa tccgtgtccg ctcgactttg gatctggtac gaatctgacc catgcttcga | 840 |
| aacatgtatc catgctcgtt tccattggat cctatggata tttgaatcca tgatcaaatt | 900 |
| tccattccta gatagctaga ttagagtaat gttccgttta gatgtcgata ttggagggtg | 960 |
| tggaattgaa ttgggttcaa ttacaaatca gccatgctat tgaaatgagt tgtaattcca | 1020 |
| atactaatgt ttggatgtca ctgaattgga gtttggaatt gtgtggtcta attccattca | 1080 |
| atacagagga gtaatgctct gtattaggag aggggggctc tagttgtagt ccaattccag | 1140 |
| gggattgggt atttgattcc aaatctcaat tatgtgcata accaaacaat agaattctag | 1200 |
| aaaagctgat ttcaattcct aattcggtgc tccaatatct acatccaaac agggtataat | 1260 |
| gcaattcttc gcttcctatg gatggtcttt tagatttgt attggctaat gatattagac | 1320 |
| gtttcttatt tttgtctttc gttgaatgtt tttcgattga tgtcggggta tgaatccatg | 1380 |

```
acttttttcca tcactagaaa atatactgtc agaaaaaata gtgctgaatt agtgaatttg    1440
atccatcata atggagttgt cattctactt tgcacttgca ctaccggcag cccgcagcag    1500
gacggctgac aagctcgcac taagtcatcg atttgtggtc actaatgcgg agctcgcact    1560
tgcgtgactc atcgagttgt gggcttgtgg ccttgtgggt ggaacggtgg aatccacctc    1620
aggatgccac agaaaaggt ttaaaaaaac tgttgcaccg agccaccgag agagcacaag     1680 accccacga ccgcaggtca agccgtactg gactggaccg gaccgacac acgcccagaa      1740 agccctgcag cagaactgca aagacacgg ccgcggcaga agagcccaaa tcacggccgc     1800
aaaagccacg cacgcggcgc ttgtcctgcg cggcgcacgg aaacccacct ccacggcggc    1860
accccgtgcg tcggctgctt gctgccccag tgccgccccg cgttcccttc gctcccgccg    1920
acaccgacgc cgccactgcc                                                1940

<210> SEQ ID NO 210
<211> LENGTH: 51
<212> TYPE: DNA
<213> ORGANISM: Arabidopsis thaliana

<400> SEQUENCE: 210
tatatcatcg ttctctctat aaactttata gaactttgtt ctgatttct c               51

<210> SEQ ID NO 211
<211> LENGTH: 1386
<212> TYPE: DNA
<213> ORGANISM: Zea mays

<400> SEQUENCE: 211
gaggtgcata aggctggcaa gacgacagtt aggaacgcat gcgagcgagg ttgacggacg      60
cgataaggtt agcgcatgcg tcgaacgcgg gctggcgagg gtggaaggca tgataaggct    120
attgggtagc gcaaaatgtg tagacagcgg gcgagtgagg atggcagtgg tggcatgcat    180
ggacgcggtt ggagcatacg cgacaagaat ggagcacgac gtagatttcg ggaggccgtg    240
gttggagcgc ccgcgggcga gatggcggcc atggttagag cgcccgtggt tacgggtggg    300
ttcatggcga gcggaggggt tgcaagattt ccagggcgct cgggtcggtt gcaagctcca    360
cggtggaggc gtgacggaga cgacgtgggg agggaggtcg tggggaaatt cggacgagca    420
gaggcgtggc aggtgtggca tggggaggga ggtcgcgggg agggcgcagg gaggtggcat    480
ggggagggag gctggggacg aagatgatgt gggcccagag ggacgcggga caaagaattg    540
cgtatgataa cgggttgatt cgtagaattt taggcggtat ttataaaaat gacgcaggac    600
agccattggt actgatactt taatatagta gagaagagat ataaattagg acgggtacaa    660
caagaccaca cgtactaaca tttttttttg tcacaggctg ctctaataca tatctctatg    720
ataagcgagc tagggatgct agcgtgtcca tttgattcct atataaatct ccaattatag    780
ctgtagcaat taatttaata aacacccaac aatagatcaa atctcatagc aaatcataat    840
catgaatgct ccaaaatcag ctagctggct ctcccttatc ttcgtttttc cttcttctcc    900
tgcaacgaaa agaaaaaaaa agaaaagaaa agaaaacggc cgcttgtggt actaactccc    960
aactacgcac ctaccgcgcg cataactctt ggccgcctgc cctcatcacc tccgcgtcgc   1020
cgtcgactca tccttatcct ccccatcacg ctcaccccgc gccgcaccg cgccatccgt    1080 actttcccgg ccgccccacc gctggccgcc ccgacgtgtc gcgccgccac cggaaggtcc   1140
cgggccgtcg ggcgggcaga gcgcctgcag cggtggaccc acgccacgct gacgcgggcg   1200
```

| | | |
|---|---|---|
| cgcgtccgtc caagaaacct gacgtaagca gtgacagaat tggcgccgcc tctcggcgtc | 1260 | |
| cacgtgtcgt ggtcaacctg tcagagtggg gctccgtgtg tgcgctaccg caggggcccg | 1320 | |
| gcgcacgggc cacacgtgtc gcggtcgacc gcggctataa atgcccggct ccgcactcgg | 1380 | |
| aacaag | 1386 | |

<210> SEQ ID NO 212
<211> LENGTH: 997
<212> TYPE: DNA
<213> ORGANISM: Zea mays

<400> SEQUENCE: 212

| | |
|---|---|
| gctgcttccg gtagcctgaa gcagaaaaaa actgaaagaa acatgacaga taattccctc | 60 |
| ggagaaactt ggcatgtttc ccgttggtca tgtaggacga cgataatgat aaattggtaa | 120 |
| gcaaagaaaa aggctactaa gctcgagcag tagaagctac ctagctcgtc gtaacgaaga | 180 |
| aacttctcgt ccttcaggta gacccttgct tgtttgcagt actttagtta gggttcggtc | 240 |
| tttaattctt ttgctgggca gcagtaaacg gagatgagaa gcgcgagctg atcattgttg | 300 |
| ccattctgtg caacgaagct aggggaccaa tgctgactcg cacgagggca tagttgctga | 360 |
| tggtcataga cgacgcgttc acttaaaata ataaagaatt ataaattgtt gtcataagtc | 420 |
| gtgcagccta atataggaga gtgcggcatt gctgtagcta attaagagag tattccggtc | 480 |
| atgcttgagc ttggagaatt tttgagggtc cgttcgcttg gagagtcgga gattttgag | 540 |
| ggcccgttcg cttgcacaat aataaacaaa gatttgttct agctcatcca aatctatata | 600 |
| aattaaagaa gtaattcggt taggaatcaa tccagagctc taattcttaa aaaccgaaca | 660 |
| gggcctgagt tgtttgtcta gacgacatta tctgattaag ttatttttcat cttcaatttc | 720 |
| aaatgtgatc tagcggcata aaacttgttg tctgacagat atttgacttc cacacgggcc | 780 |
| acagctcaat tacaaacata cttcaaacat caggcagagg cagagcacta gcagcattcg | 840 |
| ctacgtggcg gtgggcagca gtggccagca cattcgacaa ctgccacgga tcccgtacta | 900 |
| cttcaaacac gtatcgcttc cagaatccag agtcacacgt gtgcagctgc atgaacccag | 960 |
| ctcactccct aagaacagc tcgacgctca cctgtct | 997 |

<210> SEQ ID NO 213
<211> LENGTH: 1318
<212> TYPE: DNA
<213> ORGANISM: Arabidopsis thaliana

<400> SEQUENCE: 213

| | |
|---|---|
| atcaacaaat tactcctcaa tcacactcct atagaaaacg gtttaagcta tcattacatg | 60 |
| tctagttggt tttactcagc cctagaagtg ttgtttattg catcactttc cacgaagcac | 120 |
| aattttcctt ttttacaatc accagacctc acaggctcac acatatgctt tagagcacat | 180 |
| tctaaacttt gaactataaa agctgttaac actaatacac tatgcgttct ttttgctcc | 240 |
| aaacactttt gatccattat taggagacac tccacttaga aagattttct aatcctttgg | 300 |
| tcaactagga agttcaaggt ttttctaaac agaaattcat ttcacaagta atttaattta | 360 |
| taaggaaatg aatagagaaa tcaaatcatt gaagaactac aaaatataga ttcaaggtca | 420 |
| ggtctaagaa atattcctg aagctcaaaa aagagtttc ctctcacatt atagaattgg | 480 |
| cctttacttc aacattttcc cacctattcc acatttggtc agaacatttt taattacttg | 540 |
| tggatcaatt tccggttgaa atgggtttgg tgaatatccg gttcagttat atggtggccg | 600 |
| ttggaattgg cttattagtt gtggccgttg ttgaagccgt tggtattggt aagggagaag | 660 |

```
cagacttgtg gctatgagtc tatgaccatg actcgtgatt atggagctgt cttatgaccc      720
tgaccatcac cttgatctgg tggattccaa tgttttcttc ttcttctaat aaaatattat      780
ggtcaataca ggtgctaatt aagatggtaa taatttctta tgtttctgtg gtaaagtttg      840
attcaattcc gtagttttag ataatcttat ttccatacat aaattttata gttttatcta      900
ctttgttctt atgttttatc tctagccaag agttattatt attatcagaa gaagaaaaaa      960
aaaagaagca tatatacaaa aggtttaata aaatgtatta tacaaggcaa ttatccaaat     1020 ttttttttgtt ttggtttaca ttgatgctct caggatttca taaggataga gagatctatt     1080
cgtatacgtg tcacgtcatg agtgggtgtt tcgccaatcc atgaaacgca cctagatatc     1140
taaaacacat atcaattgcg aatctgcgaa gtgcgagcca ttaaccacgt aagcaaacaa     1200
acaatctaaa ccccaaaaaa aatctatgac tagccaatag caacctcaga gattgatatt     1260
tcaagataag acagtattta gatttctgta ttatatatag cgaaaatcgc atcaatac       1318
```

<210> SEQ ID NO 214
<211> LENGTH: 1500
<212> TYPE: DNA
<213> ORGANISM: Zea mays

<400> SEQUENCE: 214

```
acactttttat tatcgcgtca aatcagtacc tcaatcgata ttgtagccta gtgttcttat       60
taaatgggaa gaattcgagg acacactaat tccttgctaa cacacactta tgctccattt      120
ggatgtcgat attggagggc atggaactga attggtttca attacaaatc agccatgata      180
ttgtaatgag atgtaatttc aattctattc tttggatgtc actgaattgg agtttggaat      240
tgtgtggtcc aattccacct tatatagaag agggatgctc tgtattggga gagtgagttt      300
ctagttatag tctagcttcg ggaaattgag tctctcgttc caaatctcaa ttccatgtgc      360
aaccaaacaa tagaattctg gaaagctgat tccaattcct aattccgtgc tccaatatct      420
acatccaaac gggtgttaca taaatataga aatgacatat caaccatgca aaaccacatt      480
ggcgatgttg aacaaaggcg aacacccaca tactatgtac cgcacacggc atctctttct      540
caaaggtcga accacgtgtg ttccatgcat gcgtggaaca tgcaaggttg tcacgtatag      600
ggaatgatga cacacgagag cgcctacaag gcaacaaaca ccttacgtac cacgtagagt      660
gcattttgct accacctgcc accggatgac atgtatgcat gcatgcgttg tgtacgcata      720
cactgctgtc tgctggtgcc caaagaccat ctagaacagc atcttttaat tctccatttc      780
cctcacgcca ttgctagtgc cttgcacatg ctcgcactcc ctaacacatc ttcctccctt      840
tatttttcgt tgccaattgc tagttgttca aatgccacgt tttccttaca cagctgtagg      900
gcaccgtacc acgtagaatg cattcctcgc caccaacaga caaacacggcc gggcatatgt      960 acgtcttacg ccggaccatc accagtatat atgatgctag ggatcagtgg gcgcccttt     1020 tgcctcgtcc tcccggggcg gcattcctat gtcctaactg aagcaaccca cgcgccgcca     1080
tttctgttgc gaatgagtcc atggacatat gtgccaacag aacccctcgg aaggcaccat     1140
ctatctatct atctctcaag caatattata tttggcacct acgctcaagt acatagacag     1200
tgtgcacggc attgtgcagc tggaaagccc gcccgacacg agggctgcca aatcgacagc     1260
tccgcgccct tggaaatcct agtcacttgt tcacaattga ccaatctacc cttgaagcac     1320
acggtggatg gtactgccac atttggctta tagggggcata gaggacaatg aatgcaactg     1380
gagcgggaag gagagcttta atttgtaagt actcggtgaa cacggcacct gatgatgatg     1440
```

```
atgatggaca gcgaggaatt gttataaaag gcgcccgtcc ctcccatggc tcaagaacaa      1500

<210> SEQ ID NO 215
<211> LENGTH: 2000
<212> TYPE: DNA
<213> ORGANISM: Zea mays

<400> SEQUENCE: 215
aatgctagaa actacagggt ccaatatatg aaaatcaggg catggatgta attaatttac        60
aatagcagtg gacggcgggt taattcagta attccctagg ggcacttaag caaatatcca       120
tcgcaaaggg gtattgttgg atcccgaccg ttggatcaga tccgaaggcc gagaatagat       180
cgcgcccaca caactgcgtc gtgcactgac caccctccgg ttaagattcg acggaccaaa       240
tttaatgaaa tccaaaccac ccacagcccc acgatcagca atctacggtc cctcttaacc       300
cagatgaatc ggtatccgac ttctaatcta agcagttcct caatcgatca acgctccagg       360
gccttcttct atctcccaac gcagatcgag ctacggtcgc ttgcacccga ggaacgccga       420
cacagcgagc ggcggaccag cggttctggg taatgatttg gagcacaaac aatattggcg       480
cgacatagga atgatggcaa ctattaggtt gtgaccttac tagtgtcagc ggtgtgggca       540
gggtcgccca cgggaaacca gtgcgacggt gctcccggct tgttaatgac ggtgtgctgg       600
tcccgacacg gtgatgcccc aaacgccccc gccgtacgag aacaccgcag acgcccctgc       660
tcgactccgc cctcggcttc ccgcgcccac ctcgcacttc gacggccgca ccgaccctct       720
gacctctcct tttctctcct ttctcactcc tatcggtagc tacaacagaa gcgactccca       780
acgtggcgca aaccctcgaa gcatacggct ggggaaggtg gcagccaggt ttatatccta       840
ggcgcccgag gaaatcgtgt ggacggctgt tacgtttcgc ccgcggggcg cgattcgcgc       900
gaagaagact gtatgcgagg tagggcccac tagcagtgag ccatcaccca gggaagcgcg       960
catgcatcga ttgacacgcg accccaacag tcaggcgacc cgagtgtgca gacggtcgcg      1020
atggtgaaag tggctagctc gcgcggacgc gtaggggcat tgggccgaaa tgcgtttcag      1080
cggtccaact tctttttttc ttgtcttttt ttctttcctt ttcctttcta tttttagatt      1140
tcaaatttaa gttcaaattt tttgtggtga attttctaaa aatccacata tcagtatgaa      1200
aagaatttat atataaatct atttatttat atatttattt ttttttctatg ttatttccaa      1260 tttctaaaat gtaaattagg ttaaatcgcc atttggacac taatatatct ttattagtat      1320
tactattatt atatgcacaa ccaaataaac tccaacatga tgcatcgatt atttgtatgt      1380
cattggttaa ttattcactt taaatatgtt ccttaacgat tctcatgaaa cagaaggcca      1440
tgcacataaa gatgtatccc tttttctat attcccagag ttgggtatta caacattcat      1500
ctatgcattc taggatttca attactctca atcttttagt atttgttcct tcattgtcaa      1560
atcacttctc atctaactac tatgcttgtt taaccagcag aacaatacta caacaatatc      1620
catttataaa ggctttaata gcaaacttta catattcata tcatgttaag gttgtcacat      1680
gtgtaaaggt gaagagatca tgcatgtcat tccacataaa tgaaaagaat tcctatataa      1740
aaatgacatg ttttgttgta ggtagtggaa attatctttc cagcaaagac catataatcc      1800
gataaagctg ataactaaat gtcaaaatcg agtaagtgcc atatcatcta tatcttatct      1860
gttgtttgga aaaagacaaa atccaaaaaa aaatatatga gatctcacat gtataaatag      1920
ctcccaaatc agtagttaat acatctccca taatatttc agcattcaaa aacacaccaa      1980
gcgaagcgca ctagcaacga                                                  2000
```

<210> SEQ ID NO 216
<211> LENGTH: 1456
<212> TYPE: DNA
<213> ORGANISM: Zea mays

<400> SEQUENCE: 216

```
tgtttggact ccagaaaatt tacgggagtt ggtggagcag gtcattaagt actataaaaa      60
atcatgtagc tgaagctgca agtatttaga agacatttag ataagttatt ttatttatca     120
tttagattaa gaaaatttaa aactatttaa attgatatta taaactacag ctccacactg     180
gagctagatc ctggagtcat tacaaacacc cccttaatgg gaaaagagaa gataatgtat     240
atctaattat tgtttctgtg tcacctatag ctattagttc aaaacttcat aatcactggt     300
acaaataagc tctagagagg cggttcggaa cccattttta ttgttgtttt tcaaaaccac     360
tagtgttagg gaccgccagt ggaaactgaa acgccattgg aaattgattt tcactgatgg     420
tgagctaaga aaaccgccat tggtaatcct ttgcagaaaa cataaactag gttttaaaaa     480
tagtaaacaa atattttat taggagaggc cccacatagt cgcaccattt ttcgcgcatt     540
attcacgcgc tacgcaacca atggtaattg aacctcagag acttcactct tgtgtagcct     600
cctttgccac tccactaaac acttacttgt gtcttgattg cattttgttg cccacatatt     660
agaacaaaca gagtgtaaat tgattgtttg aggctgtaaa caaattcaaa tgaaaaagta     720
gtcaactact aaattgaata attgtttatg ttctaccact tttattttgg tacttttccc     780
atcggaggcg gtttgtaaaa tttgcatttt aagttttaca aatttcaatg aaattttgag     840
agcccaaatg atttcaaata aaaagttgt caactacaat gttttataac ttttaatttg     900
gtggttttt aaacaagctc atttgaaaaa ctaaaatgat cgattctaca tgattttag     960
gtcgattttt taaggaatcg cctgtacaaa tatttctact gacagttttt aagaaaccac    1020
ctgtggaaat catagatttg tactagcggt ttttctcaag taactgctag tagaaatatg    1080
gtggttttct taagaaaact gtttgtagga atgcacgatt tatataaatg gatttgttaa    1140
gaaaaccgct agtggaatgt tctttcaact aacggttatt gagtcgtgac agccaattta    1200
atttccttga taactaaaag cggctgtaaa aattagacca tgatgtaggc acggagctgt    1260
tttgtactga atgcgcccac tgtttttgttg gaaaagtgca tgtacttatt attcattctg    1320
tttatttcta gctggcattc agttcttaca gccacagatt atgcaaaacg cctatttctg    1380
ccagcaaatt tacaggaaaa gtcatggact ttccgggtt atttttcctat aagtacagcc    1440
attcctttca cttaca                                                    1456
```

<210> SEQ ID NO 217
<211> LENGTH: 710
<212> TYPE: DNA
<213> ORGANISM: Zea mays

<400> SEQUENCE: 217

```
ttcagcgtta tttgaacacc gtaaagcctc tccagcagat tgtgaataca cagttgtgga     60
gaacgctatt tataacgcag acactattta taatgcagat gtgtaaaagt gaaatttaaa    120
atagtagatg agataggaga gatagaatga gtaaactgct ggagagcaaa tcgtgcatat    180
gatcgtgcaa aacaccgttt ttcgtagagt gaagtttaaa atagcaggtg agagagtaga    240
taggatgagt aagctgatgg agagcaaata ttgtatatac gtggtcggtg caatagagtg    300
aaatttgaaa taactgacac agttttggtg cgtggaaata gacgaggata attctagtgc    360
aatccgcact gccagtggac cccgcccgac gataattcta cgcacgggcg gcgcactgca    420
```

```
ctactagttc atcgatcgga tgcgttagcg tgccccctcct catattgttt ccttgtacgt    480
actagtgcaa tccgtcagcc gcacggctcc agtccactcc agtccagcaa cagcgtcacc    540
tccagctccg aaaggcttat ccttgcaaca aacatcgtac gaaaaaggcg caggaaaaag    600
aaaagtgtcg aaatacgaca taaaaaaagc atcaaaatac gctgcgagtg agcgagacat    660
tggcctcccc atcccatata tatatagcta tagctatccc tcggttcttc               710
```